United States Patent
Cooper et al.

(10) Patent No.: US 12,187,702 B2
(45) Date of Patent: *Jan. 7, 2025

(54) SULFONAMIDEUREA COMPOUNDS

(71) Applicant: Inflazome Limited, Dublin (IE)

(72) Inventors: Matthew Cooper, Cambridge (GB); David Miller, Cambridge (GB); Angus MacLeod, Cambridge (GB); Jonathan Shannon, Nottingham (GB); Jokin Carrillo Arregui, Nottingham (GB); Jimmy Van Wiltenburg, Groningen (NL); Jochem Theodoor Van Herpt, Groningen (NL)

(73) Assignee: INFLAZOME LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/267,800

(22) PCT Filed: Aug. 12, 2019

(86) PCT No.: PCT/EP2019/071628
§ 371 (c)(1),
(2) Date: Feb. 10, 2021

(87) PCT Pub. No.: WO2020/035464
PCT Pub. Date: Feb. 20, 2020

(65) Prior Publication Data
US 2022/0194923 A1  Jun. 23, 2022

(30) Foreign Application Priority Data

Aug. 15, 2018 (GB) ...................................... 1813280
Feb. 20, 2019 (GB) ...................................... 1902327

(51) Int. Cl.
| | |
|---|---|
| C07D 401/12 | (2006.01) |
| C07C 311/30 | (2006.01) |
| C07D 205/04 | (2006.01) |
| C07D 207/48 | (2006.01) |
| C07D 243/08 | (2006.01) |
| C07D 295/26 | (2006.01) |
| C07D 487/04 | (2006.01) |
| C07D 487/08 | (2006.01) |
| C07D 487/10 | (2006.01) |

(52) U.S. Cl.
CPC .......... *C07D 401/12* (2013.01); *C07C 311/30* (2013.01); *C07D 205/04* (2013.01); *C07D 207/48* (2013.01); *C07D 243/08* (2013.01); *C07D 295/26* (2013.01); *C07D 487/04* (2013.01); *C07D 487/08* (2013.01); *C07D 487/10* (2013.01)

(58) Field of Classification Search
CPC .............................. C07D 207/14; A61K 31/40
See application file for complete search history.

(56) References Cited

U.S. PATENT DOCUMENTS

| | | |
|---|---|---|
| 3,242,174 A | 3/1966 | McManus et al. |
| 3,856,786 A | 12/1974 | Huber |
| 4,401,816 A | 8/1983 | Levitt |
| 4,515,620 A | 5/1985 | Bohner |
| 5,185,330 A | 2/1993 | Ochiai et al. |
| 5,214,206 A | 5/1993 | Picard et al. |
| 5,300,497 A | 4/1994 | Ochiai et al. |
| 5,486,618 A | 1/1996 | Hagen et al. |
| 6,346,359 B1 | 2/2002 | Yamada et al. |
| 10,538,487 B2 | 1/2020 | O'Neill et al. |
| 11,858,922 B2 * | 1/2024 | O'Neill ................ C07D 311/20 |

(Continued)

FOREIGN PATENT DOCUMENTS

| | | |
|---|---|---|
| AU | 2015900507 | 2/2015 |
| CH | 490350 A | 5/1970 |

(Continued)

OTHER PUBLICATIONS

Banker et al., Prodrugs, Modern Pharmaceutics, Third Edition, Revised and Expanded, pp. 451 and 596 (1996).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Alston & Bird LLP

(57) ABSTRACT

The present invention relates to compounds of formula (I): wherein Q is selected from O or S; $R^1$ and $R^3$ are each independently hydrogen or an optionally substituted hydrocarbyl group, or $R^1$ and $R^3$ together with the nitrogen atom to which they are attached may form a 3- to 12-membered optionally substituted cyclic group; and $R^2$ is a cyclic group substituted at the position, wherein $R^2$ may optionally be further substituted. The present invention further relates to salts, solvates and prodrugs of such compounds, to pharmaceutical compositions comprising such compounds, and to the use of such compounds in the treatment and prevention of medical disorders and diseases, most especially by the inhibition of NLRP3.

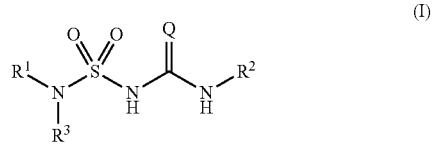

(I)

8 Claims, No Drawings

(56) References Cited

U.S. PATENT DOCUMENTS

| | | |
|---|---|---|
| 2003/0134898 A1 | 7/2003 | Reynold |
| 2018/0044287 A1 | 2/2018 | O'Neill et al. |
| 2020/0299284 A1 | 9/2020 | O'Neill et al. |
| 2022/0194923 A1 | 6/2022 | Cooper et al. |

FOREIGN PATENT DOCUMENTS

| | | |
|---|---|---|
| CN | 103159651 A | 6/2013 |
| CN | 107428696 A | 12/2017 |
| DE | 1064284 B | 8/1959 |
| EP | 0556322 A1 | 5/1993 |
| EP | 1236468 A1 | 9/2002 |
| EP | 1281399 A2 | 2/2003 |
| EP | 1354871 A1 | 10/2003 |
| EP | 1236478 A1 | 9/2020 |
| GB | 968805 A | 9/1964 |
| GB | 1031361 A | 6/1966 |
| GB | 1155936 A | 6/1969 |
| GB | 2110689 A | 6/1983 |
| JP | 2001-071647 A | 3/2001 |
| KR | 2009 0121832 A | 11/2009 |
| WO | WO 1992/08694 A1 | 5/1992 |
| WO | WO 1992/010480 A1 | 6/1992 |
| WO | WO 1998/032733 A1 | 7/1998 |
| WO | WO 2001/019390 A1 | 3/2001 |
| WO | WO 2001/96298 A2 | 12/2001 |
| WO | WO 2013/086980 A1 | 6/2013 |
| WO | WO 2018/015445 A1 | 1/2016 |
| WO | WO 2016/131098 A1 | 8/2016 |
| WO | WO 2016/150428 A1 | 9/2016 |
| WO | WO 2017/129897 A1 | 8/2017 |
| WO | WO 2017/140778 A1 | 8/2017 |
| WO | WO 2017/189651 A1 | 11/2017 |
| WO | WO 2017/189652 A1 | 11/2017 |
| WO | WO 2017/189663 A1 | 11/2017 |
| WO | WO 2017/201150 A1 | 11/2017 |
| WO | WO 2017/201152 A1 | 11/2017 |
| WO | WO 2018/215818 A1 | 11/2018 |
| WO | WO 2019/034686 A1 | 2/2019 |
| WO | WO 2019/034688 A1 | 2/2019 |
| WO | WO 2019/034692 A1 | 2/2019 |
| WO | WO 2019/034693 A1 | 2/2019 |
| WO | WO 2019/092171 A1 | 5/2019 |
| WO | WO 2019/092172 A1 | 5/2019 |
| WO | WO 2019/121691 A1 | 6/2019 |
| WO | WO 2019/166619 A1 | 9/2019 |
| WO | WO 2019/166629 A1 | 9/2019 |
| WO | WO 2019/166633 A1 | 9/2019 |
| WO | WO 2020/035464 A1 | 2/2020 |
| WO | WO 2020/035465 A1 | 2/2020 |
| WO | WO 2020/035466 A1 | 2/2020 |
| WO | WO 2020/086732 A1 | 4/2020 |
| WO | WO 2021/089768 A1 | 5/2021 |
| WO | WO 2021/089783 A1 | 5/2021 |

OTHER PUBLICATIONS

Simone, Oncology: Introduction, Cecil Textbook of Medicine, 20th Edition, vol. 1, pp. 1004-1010, 1996.*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Razonable et al., PubMed Abstract (Herpes 10(3):60-5), 2003.*
Goff, PubMed Abstract (J Gene Med. 3(6):517-28), 2001.*
PCT/EP2019/071628 International Preliminary Report on Patentability mailed Feb. 16, 2021.
PCT/EP2019/071628 Search Report and Written Opinion mailed Aug. 11, 2019.
Ronn, et al., "New Developments in the Discovery of Agents to Treat Hepatitis C," Current Topics in Medicinal Chemistry, 8, pp. 533-562, (2008).
McManus, et al., "Sulfamylurea Hypoglycemic Agents. I. Synthesis and Screening," Medical Research Laboratories, Chas. Pfizer & Co., Inc., Groton, Connecticut, pp. 766-776, (Jan. 1965).
LaPorte, et al., "Tetrhydrobenzothiophiophene inhibitors of hepatitis C virus NS5B polymerase," Bioorganic & Medincinal Chemistry Letters, 16, 100-103, (2006).
Chhabria, et al., "Discovery of Novel Acyl Coenzyme A: Cholesterol Acyltransferase Inhibitors: Pharmacophore-Based Virtual Screening, Synthesis and Pharmacology," Chem. Bio. Drug Dees., 80: 107-113, (2012).
Sarges, et al., "Sulfamylurea Hypoglycemic Agents. 6. High-Potency Derivatives," Journal of Medicinal Chemistry, American Chemical Society, US, vol. 19, No. 5, pp. 695-709, (Jan. 1976).
Wiseman, et al., "Sulfamylurea Hypoglycemic Agents. III. Drug Dynamic Studies," Medical Research Laboratories, Chas. Pfizer & Co., Inc., Groton, Connecticut, pp. 777-781, (Nov. 1965).
Belai et al "Responses of different fungal and plant species to acetolactate synthase inhibitors and their derivatives" Journal of Environmental Science and Health, Part B: Pesticides, Food Contaminants, and Agricultural Waste, B31(3):615-620 (1996).
CAS RN 1136411-26-1; STN Entry Date: Apr. 19, 2009; 1-Piperidinesulfonamide, 2,6-dimethyl-N-[(2-pyridinylamino) carbonyl]-.
CAS RN 1137082-14-4; STN Entry Date: Apr. 20, 2009; 1-Piperidinesulfonamide, N-[(2-pyridinylamino)carbonyl]-.
CAS RN 252654-28-7; STN Entry Date: Jan. 11, 2000; Urea, N-[[bis(1-methylethyl)amino]sulfonyl]-N'-2-pyridinyl-.
CAS RN 253864-92-5; STN Entry Date: Jan. 31, 2000; Thieno[3,2-c]pyridine-5(4H)-sulfonamide, 6,7-dihydro-N-[[(6-methyl-2-pyridinyl)amino]carbonyl]-4-propyl-.
CAS RN 400840-16-6; STN Entry Date: Mar. 14, 2002; 4-Morpholinesulfonamide, N-[[(5-methyl-2-pyrimidinyl)amino]carbonyl]-.
CAS RN 400840-17-7; STN Entry Date: Mar. 14, 2002; Urea, N-[(diethylamino)sulfonyl]-N'-(4,6-dimethyl-2-pyrimidinyl)-.
CAS RN 400840-33-7; STN Entry Date: Mar. 14, 2002; 1-Piperidinesulfonamide, N-[[(4,6-dimethyl-2-pyrimidinyl)amino]carbonyl]-.
CAS RN 400841-40-9; STN Entry Date: Mar. 14, 2002; 1-Piperidinesulfonamide, N-[[[4-(1,1-dimethylethyl)-6-(trifluoromethyl)-2-pyrimidinyl]amino]carbonyl]-.
CAS RN 864174-60-7; STN Entry Date: Sep. 29, 2005; 4-Morpholinesulfonamide, N-[[(4,6-dimethyl-2-pyrimidinyl)amino]carbonyl]-.
CAS RN 864389-24-2; STN Entry Date: Oct. 3, 2005; 4-Morpholinesulfonamide, N-[[[4-(1,1-dimethylethyl)-6-(trifluoromethyl)-2-pyrimidinyl]amino]carbonyl]-.
CAS RN 864424-64-6; STN Entry Date: Oct. 4, 2005; 4-Morpholinesulfonamide, N-[[(4,6-dimethoxy-2-pyrimidinyl)amino]carbonyl]-.
CAS RN 865074-37-9; STN Entry Date: Oct. 12, 2005; 1-Piperidinesulfonamide, N-[[(5-methyl-2-pyridinyl) amino]carbonyl]-.
CAS RN 956262-42-3; STN Entry Date Nov. 29, 2007; Urea, N-(4-cyano-1-phenyl-1H-pyrazol-5-yl)-N'-[(diethylamino)sulfonyl]-.
CAS RN 959321-29-0; STN Entry Date: Dec. 21, 2007; Benzo[b]thiophene-3-carboxylic acid, 2-[[[[(3,4-dihydro-2(1H)-isoquinolinyl)sulfonyl]amino]carbonyl]amino]-4,5,6,7-tetrahydro-, ethyl ester.
CAS RN 959361-83-2; STN Entry Date: Dec. 21, 2007; Benzo[b]thiophene-3-carboxylic acid, 4,5,6,7-tetrahydro-2-[[[(1-pyrrolidinylsulfonyl)amino]carbonyl]amino]-, ethyl ester.
CAS RN 959378-15-5; STN Entry Date: Dec. 21, 2007; Benzo[b]thiophene-3-carboxylic acid, 4,5,6,7-tetrahydro-6,6-dimethyl-2-[[[[(2-methyl-1H-imidazol-1-yl)sulfonyl]amino]carbonyl]amino]-, ethyl ester.

(56) References Cited

OTHER PUBLICATIONS

CAS RN 959378-16-6; STN Entry Date: Dec. 21, 2007; Benzo[b]thiophene-3-carboxylic acid, 4,5,6,7-tetrahydro-2-[[[(4-morpholinylsulfonyl)amino]carbonyl]amino]-, ethyl ester.
CAS RN 959378-20-2; STN Entry Date: Dec. 21, 2007; Benzo[b]thiophene-3-carboxylic acid, 4,5,6,7-tetrahydro-2-[[[(1-piperidinylsulfonyl)amino]carbonyl]amino]-, ethyl ester.
CAS RN 959663-63-9; STN Entry Date: Dec. 28, 2007; Benzo[b]thiophene-3-carboxylic acid, 4,5,6,7-tetrahydro-2-[[[[(4-methyl-1-piperazinyl)sulfonyl]amino]carbonyl]amino]-, ethyl ester.
CAS RN 959664-76-7; STN Entry Date: Dec. 28, 2007; Benzo[b]thiophene-3-carboxylic acid, 4,5,6,7-tetrahydro-6,6-dimethyl-2-[[[[(5-methyl-1H-pyrazol-1-yl)-sulfonyl]amino]carbonyl]amino]-, ethyl ester.
CAS RN 959670-14-5; STN Entry Date: Dec. 28, 2007; Benzo[b]thiophene-3-carboxylic acid, 2-[[[[(4-acetyl-1-piperazinyl) sulfonyl]amino]carbonyl]amino]-4,5,6,7-tetrahydro-, ethyl ester.
CAS RN 687986-77-2; May 31, 2004.
CAS 210826-40-7; Sep. 3, 1998.
CAS 256373-96-3; Feb. 18, 2000.
CAS RN 65304-32-7; CAS Doc No. 88:74272; STN Entry 1977; Wu—Journal ref: Wu et al. "Synthesis of sulfonylureas. I. 1-Substituted benzenesulfonyl-3-heterocyclyl ureas" Taiwan Yaoxue Zazhi, 28(1-2):56-61 (1977).
El-Akri et al. "Physicochemical 2D-Qsar and 3D molecular docking studies on N-chlorosulfonyl isocyanate analogs as sterol O-acyl-transferase-1 "Soat-1" Inhibitors" Open Journal of Medicinal Chemistry, 3:100-120 (2013).
Lather et al. "Predicting Acyl-Coenzyme A: Cholesterol O-acyltransferase inhibitory activity: Computational approach using topological descriptors" Drug Design and Discovery, 18:117-122 (2003).
Patankar et al. "Prediction of IC50 values for ACAT inhibitors from molecular structure" J. Chem. Inf. Comput. Sci., 40:706-723 (2000).
Petersen, "New reactions of sulphonamides," Chemische Berichte, 83(6):551-558, (1950), no translation available.
Picard et al., "Inhibitors of Acyl-CoA: Cholesterol O-Acyltransferase. 17. Structure-Activity Relationships of Several Series of Compounds Derived from N-Chlorosulfonyl Isocyanate" Journal of Medicinal Chemistry, 39(6): 1243-1252 (1996).
Rakel et al., "Beneficial effects of gliclazide modified release compared with glibenclamide on endothelial activation and low-grade inflammation in patients with type 2 diabetes" Diabetes, Obesity and Metabolism, 9(1):127-129 (2007).
So et al. "Evaluation of designed ligands by a multiple screening method: Application to glycogen phosphorylase inhibitors constructed with a variety of approaches" Journal of Computer Aided Design, 2001, 15, pp. 615-647.
Ettmayer et al., "Lessons learned from marketed and investigational prodrugs" J. Med. Chem., 47(10):2394-2404 (2004).
Himiceskij, Chemical Encyclopedia, (1983), p. 130-131, Brief Statement of Relevance.
Stella, "Prodrugs as therapeutics" Expert Opinion of therapeutic patents, 14(3): 277-280 (2004).
Testa, "Prodrug Research: futile or fertile?" Biochemical Pharmacology, 68 (2004) 2097-2106.
Zawilska et al., Prodrugs: a challenge for the drug development, Pharmacological Reports, 2013, vol. 65, No. 1, pp. 1-14.
Parajuli et al., Prodrug as a novel approach of drug delivery—a review, Journal of Drug Delivery & Therapeutics, 2015, 5(3), pp. 5-9.
Belikov, "Pharmaceutical chemistry", chapter 2.6 "The interconnection between chemical structure, properties of substances and their effect on the body", MEDpress-inform, Moscow, 2007, p. 27-29, Brief Statement of Relevance.
Solvation—Wikipedia, retrieved from the internet on Jan. 15, 2022 at: https://en.wikipedia.org/wiki/Solvation.
Disease—Wikipedia, retrieved from the internet on Feb. 2, 2022 at: https://en.wikipedia.org/wiki/Disease.

Han, "Targeted prodrug design to optimize drug delivery" AAPS Pharmsci. 2(1) Article 6: 1-11, (2000).
Kelley et al. "the NLRP3 inflammasome: an overview of mechanisms of activation and regulation" International Journal of Molecular Sciences, 2019, vol. 20, Article 3328, pp. 1-24.
Coll, et al., "The Cytokine Release Inhibitory Drug CRID3 Targets ASC Oligomerisation in the NLRP3 and AIM2 Inflammasomes," PloS ONE, vol. 6, Issue 12, e29539, (Dec. 2011) and correction.
PCT/EP2017/053498 International Search Report and Written Opinion mailed Mar. 29, 2017.
PCT/EP2017/053498 International Preliminary Report on Patentability mailed Aug. 21, 2018.
AU2015/900506 Search Report mailed Jul. 21, 2015.
U.S. Appl. No. 16/535,002 Notice of allowance mailed May 19, 2021.
U.S. Appl. No. 16/629,006 Non-final Office Action mailed Dec. 8, 2020.
Balant, ed in Wolff et al. Burger's Medicinal Chemistry and drug discovery, 5th Ed., vol. 1. Principles and practice, pp. 949-982, 1995.
Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.
Banker et al., Prodrugs, Modern Pharmaceutics, 3rd edition, Revised and Expanded, pp. 451 and 596, (1995).
Bundgaard, "Design of Prodrugs," Chapter1, p. 1, (1985).
CAS RN 210826-40-7; Sep. 3, 1998.
Coll et al., "A small-molecule inhibitor of the NLRP3 inflammasome for the treatment of inflammatory diseases," Nature Medicine, 21(3):248-255, (2015).
EP 1169038 Decision of the Opposition Division of the European Patent Office posted Feb. 9, 2016.
Ettmayer, et al., " Perspective, Lessons Learned from Marketed and Investigational Prodrugs," Journal of Medicinal Chemistry, vol. 47, No. 10, 2393-2404, (May 6, 2004).
Luo, et al., "NLRP3 gene silencing ameliorates diabetic cardiomyopathy in a type 2 diabetes rat model", PloS One, vol. 9(8), e104771, (2014).
Pan, et al., "Microglial NLRP3 inflammasome activation mediates IL-1β-related inflammation in prefrontal cortex of depressive rats", Brain, Behavior, and Immunity, vol. 41, pp. 90-100, (2014).
Silverman, "The Organic Chemistry of Drug Design and Drug Action," Prodrugs and Drug Delivery Stystem, The Organic Chemistry of Drug Design and Drug Action, Chapter 8, pp. 352-400, (1992).
Silverman, Prodrugs and drug delivery systems, The organic chemistry of drug design and drug action, Chapter 8, pp. 352-400, 1992.
The Library of Trinity College Dublin—Trinity College Dublin, Classic Catalogue, Thesis 9801 unavailable, retrived from the internet at: library.catalogue.tcd.ie/search on Jan. 17, 2022.
WO 1998/032733 A1, Claim 5 structures, cited by the opponent in opposition of EP1169038.
WO 2001/019390 A1, Claim 14 structures, cited by the opponent in opposition of EP1169038.
Zhao, et al., "Bay11-7082 attenuates murine lupus nephritis via inhibiting NLRP3 inflammasome and NF-KB activation", International Immunopharmacology, vol. 17, pp. 116-122, (2013).
IL 273065 Examination Report mailed Jan. 17, 2022,.
U.S. Appl. No. 15/999,424, Final Office Action and Interview Summary mailed May 16, 2022.
U.S. Appl. No. 15/999,424, Non-Final Office Action mailed Feb. 12, 2021.
U.S. Appl. No. 15/999,424, Non-Final Office Action mailed Sep. 21, 2021.
U.S. Appl. No. 15/999,424, Non-Final Office Action mailed Nov. 30, 2022.
U.S. Appl. No. 15/999,424, Notice of Allowance mailed Apr. 14, 2023.
U.S. Appl. No. 15/999,424, Requirement for Restriction/Election mailed Jul. 31, 2020.
U.S. Appl. No. 15/999,424, Notice of Allowance mailed Sep. 6, 2023.

(56) References Cited

OTHER PUBLICATIONS

JP Application 2021-507616 Notice of Reasons for Rejection mailed Aug. 1, 2023, English translation only.

Leszczyriska et al., "The NLRP3 inflammasome as a new target in respiratory disorders treatment," Front. Immunol. vol. 13, (Sep. 2022).

Yan et al., "CSB6B prevents β-amyloid-associated neuroinflammation and cognitive impairments via inhibiting NF-κB and NLRP3 in microglia cells," International Immunopharmacology 81 (2020) 106263.

Ridker, et al., "Antiinflammatory Therapy with Canakinumab for Atherosclerotic Disease," Engl J Med, 377(12):1119-1131, (Sep. 2017).

Ridker, et al., "Effect of interleukin-1β inhibition with canakinumab on incident lung cancer in patients with atherosclerosis: exploratory results from a randomised, double-blind, placebo-controlled trial," Published online (Aug. 2017) at http://dx.doi.org/10.1016/S0140-6736(17)32247-X.

\* cited by examiner

SULFONAMIDEUREA COMPOUNDS

CROSS-REFERENCE TO RELATED APPLICATIONS

This application is a national stage entry of PCT/EP2019/071628 filed Aug. 12, 2019, which claims the benefit of GB Application No. 1813280.3 filed Aug. 15, 2018 and GB Application No. 1902327.4 filed Feb. 20, 2019.

FIELD OF THE INVENTION

The present invention relates to sulfonylureas and sulfonylthioureas comprising an N-linked substituent attached to the sulfur atom of the sulfonylurea or sulfonylthiourea group and an α-substituted cyclic group attached to the nitrogen atom of the urea or thiourea group, and to associated salts, solvates, prodrugs and pharmaceutical compositions. The present invention further relates to the use of such compounds in the treatment and prevention of medical disorders and diseases, most especially by NLRP3 inhibition.

BACKGROUND OF THE INVENTION

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signalling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al., J Pharmacol Exp Ther, 299: 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184623 A1, WO 2017/184624 A1, WO 2018/015445 A1, WO 2018/136890 A1, WO 2018/215818 A1, WO 2019/008025 A1, WO 2019/008029 A1, WO 2019/034686 A1, WO 2019/034688 A1, WO 2019/034690 A1, WO 2019/034692 A1, WO 2019/034693 A1, WO 2019/034696 A1, WO 2019/034697 A1, WO 2019/043610 A1, WO 2019/092170 A1, WO 2019/092171 A1, and WO 2019/092172 A1). In addition, WO 2017/184604 A1 and WO 2019/079119 A1 disclose a number of sulfonylamide-containing compounds as inhibitors of NLRP3. Certain sulfoximine-containing compounds are also disclosed as inhibitors of NLRP3 (WO 2018/225018 A1, WO 2019/023145 A1, WO 2019/023147 A1, and WO 2019/068772 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

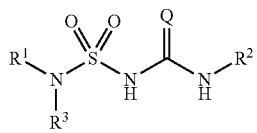

Formula (I)

wherein:
Q is selected from O or S;
$R^1$ and $R^3$ are each independently hydrogen or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
wherein optionally $R^1$ and $R^3$ together with the nitrogen atom to which they are attached may form a 3- to 12-membered cyclic group, wherein the cyclic group may optionally be substituted; and
$R^2$ is a cyclic group substituted at the α-position, wherein $R^2$ may optionally be further substituted.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

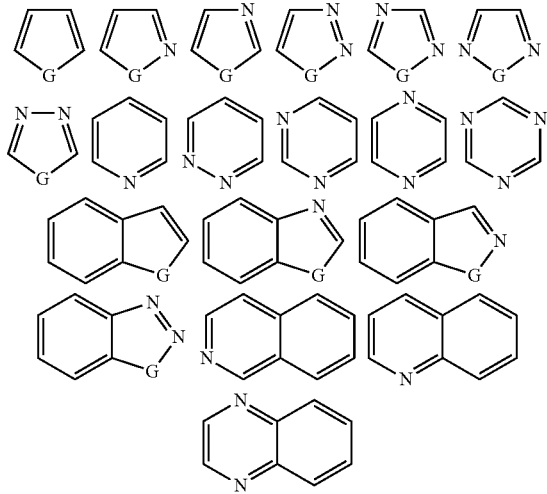

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or (ii) any two hydrogen atoms attached to the same carbon or nitrogen atom may optionally be replaced by a π-bonded substituent independently selected from oxo (=O), =S, =NH or =NR$^\beta$; and/or (iii) any sulfur atom may optionally be substituted with one or two π-bonded substituents independently selected from oxo (=O), =NH or =NR$^\beta$; and/or (iv) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$- or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$-.

Where reference is made to a —R$^\alpha$—C(N$_2$)R$^\beta$ group, what is intended is:

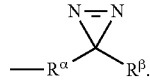

Typically, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH;

—$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$N^+(R^\beta)_3$; —$R^\alpha$—$NH_2$; —$R^\alpha$—$NHR^\beta$; —$R^\alpha$—$N(R^\beta)_2$; —$R^\alpha$—$N^+(R^\beta)_3$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$; and/or (ii) any two hydrogen atoms attached to the same carbon atom may optionally be replaced by a π-bonded substituent independently selected from oxo (═O), ═S, ═NH or ═$NR^\beta$; and/or (iii) any two hydrogen atoms attached to the same or different atoms, within the same optionally substituted group or moiety, may optionally be replaced by a bridging substituent independently selected from —O—, —S—, —NH—, —$N(R^\beta)$—, —$N^+(R^\beta)_2$- or —$R^\alpha$—;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein a single —$CH_2$— group in the backbone of the alkylene, alkenylene or alkynylene group may optionally be replaced by a —$N^+(R^\beta)_2$— group, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two or three —$R^\beta$ attached to the same nitrogen atom may, together with the nitrogen atom to which they are attached, form a $C_2$-$C_7$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (═O), or 4- to 6-membered heterocyclic group.

Typically, in an optionally substituted group or moiety:

(i) each hydrogen atom may optionally be replaced by a group independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R^\beta)_2$; —$R^\alpha$—$NH_2$; —$R^\alpha$—$NHR^\beta$; —$R^\alpha$—$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; or —$R^\alpha$—$OCOR^\beta$; and/or (ii) any two hydrogen atoms attached to the same carbon atom may optionally be replaced by a π-bonded substituent independently selected from oxo (═O), ═S, ═NH or ═$NR^\beta$; and/or (iii) any two hydrogen atoms attached to the same or different atoms, within the same optionally substituted group or moiety, may optionally be replaced by a bridging substituent independently selected from —O—, —S—, —NH—, —$N(R^\beta)$— or —$R^\alpha$—;

wherein each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two —$R^\beta$ attached to the same nitrogen atom may, together with the nitrogen atom to which they are attached, form a $C_2$-$C_6$ cyclic group, and wherein any —$R^\beta$ may optionally be substituted with one or more $C_1$-$C_4$ alkyl, halo, —OH, or 4- to 6-membered heterocyclic group.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —$N(R^\beta)$—, —$N(O)(R^\beta)$—, —$N^+(R^\beta)_2$— or —$R^\alpha$—) of an optionally substituted group or moiety (e.g. $R^1$) must only be attached to the specified group or moiety and may not be attached to a second group or moiety (e.g. $R^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Similarly, unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Unless stated otherwise, any reference to a compound or group is to be considered a reference to all tautomers of that compound or group.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

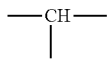

is replaced by

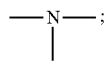

—CH$_2$— is replaced by —NH—, —O— or —S—;
—CH$_3$ is replaced by —NH$_2$, —OH or —SH;
—CH= is replaced by —N=;
CH$_2$= is replaced by NH=, O= or S=; or
CH≡ is replaced by N≡;

provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:

—CH$_2$— is replaced by

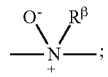

or

—CH$_2$— is replaced by

In the context of the present specification, unless otherwise stated, a C$_x$-C$_y$ group is defined as a group containing from x to y carbon atoms. For example, a C$_1$-C$_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are to be counted as carbon atoms when calculating the number of carbon atoms in a C$_x$-C$_y$ group. For example, a morpholinyl group is to be considered a C$_6$ heterocyclic group, not a C$_4$ heterocyclic group.

For the purposes of the present specification, where it is stated that a first atom or group is "directly attached" to a second atom or group it is to be understood that the first atom or group is covalently bonded to the second atom or group with no intervening atom(s) or group(s) being present. So, for example, for the group —(C=O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

For the avoidance of doubt, where it is stated that a compound or a group, such as R$^1$ or R$^2$, contains from x to y atoms other than hydrogen, it is to be understood that the compound or group as a whole, including any optional substituents, contains from x to y atoms other than hydrogen. Such a compound or group may contain any number of hydrogen atoms.

R$^1$ and R$^3$ are each independently hydrogen or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; wherein optionally R$^1$ and R$^3$ together with the nitrogen atom to which they are attached may form a 3- to 12-membered cyclic group, wherein the cyclic group may optionally be substituted.

In one embodiment, R$^1$ and R$^3$ are not both hydrogen.

In one embodiment, R$^1$ and R$^3$ are each independently hydrogen or a saturated or unsaturated C$_1$-C$_{20}$ (or C$_1$-C$_{18}$ or C$_1$-C$_{16}$ or C$_1$-C$_{14}$ or C$_1$-C$_{12}$ or C$_1$-C$_{10}$) hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton.

In one embodiment, R$^1$ and R$^3$ together with the nitrogen atom to which they are attached forms a 3- to 12-membered (or 3- to 10-membered, or 3- to 8-membered, or 3- to 7-membered) cyclic group, wherein the cyclic group may optionally be substituted. The cyclic group may be monocyclic, bicyclic (e.g. bridged, fused or spiro), or polycyclic.

In one embodiment, R$^1$ and R$^3$ together with the nitrogen atom to which they are attached forms a monocyclic 3- to 8-membered (or 4- to 7-membered) cyclic group, wherein the cyclic group may optionally be substituted.

In one embodiment, R$^1$ and R$^3$ together with the nitrogen atom to which they are attached forms a bicyclic 4- to 12-membered (or 6- to n-membered, or 7- to 10-membered) cyclic group, wherein the cyclic group may optionally be substituted. The bicyclic group may be bridged, fused or spiro.

In the above embodiments, R$^1$ may be substituted with one or more substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si (R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —CORP; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$;

—CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (═O), or 4- to 6-membered heterocyclic group.

Alternatively, R$^1$ may be substituted with one or more substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein a single —CH$_2$— group in the backbone of the alkylene, alkenylene or alkynylene group may optionally be replaced by a —N$^+$(R$^\beta$)$_2$— group, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (═O), or 4- to 6-membered heterocyclic group.

Alternatively, R$^1$ may be substituted with one or more substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two —R$^\beta$ attached to the same nitrogen atom may, together with the nitrogen atom to which they are attached, form a C$_2$-C$_6$ cyclic group, and wherein any —R$^\beta$ may optionally be substituted with one or more C$_1$-C$_4$ alkyl, halo, —OH, or 4- to 6-membered heterocyclic group.

In one aspect of any of the above embodiments, R$^1$ contains from 1 to 20 atoms other than hydrogen. More typically, R$^1$ contains from 1 to 15 atoms other than hydrogen. More typically, R$^1$ contains from 1 to 12 atoms other than hydrogen. More typically, R$^1$ contains from 1 to 10 atoms other than hydrogen.

In one aspect of any of the above embodiments, R$^3$ contains from 1 to 20 atoms other than hydrogen. More typically, R$^3$ contains from 1 to 15 atoms other than hydrogen. More typically, R$^3$ contains from 1 to 12 atoms other than hydrogen. More typically, R$^3$ contains from 1 to 10 atoms other than hydrogen.

In one embodiment of the first aspect of the invention, the invention provides a compound of formula (IA):

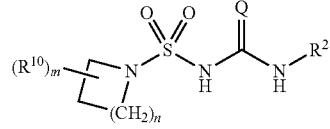

Formula (IA)

wherein:
m is 1, 2 or 3;
n is 1, 2 or 3;
each $R^{10}$ is independently selected from —$(CH_2)_p$—$NH_2$, —$(CH_2)_p$—$NHR^{11}$, —$(CH_2)_p$—$N(R^{11})_2$, or a 4- to 6-membered saturated heterocyclic group comprising one or two ring nitrogen atoms, wherein the heterocyclic group may optionally be substituted with one or two $C_1$-$C_3$ alkyl groups; or two $R^{10}$ together with the atom(s) to which they are attached form a 3- to 6-membered saturated heterocyclic group comprising one or two ring nitrogen atoms, wherein the heterocyclic group may optionally be substituted with one or two $C_1$-$C_3$ alkyl groups;

each $R^{11}$ is independently selected from $C_1$-$C_3$ alkyl or cyclopropyl; or two $R^{11}$ which are attached to the same nitrogen atom, may together form a $C_2$-$C_5$ alkylene;

p is 0, 1 or 2; and $R^2$ is a cyclic group substituted at the α- and α'-positions, wherein $R^2$ may optionally be further substituted.

For the avoidance of doubt, it is noted that $R^{10}$ may be directly attached to any of the ring carbon atoms of the azetidinyl, pyrrolidinyl or piperidinyl group to which $R^{10}$ is attached.

In one embodiment, n is 1 and the compound of formula (IA) is a compound of formula (IA1):

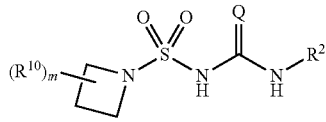

Formula (IA$_1$)

wherein $R^2$, $R^{10}$ and m are as defined with reference to formula (IA).

In one embodiment, n is 2 and the compound of formula (IA) is a compound of formula (IA2):

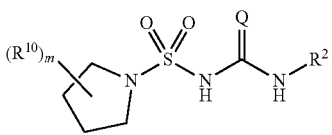

Formula (IA$_2$)

wherein $R^2$, $R^{10}$ and m are as defined with reference to formula (IA).

In one embodiment, n is 3 and the compound of formula (IA) is a compound of formula (IA3):

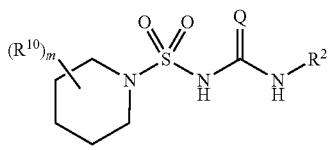

Formula (IA$_3$)

wherein $R^2$, $R^{10}$ and m are as defined with reference to formula (IA).

In one embodiment, each $R^{10}$ is independently selected from —$(CH_2)_p$—$NH_2$, —$(CH_2)_p$—$NHR^{11}$, —$(CH_2)_p$—$N(R^{11})_2$, or a 4- to 6-membered saturated heterocyclic group, wherein the ring atoms of the heterocyclic group consist of three, four or five ring carbon atoms and one or two ring nitrogen atoms, and wherein the heterocyclic group may optionally be substituted with one or two $C_1$-$C_3$ alkyl groups. In one embodiment, the 4- to 6-membered saturated heterocyclic group is selected from an azetidinyl, pyrrolidinyl, imidazolinyl, pyrazolinyl, piperidinyl or piperazinyl group, all optionally substituted with one or two $C_1$-$C_3$ alkyl groups. In one embodiment, the 4- to 6-membered saturated heterocyclic group is selected from an azetidinyl, pyrrolidinyl or piperidinyl group, all optionally substituted with one $C_1$-$C_3$ alkyl group independently selected from methyl, ethyl, n-propyl or iso-propyl. In one embodiment, the 4- to 6-membered saturated heterocyclic group is selected from an unsubstituted azetidinyl, pyrrolidinyl or piperidinyl group. In one embodiment, p is 0 or 1. In one embodiment, each $R^{11}$ is independently selected from $C_1$-$C_3$ alkyl. In one embodiment, each $R^{11}$ is independently selected from methyl, ethyl, n-propyl or iso-propyl. In one embodiment, each $R^{11}$ is independently selected from methyl or ethyl.

In one embodiment, m is 1 or 2. In one embodiment, m is 1. In another embodiment, m is 2.

In one embodiment, each $R^{10}$ is independently selected from —$(CH_2)_p$—$NH_2$, —$(CH_2)_p$—$NHR^{11}$, —$(CH_2)_p$—$N(R^{11})_2$, or a 4- to 6-membered saturated heterocyclic group selected from an azetidinyl, pyrrolidinyl, imidazolinyl, pyrazolinyl, piperidinyl or piperazinyl group, all optionally substituted with one or two $C_1$-$C_3$ alkyl groups; wherein p is 0, 1 or 2, and each $R^{11}$ is independently selected from methyl, ethyl, n-propyl or iso-propyl. In one embodiment, m is 1 or 2. In one embodiment, m is 1. In another embodiment, m is 2.

In one embodiment, each $R^{10}$ is independently selected from —$(CH_2)_p$—$NHR^{11}$, —$(CH_2)_p$—$N(R^1)_2$, or a 4- to 6-membered saturated heterocyclic group selected from an azetidinyl, pyrrolidinyl or piperidinyl group, all optionally substituted with one $C_1$-$C_3$ alkyl group independently selected from methyl, ethyl, n-propyl or iso-propyl; wherein p is 0 or 1, and each $R^{11}$ is independently selected from methyl, ethyl, n-propyl or iso-propyl. In one embodiment, m is 1 or 2. In one embodiment, m is 1. In another embodiment, m is 2.

In one embodiment, each $R^{10}$ is independently selected from —$(CH_2)_p$—$N(R^{11})_2$, or a 4- to 6-membered saturated heterocyclic group selected from an unsubstituted azetidinyl, pyrrolidinyl or piperidinyl group; wherein p is 0 or 1, and each $R^{11}$ is independently selected from methyl, ethyl, n-propyl or iso-propyl. In one embodiment, m is 1 or 2. In one embodiment, m is 1. In another embodiment, m is 2.

When two $R^{10}$ together with the atom(s) to which they are attached form a 3- to 6-membered saturated heterocyclic group, the 3- to 6-membered saturated heterocyclic group and the azetidinyl, pyrrolidinyl or piperidinyl group it is attached to, together form a bicyclic ring structure which may be bridged, fused or spiro. In one embodiment, the bicyclic ring structure is fused or spiro.

In one embodiment, when two $R^{10}$ together with the atom(s) to which they are attached form a 3- to 6-membered saturated heterocyclic group, the ring atoms of the heterocyclic group consist of two, three, four or five ring carbon atoms and one or two ring nitrogen atoms, wherein the heterocyclic group may optionally be substituted with one or two $C_1$-$C_3$ alkyl groups. In one embodiment, two $R^{10}$ together with the atom(s) to which they are attached form a 4- to 6-membered saturated heterocyclic group, wherein the ring atoms of the heterocyclic group consist of three, four or five ring carbon atoms and one or two ring nitrogen atoms, and wherein the heterocyclic group may optionally be substituted with one or two $C_1$-$C_3$ alkyl groups.

In one embodiment, two $R^{10}$ together form a divalent substituent selected from —N($R^{16}$)—$CH_2$—, —N($R^{16}$)—$CH_2CH_2$—, —$CH_2$—N($R^{16}$)—$CH_2$—, —N($R^{16}$)—$CH_2CH_2CH_2$—, or —$CH_2$—N($R^{16}$)—$CH_2CH_2$—; wherein $R^{16}$ is selected from hydrogen or $C_1$-$C_3$ alkyl. In one embodiment, $R^{16}$ is selected from hydrogen, methyl, ethyl, n-propyl or iso-propyl. In one embodiment, $R^{16}$ is selected from methyl, ethyl, n-propyl or iso-propyl. Typically in such an embodiment, the divalent substituent of two $R^{10}$ and the azetidinyl, pyrrolidinyl or piperidinyl group it is attached to, together form a bicyclic ring structure which may be bridged, fused or spiro. In one embodiment, the bicyclic ring structure is fused or spiro.

In another embodiment of the first aspect of the invention, the invention provides a compound of formula (IB):

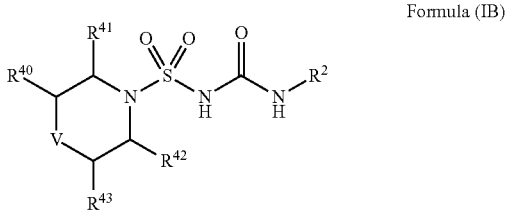

Formula (IB)

wherein:
V is $CR^{44}R^{46}$, $NR^{44}$ or $NR^{48}$;
one of $R^{40}$ and $R^{42}$, or $R^{40}$ and $R^{43}$, or $R^{41}$ and $R^{42}$, or $R^{41}$ and $R^{44}$ together form —$CH_2$—, —$CH_2CH_2$—, —O—$CH_2$—, or —$NR^{45}$—$CH_2$—, and the remaining of $R^{40}$, $R^{41}$, $R^{42}$, $R^{43}$ and, when present, $R^{44}$ are hydrogen;
$R^{45}$ is selected from hydrogen, methyl or ethyl;
$R^{46}$ is selected from —$(CH_2)_q$—$NH_2$, —$(CH_2)_q$—$NHR^{47}$, —$(CH_2)_q$—$N(R^{47})_2$, or a 4- to 6-membered saturated heterocyclic group comprising one or two ring nitrogen atoms, wherein the heterocyclic group may optionally be substituted with one or two $C_1$-$C_3$ alkyl groups;
each $R^{47}$ is independently selected from $C_1$-$C_3$ alkyl or cyclopropyl; or two $R^{47}$ together may form a $C_2$-$C_5$ alkylene;
q is 0, 1 or 2;
$R^{48}$ is selected from $C_1$-$C_4$ alkyl or $C_3$-$C_4$ cycloalkyl; and
$R^2$ is a cyclic group substituted at the α- and α'-positions, wherein $R^2$ may optionally be further substituted.

For the avoidance of doubt, it is noted that when V is $NR^{44}$, and $R^{41}$ and $R^{44}$ together form —O—$CH_2$— or —$NR^{45}$—$CH_2$—, the nitrogen atom of $NR^{44}$ is not directly attached to the oxygen atom of —O—$CH_2$— or the nitrogen atom of —$NR^{45}$—$CH_2$—.

In one embodiment, V is $CHR^{46}$ or $NR^{48}$.

In one embodiment, V is $NR^{48}$. In one embodiment, $R^{48}$ is selected from $C_1$-$C_3$ alkyl or cyclopropyl. In one embodiment, $R^{48}$ is selected from methyl, ethyl, n-propyl, iso-propyl or cyclopropyl.

In one embodiment, V is $CHR^{46}$. In one embodiment, $R^{46}$ is selected from —$(CH_2)_q$—$NH_2$, —$(CH_2)_q$—$NHR^{47}$, —$(CH_2)_q$—$N(R^{47})_2$, or a 4- to 6-membered saturated heterocyclic group, wherein the ring atoms of the heterocyclic group consist of three, four or five ring carbon atoms and one or two ring nitrogen atoms, and wherein the heterocyclic group may optionally be substituted with one or two $C_1$-$C_3$ alkyl groups. In one embodiment, the 4- to 6-membered saturated heterocyclic group is selected from an azetidinyl, pyrrolidinyl, imidazolinyl, pyrazolinyl, piperidinyl or piperazinyl group, all optionally substituted with one or two $C_1$-$C_3$ alkyl groups. In one embodiment, the 4- to 6-membered saturated heterocyclic group is selected from an azetidinyl, pyrrolidinyl or piperidinyl group, all optionally substituted with one $C_1$-$C_3$ alkyl group independently selected from methyl, ethyl, n-propyl or iso-propyl. In one embodiment, the 4- to 6-membered saturated heterocyclic group is selected from an unsubstituted azetidinyl, pyrrolidinyl or piperidinyl group. In one embodiment, q is 0 or 1. In one embodiment, q is 0. In one embodiment, each $R^{47}$ is independently selected from $C_1$-$C_3$ alkyl. In one embodiment, each $R^{47}$ is independently selected from methyl, ethyl, n-propyl or iso-propyl. In one embodiment, each $R^{47}$ is independently selected from methyl or ethyl.

In one embodiment, V is $CHR^{46}$, and $R^{46}$ is selected from —$(CH_2)_q$—$NH_2$, —$(CH_2)_q$—$NHR^{47}$, —$(CH_2)_q$—$N(R^{47})_2$, or a 4- to 6-membered saturated heterocyclic group selected from an azetidinyl, pyrrolidinyl, imidazolinyl, pyrazolinyl, piperidinyl or piperazinyl group, all optionally substituted with one or two $C_1$-$C_3$ alkyl groups; wherein q is 0, 1 or 2, and each $R^{47}$ is independently selected from methyl, ethyl, n-propyl or iso-propyl.

In one embodiment, V is $CHR^{46}$, and $R^{46}$ is selected from —$(CH_2)_q$—$NHR^{47}$, —$(CH_2)_q$—$N(R^{47})_2$, or a 4- to 6-membered saturated heterocyclic group selected from an azetidinyl, pyrrolidinyl or piperidinyl group, all optionally substituted with one $C_1$-$C_3$ alkyl group independently selected from methyl, ethyl, n-propyl or iso-propyl; wherein q is 0 or 1, and each $R^{47}$ is independently selected from methyl, ethyl, n-propyl or iso-propyl.

In one embodiment, V is $CHR^{46}$, and $R^{46}$ is selected from —$(CH_2)_q$—$N(R^{47})_2$, or a 4- to 6-membered saturated heterocyclic group selected from an unsubstituted azetidinyl, pyrrolidinyl or piperidinyl group; wherein q is 0 or 1, and each $R^{47}$ is independently selected from methyl, ethyl, n-propyl or iso-propyl.

In one embodiment, V is $CHR^{46}$, and $R^{46}$ is selected from $NMe_2$, $NEt_2$ or pyrrolidinyl.

In one embodiment, one of $R^{40}$ and $R^{42}$, or $R^{40}$ and $R^{43}$, or $R^{41}$ and $R^{42}$, or $R^{41}$ and $R^{44}$ together form —$CH_2$— or —$CH_2CH_2$—, and the remaining of $R^{40}$, $R^{41}$, $R^{42}$, $R^{43}$ and, when present, $R^{44}$ are hydrogen.

In one embodiment, the compound of formula (IB) is a compound of formula (IB1), (IB2), (IB3) or (IB4):

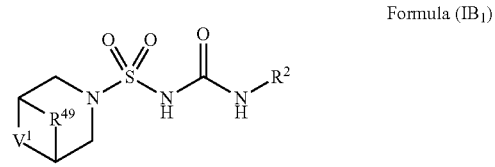

Formula (IB$_1$)

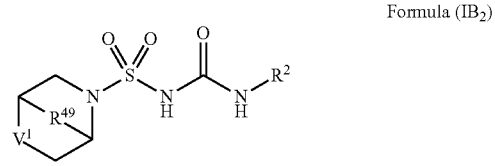

Formula (IB$_2$)

-continued

Formula (IB3)

Formula (IB4)

wherein:
R$^{49}$ is —CH$_2$— or —CH$_2$CH$_2$—;
V$^1$ is CHR$^{46}$, NH or NR$^{48}$;
V$^2$ is CR$^{46}$ or N; and
R$^{46}$, R$^{48}$ and R$^2$ are as defined with reference to formula (IB).

In another embodiment of the first aspect of the invention, the invention provides a compound of formula (IC):

Formula (IC)

wherein:
W, X, Y and Z are each independently selected from —CH$_2$—, —CH(R$^{18}$)—, —C(R$^{18}$)$_2$—, —NH— or —N(R$^{18}$)—, provided that no two ring nitrogen atoms are directly attached to each other;
each R$^{18}$ is independently selected from C$_1$-C$_3$ alkyl or cyclopropyl; or two R$^{18}$ together may form a C$_2$-C$_6$ alkylene; and
R$^2$ is a cyclic group substituted at the α- and α'-positions, wherein R$^2$ may optionally be further substituted.

In one embodiment, three of W, X, Y and Z are —CH$_2$—, and one of W, X, Y and Z is —N(R$^{18}$)—.

In one embodiment, each R$^{18}$ is independently selected from C$_1$-C$_3$ alkyl or cyclopropyl. In one embodiment, each R$^{18}$ is independently selected from C$_1$-C$_3$ alkyl. In one embodiment, each R$^{18}$ is independently selected from methyl, ethyl, n-propyl or iso-propyl. In one embodiment, each R$^{18}$ is independently selected from methyl or ethyl. In one embodiment, each R$^{18}$ is methyl.

In another embodiment of the first aspect of the invention, the invention provides a compound of formula (ID):

Formula (ID)

wherein:
R$^{20}$ is selected from a bond or C$_1$-C$_5$ alkylene;
R$^{21}$ is N(R$^{22}$)$_2$ or a 4- to 6-membered saturated heterocyclic group comprising one or two ring nitrogen atoms, wherein the heterocyclic group may optionally be substituted with one or two C$_1$-C$_4$ alkyl groups;
each R$^{22}$ is independently selected from hydrogen, C$_1$-C$_5$ alkyl or C$_3$-C$_5$ cycloalkyl; or two R$^{22}$ together may form a C$_2$-C$_5$ alkylene;
R$^{23}$ is selected from hydrogen, C$_1$-C$_5$ alkyl, C$_3$-C$_5$ cycloalkyl or —(CH$_2$)$_t$-Ph;
t is 0, 1, 2, 3 or 4; and
R$^2$ is a cyclic group substituted at the α- and α'-positions, wherein R$^2$ may optionally be further substituted;
provided that when R$^{21}$ is N(R$^{22}$)$_2$, then R$^{20}$ is selected from C$_1$-C$_5$ alkylene.

For the avoidance of doubt, it is noted that when R$^{20}$ is a bond and R$^{21}$ is a 4- to 6-membered saturated heterocyclic group, it is a ring carbon atom of the 4- to 6-membered saturated heterocyclic group of R$^{21}$ that is directly attached to the nitrogen atom of the remainder of the compound.

In one embodiment, R$^{20}$ is selected from a bond or C$_1$-C$_4$ alkylene. In one embodiment, R$^{20}$ is selected from a bond, —CH$_2$—, —CH$_2$CH$_2$—, —CH$_2$CH$_2$CH$_2$—, —CH$_2$CH$_2$CH$_2$CH$_2$—, —CHMe-, —CMe$_2$-, —CHMe-CH$_2$—, —CH$_2$—CHMe-, —CHMe-CHMe-, —CMe$_2$-CH$_2$—, —CH$_2$—CMe$_2$-, —CHMe-CH$_2$CH$_2$—, —CH$_2$—CHMe-CH$_2$—, —CH$_2$CH$_2$—CHMe-, —CHMe-CHMe-CH$_2$—, —CHMe-CH$_2$—CHMe-, —CH$_2$—CHMe-CHMe-, —CMe$_2$-CH$_2$CH$_2$—, —CH$_2$—CMe$_2$-CH$_2$—, or —CH$_2$CH$_2$—CMe$_2$-. In one embodiment, R$^{20}$ is selected from a bond, —CH$_2$—, —CH$_2$CH$_2$—, —CH$_2$CH$_2$CH$_2$—, —CH$_2$CH$_2$CH$_2$CH$_2$—, —CHMe-CH$_2$—, —CH$_2$—CHMe-, —CMe$_2$-CH$_2$—, or —CH$_2$—CMe$_2$-.

In one embodiment, R$^{21}$ is N(R$^{22}$)$_2$, R$^{20}$ is selected from —CH$_2$CH$_2$—, —CH$_2$CH$_2$CH$_2$—, —CH$_2$CH$_2$CH$_2$CH$_2$—, —CHMe-CH$_2$—, —CH$_2$—CHMe-, —CMe$_2$-CH$_2$—, or —CH$_2$—CMe$_2$-.

In one embodiment, when R$^{21}$ is a 4- to 6-membered saturated heterocyclic group, R$^{20}$ is selected from a bond, —CH$_2$— or —CH$_2$CH$_2$—.

In one embodiment, R$^{21}$ is N(R$^{22}$)$_2$, and each R$^{22}$ is independently selected from hydrogen, C$_1$-C$_5$ alkyl or C$_3$-C$_5$ cycloalkyl. In one embodiment, R$^{21}$ is N(R$^{22}$)$_2$, and each R$^{22}$ is independently selected from hydrogen or C$_1$-C$_5$ alkyl. In one embodiment, R$^{21}$ is N(R$^{22}$)$_2$, and each R$^{22}$ is independently selected from hydrogen, methyl, ethyl, n-propyl, iso-propyl, n-butyl, iso-butyl, sec-butyl or t-butyl, provided that not both R$^{22}$ are hydrogen. In one embodiment, R$^{21}$ is N(R$^{22}$)$_2$, and each R$^{22}$ is independently selected from hydrogen, methyl, ethyl, iso-propyl or t-butyl, provided that not both R$^{22}$ are hydrogen. In one embodiment, R$^{21}$ is NHMe, NHEt, NH$^i$Pr, NH$^t$Bu, NMe$_2$, NMeEt, or NEt$_2$. In one embodiment, R$^{21}$ is NHEt, NH$^i$Pr, NH$^t$Bu, NMe$_2$, NMeEt, or NEt$_2$.

In one embodiment, R$^{21}$ is a 4- to 6-membered saturated heterocyclic group comprising one or two ring nitrogen atoms, wherein the heterocyclic group may optionally be substituted with one or two C$_1$-C$_4$ alkyl groups. In one embodiment, the ring atoms of the 4- to 6-membered saturated heterocyclic group consist of three, four or five ring carbon atoms and one or two ring nitrogen atoms, and the heterocyclic group may optionally be substituted with one or two C$_1$-C$_3$ alkyl groups. In one embodiment, the 4- to 6-membered saturated heterocyclic group is selected from an azetidinyl, pyrrolidinyl, imidazolinyl, pyrazolinyl, piperidinyl or piperazinyl group, all optionally substituted with one or two C$_1$-C$_3$ alkyl groups. In one embodiment, the 4- to 6-membered saturated heterocyclic group is selected from an azetidinyl, pyrrolidinyl or piperidinyl group, all optionally substituted with one or two C$_1$-C$_3$ alkyl groups independently selected from methyl, ethyl, n-propyl or iso-propyl. In one embodiment, the 4- to 6-membered saturated heterocyclic group is selected from an azetidinyl, pyrrolidinyl or piperidinyl group, all optionally substituted on the ring nitrogen atom with one $C_1$-$C_3$ alkyl group selected from methyl, ethyl, n-propyl or iso-propyl.

In one embodiment, the 4- to 6-membered saturated heterocyclic group of $R^{21}$ is substituted with one $C_1$-$C_3$ alkyl group. In one embodiment, the 4- to 6-membered saturated heterocyclic group of $R^{21}$ is substituted with one $C_1$-$C_3$ alkyl group selected from methyl, ethyl, n-propyl or iso-propyl. In one embodiment, the substituent on the 4- to 6-membered saturated heterocyclic group of $R^{21}$ is on a ring nitrogen atom.

In one embodiment, $R^{23}$ is selected from hydrogen, $C_1$-$C_5$ alkyl or —$(CH_2)_t$-Ph, wherein t is 0, 1, 2, 3 or 4. In one embodiment, $R^{23}$ is selected from hydrogen, $C_1$-$C_4$ alkyl or —$(CH_2)_t$-Ph, wherein t is 1, 2 or 3. In one embodiment, $R^{23}$ is selected from hydrogen, methyl, ethyl, n-propyl, iso-propyl, n-butyl, iso-butyl, sec-butyl, t-butyl or —$(CH_2)_t$-Ph, wherein t is 1, 2 or 3. In one embodiment, $R^{23}$ is selected from hydrogen, methyl, ethyl, n-propyl, iso-propyl or —$(CH_2)_t$-Ph, wherein t is 1, 2 or 3. In one embodiment, $R^{23}$ is selected from hydrogen, methyl, ethyl, n-propyl, iso-propyl or —$(CH_2)_t$-Ph, wherein t is 2 or 3.

In one embodiment, when $R^{21}$ is $N(R^{22})_2$, $R^{23}$ is selected from hydrogen, $C_1$-$C_5$ alkyl or —$(CH_2)_t$-Ph, wherein t is 0, 1, 2, 3 or 4. In one embodiment, when $R^{21}$ is $N(R^{22})_2$, $R^{23}$ is selected from hydrogen, $C_1$-$C_4$ alkyl or —$(CH_2)_t$-Ph, wherein t is 1, 2 or 3. In one embodiment, when $R^{21}$ is $N(R^{22})_2$, $R^{23}$ is selected from hydrogen, methyl, ethyl, n-propyl, iso-propyl, n-butyl, iso-butyl, sec-butyl, t-butyl or —$(CH_2)_t$-Ph, wherein t is 1, 2 or 3. In one embodiment, when $R^{21}$ is $N(R^{22})_2$, $R^{23}$ is selected from hydrogen, methyl, ethyl, n-propyl, iso-propyl or —$(CH_2)_t$-Ph, wherein t is 1, 2 or 3. In one embodiment, when $R^{21}$ is $N(R^{22})_2$, $R^{23}$ is selected from hydrogen, methyl, ethyl, n-propyl, iso-propyl or —$(CH_2)_t$-Ph, wherein t is 2 or 3.

In one embodiment, when $R^{21}$ is a 4- to 6-membered saturated heterocyclic group, $R^{23}$ is selected from hydrogen or $C_1$-$C_4$ alkyl. In one embodiment, when $R^{21}$ is a 4- to 6-membered saturated heterocyclic group, $R^{23}$ is selected from hydrogen, methyl, ethyl, n-propyl, iso-propyl, n-butyl, iso-butyl, sec-butyl or t-butyl. In one embodiment, when $R^{21}$ is a 4- to 6-membered saturated heterocyclic group, $R^{23}$ is selected from hydrogen, methyl, ethyl, n-propyl or iso-propyl. In one embodiment, when $R^{21}$ is a 4- to 6-membered saturated heterocyclic group, $R^{23}$ is selected from hydrogen, methyl or ethyl. In one embodiment, when $R^{21}$ is a 4- to 6-membered saturated heterocyclic group, $R^{23}$ is selected from hydrogen or methyl.

In one embodiment, t is 0, 1, 2 or 3. In one embodiment, t is 1, 2 or 3.

In another embodiment of the first aspect of the invention, the invention provides a compound of formula (IE):

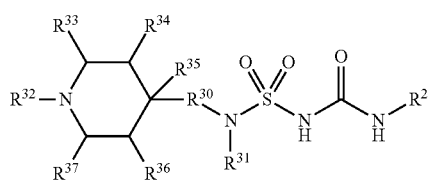

Formula (IE)

wherein:
$R^{30}$ is selected from a bond or $C_1$-$C_3$ alkylene;
$R^{31}$ is selected from hydrogen, $C_1$-$C_3$ alkyl or cyclopropyl;
one of $R^{32}$ and $R^{34}$, or $R^{32}$ and $R^{35}$, or $R^{33}$ and $R^{35}$, or $R^{33}$ and $R^{36}$, or $R^{33}$ and $R^{37}$, or $R^{34}$ and $R^{36}$ together form —$CH_2$—, —$CH_2CH_2$—, —$O$—$CH_2$—, or —$NR^{38}$—$CH_2$—, and the remaining of $R^{33}$, $R^{34}$, $R^{35}$, $R^{36}$ and $R^{37}$ are hydrogen, and $R^{32}$, if remaining, is selected from hydrogen, $C_1$-$C_4$ alkyl or $C_3$-$C_4$ cycloalkyl;
$R^{38}$ is selected from hydrogen, methyl or ethyl; and
$R^2$ is a cyclic group substituted at the α- and α'-positions, wherein $R^2$ may optionally be further substituted.

For the avoidance of doubt, it is noted that when $R^{32}$ and $R^{34}$, or $R^{32}$ and $R^{35}$ together form —$O$—$CH_2$— or —$NR^{38}$—$CH_2$—, the nitrogen atom of $NR^{32}$ is not directly attached to the oxygen atom of —$O$—$CH_2$— or the nitrogen atom of —$NR^{38}$—$CH_2$—.

In one embodiment, $R^{30}$ is selected from a bond or $C_1$-$C_2$ alkylene. In one embodiment, $R^{30}$ is selected from a bond, —$CH_2$—, or —$CH_2CH_2$—. In one embodiment, $R^{30}$ is selected from a bond or —$CH_2$—. In one embodiment, $R^{30}$ is a bond.

In one embodiment, $R^{31}$ is selected from hydrogen or $C_1$-$C_3$ alkyl. In one embodiment, $R^{31}$ is selected from hydrogen, methyl, ethyl, n-propyl or iso-propyl. In one embodiment, $R^{31}$ is selected from hydrogen, methyl or ethyl. In one embodiment, $R^{31}$ is selected from hydrogen or methyl. In one embodiment, $R^{31}$ is hydrogen.

In one embodiment, $R^{32}$ is selected from hydrogen or $C_1$-$C_4$ alkyl. In one embodiment, $R^{32}$ is selected from hydrogen or $C_1$-$C_3$ alkyl. In one embodiment, $R^{32}$ is selected from methyl, ethyl, n-propyl or iso-propyl. In one embodiment, $R^{32}$ is selected from methyl, ethyl or iso-propyl.

In one embodiment, one of $R^{32}$ and $R^{34}$, or $R^{32}$ and $R^{35}$, or $R^{33}$ and $R^{35}$, or $R^{33}$ and $R^{36}$, or $R^{33}$ and $R^{37}$, or $R^{34}$ and $R^{36}$ together form —$CH_2$— or —$CH_2CH_2$—, and the remaining of $R^{33}$, $R^{34}$, $R^{35}$, $R^{36}$ and $R^{37}$ are hydrogen, and $R^{32}$, if remaining, is selected from $C_1$-$C_4$ alkyl or $C_3$-$C_4$ cycloalkyl. In one embodiment, one of $R^{32}$ and $R^{34}$, or $R^{32}$ and $R^{35}$, or $R^{33}$ and $R^{35}$, or $R^{33}$ and $R^{36}$, or $R^{33}$ and $R^{37}$, or $R^{34}$ and $R^{36}$ together form —$CH_2CH_2$—, and the remaining of $R^{33}$, $R^{34}$, $R^{35}$, $R^{36}$ and $R^{37}$ are hydrogen, and $R^{32}$, if remaining, is selected from methyl, ethyl, n-propyl or iso-propyl.

In one embodiment, the compound of formula (IE) is a compound of formula (IE1), (IE2), (IE3), (IE4), (IE5) or (IE6):

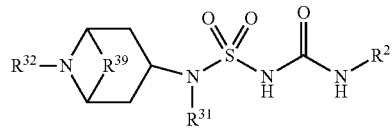

Formula (IE$_1$)

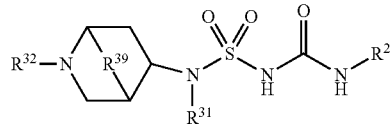

Formula (IE$_2$)

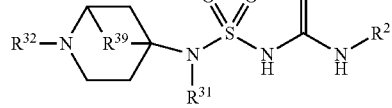

Formula (IE$_3$)

Formula (IE4)

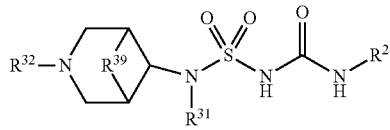

Formula (IE5)

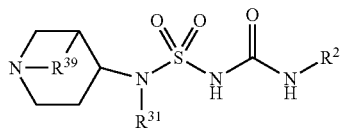

Formula (IE6)

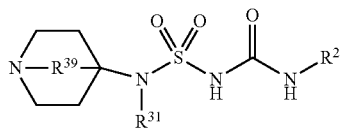

wherein R$^{39}$ is selected from —CH$_2$— or —CH$_2$CH$_2$—; and R$^2$, R$^{31}$ and R$^{32}$ are as defined with reference to formula (IE). In one embodiment, R$^{39}$ is —CH$_2$CH$_2$—.

In another embodiment of the first aspect of the invention, the invention provides a compound of formula (IF):

Formula (IF)

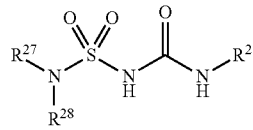

wherein:
R$^{27}$ is a 5-membered heteroaromatic group comprising one, two or three ring nitrogen atoms, wherein the heteroaromatic group may optionally be substituted with one or two C$_1$-C$_4$ alkyl or C$_3$-C$_4$ cycloalkyl groups;
R$^{28}$ is selected from hydrogen, C$_1$-C$_3$ alkyl or cyclopropyl; and
R$^2$ is a cyclic group substituted at the α- and α'-positions, wherein R$^2$ may optionally be further substituted.

For the avoidance of doubt, it is noted that it is a ring carbon atom of the 5-membered heteroaromatic group of R$^{27}$ that is directly attached to the nitrogen atom of the remainder of the compound.

In one embodiment, R$^{27}$ is a 5-membered heteroaromatic group, wherein the ring atoms of the heteroaromatic group consist of two, three or four ring carbon atoms and one, two or three ring nitrogen atoms, and wherein the heteroaromatic group may optionally be substituted with one or two C$_1$-C$_4$ alkyl groups. In one embodiment, the 5-membered heteroaromatic group is selected from a pyrrolyl, pyrazolyl, imidazolyl or triazolyl group, all optionally substituted with one or two C$_1$-C$_4$ alkyl groups. In one embodiment, the 5-membered heteroaromatic group is selected from a pyrrolyl, pyrazolyl, imidazolyl or triazolyl group, all optionally substituted with one or two C$_1$-C$_3$ alkyl groups. In one embodiment, the 5-membered heteroaromatic group is selected from a pyrazolyl or imidazolyl group, both optionally substituted with one or two C$_1$-C$_3$ alkyl groups. In one embodiment, the 5-membered heteroaromatic group is a pyrazolyl group, optionally substituted with one or two C$_1$-C$_3$ alkyl groups independently selected from methyl, ethyl, n-propyl or iso-propyl. In one embodiment, the 5-membered heteroaromatic group is a pyrazolyl group, optionally substituted on a ring nitrogen atom with one C$_1$-C$_3$ alkyl group selected from methyl, ethyl, n-propyl or iso-propyl.

In one embodiment, the 5-membered heteroaromatic group of R$^{27}$ is substituted with one C$_1$-C$_3$ alkyl group. In one embodiment, the 5-membered heteroaromatic group of R$^{27}$ is substituted with one C$_1$-C$_3$ alkyl group selected from methyl, ethyl, n-propyl or iso-propyl. In one embodiment, the 5-membered heteroaromatic group of R$^{27}$ is substituted with one C$_1$-C$_3$ alkyl group selected from methyl, ethyl or iso-propyl. In one embodiment, the substituent on the 5-membered heteroaromatic group is on a ring nitrogen atom.

In one embodiment, R$^{28}$ is selected from hydrogen or C$_1$-C$_3$ alkyl. In one embodiment, R$^{28}$ is selected from hydrogen, methyl, ethyl, n-propyl or iso-propyl. In one embodiment, R$^{28}$ is selected from hydrogen, methyl or ethyl. In one embodiment, R$^{28}$ is selected from hydrogen or methyl. In one embodiment, R$^{28}$ is hydrogen.

In the compounds of formula (I), R$^2$ is a cyclic group substituted at the α-position, wherein R$^2$ may optionally be further substituted. In the compounds of formula (IA), (IA1), (IA2), (IA3), (IB), (IB1), (IB2), (IB3), (IB4), (IC), (ID), (IE), (IE1), (IE2), (IE3), (IE4), (IE5), (IE6) and (IF), R$^2$ is a cyclic group substituted at the α- and α'-positions, wherein R$^2$ may optionally be further substituted. For the avoidance of doubt, it is noted that it is a ring atom of the cyclic group of R$^2$ that is directly attached to the nitrogen atom of the urea or thiourea group, not any substituent.

In one embodiment of the first aspect of the invention, R$^2$ is an aryl or a heteroaryl group, wherein the aryl or the heteroaryl group is substituted at the α-position, and wherein R$^2$ may optionally be further substituted. Typically, R$^2$ is a phenyl or a 5- or 6-membered heteroaryl group, wherein the phenyl or the heteroaryl group is substituted at the α-position, and wherein R$^2$ may optionally be further substituted. Typically, R$^2$ is an aryl or a heteroaryl group, wherein the aryl or the heteroaryl group is substituted at the α and α' positions, and wherein R$^2$ may optionally be further substituted. Typically, R$^2$ is a phenyl or a 5- or 6-membered heteroaryl group, wherein the phenyl or the heteroaryl group is substituted at the α and α' positions, and wherein R$^2$ may optionally be further substituted. For example, R$^2$ may be a phenyl group substituted at the 2- and 6-positions or a phenyl group substituted at the 2-, 4- and 6-positions.

In one embodiment, the parent phenyl or 5- or 6-membered heteroaryl group of R$^2$ may be selected from phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl. Typically, the parent phenyl or 5- or 6-membered heteroaryl group of R$^2$ may be selected from phenyl, pyridinyl, pyridazinyl, pyrimidinyl, pyrrolyl, pyrazolyl, imidazolyl or triazolyl. Typically, the parent phenyl or 5- or 6-membered heteroaryl group of R$^2$ may be selected from phenyl, pyridinyl, pyridazinyl, pyrimidinyl or pyrazolyl.

As used herein, the nomenclature α, β, α', β' refers to the position of the atoms of a cyclic group, such as —R$^2$, relative to the point of attachment of the cyclic group to the remainder of the molecule. For example, where —R$^2$ is a 1,2,3,5,6,7-hexahydro-s-indacen-4-yl moiety, the α, β, α' and β' positions are as follows:

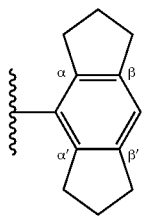 [SMILES: *c1c2c(cc3c1CCC3)CCC2]

For the avoidance of doubt, where it is stated that a cyclic group, such as an aryl or a heteroaryl group, is substituted at the α and/or α' positions, it is to be understood that one or more hydrogen atoms at the α and/or α' positions respectively are replaced by one or more substituents, such as any optional substituent as defined above. Unless stated otherwise, the term 'substituted' does not include the replacement of one or more ring carbon atoms by one or more ring heteroatoms.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions may be independently selected from $-R^4$, $-OR^4$ and $-COR^4$ groups, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, at least one substituent at the α and/or α' positions comprises a carbon atom. Typically, each substituent at the α and/or α' positions comprises a carbon atom. More typically, $R^2$ is substituted at the α and α' positions and both substituents at the α and α' positions comprise a carbon atom.

In a further aspect of any of the above embodiments, at least one substituent at the α and/or α' positions comprises a $sp^2$ or $sp^3$ hybridised carbon atom. Typically, each substituent at the α and/or α' positions comprises a $sp^2$ or $sp^3$ hybridised carbon atom.

More typically, $R^2$ is substituted at the α and α' positions and both substituents at the α and α' positions comprise a $sp^2$ or $sp^3$ hybridised carbon atom.

Typically, at least one substituent at the α and/or α' positions comprises a $sp^3$ hybridised carbon atom.

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α', β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the aryl or heteroaryl group across the α,β positions. Typically, the aryl or heteroaryl group is also substituted at the α' position, for example with a substituent selected from $-R^4$, $-OR^4$ and $-COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

More typically, $R^2$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure. Typically, the phenyl or the 5- or 6-membered heteroaryl group is also substituted at the α' position, for example with a substituent selected from $-R^4$, $-OR^4$ and $-COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically in such an embodiment, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted. Typically in such an embodiment, $R^2$ is tricyclic.

More typically, $R^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α', β' positions so as to form a second 4- to 6-membered fused ring structure, wherein $R^2$ may optionally be further substituted. Typically in such an embodiment, $R^2$ is tricyclic.

In one embodiment, $-R^2$ has a formula selected from:

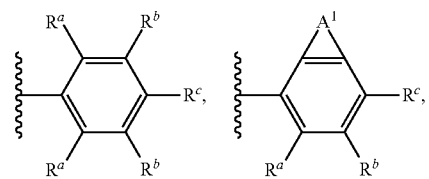

-continued

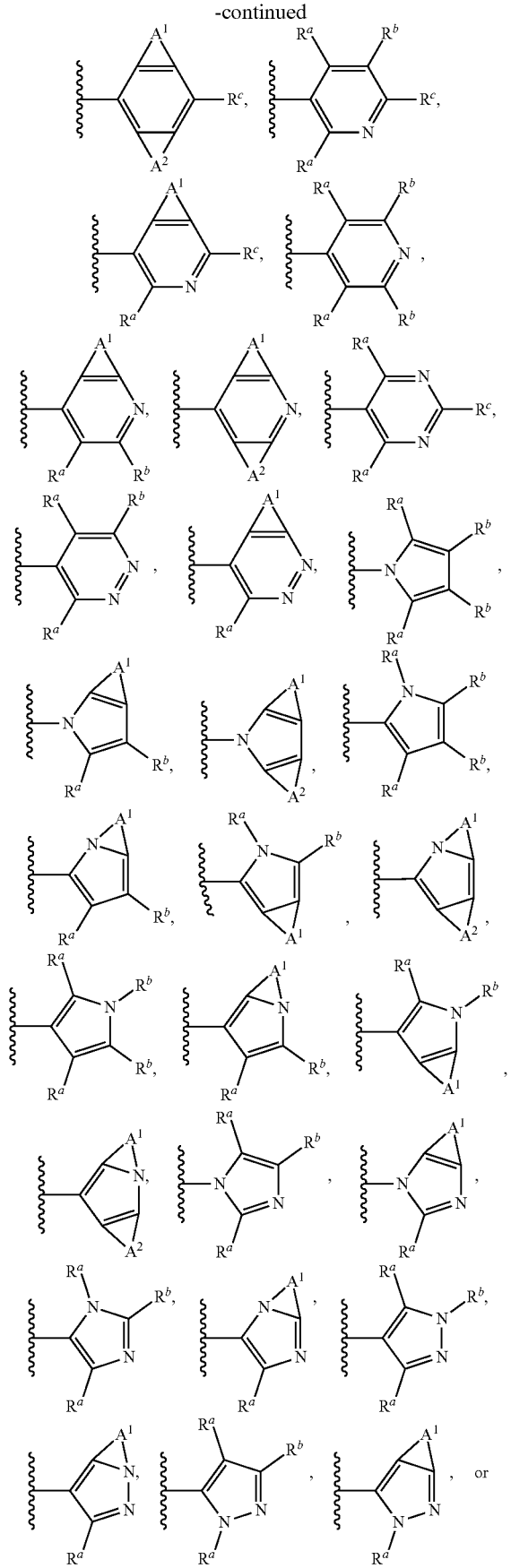

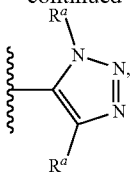

wherein:
A¹ and A² are each independently selected from an optionally substituted alkylene or alkenylene group, wherein one or more carbon atoms in the backbone of the alkylene or alkenylene group may optionally be replaced by one or more heteroatoms N, O or S;
each $R^a$ is independently selected from —$R^{aa}$, —$OR^{aa}$ or —$COR^{aa}$;
each $R^b$ is independently selected from hydrogen, halo, —$NO_2$, —CN, —$R^{aa}$, —$OR^{aa}$ or —$COR^{aa}$;
provided that any $R^a$ or $R^b$ that is directly attached to a ring nitrogen atom is not halo, —$NO_2$, —CN or —$OR^{aa}$;
each $R^c$ is independently selected from hydrogen, halo, —OH, —$NO_2$, —CN, —R—, —$OR^{cc}$, —$COR^c$, —$COOR^c$, —$CONH_2$, —$CONHR^{cc}$ or —$CON(R^c)_2$;
each $R^{aa}$ is independently selected from a $C_1$-$C_6$ alkyl, $C_2$-$C_6$ alkenyl, $C_2$-$C_6$ alkynyl or a 3- to 7-membered cyclic group, wherein each $R^{aa}$ is optionally substituted; and
each $R^{cc}$ is independently selected from a $C_1$-$C_6$ alkyl, $C_2$-$C_6$ alkenyl, $C_2$-$C_6$ alkynyl or a 3- to 7-membered cyclic group, or any two $R^{cc}$ attached to the same nitrogen atom may, together with the nitrogen atom to which they are attached, form a 3- to 7-membered heterocyclic group, wherein each $R^{cc}$ is optionally substituted.

Typically, any ring containing A¹ or A² is a 5- or 6-membered ring. Typically, A¹ and A² are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A¹ and A² are each independently selected from an optionally substituted straight-chained alkylene group, wherein one carbon atom in the backbone of the alkylene group may optionally be replaced by an oxygen atom. Typically, no heteroatom in A¹ or A² is directly attached to another ring heteroatom. Typically, A¹ and A² are unsubstituted or substituted with one or more substituents independently selected from halo, —OH, —CN, —$NO_2$, $C_1$-$C_4$ alkyl, $C_1$-$C_4$ haloalkyl, —O($C_1$-$C_4$ alkyl) or —O($C_1$-$C_4$ haloalkyl). More typically, A¹ and A² are unsubstituted or substituted with one or more fluoro and/or chloro groups. Where $R^2$ contains both A¹ and A² groups, A¹ and A² may be the same or different. Typically, A¹ and A² are the same.

Where $R^{aa}$ is a substituted $C_1$-$C_6$ alkyl, $C_2$-$C_6$ alkenyl or $C_2$-$C_6$ alkynyl group, typically the $C_1$-$C_6$ alkyl, $C_2$-$C_6$ alkenyl or $C_2$-$C_6$ alkynyl group is substituted with one or more (e.g. one or two) substituents independently selected from halo, —OH, —CN, —$NO_2$, —O($C_1$-$C_4$ alkyl) or —O($C_1$-$C_4$ haloalkyl).

Where $R^{aa}$ is a substituted 3- to 7-membered cyclic group, typically the 3- to 7-membered cyclic group is substituted with one or more (e.g. one or two) substituents independently selected from halo, —OH, —$NH_2$, —CN, —$NO_2$, —B$^1$, —OB$^1$, —NHB$^1$, —N(B$^1$)$_2$, —CONH$_2$, —CONHB$^1$, —CON(B$^1$)$_2$, —NHCOB$^1$, —NB$^1$COB$^1$, or —B$^{11}$—;

wherein each B$^1$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B$^1$ may optionally be halo-substituted and/or substituted with one or two substituents independently selected from —OH, —NH$_2$, —OB$^{12}$, —NHB$^{12}$ or —N(B$^{12}$)$_2$;

wherein each B$^{11}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and wherein each B$^{12}$ is independently selected from a C$_1$-C$_3$ alkyl or C$_1$-C$_3$ haloalkyl group. Typically, any divalent group —B$^{11}$— forms a 4- to 6-membered fused ring.

Typically, each R$^a$ is —R$^{aa}$. More typically, each R$^a$ is independently selected from a C$_1$-C$_6$ alkyl (in particular C$_3$-C$_6$ branched alkyl) or C$_3$-C$_6$ cycloalkyl group, wherein each R$^a$ is optionally further substituted with one or more halo groups. More typically, each R$^a$ is independently selected from a C$_1$-C$_4$ alkyl, C$_1$-C$_4$ haloalkyl, C$_3$-C$_4$ cycloalkyl or C$_3$-C$_4$ halocycloalkyl group. Where a group R$^a$ is present at both the α- and α'-positions, each R$^a$ may be the same or different. Typically, each R$^a$ is the same.

Typically, each R$^b$ is independently selected from hydrogen or halo. More typically, each R$^b$ is hydrogen.

Typically, each R$^c$ is independently selected from hydrogen, halo, —OH, —NO$_2$, —CN, —R$^{cc}$ or —OR$^{cc}$. More typically, each R$^{cc}$ is independently selected from hydrogen, halo, —CN, C$_1$-C$_3$ alkyl, C$_1$-C$_3$ haloalkyl, cyclopropyl or halocyclopropyl. Most typically, each R$^c$ is independently selected from hydrogen or halo.

Typically, each R$^{cc}$ is independently selected from a C$_1$-C$_4$ alkyl or C$_3$-C$_6$ cycloalkyl group, or any two R$^{cc}$ attached to the same nitrogen atom may, together with the nitrogen atom to which they are attached, form a 3- to 6-membered saturated heterocyclic group, wherein each R$^c$ is optionally substituted. Where R$^{cc}$ is substituted, typically R$^{cc}$ is substituted with one or more halo, —OH, —CN, —NO$_2$, —O(C$_1$-C$_4$ alkyl) or —O(C$_1$-C$_4$ haloalkyl) groups. More typically, each R$^c$ is independently selected from a C$_1$-C$_4$ alkyl, C$_1$-C$_4$ haloalkyl, C$_3$-C$_4$ cycloalkyl or C$_3$-C$_4$ halocycloalkyl group.

In one embodiment, —R$^2$ has a formula selected from:

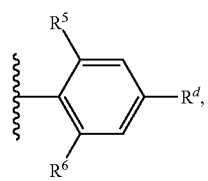

wherein R$^5$ and R$^6$ are independently selected from C$_1$-C$_4$ alkyl, C$_1$-C$_4$ haloalkyl, C$_3$-C$_4$ cycloalkyl and C$_3$-C$_4$ halocycloalkyl, and R$^d$ is hydrogen, halo, —OH, —NO$_2$, —CN, —R$^{dd}$, —OR$^{dd}$, —COR$^{dd}$, —COOR$^{dd}$, —CONH$_2$, —CONHR$^{dd}$ or —CON(R$^{dd}$)$_2$, wherein each —R$^{dd}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^5$ and R$^6$ are independently selected from C$_1$-C$_4$ alkyl, and R$^d$ is hydrogen, halo, —CN, C$_1$-C$_3$ alkyl, C$_1$-C$_3$ haloalkyl, cyclopropyl or halocyclopropyl. More typically, R$^5$ and R$^6$ are independently selected from C$_1$-C$_4$ alkyl, and R$^d$ is hydrogen or halo.

Typically, —R$^2$ has a formula selected from:

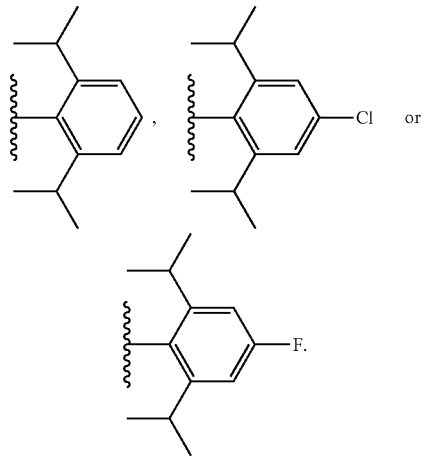

In one embodiment, —R$^2$ has a formula selected from:

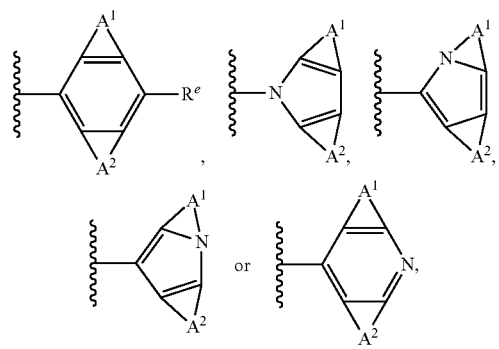

wherein A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S, and wherein R$^e$ is hydrogen or any optional substituent. R$^e$ and any optional substituent attached to A$^1$ or A$^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to A$^1$ and any optional substituent attached to A$^2$ may also together with the atoms to which they are attached form a further fused cycloalkyl, cycloalkenyl, non-aromatic heterocyclic, aryl or heteroaryl ring which may itself be optionally substituted.

In one embodiment, R$^e$ is hydrogen, halo, —OH, —NO$_2$, —CN, —R$^{ee}$, —OR$^{ee}$, —COR$^{ee}$, —COOR$^{ee}$, —CONH$_2$, —CONHR$^{ee}$ or —CON(R$^{ee}$)$_2$, wherein each —R$^{ee}$ is independently selected from C$_1$-C$_4$ alkyl, C$_1$-C$_4$ haloalkyl, C$_3$-C$_4$ cycloalkyl and C₃-C₄ halocycloalkyl. Typically, $R^e$ is hydrogen or a halo, hydroxyl, —CN, —NO₂, —$R^{ee}$ or —O$R^{ee}$ group, wherein $R^{ee}$ is a C₁-C₄ alkyl group which may optionally be halo-substituted. More typically, $R^e$ is hydrogen or halo.

Typically, any ring containing $A^1$ or $A^2$ is a 5- or 6-membered ring.

Typically, $A^1$ and $A^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, $A^1$ and $A^2$ are each independently selected from an optionally substituted straight-chained alkylene group, wherein one carbon atom in the backbone of the alkylene group may optionally be replaced by an oxygen atom. Typically, no heteroatom in $A^1$ or $A^2$ is directly attached to another ring heteroatom. Typically, $A^1$ and $A^2$ are unsubstituted or substituted with one or more halo, hydroxyl, —CN, —NO₂, —$B^3$ or —O$B^3$ groups, wherein $B^3$ is a C₁-C₄ alkyl group which may optionally be halo-substituted. More typically, $A^1$ and $A^2$ are unsubstituted or substituted with one or more fluoro and/or chloro groups. Where $R^2$ contains both $A^1$ and $A^2$ groups, $A^1$ and $A^2$ may be the same or different. Typically, $A^1$ and $A^2$ are the same.

In a further embodiment, —$R^2$ has a formula selected from:

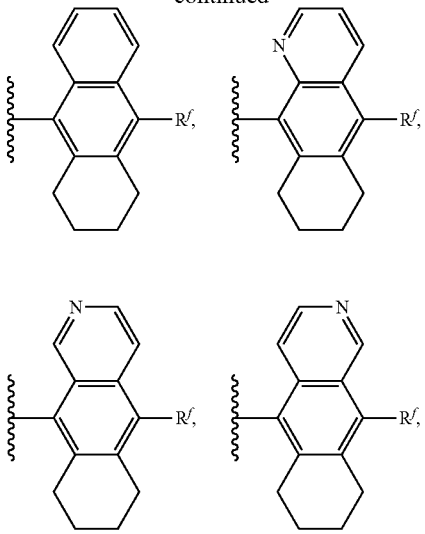

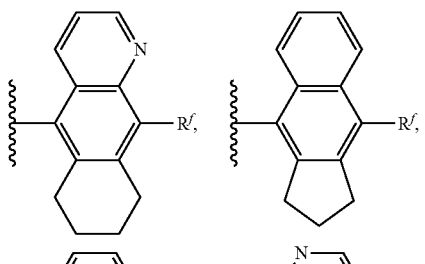

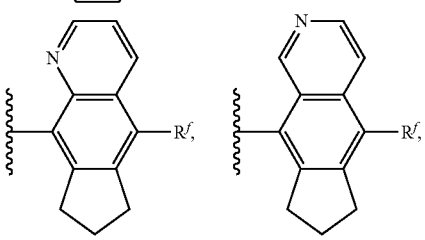

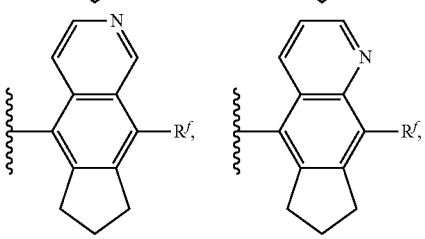

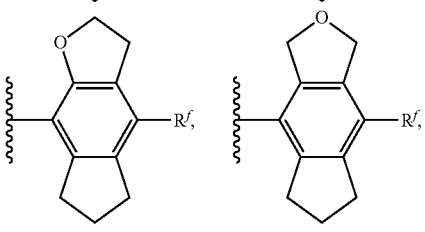

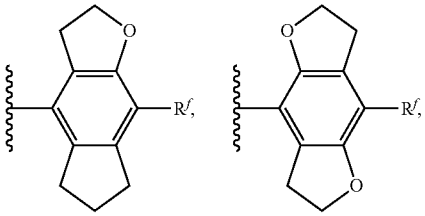

31

-continued

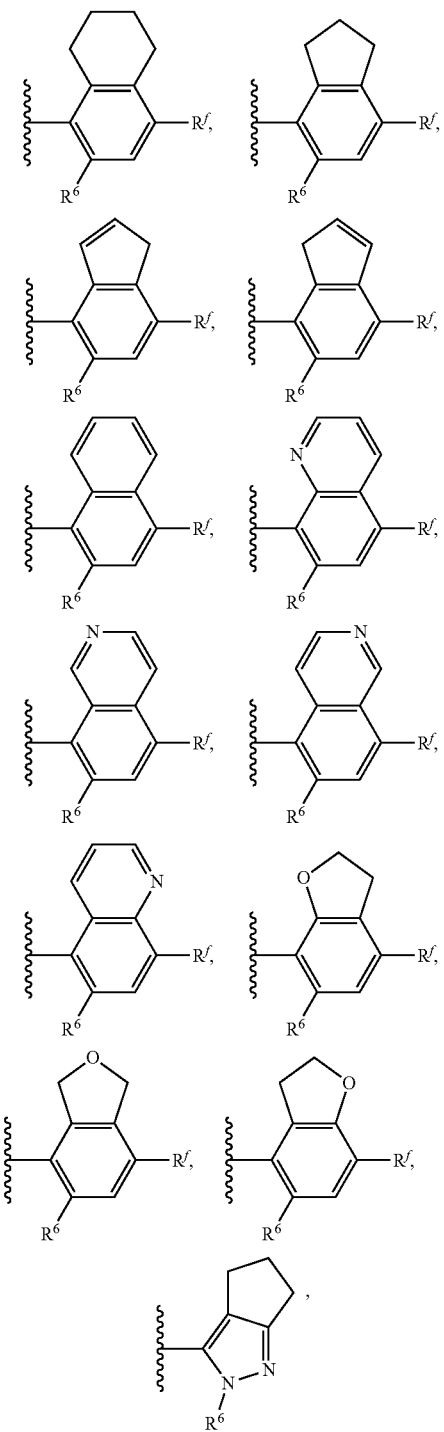

wherein $R^6$ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —NO$_2$, —CN, —R$^{ff}$, —OR$^{ff}$, —COR$^{ff}$, —COOR$^{ff}$, —CONH$_2$, —CONHR$^{ff}$ or —CON(R$^{ff}$)$_2$, wherein each —R$^{ff}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^6$ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, $R^6$ is $C_1$-$C_4$ alkyl, and $R^f$ is hydrogen or halo.

32

Typically, —$R^2$ has the formula:

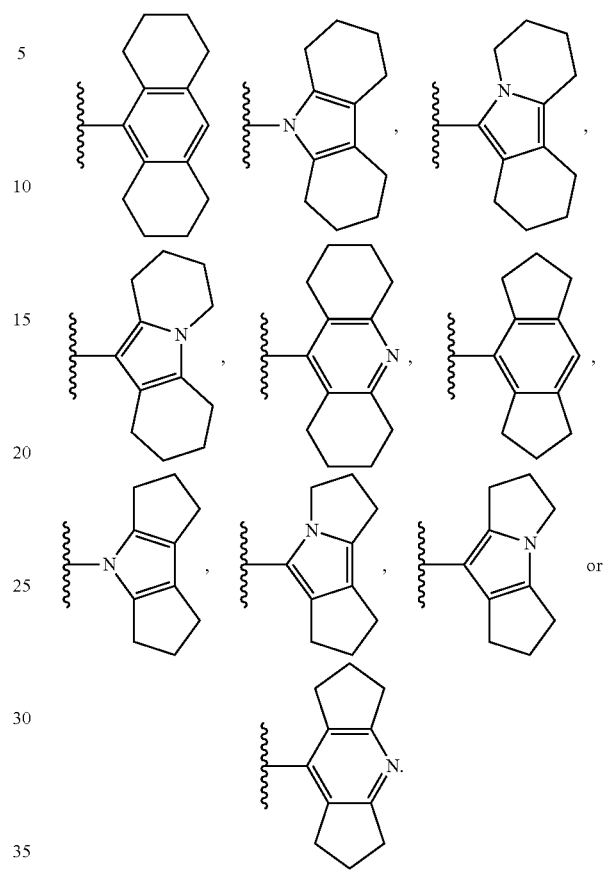

More typically, —$R^2$ has the formula:

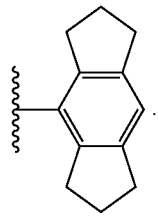 [SMILES: *c1c2c(cc3c1CCC3)CCC2]

Yet other typical substituents at the α-position of the parent cyclic group of $R^2$ may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such $R^2$ groups are described in greater detail below.

In one embodiment, the α-substituted parent cyclic group of $R^2$ is a 5- or 6-membered cyclic group, wherein the cyclic group may optionally be further substituted. In one embodiment, the α-substituted parent cyclic group of $R^2$ is an aryl or a heteroaryl group, all of which may optionally be further substituted. In one embodiment, the α-substituted parent cyclic group of $R^2$ is a phenyl or a 5- or 6-membered heteroaryl group, all of which may optionally be further substituted. In one embodiment, the α-substituted parent cyclic group of $R^2$ is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of $R^2$ is a phenyl or pyrazolyl group, both of which may optionally be further substituted. In a further embodiment, the α-substituted parent cyclic group of $R^2$ is a phenyl group, which may optionally be further substituted.

In one embodiment, the α-substituted parent cyclic group of $R^2$ is substituted at the α and α' positions, and may optionally be further substituted. For example, the α-substituted parent cyclic group of $R^2$ may be a phenyl group substituted at the 2- and 6-positions or a phenyl group substituted at the 2-, 4- and 6-positions.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, piperazinyl, 1,4-dioxanyl, thianyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH$_2$, —CN, —NO$_2$, —B$^4$, —OB$^4$, —NHB$^4$, —N(B$^4$)$_2$, —CONH$_2$, —CONHB$^4$, —CON(B$^4$)$_2$, —NHCOB$^4$, —NB$^4$COB$^4$, or —B$^{44}$—;

wherein each B$^4$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^4$ together with the nitrogen atom to which they are attached may form a 4- to 6-membered heterocyclic group containing one or two ring heteroatoms N and/or O, wherein any B$^4$ may optionally be halo-substituted and/or substituted with one or two substituents independently selected from —OH, —NH$_2$, —OB$^{45}$, —NHB$^{45}$ or —N(B$^{45}$)$_2$;

wherein each B$^{44}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{45}$, —NHB$^{45}$ or —N(B$^{45}$)$_2$; and wherein each B$^{45}$ is independently selected from a $C_1$-$C_3$ alkyl or $C_1$-$C_3$ haloalkyl group.

Typically, any divalent group —B$^{44}$— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a $C_1$-$C_4$ alkyl, $C_2$-$C_4$ alkenyl or $C_2$-$C_4$ alkynyl group all of which may optionally be halo-substituted.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of $R^2$. Such further substituents may be independently selected from halo, —R$^6$, —OR$^6$ or —COR$^6$ groups, wherein each R$^6$ is independently selected from a C$_1$-C$_6$ alkyl, C$_2$-C$_6$ alkenyl, C$_2$-C$_6$ alkynyl or C$_2$-C$_6$ cyclic group and wherein each R$^6$ is optionally further substituted with one or more halo groups. Typically, such further substituents on the α-substituted parent cyclic group of R$^2$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

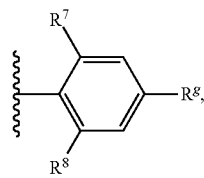

wherein R$^7$ is C$_1$-C$_4$ alkyl, C$_1$-C$_4$ haloalkyl, C$_3$-C$_6$ cycloalkyl or C$_3$-C$_6$ halocycloalkyl, R$^8$ is a 5- or 6-membered, optionally substituted heterocyclic or aromatic group, and R$^g$ is hydrogen, halo, —OH, —NO$_2$, —CN, —R$^{gg}$, —OR$^{gg}$, —COR$^{gg}$, —COOR$^{gg}$, —CONH$_2$, —CONHR$^{gg}$ or —CON(R$^{gg}$)$_2$, wherein each —R$^{gg}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B$^5$, —OB$^5$, —NHB$^5$, —N(B$^5$)$_2$, —CONH$_2$, —CONHB$^5$, —CON(B$^5$)$_2$, —NHCOB$^5$, —NB$^5$COB$^5$, or —B$^{55}$—;
  wherein each B$^5$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^5$ together with the nitrogen atom to which they are attached may form a 4- to 6-membered heterocyclic group containing one or two ring heteroatoms N and/or O, wherein any B$^5$ may optionally be halo-substituted and/or substituted with one or two substituents independently selected from —OH, —NH$_2$, —OB$^{56}$, —NHB$^{56}$ or —N(B$^{56}$)$_2$;
  wherein each B$^{55}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{56}$, —NHB$^{56}$ or —N(B$^{56}$)$_2$; and
  wherein each B$^{56}$ is independently selected from a C$_1$-C$_3$ alkyl or C$_1$-C$_3$ haloalkyl group.

Typically, any divalent group —B$^{55}$— forms a 4- to 6-membered fused ring. Typically, R$^7$ is C$_1$-C$_4$ alkyl, R$^8$ is a 5- or 6-membered, optionally substituted heterocyclic or aromatic group, and R$^g$ is hydrogen, halo, —CN, C$_1$-C$_3$ alkyl, C$_1$-C$_3$ haloalkyl, cyclopropyl or halocyclopropyl. More typically, R$^7$ is C$_1$-C$_4$ alkyl, R$^8$ is a 5- or 6-membered, optionally substituted heterocyclic or aromatic group, and R$^g$ is hydrogen or halo. In one embodiment, the optional substituents on the heterocyclic or aromatic group are independently selected from halo, —OH, —NH$_2$, —CN, —NO$_2$, —B$^5$, —OB$^5$, —NHB$^5$ or —N(B$^5$)$_2$, wherein each B$^5$ is independently selected from a C$_1$-C$_4$ alkyl, C$_2$-C$_4$ alkenyl or C$_2$-C$_4$ alkynyl group all of which may optionally be halo-substituted.

Typically, —R$^2$ has a formula selected from:

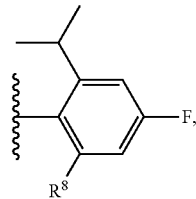

wherein R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^6$, —OB$^6$, —NHB$^6$, —N(B$^6$)$_2$, —CONH$_2$, —CONHB$^6$, —CON(B$^6$)$_2$, —NHCOB$^6$, —NB$^6$COB$^6$, or —B$^{66}$—;
  wherein each B$^6$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^6$ together with the nitrogen atom to which they are attached may form a 4- to 6-membered heterocyclic group containing one or two ring heteroatoms N and/or O, wherein any B$^6$ may optionally be halo-substituted and/or substituted with one or two substituents independently selected from —OH, —NH$_2$, —OB$^{67}$, —NHB$^{67}$ or —N(B$^{67}$)$_2$;
  wherein each B$^{66}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{67}$, —NHB$^{67}$ or —N(B$^{67}$)$_2$; and
  wherein each B$^{67}$ is independently selected from a C$_1$-C$_3$ alkyl or C$_1$-C$_3$ haloalkyl group.

Typically, any divalent group —B$^{66}$— forms a 4- to 6-membered fused ring. Typically, the optional substituents on the heterocyclic or aromatic group are independently selected from halo, —OH, —NH$_2$, —CN, —NO$_2$, —B$^6$, —OB$^6$, —NHB$^6$ or —N(B$^6$)$_2$, wherein each B$^6$ is independently selected from a C$_1$-C$_4$ alkyl, C$_2$-C$_4$ alkenyl or C$_2$-C$_4$ alkynyl group all of which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of R$^2$ also include cycloalkyl, cycloalkenyl, non-aromatic heterocyclic, aryl or heteroaryl rings which are fused to the α-substituted parent cyclic group of R$^2$. Typically, the cycloalkyl, cycloalkenyl, non-aromatic heterocyclic, aryl or heteroaryl rings are ortho-fused to the α-substituted parent cyclic group of R$^2$, i.e. each fused cycloalkyl, cycloalkenyl, non-aromatic heterocyclic, aryl or heteroaryl ring has only two atoms and one bond in common with the α-substituted parent cyclic group of $R^2$. Typically, the cycloalkyl, cycloalkenyl, non-aromatic heterocyclic, aryl or heteroaryl rings are ortho-fused to the α-substituted parent cyclic group of $R^2$ across the α',β' positions.

In one embodiment, —$R^2$ has a formula selected from:

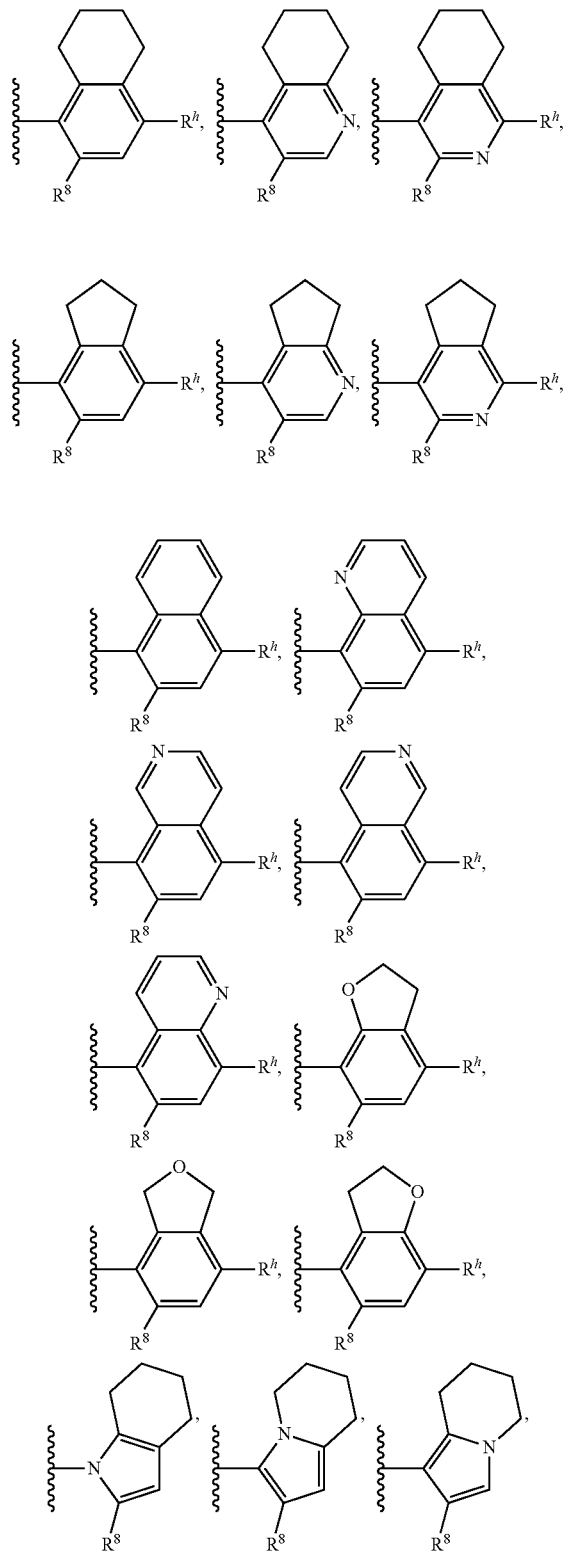

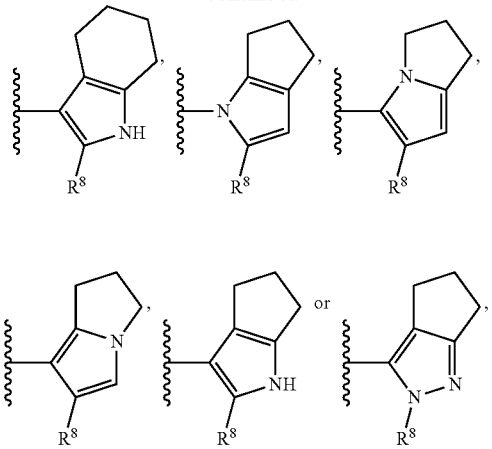

wherein $R^8$ is a 5- or 6-membered, optionally substituted heterocyclic or aromatic group, and $R^h$ is hydrogen, halo, —OH, —$NO_2$, —CN, —$R^{hh}$, —$OR^{hh}$, —$COR^{hh}$, —CO-$OR^{hh}$, —$CONH_2$, —$CONHR^{hh}$ or —$CON(R^{hh})_2$, wherein each —$R^{hh}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —$NH_2$, —CN, —$NO_2$, —$B^7$, —$OB^7$, —$NHB^7$, —$N(B^7)_2$, —$CONH_2$, —$CONHB^7$, —$CON(B^7)_2$, —$NHCOB^7$, —$NB^7COB^7$, or —$B^{77}$—;

wherein each $B^7$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^7$ together with the nitrogen atom to which they are attached may form a 4- to 6-membered heterocyclic group containing one or two ring heteroatoms N and/or O, wherein any $B^7$ may optionally be halo-substituted and/or substituted with one or two substituents independently selected from —OH, —$NH_2$, —$OB^{78}$, —$NHB^{78}$ or —$N(B^{78})_2$;

wherein each $B^{77}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —$NH_2$, —$OB^{78}$, —$NHB^{78}$ or —$N(B^{78})_2$; and wherein each $B^{78}$ is independently selected from a $C_1$-$C_3$ alkyl or $C_1$-$C_3$ haloalkyl group.

Typically, any divalent group —$B^{77}$— forms a 4- to 6-membered fused ring. Typically, $R^h$ is hydrogen, halo, —CN, $C_1$-$C_3$ alkyl, $C_1$-$C_3$ haloalkyl, cyclopropyl or halocyclopropyl. More typically, $R^h$ is hydrogen or halo. Typically, the optional substituents on the heterocyclic or aromatic group are independently selected from halo, —OH, —$NH_2$, —CN, —$NO_2$, —$B^7$, —$OB^7$, —$NHB^7$ or —$N(B^7)_2$, wherein each $B^7$ is independently selected from a $C_1$-$C_4$ alkyl, $C_2$-$C_4$ alkenyl or $C_2$-$C_4$ alkynyl group all of which may optionally be halo-substituted.

In one embodiment, —$R^2$ has a formula selected from:

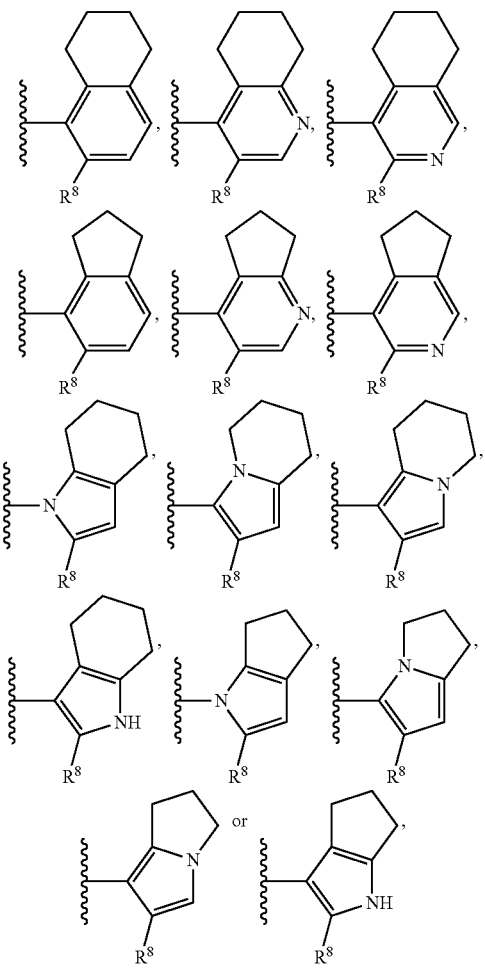

wherein $R^8$ is a 5- or 6-membered, optionally substituted heterocyclic or aromatic group. In one embodiment, the optional substituents on the heterocyclic or aromatic group are independently selected from halo, —OH, —$NH_2$, —CN, —$NO_2$, —$B^8$, —$OB^8$, —$NHB^8$, —$N(B^8)_2$, —$CONH_2$, —$CONHB^8$, —$CON(B^8)_2$, —$NHCOB^8$, —$NB^8COB^8$, or —$B^{88}$—;

wherein each $B^8$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^8$ together with the nitrogen atom to which they are attached may form a 4- to 6-membered heterocyclic group containing one or two ring heteroatoms N and/or O, wherein any $B^8$ may optionally be halo-substituted and/or substituted with one or two substituents independently selected from —OH, —$NH_2$, —$OB^{89}$, —$NHB^{89}$ or —$N(B^{89})_2$;

wherein each $B^{88}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —$NH_2$, —$OB^{89}$, —$NHB^{89}$ or —$N(B^{89})_2$; and wherein each $B^{89}$ is independently selected from a $C_1$-$C_3$ alkyl or $C_1$-$C_3$ haloalkyl group.

Typically, any divalent group —$B^{88}$— forms a 4- to 6-membered fused ring. Typically, the optional substituents on the heterocyclic or aromatic group are independently selected from halo, —OH, —$NH_2$, —CN, —$NO_2$, —$B^8$, —$OB^8$, —$NHB^8$ or —$N(B^8)_2$, wherein each $B^8$ is independently selected from a $C_1$-$C_4$ alkyl, $C_2$-$C_4$ alkenyl or $C_2$-$C_4$ alkynyl group all of which may optionally be halo-substituted.

Typically, —$R^2$ has a formula selected from:

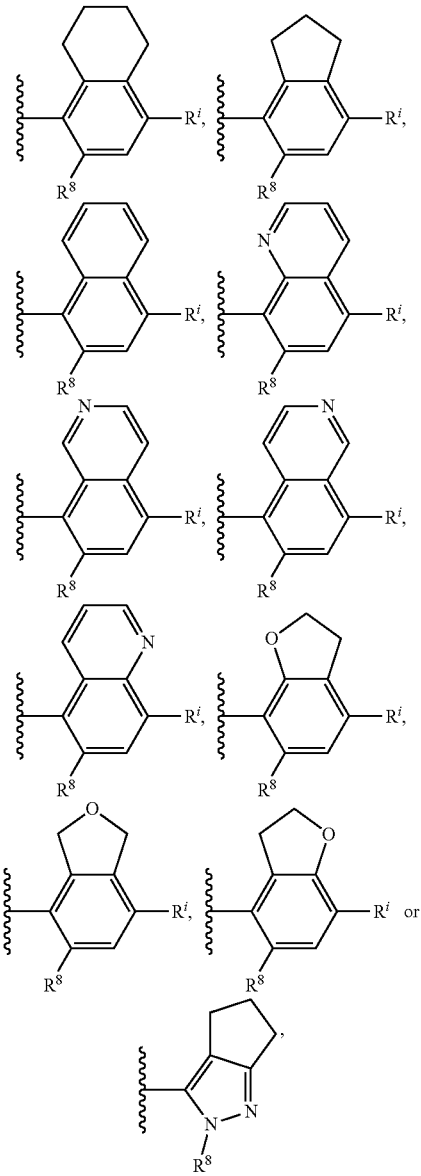

wherein $R^8$ is a 5- or 6-membered, optionally substituted heterocyclic or aromatic group, and $R^1$ is hydrogen, halo, —OH, —$NO_2$, —CN, —$R^{11}$, —$OR^{11}$, —$COR^{11}$, —$COOR^{11}$, —$CONH_2$, —$CONHR^{11}$ or —$CON(R^{11})_2$, wherein each —$R^{11}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —$NH_2$, —CN, —$NO_2$, —$B^9$, —$OB^9$, —$NHB^9$, —$N(B^9)_2$, —$CONH_2$, —$CONHB^9$, —$CON(B^9)_2$, —$NHCOB^9$, —$NB^9COB^9$, or —$B^{99}$—;
  wherein each $B^9$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^9$ together with the nitrogen atom to which they are attached may form a 4- to 6-membered heterocyclic group containing one or two ring heteroatoms N and/or O, wherein any $B^9$ may optionally be halo-substituted and/or substituted with one or two substituents independently selected from —OH, —$NH_2$, —$OB^{98}$, —$NHB^{98}$ or —$N(B^{98})_2$;
  wherein each $B^{99}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —$NH_2$, —$OB^{98}$, —$NHB^{98}$ or —$N(B^{98})_2$; and
  wherein each $B^{98}$ is independently selected from a $C_1$-$C_3$ alkyl or $C_1$-$C_3$ haloalkyl group. Typically, any divalent group —$B^{99}$— forms a 4- to 6-membered fused ring. Typically, $R^1$ is hydrogen, halo, —CN, $C_1$-$C_3$ alkyl, $C_1$-$C_3$ haloalkyl, cyclopropyl or halocyclopropyl. More typically, $R^1$ is hydrogen or halo. Typically, the optional substituents on the heterocyclic or aromatic group are independently selected from halo, —OH, —$NH_2$, —CN, —$NO_2$, —$B^9$, —$OB^9$, —$NHB^9$ or —$N(B^9)_2$, wherein each $B^9$ is independently selected from a $C_1$-$C_4$ alkyl, $C_2$-$C_4$ alkenyl or $C_2$-$C_4$ alkynyl group all of which may optionally be halo-substituted.

In one embodiment, $R^2$ is phenyl or a 5- or 6-membered heteroaryl group (such as phenyl, pyridinyl, pyridazinyl, pyrimidinyl or pyrazinyl); wherein
  (i) the phenyl or 5- or 6-membered heteroaryl group is substituted at the α position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and
  optionally the phenyl or 5- or 6-membered heteroaryl group is further substituted at the α' position with a substituent selected from —$R^{14}$, —$OR^{14}$ and —$COR^{14}$, wherein $R^{14}$ is selected from a $C_1$-$C_6$ alkyl, $C_2$-$C_6$ alkenyl, $C_2$-$C_6$ alkynyl or $C_2$-$C_6$ cyclic group and wherein $R^{14}$ is optionally substituted with one or more halo groups; and
  optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or
  (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and
  optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and
  optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or
  (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and
  optionally the phenyl group is further substituted (typically with a substituent selected from halo, —$NO_2$, —CN, —$COOR^{15}$, —$CONH_2$, —$CONHR15$ or —$CON(R^{15})_2$, wherein each —$R^{15}$ is independently selected from a $C_1$-$C_4$ alkyl or $C_1$-$C_4$ haloalkyl group); or
  (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and
  optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and
  optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or
  (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —R$^{12}$—OR$^{13}$, —R$^{12}$—N(R$^{13}$)$_2$, —R$^{12}$—CN or —R$^{12}$—C≡CR$^{13}$, and wherein a ring atom of the monovalent heterocyclic or aromatic group is directly attached to the α-ring atom of the parent phenyl or 5- or 6-membered heteroaryl group;

wherein R$^{12}$ is independently selected from a bond or a C$_1$-C$_3$ alkylene group; and R$^{13}$ is independently selected from hydrogen or a C$_1$-C$_3$ alkyl or C$_1$-C$_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α', β' positions and which is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group).

In the embodiment directly above, where a group or moiety is optionally substituted with one or more halo groups, it may be substituted for example with one, two, three, four, five or six halo groups.

In one aspect of any of the above embodiments, R$^2$ contains from 10 to 50 atoms other than hydrogen. More typically, R$^2$ contains from 10 to 40 atoms other than hydrogen.

More typically, R$^2$ contains from 10 to 35 atoms other than hydrogen. Most typically, R$^2$ contains from 12 to 30 atoms other than hydrogen.

Q is selected from O or S. In one embodiment of the first aspect of the invention, Q is O.

In one aspect of any of the above embodiments, the compound of formula (I) has a molecular weight of from 250 to 2000 Da. Typically, the compound of formula (I) has a molecular weight of from 280 to 900 Da. More typically, the compound of formula (I) has a molecular weight of from 310 to 550 Da.

A second aspect of the invention provides a compound selected from the group consisting of:

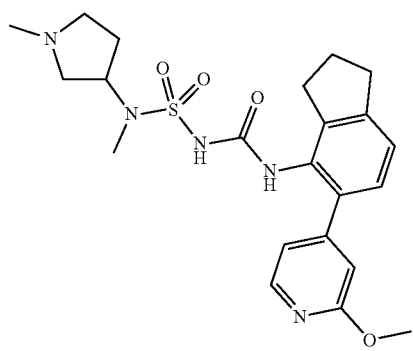

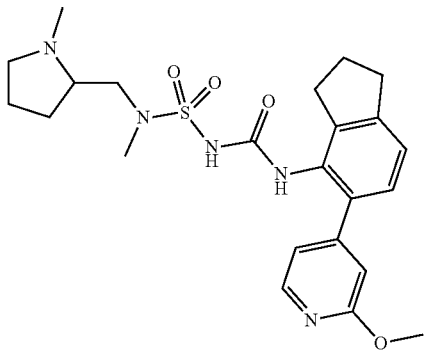

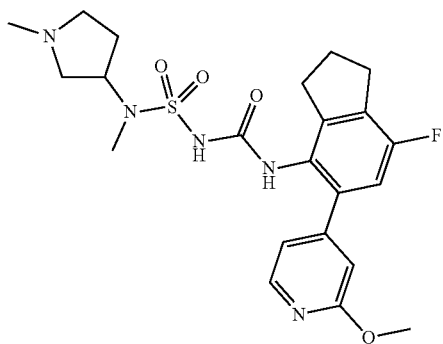

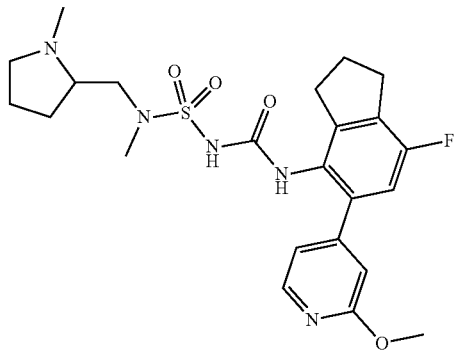

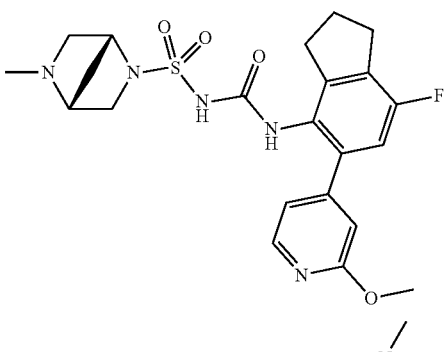

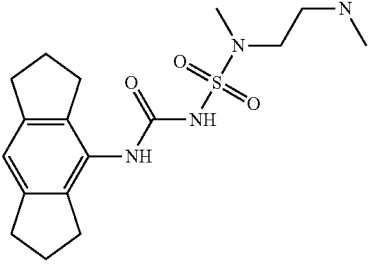

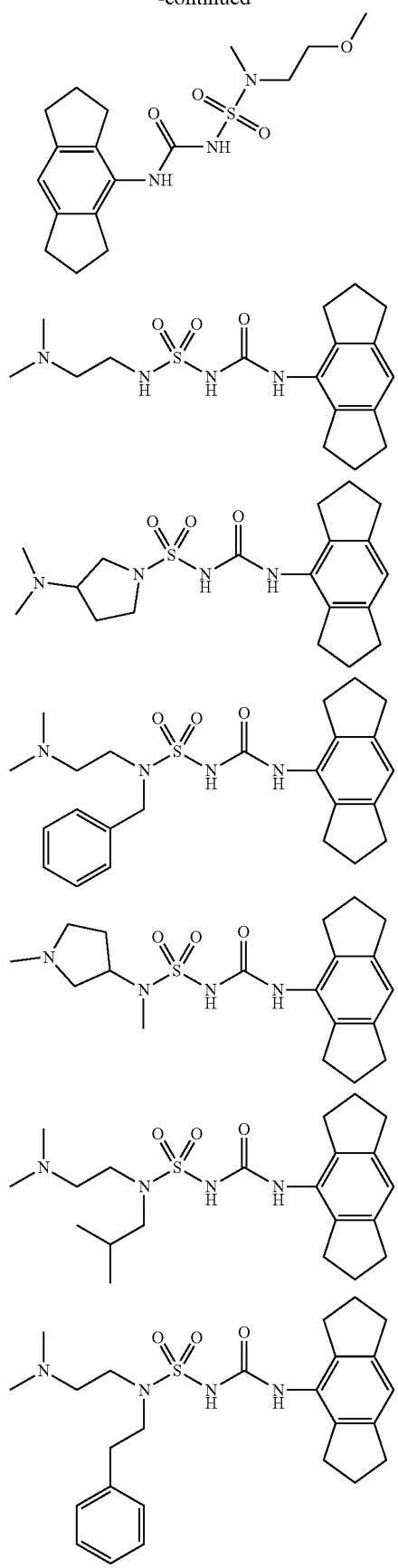
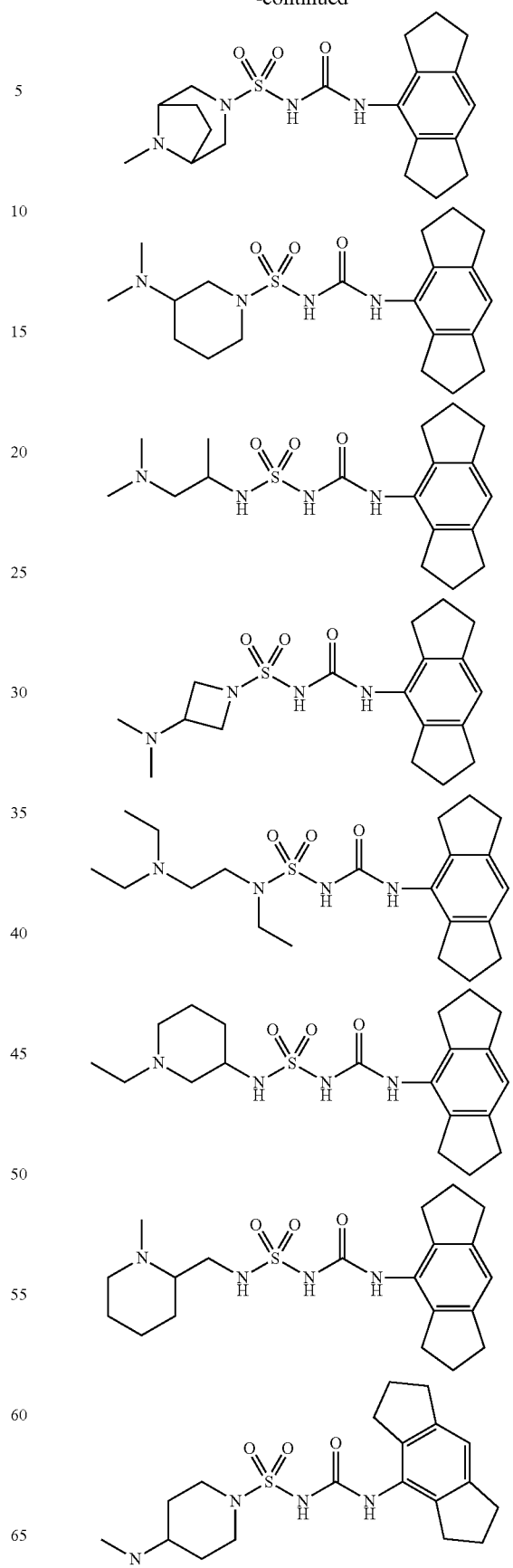

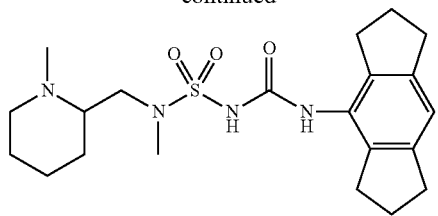
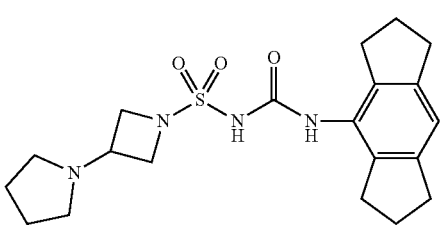
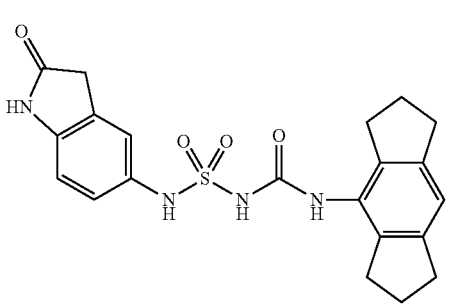
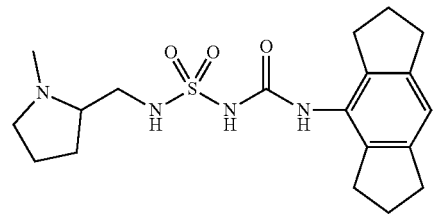
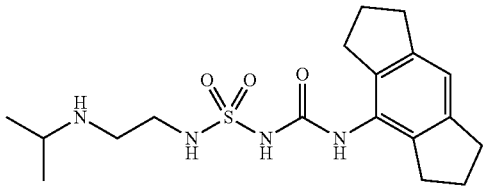
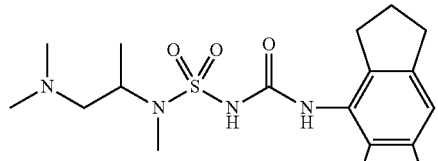
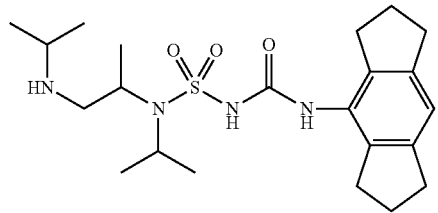
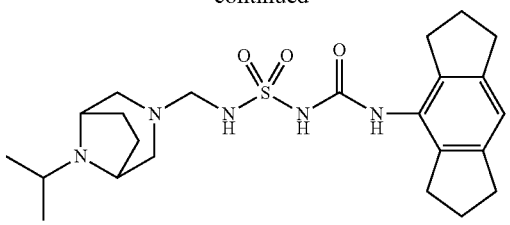
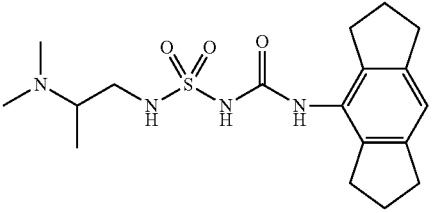
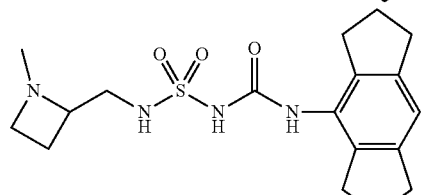
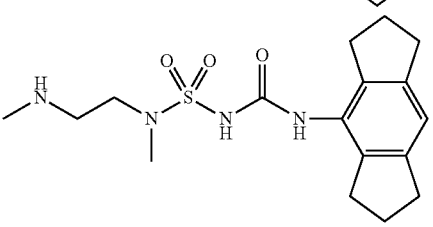
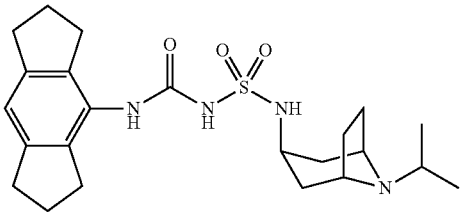
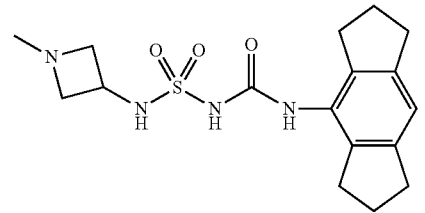
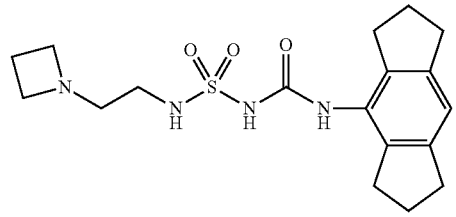
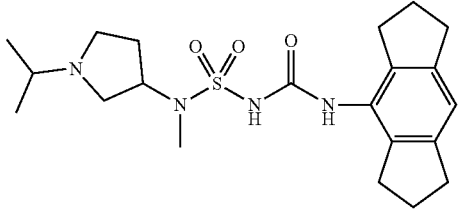

49
-continued
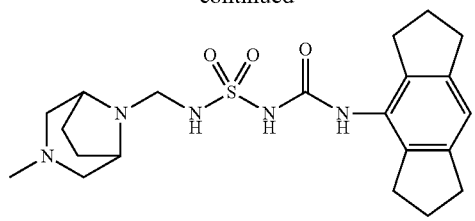
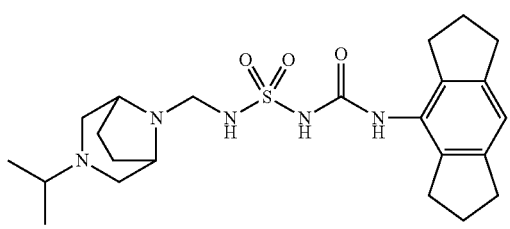
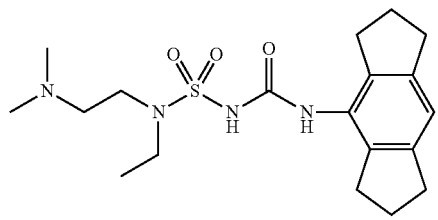
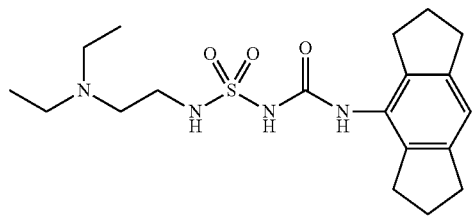
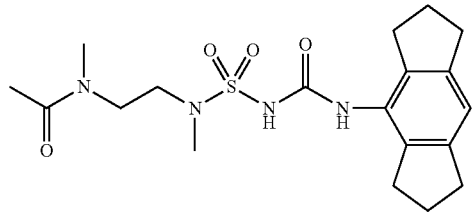
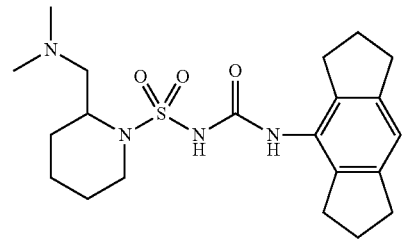
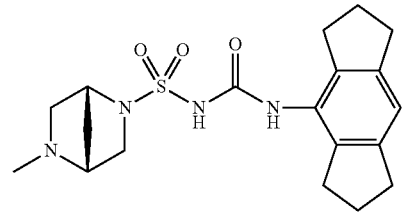
50
-continued
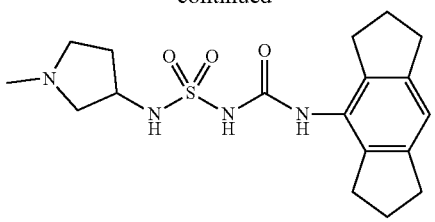

51
-continued
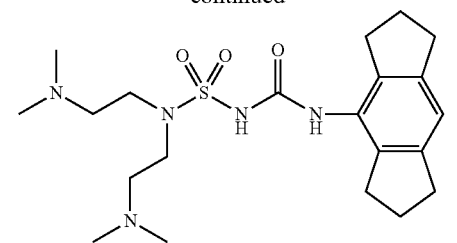
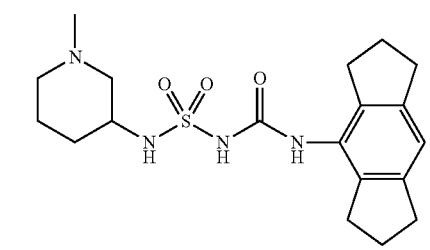
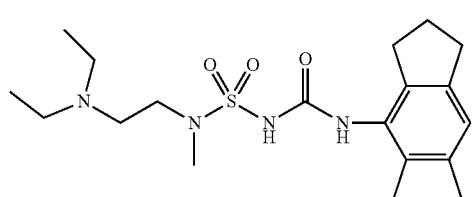
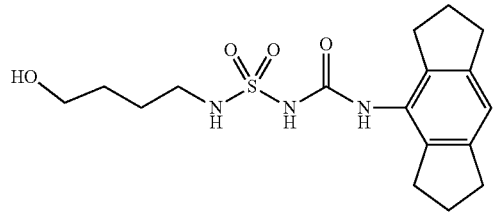
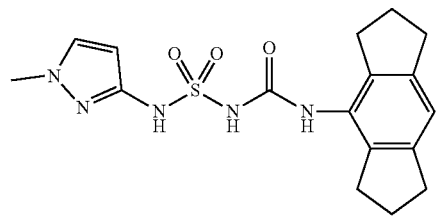
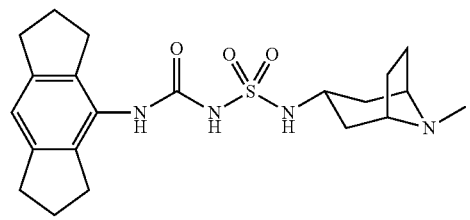
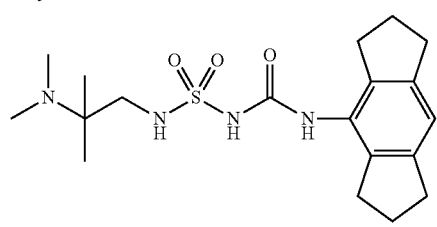
52
-continued
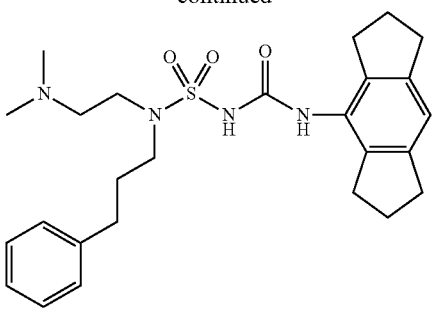
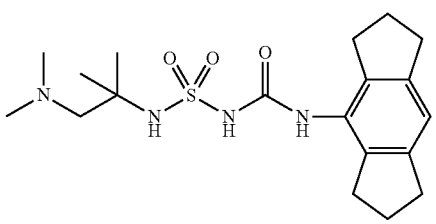
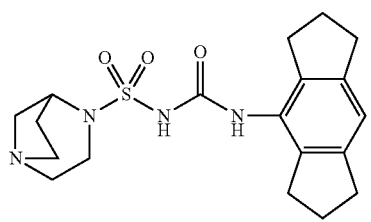
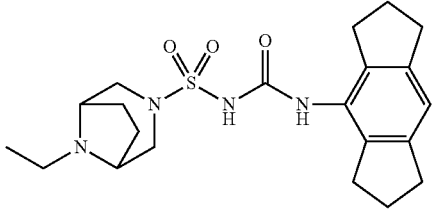
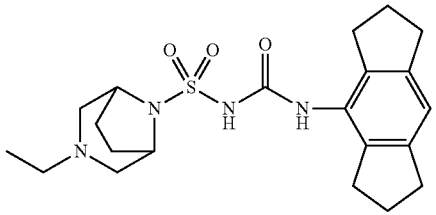
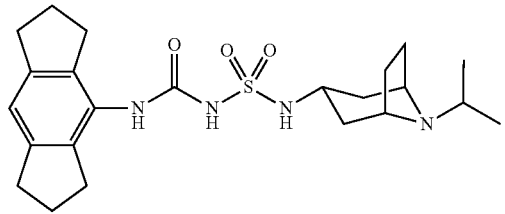
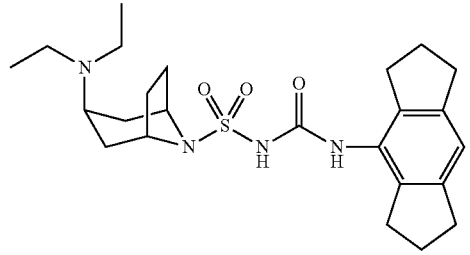

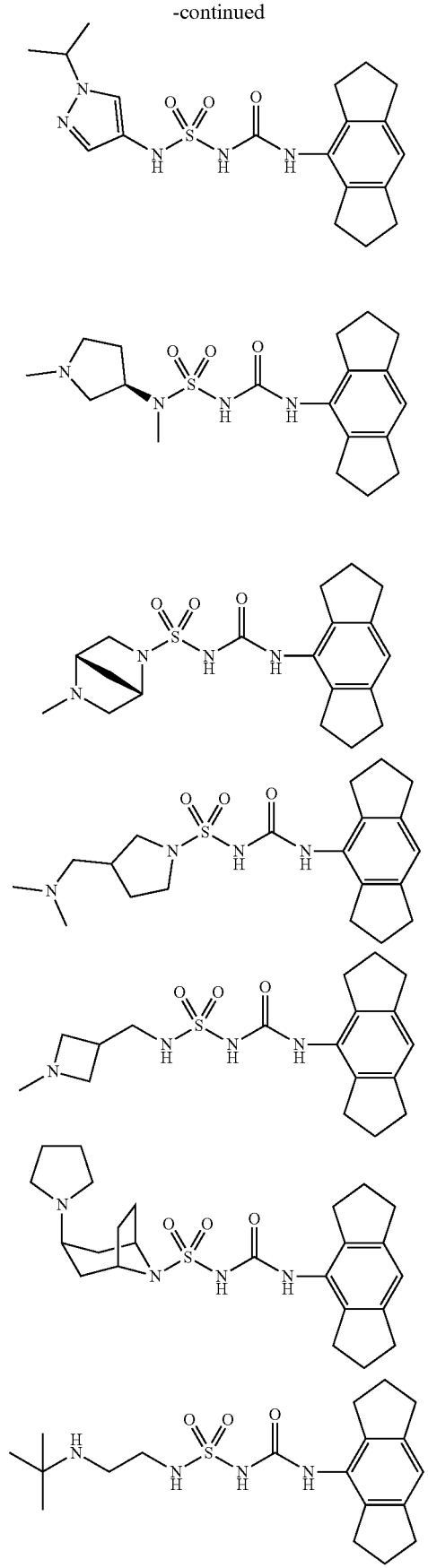
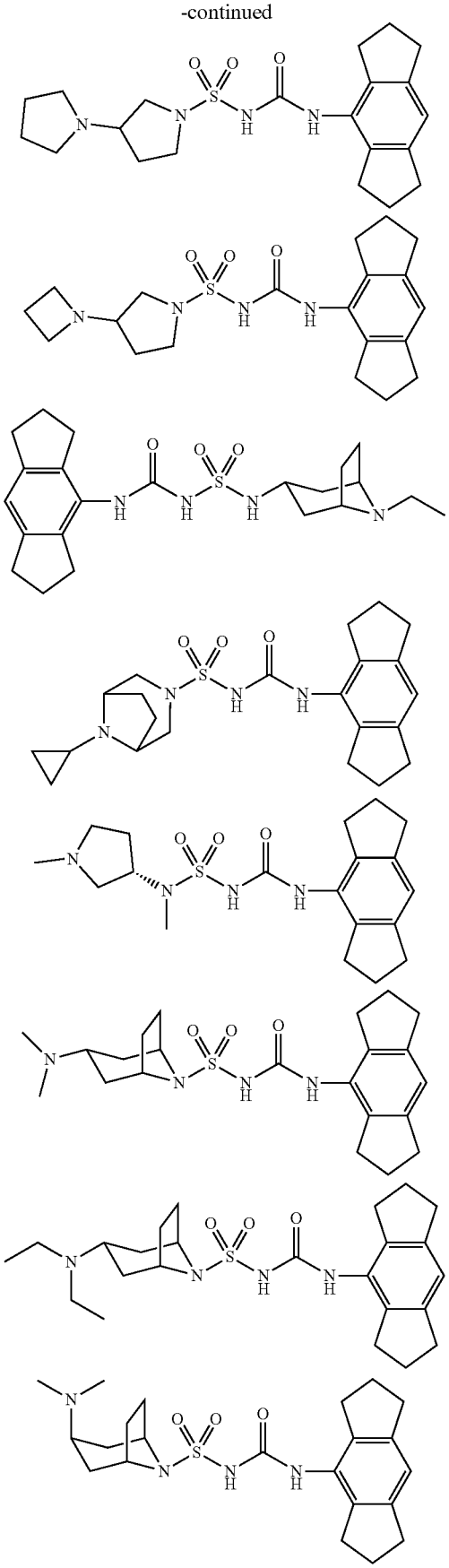

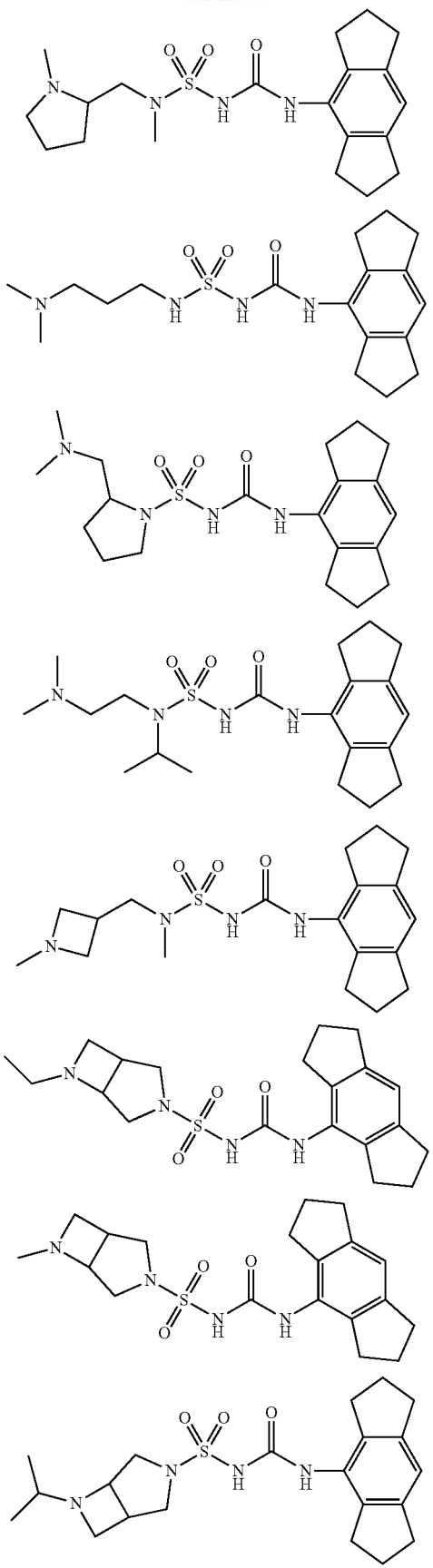
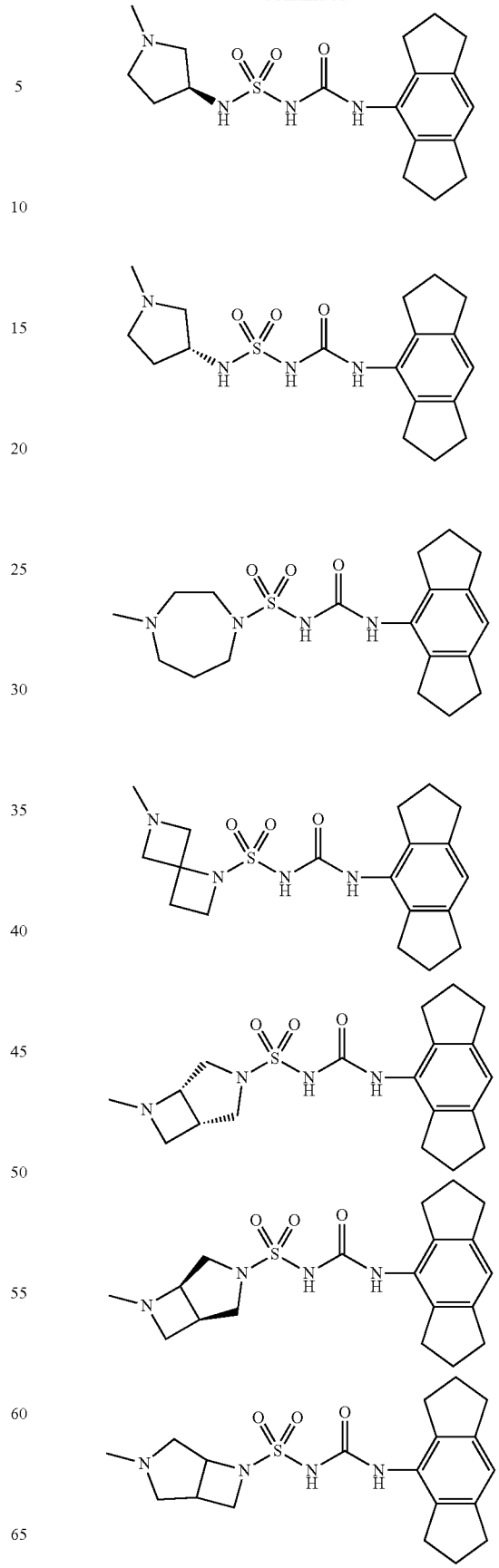

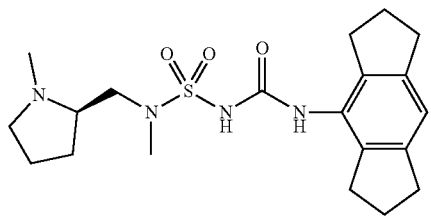
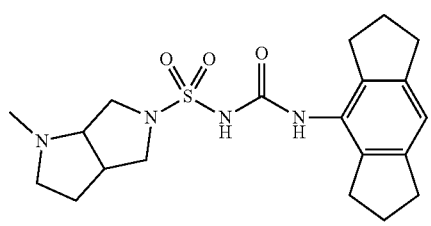
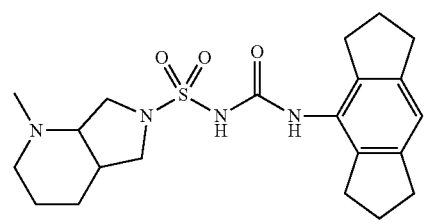
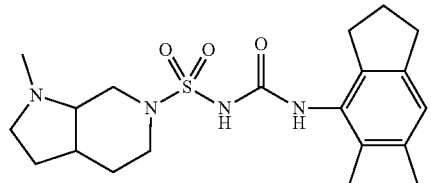
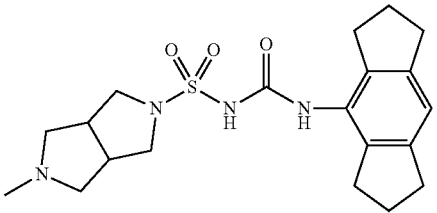
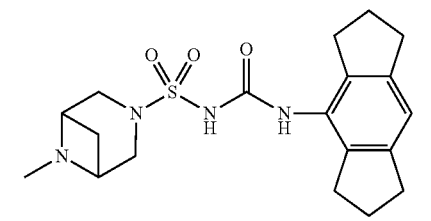
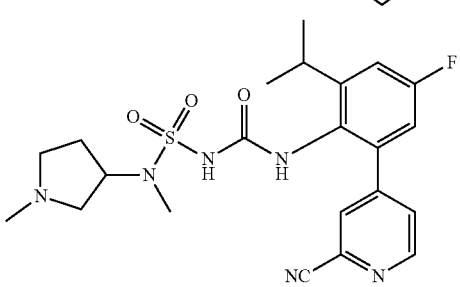
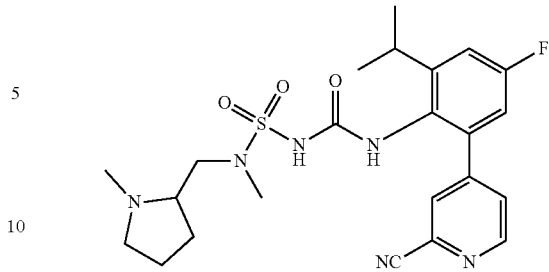
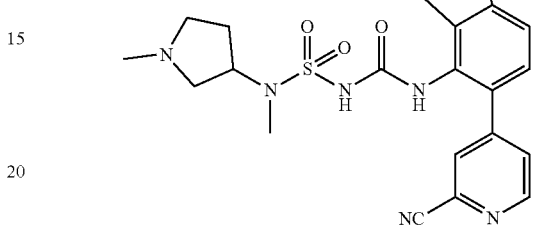
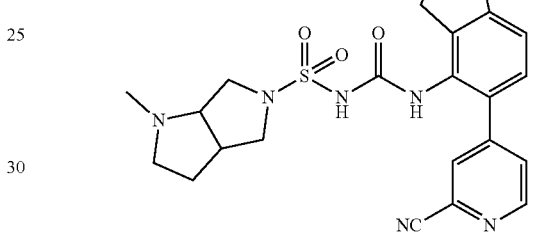
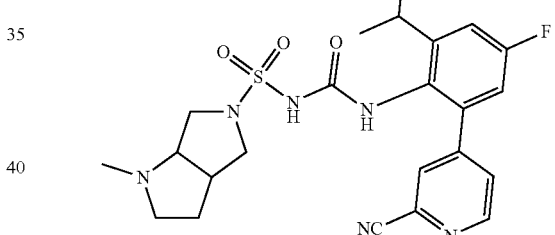
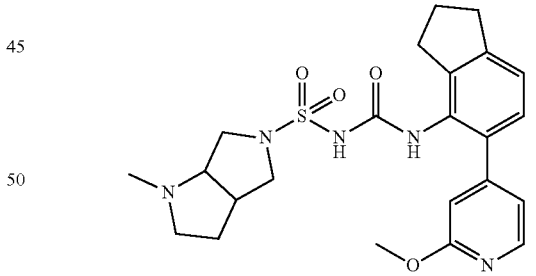
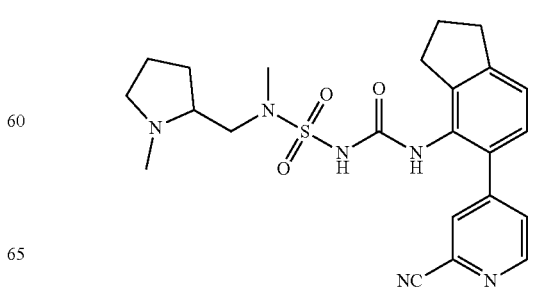

-continued

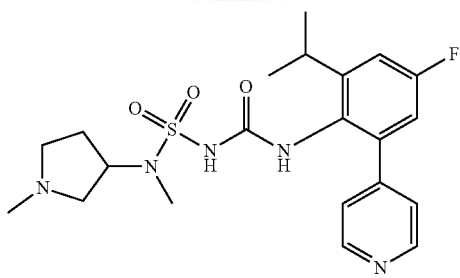

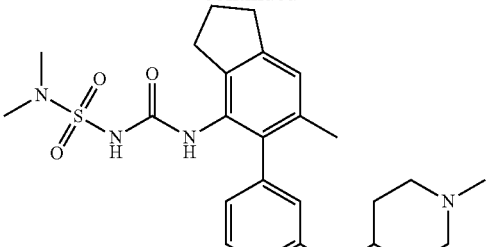

and

A third aspect of the invention provides a pharmaceutically acceptable salt, solvate or prodrug of any compound of the first or second aspect of the invention.

The compounds of the present invention can be used both, in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter

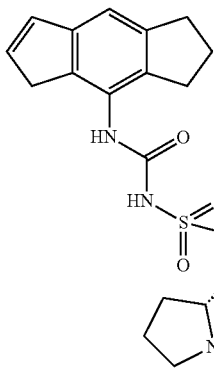

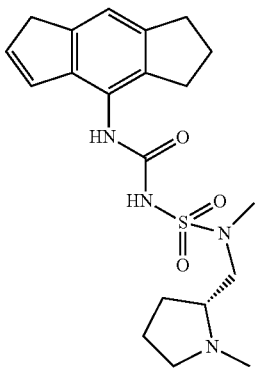

ion. Examples of suitable counter ions include the conjugate bases of the protic acids discussed above in relation to acid addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such other solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptom, the amelioration or palliation of a condition/symptom, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant (p≤0.05) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL-1β and IL-18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481: 278-286, 2012).

Genetic diseases in which a role for NLRP3 has been suggested include sickle cell disease (Vogel et al., Blood, 130(Suppl 1): 2234, 2017), and Valosin Containing Protein disease (Nalbandian et al., Inflammation, 40(1): 21-41, 2017).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur J Immunol, 40: 595-653, 2010). In particular, NLRP3 mutations have been found to be responsible for a set of rare autoinflammatory diseases known as CAPS (Ozaki et al., J Inflammation Research, 8: 15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type 1 diabetes (T1D), psoriasis, rheumatoid arthritis (RA), Behcet's disease, Schnitzler's syndrome, macrophage activation syndrome (Masters, Clin Immunol, 147(3): 223-228, 2013; Braddock et al., Nat Rev Drug Disc, 3: 1-10, 2004; Inoue et al., Immunology, 139: 11-18, 2013; Coll et al., Nat Med, 21(3): 248-55, 2015; Scott et al., Clin Exp Rheumatol, 34(1): 88-93, 2016; and Guo et al., Clin Exp Immunol, 194(2): 231-243, 2018), systemic lupus erythematosus (Lu et al., J Immunol, 198(3): 1119-29, 2017) including lupus nephritis (Zhao et al., Arthritis and Rheumatism, 65(12): 3176-3185, 2013), multiple sclerosis (Xu et al., J Cell Biochem, 120(4): 5160-5168, 2019), and systemic sclerosis (Artlett et al., Arthritis Rheum, 63(11): 3563-74, 2011).

NLRP3 has also been shown to play a role in a number of lung diseases including chronic obstructive pulmonary disorder (COPD), asthma (including steroid-resistant asthma and eosinophilic asthma), asbestosis, and silicosis (De Nardo et al., Am J Pathol, 184: 42-54, 2014; Lv et al., J Biol Chem, 293(48): 18454, 2018; and Kim et al., Am J Respir Crit Care Med, 196(3): 283-97, 2017).

NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al., Brain Behav Immun, 61: 306-316, 2017), intracranial aneurysms (Zhang et al., J Stroke & Cerebrovascular Dis, 24(5): 972-979, 2015), intracerebral haemorrhages (ICH) (Ren et al., Stroke, 49(1): 184-192, 2018), cerebral ischemia-reperfusion injuries (Fauzia et al., Front Pharmacol, 9: 1034, 2018), sepsis-associated encephalopathy (SAE) (Fu et al., Inflammation, 42(1): 306-318, 2019), postoperative cognitive dysfunction (POCD) (Fan et al., Front Cell Neurosci, 12: 426, 2018), early brain injury (subarachnoid haemorrhage SAH) (Luo et al., Brain Res Bull, 146: 320-326, 2019), and traumatic brain injury (Ismael et al., J Neurotrauma, 35(11): 1294-1303, 2018).

NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (NASH) (Mridha et al., J Hepatol, 66(5): 1037-46, 2017).

A role for NLRP3 via IL-1β has also been suggested in atherosclerosis, myocardial infarction (van Hout et al., Eur Heart J, 38(11): 828-36, 2017), cardiovascular disease (Janoudi et al., European Heart Journal, 37(25): 1959-1967, 2016), cardiac hypertrophy and fibrosis (Gan et al., Biochim Biophys Acta, 1864(1): 1-10, 2018), heart failure (Sano et al., J Am Coll Cardiol, 71(8): 875-66, 2018), aortic aneurysm and dissection (Wu et al., Arterioscler Thromb Vasc Biol, 37(4): 694-706, 2017), cardiac injury induced by metabolic dysfunction (Pavillard et al., Oncotarget, 8(59): 99740-99756, 2017), atrial fibrillation (Yao et al., Circulation, 138(20): 2227-2242, 2018), hypertension (Gan et al., Biochim Biophys Acta, 1864(1): 1-10, 2018), and other cardiovascular events (Ridker et al., N Engl J Med, doi: 10.1056/NEJMoa1707914, 2017).

Other diseases in which NLRP3 has been shown to be involved include:

ocular diseases such as both wet and dry age-related macular degeneration (Doyle et al., Nature Medicine, 18: 791-798, 2012; and Tarallo et al., Cell, 149(4): 847-59, 2012), diabetic retinopathy (Loukovaara et al., Acta Ophthalmol, 95(8): 803-808, 2017) and optic nerve damage (Puyang et al., Sci Rep, 6: 20998, 2016 Feb. 19);

liver diseases including non-alcoholic steatohepatitis (NASH) (Henao-Meija et al., Nature, 482: 179-185, 2012), ischemia reperfusion injury of the liver (Yu et al., Transplantation, 103(2): 353-362, 2019), fulminant hepatitis (Pourcet et al., Gastroenterology, 154(5): 1449-1464, e20, 2018), liver fibrosis (Zhang et al., Parasit Vectors, 12(1): 29, 2019), and liver failure (Wang et al., Hepatol Res, 48(3): E194-E202, 2018);

kidney diseases including nephrocalcinosis (Anders et al., Kidney Int, 93(3): 656-669, 2018), kidney fibrosis including chronic crystal nephropathy (Ludwig-Portugall et al., Kidney Int, 90(3): 525-39, 2016), and renal hypertension (Krishnan et al., Br J Pharmacol, 173(4): 752-65, 2016);

conditions associated with diabetes including diabetic encephalopathy (Zhai et al., Molecules, 23(3): 522, 2018), diabetic retinopathy (Zhang et al., Cell Death Dis, 8(7): e2941, 2017), and diabetic hypoadiponectinemia (Zhang et al., Biochimica et Biophysica Acta (BBA)—Molecular Basis of Disease, 1863(6): 1556-1567, 2017);

inflammatory reactions in the lung and skin (Primiano et al., J Immunol, 197(6): 2421-33, 2016) including lung ischemia-reperfusion injury (Xu et al., Biochemical and Biophysical Research Communications, 503(4): 3031-3037, 2018), epithelial to mesenchymal transition (EMT) (Li et al., Experimental Cell Research, 362(2): 489-497, 2018), contact hypersensitivity (such as bullous pemphigoid (Fang et al., J Dermatol Sci, 83(2): 116-23, 2016)), atopic dermatitis (Niebuhr et al., Allergy, 69(8): 1058-67, 2014), Hidradenitis suppurativa (Alikhan et al., J Am Acad Dermatol, 60(4): 539-61, 2009), acne vulgaris (Qin et al., J Invest Dermatol, 134(2): 381-88, 2014), and sarcoidosis (Jager et al., Am J Respir Crit Care Med, 191: A5816, 2015);

inflammatory reactions in the joints (Braddock et al., Nat Rev Drug Disc, 3: 1-10, 2004) and osteoarthritis (Jin et al., PNAS, 108(36): 14867-14872, 2011);

amyotrophic lateral sclerosis (Gugliandolo et al., Inflammation, 41(1): 93-103, 2018);

cystic fibrosis (Iannitti et al., Nat Commun, 7: 10791, 2016);

stroke (Walsh et al., Nature Reviews, 15: 84-97, 2014);

chronic kidney disease (Granata et al., PLoS One, 10(3): eo122272, 2015);

Sjogren's syndrome (Vakrakou et al., Journal of Autoimmunity, 91: 23-33, 2018);

sickle cell disease (Vogel et al., Blood, 130(Suppl 1): 2234, 2017); and colitis and inflammatory bowel diseases including ulcerative colitis and Crohn's disease (Braddock et al., Nat Rev Drug Disc, 3: 1-10, 2004; Neudecker et al., J Exp Med, 214(6): 1737-52, 2017; Wu et al., Mediators Inflamm, 2018: 3048532, 2018; and Lazaridis et al., Dig Dis Sci, 62(9): 2348-56, 2017), and sepsis (intestinal epithelial disruption) (Zhang et al., Dig Dis Sci, 63(1): 81-91, 2018).

Genetic ablation of NLRP3 has been shown to protect from HSD (high sugar diet), HFD (high fat diet) and HSFD-induced obesity (Pavillard et al., Oncotarget, 8(59): 99740-99756, 2017).

The NLRP3 inflammasome has been found to be activated in response to oxidative stress, sunburn (Hasegawa et al., Biochemical and Biophysical Research Communications, 477(3): 329-335, 2016), and UVB irradiation (Schroder et al., Science, 327: 296-300, 2010).

NLRP3 has also been shown to be involved in inflammatory hyperalgesia (Dolunay et al., Inflammation, 40: 366-386, 2017), wound healing (Ito et al., Exp Dermatol, 27(1): 80-86, 2018), pain including multiple sclerosis-associated neuropathic pain (Khan et al., Inflammopharmacology, 26(1): 77-86, 2018), and intra-amniotic inflammation/infection associated with preterm birth (Faro et al., Biol Reprod, 100(5): 1290-1305, 2019; and Gomez-Lopez et al., Biol Reprod, 100(5): 1306-1318, 2019).

The inflammasome, and NLRP3 specifically, has also been proposed as a target for modulation by various pathogens including bacterial pathogens such as *Staphylococcus aureus* (Cohen et al., Cell Reports, 22(9): 2431-2441, 2018), *Bacillus cereus* (Mathur et al., Nat Microbiol, 4: 362-374, 2019), *Salmonella typhimurium* (Diamond et al., Sci Rep, 7(1): 6861, 2017), and group A *streptococcus* (LaRock et al., Science Immunology, 1(2): eaah3539, 2016); viruses such as DNA viruses (Amsler et al., Future Virol, 8(4): 357-370, 2013), influenza A virus (Coates et al., Front Immunol, 8: 782, 2017), chikungunya, Ross river virus, and alpha viruses (Chen et al., Nat Microbiol, 2(10): 1435-1445, 2017); fungal pathogens such as *Candida albicans* (Tucey et al., mSphere, 1(3), pii: eo0074-16, 2016); and other pathogens such as *T. gondii* (Gov et al., J Immunol, 199(8): 2855-2864, 2017), helminth worms (Alhallaf et al., Cell Reports, 23(4): 1085-1098, 2018), leishmania (Novais et al., PLoS Pathogens, 13(2): e1006196, 2017), and plasmodium (Strangward et al., PNAS, 115(28): 7404-7409, 2018). NLRP3 has been shown to be required for the efficient control of viral, bacterial, fungal, and helminth pathogen infections (Strowig et al., Nature, 481: 278-286, 2012).

NLRP3 has also been implicated in the pathogenesis of many cancers (Menu et al., Clinical and Experimental Immunology, 166: 1-15, 2011; and Masters, Clin Immunol, 147(3): 223-228, 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al., Lancet, S0140-6736(17)32247-X, 2017). Inhibition of the NLRP3 inflammasome or IL-1β has also been shown to inhibit the proliferation and migration of lung cancer cells in vitro (Wang et al., Oncol Rep, 35(4): 2053-64, 2016). A role for the NLRP3 inflammasome has been suggested in myelodysplastic syndromes (Basiorka et al., Blood, 128(25): 2960-2975, 2016) and also in the carcinogenesis of various other cancers including glioma (Li et al., Am J Cancer Res, 5(1): 442-449, 2015), colon cancer (Allen et al., J Exp Med, 207(5): 1045-56, 2010), melanoma (Dunn et al., Cancer Lett, 314(1): 24-33, 2012), breast cancer (Guo et al., Scientific Reports, 6: 36107, 2016), inflammation-induced tumours (Allen et al., J Exp Med, 207(5): 1045-56, 2010; and Hu et al., PNAS, 107(50): 21635-40, 2010), multiple myeloma (Li et al., Hematology, 21(3): 144-51, 2016), and squamous cell carcinoma of the head and neck (Huang et al., J Exp Clin Cancer Res, 36(1): 116, 2017). Activation of the NLRP3 inflammasome has also been shown to mediate chemoresistance of tumour cells to 5-fluorouracil (Feng et al., J Exp Clin Cancer Res, 36(1): 81, 2017), and activation of the NLRP3 inflammasome in peripheral nerves contributes to chemotherapy-induced neuropathic pain (Jia et al., Mol Pain, 13: 1-11, 2017).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behcet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler's syndrome, macrophage activation syndrome, Blau syndrome, vitiligo or vulvodynia; (iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, intracerebral haemorrhages, sepsis-associated encephalopathy, postoperative cognitive dysfunction, early brain injury, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, cardiac hypertrophy and fibrosis, embolism, aneurysms including abdominal aortic aneurysm, and pericarditis including Dressler's syndrome;

(viii) respiratory diseases including chronic obstructive pulmonary disorder (COPD), asthma such as allergic asthma, eosinophilic asthma, and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD) and non-alcoholic steatohepatitis (NASH) including advanced fibrosis stages F3 and F4, alcoholic fatty liver disease (AFLD), alcoholic steatohepatitis (ASH), ischemia reperfusion injury of the liver, fulminant hepatitis, liver fibrosis, and liver failure;

(x) renal diseases including chronic kidney disease, oxalate nephropathy, nephrocalcinosis, glomerulonephritis, diabetic nephropathy, kidney fibrosis including chronic crystal nephropathy, and renal hypertension;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease;

(xiv) psychological disorders such as depression and psychological stress;

(xv) graft versus host disease;

(xvi) allodynia including mechanical allodynia;

(xvii) conditions associated with diabetes including diabetic encephalopathy, diabetic retinopathy, and diabetic hypoadiponectinemia; and (xviii) any disease where an individual has been determined to carry a germline or somatic non-silent mutation in NLRP3.

In one embodiment, the disease, disorder or condition is selected from:
(i) cancer;
(ii) an infection;
(iii) a central nervous system disease;
(iv) a cardiovascular disease;
(v) a liver disease;
(vi) an ocular disease; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);

(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) sickle cell disease;
(xxx) systemic juvenile idiopathic arthritis;
(xxxi) systemic lupus erythematosus;
(xxxii) traumatic brain injury;
(xxxiii) transient ischemic attack;
(xxxiv) ulcerative colitis; or
(xxxv) Valosin Containing Protein disease.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
  (i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
  (ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
  (iii) a muscular condition such as polymyositis or myasthenia gravis;
  (iv) a gastrointestinal tract condition such as inflammatory bowel disease (including Crohn's disease and ulcerative colitis), colitis, gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);
  (v) a respiratory system condition such as chronic obstructive pulmonary disease (COPD), asthma (including eosinophilic, bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;
  (vi) a vascular condition such as atherosclerosis, Behcet's disease, vasculitides, or Wegener's granulomatosis;
  (vii) an autoimmune condition such as systemic lupus erythematosus, Sjögren's syndrome, systemic sclerosis, Hashimoto's thyroiditis, type I diabetes, idiopathic thrombocytopenia purpura, or Graves disease;
  (viii) an ocular condition such as uveitis, allergic conjunctivitis, or vernal conjunctivitis;
  (ix) a nervous condition such as multiple sclerosis or encephalomyelitis;
  (x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *legionella*, Lyme disease, influenza A, Epstein-Barr virus infection, viral encephalitis/aseptic meningitis, or pelvic inflammatory disease;
  (xi) a renal condition such as mesangial proliferative glomerulonephritis, nephrotic syndrome, nephritis, glomerular nephritis, acute renal failure, uremia, nephritic syndrome, kidney fibrosis including chronic crystal nephropathy, or renal hypertension;
  (xii) a lymphatic condition such as Castleman's disease;
  (xiii) a condition of, or involving, the immune system, such as hyper IgE syndrome, lepromatous leprosy, familial hemophagocytic lymphohistiocytosis, or graft versus host disease;
  (xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH), primary biliary cirrhosis, fulminant hepatitis, liver fibrosis, or liver failure;
  (xv) a cancer, including those cancers listed above;
  (xvi) a burn, wound, trauma, haemorrhage or stroke;
  (xvii) radiation exposure;
  (xviii) obesity; and/or
  (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
  (i) chemotherapeutic agents;
  (ii) antibodies;
  (iii) alkylating agents;
  (iv) anti-metabolites;
  (v) anti-angiogenic agents;
  (vi) plant alkaloids and/or terpenoids;
  (vii) topoisomerase inhibitors;
  (viii) mTOR inhibitors;
  (ix) stilbenoids;
  (x) STING agonists;
  (xi) cancer vaccines;
  (xii) immunomodulatory agents;

(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPRio9881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulfonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, *Catharanthus roseus* (formerly known as *Vinca rosea*), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDRooi (PD1), BMS-986016, MGA271, lirilumab, IPH2201, emactuzumab, INCBo24360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, daloprisin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disease, disorder or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES—COMPOUND SYNTHESIS

All solvents, reagents and compounds were purchased and used without further purification unless stated otherwise.

Abbreviations

2-MeTHF 2-methyltetrahydrofuran
$Ac_2O$ acetic anhydride
AcOH acetic acid
aq aqueous
$B_2Pin_2$ bis(pinacolato)diboron
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMA dimethylacetamide
DMAP 4-dimethylaminopyridine, also called N,N-dimethylpyridin-4-amine
DME dimethoxyethane
DMF N,N-dimethylformamide
DMSO dimethyl sulfoxide
EDC 1-ethyl-3-(3-dimethylaminopropyl)carbodiimide
eq or equiv equivalent
(ES$^+$) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)$^+$ protonated molecular ion MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaOtBu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
$Pd_2(dba)_3$ tris(dibenzylideneacetone) dipalladium(0)
$Pd(dppf)Cl_2$ [1,1'-bis(diphenylphosphino)ferrocene]dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
sat saturated
SCX solid supported cation exchange (resin)
sept septuplet
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight
Xphos 2-dicyclohexylphosphino-2',4',6'-triisopropylbiphenyl Experimental Methods Nuclear Magnetic Resonance NMR spectra were recorded at 300, 400 or 500 MHz. Spectra were measured at 298 K, unless indicated otherwise, and were referenced relative to the solvent resonance. The chemical shifts are reported in parts per million. Spectra were recorded using one of the following machines:
- a Bruker Avance III spectrometer at 400 MHz fitted with a BBO 5 mm liquid probe,
- a Bruker 400 MHz spectrometer using ICON-NMR, under TopSpin program control,
- a Bruker Avance III HD spectrometer at 500 MHz, equipped with a Bruker 5 mm SmartProbe™,
- an Agilent VNMRS 300 instrument fitted with a 7.05 Tesla magnet from Oxford instruments, indirect detection probe and direct drive console including PFG module, or
- an Agilent MercuryPlus 300 instrument fitted with a 7.05 Tesla magnet from Oxford instruments, 4 nuclei autoswitchable probe and Mercury plus console.

LC-MS

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% $NH_3$—$H_2O$ in water (v/v); B: acetonitrile. Column: Kinetex EVO C18 2.1×30 mm, 5 µm.

Reversed Phase HPLC Conditions for the LCMS Analytical Methods

Methods 1a and 1b: Waters Xselect CSH C18 XP column (4.6×30 mm, 2.5 µm) at 40° C.; flow rate 2.5-4.5 mL min$^{-1}$ eluted with a $H_2O$-MeCN gradient containing either 0.1% v/v formic acid (Method 1a) or 10 mM $NH_4HCO_3$ in water (Method 1b) over 4 min employing UV detection at 254 nm. Gradient information: 0-3.00 min, ramped from 95% water-5% acetonitrile to 5% water-95% acetonitrile; 3.00-3.01 min, held at 5% water-95% acetonitrile, flow rate increased to 4.5 mL min$^{-1}$; 3.01-3.50 min, held at 5% water-95% acetonitrile; 3.50-3.60 min, returned to 95% water-5% acetonitrile, flow rate reduced to 3.50 mL min$^{-1}$; 3.60-3.90 min, held at 95% water-5% acetonitrile; 3.90-4.00 min, held at 95% water-5% acetonitrile, flow rate reduced to 2.5 mL min$^{-1}$.

Method 1c: Agilent 1290 series with UV detector and HP 6130 MSD mass detector using Waters XBridge BEH C18 XP column (2.1×50 mm, 2.5 µm) at 35° C.; flow rate 0.6 mL/min; mobile phase A: ammonium acetate (10 mM); water/MeOH/acetonitrile (900:60:40); mobile phase B: ammonium acetate (10 mM); water/MeOH/acetonitrile (100:540:360); over 4 min employing UV detection at 215 and 238 nm. Gradient information: 0-0.5 min, held at 80% A-20% B; 0.5-2.0 min, ramped from 80% A-20% B to 100% B.

Reversed Phase HPLC Conditions for the UPLC Analytical Methods

Methods 2a and 2b: Waters BEH C18 (2.1×30 mm, 1.7 µm) at 40° C.; flow rate 0.77 mL min$^{-1}$ eluted with a $H_2O$-MeCN gradient containing either 0.1% v/v formic acid (Method 2a) or 10 mM $NH_4HCO_3$ in water (Method 2b) over 3 min employing UV detection at 254 nm. Gradient information: 0-0.11 min, held at 95% water-5% acetonitrile, flow rate 0.77 mL min$^{-1}$; 0.11-2.15 min, ramped from 95% water-5% acetonitrile to 5% water-95% acetonitrile; 2.15-2.49 min, held at 5% water-95% acetonitrile, flow rate 0.77 mL min$^{-1}$; 2.49-2.56 min, returned to 95% water-5% acetonitrile; 2.56-3.00 min, held at 95% water-5% acetonitrile, flow rate reduced to 0.77 mL min$^{-1}$.

Preparative Reversed Phase HPLC General Methods

Method 1 (acidic preparation): Waters X-Select CSH column C18, 5 µm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Method 2 (basic preparation): Waters X-Bridge Prep column C18, 5 µm (19×50 mm), flow rate 28 mL min$^{-1}$ eluting with a 10 mM $NH_4HCO_3$-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

Method 3: Phenomenex Gemini column, 10 µm (150×25 mm), flow rate=25 mL/min eluting with a water-acetonitrile gradient containing 0.04% $NH_3$ at pH 10 over 9 minutes using UV detection at 220 and 254 nm. Gradient information: 0-9 minutes, ramped from 8% to 35% acetonitrile;

9-9.2 minutes, ramped from 35% to 100% acetonitrile; 9.2-15.2 minutes, held at 100% acetonitrile.

Method 4: Revelis C18 reversed-phase 12 g cartridge [carbon loading 18%; surface area 568 m²/g; pore diameter 65 Angstrom; pH (5% slurry) 5.1; average particle size 40 μm], flow rate=30 mL/min eluting with a water-methanol gradient over 35 minutes using UV detection at 215, 235, 254 and 280 nm. Gradient information: 0-5 minutes, held at 0% methanol; 5-30 minutes, ramped from 0% to 70% methanol; 30-30.1 minutes, ramped from 70% to 100% methanol; 30.1-35 minutes, held at 100% methanol.

Synthesis of Intermediates

Intermediate A1: 7-Fluoro-5-(2-methoxypyridin-4-yl)-2,3-dihydro-1H-inden-4-amine Step A:
N-(7-Fluoro-2,3-dihydro-1H-inden-4-yl)pivalamide

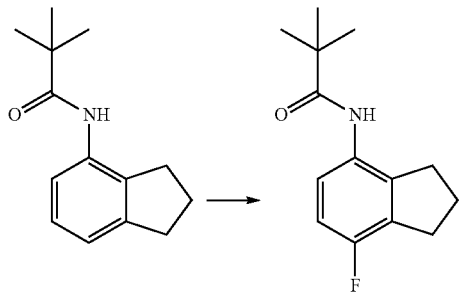 [SMILES: CC(C)(C)C(=O)Nc1cccc2c1CCC2 ; CC(C)(C)C(=O)Nc1ccc(F)c2c1CCC2]

To an ice-cooled solution of N-(2,3-dihydro-1H-inden-4-yl)pivalamide (2.5 g, 11.50 mmol) in dry dichloromethane (50 mL) was added pyridine hydrofluoride (9 ml, 69.9 mmol). The pale yellow mixture was stirred for 30 minutes at 0° C. A solution of bis(tert-butylcarbonyloxy)iodobenzene (7.5, 17.91 mmol) in dichloromethane (10 mL) was then slowly added over 10 minutes to the mixture. The reaction was slowly allowed to reach room temperature and stirred overnight. It was then quenched with triethylamine (0.5 ml, 3.58 mmol) and the whole mixture was absorbed onto silica gel and purified by chromatography on silica gel (120 g column, 0-30% EtOAc/isohexane) to afford the title compound (0.635 g, 22%) as a yellow crystalline solid.

$^1$H NMR (CDCl$_3$) δ 7.68 (dd, J=8.8, 4.5 Hz, 1H), 7.14 (s, 1H), 6.87 (t, J=8.6 Hz, 1H), 3.01 (t, J=7.5 Hz, 2H), 2.85 (t, J=7.5 Hz, 2H), 2.18 (p, J=7.5 Hz, 2H), 1.34 (s, 9H).

LCMS m/z 236.3 (M+H)$^+$ (ES$^+$); 234.2 (M–H)$^-$ (ES$^-$).

Step B: 7-Fluoro-2,3-dihydro-1H-inden-4-amine

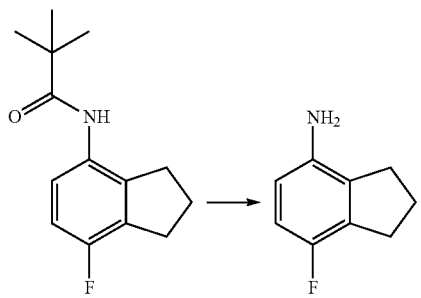 [SMILES: CC(C)(C)C(=O)Nc1ccc(F)c2c1CCC2 ; Nc1ccc(F)c2c1CCC2]

N-(7-Fluoro-2,3-dihydro-1H-inden-4-yl)pivalamide (0.632 g, 2.69 mmol) was dissolved in ethanol (5 mL) and stirred at room temperature. H$_2$SO$_4$ (95% aq.) (5 ml, 89 mmol) was slowly added to water (5 mL) and this mixture was then added to the reaction mixture. The slurry was heated to 100° C. (bath temperature) over the weekend. The reaction mixture was cooled to room temperature, diluted with water (10 mL) and then basified with 2M aq. NaOH. The mixture was extracted with dichloromethane (3×100 mL). The combined organics were washed, dried by passing through a hydrophobic frit and concentrated in vacuo. The crude product was purified by chromatography on silica gel (24 g column, 0-30% EtOAc/isohexane) to afford the title compound (350 mg, 82%) as a pale pink oil that solidified on standing.

$^1$H NMR (CDCl$_3$) δ 6.71 (dd, J=9.0, 8.2 Hz, 1H), 6.46 (dd, J=8.5, 3.9 Hz, 1H), 3.45 (s, 2H), 2.96 (t, J=7.6 Hz, 2H), 2.77 (t, J=7.5 Hz, 2H), 2.16 (p, J=7.6 Hz, 2H).

LCMS m/z 152.3 (M+H)$^+$ (ES$^+$).

Step C:
5-Bromo-7-fluoro-2,3-dihydro-1H-inden-4-amine

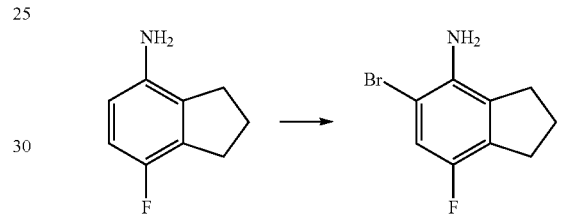

7-Fluoro-2,3-dihydro-1H-inden-4-amine (345 mg, 2.282 mmol) was dissolved in dichloromethane (10 mL). NBS (450 mg, 2.53 mmol) was added at room temperature in a single portion. The mixture turned dark brown immediately and was stirred for 15 minutes at room temperature. The reaction mixture was partitioned between dichloromethane and 1M aq. NaOH (20 mL) and stirred for 15 minutes. The organic phase was separated and washed with brine (10 mL), and then dried by passing through a hydrophobic frit. The solvent was removed in vacuo to give a dark brown oil. The crude product was purified by chromatography on silica gel (24 g column, 0-20% EtOAc/isohexane) to afford the title compound (323 mg, 55%) as a dark purple oil.

$^1$H NMR (CDCl$_3$) δ 7.08 (d, J=7.8 Hz, 1H), 3.06 (t, J=7.5 Hz, 2H), 2.95 (t, J=7.5 Hz, 2H), 2.20 (p, J=7.6 Hz, 2H), NH$_2$ not observed.

Step D: 7-Fluoro-5-(2-methoxypyridin-4-yl)-2,3-dihydro-1H-inden-4-amine

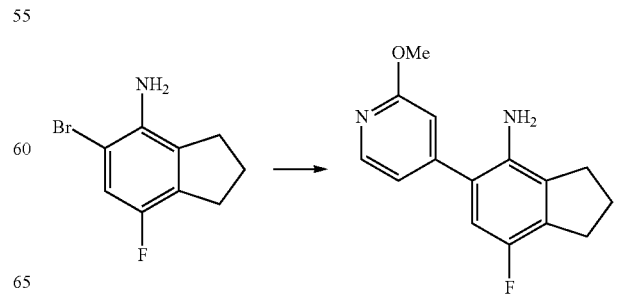

5-Bromo-7-fluoro-2,3-dihydro-1H-inden-4-amine (320 mg, 1.391 mmol) was dissolved in dioxane (5 mL). A solution of potassium carbonate (600 mg, 4.34 mmol) in water (1 mL) and solid (2-methoxypyridin-4-yl)boronic acid (250 mg, 1.635 mmol) were added. The mixture was degassed with nitrogen for 15 minutes before Pd(dppf)Cl$_2$.CH$_2$Cl$_2$ (60 mg, 0.073 mmol) was added. The reaction mixture was heated to 80° C. (bath temperature) for 24 hours. The mixture was cooled to room temperature and partitioned between dichloromethane (30 mL) and water (20 mL). The organic phase was dried by passing through a hydrophobic frit and concentrated in vacuo to give a brown oil. The crude product was purified by chromatography on silica gel (12 g column, 0-50% EtOAc/isohexane) to afford the title compound (0.185 g, 49%) as a pale brown oil that crystallized on standing.

$^1$H NMR (CDCl$_3$) δ 8.27 (d, J=5.4 Hz, 1H), 7.06 (d, J=5.3 Hz, 1H), 6.95 (s, 1H), 6.73 (d, J=9.0 Hz, 1H), 4.03 (s, 3H), 3.00 (t, J=7.5 Hz, 2H), 2.85 (t, J=7.4 Hz, 2H), 2.23 (p, J=7.5 Hz, 2H), NH$_2$ not observed.

LCMS m/z 259.3 (M+H)$^+$ (ES$^+$).

Intermediate A2: 5-(2-Methoxypyridin-4-yl)-2,3-dihydro-1H-inden-4-amine

Step A:
N-(5-Bromo-2,3-dihydro-1H-inden-4-yl)pivalamide

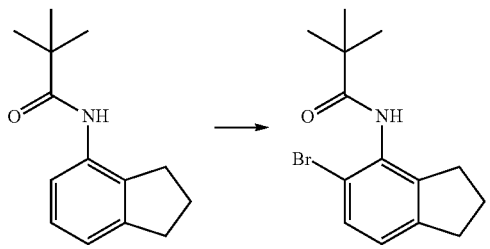 [SMILES: CC(C)(C)C(=O)Nc1cccc2c1CCC2 ; CC(C)(C)C(=O)Nc1c(Br)ccc2c1CCC2]

N-(2,3-Dihydro-1H-inden-4-yl)pivalamide (1 g, 4.60 mmol), p-toluenesulfonic acid monohydrate (0.45 g, 2.366 mmol), Pd(OAc)$_2$ (0.05 g, 0.223 mmol), and NBS (0.9 g, 5.06 mmol) were suspended in toluene (20 mL) and stirred under air for 16 hours. The dark green mixture was diluted with EtOAc (20 mL), and then washed with saturated aq. NaHCO$_3$ (2×10 mL), water (2×10 mL) and brine (10 mL). The organic phase was dried (Na$_2$SO$_4$), filtered and concentrated in vacuo to give a dark green amorphous solid. The crude product was purified by chromatography on silica gel (40 g column, 0-30% EtOAc/isohexane) to afford the title compound (1.662 g, 100%) as a colourless crystalline solid that was contaminated with a small amount of reaction byproducts.

LCMS m/z 296.3/298.3 (M+H)$^+$ (ES$^+$).

Step B: 5-Bromo-2,3-dihydro-1H-inden-4-amine

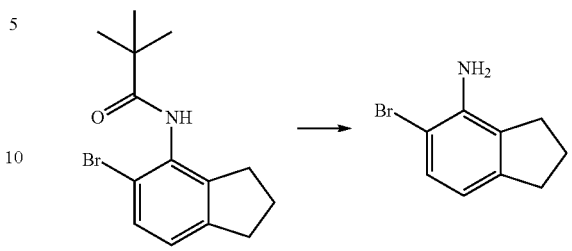

N-(5-Bromo-2,3-dihydro-1H-inden-4-yl)pivalamide (0.632 g, 2.134 mmol) was dissolved in ethanol (5 mL) and stirred at room temperature. H$_2$SO$_4$ (95% aq.) (5 ml, 89 mmol) was slowly added to water (5 mL) and this mixture was then added to the reaction mixture. The slurry was heated to 100° C. (bath temperature) at which point the mixture became homogeneous and it was stirred at this temperature over the weekend. The mixture was cooled to room temperature and then basified with 2M aq. NaOH. The mixture was extracted with dichloromethane (3×20 mL). The organic phase was dried by passing through a hydrophobic frit, and then concentrated in vacuo. The crude product was purified by chromatography on silica gel (40 g column, 0-50% EtOAc/isohexane) to afford the title compound (0.138 g, 29%).

$^1$H NMR (CDCl$_3$) δ 7.23 (d, J=7.9 Hz, 1H), 6.57 (d, J=8.0 Hz, 1H), 3.92 (s, 2H), 2.89 (t, J=7.6 Hz, 2H), 2.77 (t, J=7.4 Hz, 2H), 2.15 (p, J=7.5 Hz, 2H).

Step C: 5-(2-Methoxypyridin-4-yl)-2,3-dihydro-1H-inden-4-amine

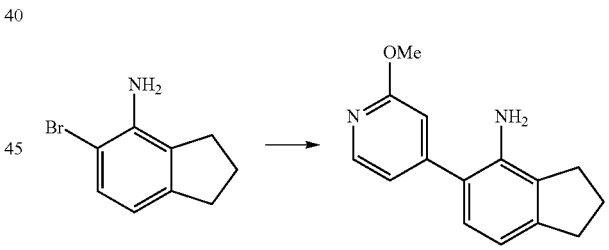

5-Bromo-2,3-dihydro-1H-inden-4-amine (280 mg, 1.320 mmol) was dissolved in dioxane (5 mL). A solution of potassium carbonate (600 mg, 4.34 mmol) in water (1 mL) and (2-methoxypyridin-4-yl)boronic acid (250 mg, 1.635 mmol) were added. The mixture was degassed with nitrogen for 15 minutes before Pd(dppf)Cl$_2$.CH$_2$Cl$_2$ (60 mg, 0.073 mmol) was added. The reaction mixture was heated to 80° C. (bath temperature) for 2 hours. The mixture was cooled to room temperature and partitioned between dichloromethane (30 mL) and water (20 mL). The organic phase was dried by passing through a hydrophobic frit and concentrated in vacuo to give a brown oil. The crude product was purified by chromatography on silica gel (12 g column, 0-50% EtOAc/isohexane) to afford the title compound (0.289 g, 87%) as a pale yellow crystalline solid.

$^1$H NMR (CDCl$_3$) δ 8.26 (d, J=5.4 Hz, 1H), 7.11 (d, J=5.0 Hz, 1H), 7.01 (d, J=7.7 Hz, 1H), 6.97 (s, 1H), 6.80 (d, J=7.6 Hz, 1H), 4.06 (s, 3H), 2.98 (t, J=7.6 Hz, 2H), 2.80 (t, J=7.4 Hz, 2H), 2.19 (p, J=7.5 Hz, 2H), NH$_2$ not observed.

LCMS m/z 241.3 (M+H)$^+$ (ES$^+$).

Intermediate A3:
4-Isocyanato-1,2,3,5,6,7-hexahydro-s-indacene

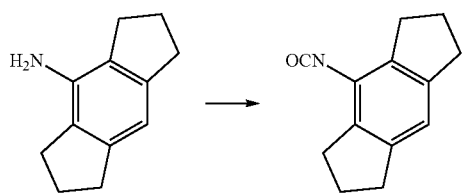

To a solution of phosgene (4.45 mL, 20% weight in toluene, 8.4 mmol) in EtOAc (90 mL) was added drop-wise a solution of 1,2,3,5,6,7-hexahydro-s-indacen-4-amine (589 mg, 3.4 mmol) in EtOAc (45 mL) at ambient temperature. The resulting reaction mixture was then heated to reflux for 3 hours and upon cooling was filtered and concentrated in vacuo to afford the title compound as a brown oil (756 mg, 100%). The crude product was used directly in the next step without further purification.

$^1$H NMR (CDCl$_3$) δ 6.8 (s, 1H), 2.89 (m, 8H) and 2.09 (m, 4H).

Intermediate A4:
((1,2,3,5,6,7-Hexahydro-s-indacen-4-yl)carbamoyl) sulfamoyl chloride

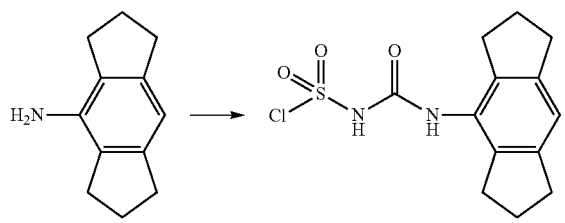 [SMILES: Nc1c2c(cc3c1CCC3)CCC2 ; O=C(Nc1c2c(cc3c1CCC3)CCC2)NS(=O)(=O)Cl]

A stirred solution of chlorosulfonyl isocyanate (0.53 ml, 6.1 mmol) in tert-butyl methyl ether (10 mL) was cooled to −20° C., then a solution of 1,2,3,5,6,7-hexahydro-s-indacen-4-amine (1 g, 5.8 mmol) in tert-butyl methyl ether (20 mL) was added slowly over 10 minutes. The reaction was stirred for 1 hour at −20° C. and then allowed to reach room temperature overnight. Subsequently most of the solvent was removed in vacuo and the material was dried overnight to afford the crude title compound (1.5 g, 82%), which was used without additional purification.

$^1$H NMR (CDCl$_3$) δ 7.95 (s, 1H), 7.10 (s, 1H), 2.93 (t, J=7.5 Hz, 4H), 2.86 (t, 4H), 2.11 (m, 4H).

Intermediate A5:
1,2,3,5-Tetrahydro-s-indacen-4-amine

Step A: 4-Nitro-1,2,3,5-tetrahydro-s-indacene

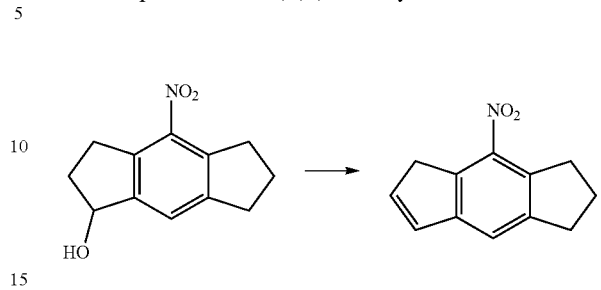

To a suspension of 4-nitro-1,2,3,5,6,7-hexahydro-s-indacen-1-ol (174 mg, 0.794 mmol) in anhydrous toluene (2 mL) were added 3 molecular sieves 3A and p-toluenesulfonic acid monohydrate (29 mg, 0.151 mmol). The reaction mixture was refluxed for 1.5 hours, and then diluted with EtOAc and washed with saturated aq. NaHCO$_3$ (5 mL) and brine (5 mL). The organic layer was dried over Na$_2$SO$_4$, filtered and concentrated under reduced pressure. The residue was purified by flash column chromatography (heptane:EtOAc) to afford the title compound (92 mg, 59%) as a yellow solid.

$^1$H NMR (CDCl$_3$) δ 7.50 (s, 1H), 6.85 (m, 1H), 6.66 (m, 1H), 3.83 (s, 2H), 3.38 (t, 2H), 3.02 (t, 2H), 2.18 (m, 2H).

Step B: 1,2,3,5-Tetrahydro-s-indacen-4-amine

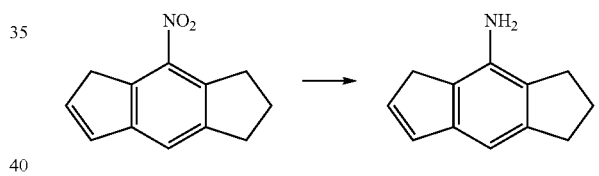

To a solution of 4-nitro-1,2,3,5-tetrahydro-s-indacene (85 mg, 42 mmol) in a 1/0.6/0.4 mixture of 1,4-dioxane/EtOH/H$_2$O (11.9 mL) was added Fe (144.5 mg, 2.55 mmol) and ammonium chloride (110.5 mg, 2.12 mmol). The reaction mixture was stirred at reflux for 1 hour, and then filtered through a plug of Celite® and concentrated under reduced pressure. The residue was purified by flash column chromatography (heptane:EtOAc) to afford the title compound (29 mg, 40%) as a yellow solid.

$^1$H NMR (CDCl$_3$) δ 6.94 (s, 1H), 6.82 (m, 1H), 6.50 (m, 1H), 3.32 (d, 2H), 2.92 (dd, 4H), 2.17 (q, 2H).

Intermediate A6: 6-Methyl-5-(2-((1-methylpiperidin-4-yl)oxy)pyridin-4-yl)-2,3-dihydro-1H-inden-4-amine Step A: N-(6-Bromo-4-nitro-2,3-dihydro-1H-inden-5-yl)acetamide

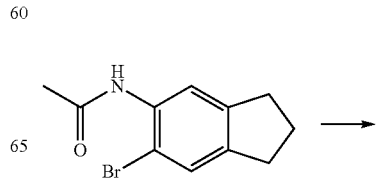

89

-continued

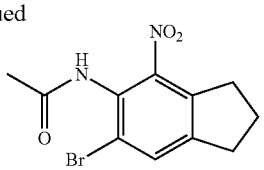

Nitric acid (150 mL, 2350 mmol) was slowly added to sulfuric acid (150 mL) cooled to 0° C., while keeping the temperature below 20° C. The mixture was stirred for 10 minutes and then added dropwise to a stirred mixture of N-(6-bromo-2,3-dihydro-1H-inden-5-yl)acetamide (58 g, 228 mmol) in AcOH (300 mL) and sulfuric acid (150 mL), while keeping the temperature below 30° C. The mixture was stirred at room temperature for 4 hours and then poured onto ice/water (4.5 L total volume, 2.5 kg ice) and left to stand at room temperature for 18 hours. The solid was filtered, washed with water (2.5 L) and dried to afford the title compound (55 g, 80%) as an ochre powder.

$^1$H NMR (DMSO-d6) δ 9.99 (s, 1H), 7.85 (s, 1H), 3.01-2.88 (m, 4H), 2.07 (p, J=7.5 Hz, 2H), 2.00 (s, 3H).

LCMS m/z 299.0/301.0 (M+H)$^+$ (ES$^+$).

Step B: N-(6-Methyl-4-nitro-2,3-dihydro-1H-inden-5-yl)acetamide

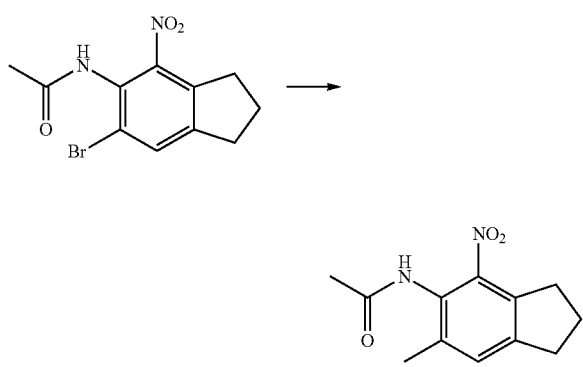

A mixture of N-(6-bromo-4-nitro-2,3-dihydro-1H-inden-5-yl)acetamide (30 g, 100 mmol), 2,4,6-trimethyl-1,3,5,2,4,6-trioxatriborinane (14.02 mL, 100 mmol) and K$_2$CO$_3$ (34.7 g, 251 mmol) in dioxane (500 mL) and H$_2$O (140 mL) was degassed with N$_2$ for 15 minutes. Then PdCl$_2$(dppf).DCM (4.10 g, 5.01 mmol) was added and the reaction was heated at 100° C. for 16 hours, diluted with brine (300 mL) and extracted with EtOAc (2×800 mL). The organic layers were dried (MgSO$_4$) and evaporated. The residue was triturated with EtOAc/isohexanes (1:1 mixture, 400 mL) and the resultant solid was filtered, rinsing with hexanes, and dried in vacuo to afford the title compound (15.33 g, 56%) as a brown solid.

$^1$H NMR (DMSO-d6) δ 9.65 (s, 1H), 7.41 (s, 1H), 2.98-2.87 (m, 4H), 2.20 (s, 3H), 2.07-2.03 (m, 2H), 1.99 (s, 3H).

LCMS m/z 235.2 (M+H)$^+$ (ES$^+$).

90

Step C:
6-Methyl-4-nitro-2,3-dihydro-1H-inden-5-amine

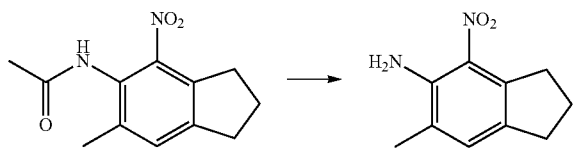 [SMILES: CC(=O)Nc1c(C)cc2c(c1[N+](=O)[O-])CCC2 ; Cc1cc2c(c([N+](=O)[O-])c1N)CCC2]

N-(6-Methyl-4-nitro-2,3-dihydro-1H-inden-5-yl)acetamide (15.33 g, 65.4 mmol) was suspended in a mixture of EtOH (126 mL) and concentrated aqueous HCl (126 mL). The mixture was heated to reflux overnight and concentrated in vacuo. The residue was basified by portionwise addition of 2M aq NaOH (~500 mL). The aqueous layer was extracted with DCM (5×200 mL), dried (MgSO$_4$) and concentrated in vacuo to afford the title compound (15.18 g, 84%) as a brown solid.

$^1$H NMR (DMSO-d6) δ 7.21 (s, 1H), 6.61 (s, 2H), 3.16 (t, J=7.5 Hz, 2H), 2.76 (t, J=7.6 Hz, 2H), 2.16 (s, 3H), 2.00-1.94 (m, 2H).

LCMS m/z 193.4 (M+H)$^+$ (ES$^+$).

Step D:
5-Bromo-6-methyl-4-nitro-2,3-dihydro-1H-indene

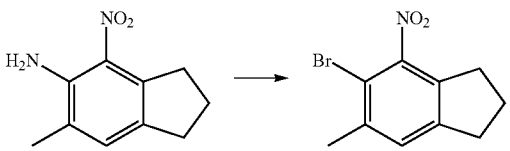

A solution of 6-methyl-4-nitro-2,3-dihydro-1H-inden-5-amine (4.9 g, 20.39 mmol) and isopentyl nitrite (3 mL, 22.33 mmol) in MeCN (400 mL) was heated to 55° C., whereupon CuBr$_2$ (4.56 g, 20.39 mmol) was added. The mixture was heated to 70° C. and stirred for 1 hour. Then the reaction was allowed to cool to room temperature and 1M HCl (200 mL) was added. The reaction mixture was extracted with DCM (3×200 mL). The organic phases were concentrated in vacuo and the crude product was purified by chromatography on silica gel (220 g column, 0-20% EtOAc/isohexane) to afford the title compound (3.2 g, 60%) as a pale yellow solid.

$^1$H NMR (DMSO-d6) δ 7.50 (s, 1H), 2.94-2.86 (m, 4H), 2.41 (s, 3H), 2.09 (p, J=7.6 Hz, 2H).

LCMS m/z 279.2 (M+Na)+(ES$^+$).

Step E:
4-Bromo-2-((1-methylpiperidin-4-yl)oxy)pyridine

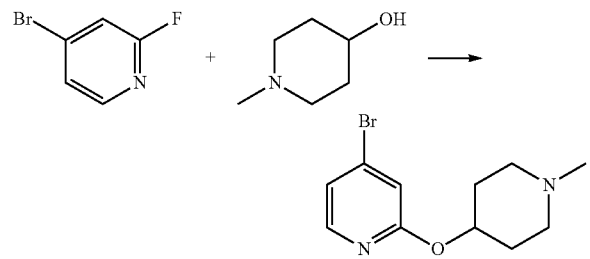

1-Methylpiperidin-4-ol (0.75 g, 6.51 mmol) was added to a mixture of KO^tBu (0.96 g, 8.56 mmol) in THF (10 mL) at room temperature. The mixture was stirred for 1 hour, cooled to 0° C. and then a solution of 4-bromo-2-fluoropyridine (1.00 g, 5.68 mmol) in THF (5 mL) was added. The mixture was warmed to room temperature, stirred for 22 hours, and then partitioned between EtOAc (100 mL) and water (100 mL). The organic layer was washed with water (50 mL), dried (MgSO$_4$) and evaporated in vacuo. The crude product was purified by chromatography on silica gel (24 g column, 0-10% (0.7 M ammonia/MeOH)/DCM) to afford the title compound (1.43 g, 76%) as a pale yellow oil.

$^1$H NMR (DMSO-d6) δ 8.05 (d, J=5.5 Hz, 1H), 7.19 (dd, J=5.5, 1.7 Hz, 1H), 7.08 (d, J=1.6 Hz, 1H), 5.12-4.86 (m, 1H), 2.71-2.56 (m, 2H), 2.21-2.08 (m, 5H), 1.99-1.86 (m, 2H), 1.76-1.59 (m, 2H).

LCMS m/z 271.0/273.0 (M+H)$^+$ (ES$^+$).

Step F: 4-(6-Methyl-4-nitro-2,3-dihydro-1H-inden-5-yl)-2-((1-methylpiperidin-4-yl)oxy)pyridine

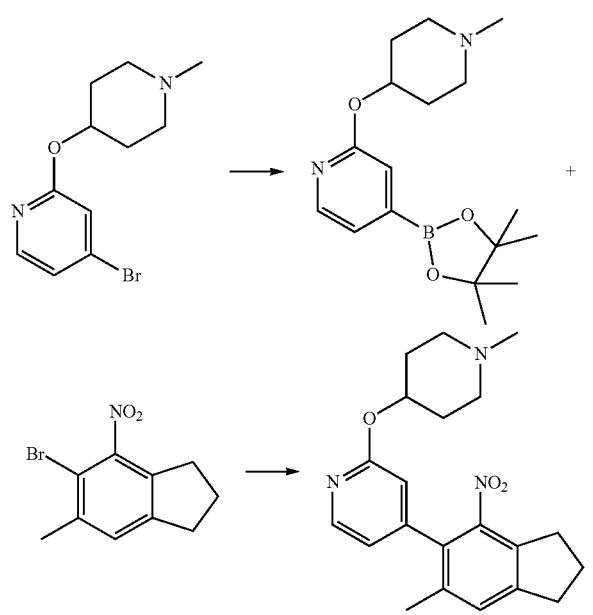

To a solution of 4-bromo-2-((1-methylpiperidin-4-yl)oxy)pyridine (step E) (2.485 g, 9.17 mmol) in dioxane (42 mL) was added B$_2$Pin$_2$ (2.56 g, 10.08 mmol) followed by KOAc (3.60 g, 36.7 mmol). The reaction mixture was heated to 60° C. and degassed with N$_2$. PdCl$_2$(dppf).DCM (0.374 g, 0.458 mmol) was added to the reaction mixture and the temperature was increased to 100° C. for 2 hours. 5-Bromo-6-methyl-4-nitro-2,3-dihydro-1H-indene (step D) (2.42 g, 9.17 mmol) was added, followed by a solution of K$_2$CO$_3$ (5.07 g, 36.7 mmol) in water (10 mL). The solution was stirred at 100° C. for 1 hour, cooled to room temperature, filtered through a plug of Celite®, diluted with EtOAc (200 mL) and washed with brine (100 mL). The organic layers were dried (MgSO$_4$), concentrated in vacuo and purified by chromatography on silica gel (120 g column, 0-10% (0.7 M ammonia/MeOH)/DCM) to afford the title compound (1.88 g, 51 20%) as a brown gum.

$^1$H NMR (DMSO-d6) δ 8.20 (d, J=5.2 Hz, 1H), 7.49 (s, 1H), 6.81 (dd, J=5.2, 1.5 Hz, 1H), 6.60 (s, 1H), 5.07-4.85 (m, 1H), 3.03-2.89 (m, 4H), 2.74-2.57 (m, 2H), 2.25-2.03 (m, 9H), 2.04-1.95 (m, 3H), 1.75-1.59 (m, 2H).

LCMS m/z 368.3 (M+H)$^+$ (ES$^+$).

Step G: 6-Methyl-5-(2-((1-methylpiperidin-4-yl)oxy)pyridin-4-yl)-2,3-dihydro-1H-inden-4-amine

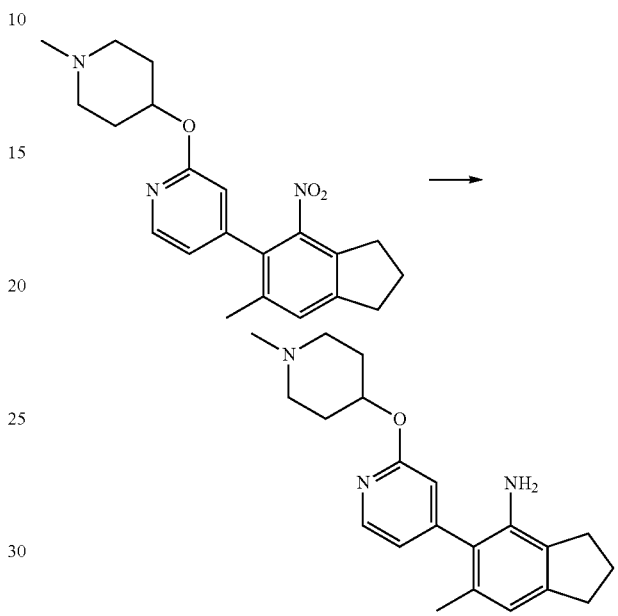

A mixture of 4-(6-methyl-4-nitro-2,3-dihydro-1H-inden-5-yl)-2-((1-methylpiperidin-4-yl)oxy)pyridine (1.88 g, 4.66 mmol) and 5% Pd—C(Type 87L, 58-5% moisture) (0.478 g, 0.093 mmol) in EtOH (30 mL) was hydrogenated at 1 bar for 22 hours. The mixture was filtered through a pad of Celite®, rinsing with MeOH (2×30 mL). The filtrate was concentrated in vacuo to afford the title compound (1.70 g, 94%) as a sticky brown tar.

$^1$H NMR (DMSO-d6) δ 8.21 (d, J=5.1 Hz, 1H), 6.73 (dd, J=5.2, 1.4 Hz, 1H), 6.55-6.47 (m, 1H), 6.45 (s, 1H), 5.01 (tt, J=8.8, 4.2 Hz, 1H), 4.14 (s, 2H), 2.78 (t, J=7.5 Hz, 2H), 2.74-2.58 (m, 4H), 2.27-2.09 (m, 5H), 2.06-1.93 (m, 4H), 1.88 (s, 3H), 1.76-1.63 (m, 2H).

LCMS m/z 338.2 (M+H)$^+$ (ES$^+$).

Intermediate A7: 5-(2-Methoxypyridin-4-yl)-6-methyl-2,3-dihydro-1H-inden-4-amine Step A: 2-Methoxy-4-(6-methyl-4-nitro-2,3-dihydro-1H-inden-5-yl)pyridine

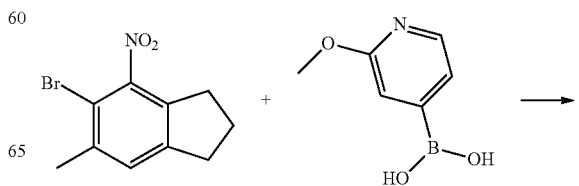

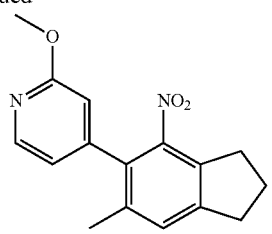

A mixture of 5-bromo-6-methyl-4-nitro-2,3-dihydro-1H-indene (Intermediate A6, Step D) (910 mg, 3.55 mmol) and (2-methoxypyridin-4-yl)boronic acid (652 mg, 4.26 mmol) was dissolved in dioxane (20 mL) and a solution of $K_2CO_3$ (1473 mg, 10.66 mmol) in water (4 mL) was added. The reaction mixture was degassed with $N_2$ for 15 minutes. Pd(dppf)$Cl_2$.DCM (290 mg, 0.355 mmol) was added and the reaction mixture was heated to 80° C. for 4 hours. The reaction was cooled to room temperature and partitioned between EtOAc (100 mL) and brine (50 mL). The organic layers were concentrated in vacuo. The crude product was purified by chromatography on silica gel (24 g column, 0-20% EtOAc/isohexane) to afford the title compound (888 mg, 83%) as a yellow oil.

$^1$H NMR (DMSO-d6) δ 8.24 (d, J=5.2 Hz, 1H), 7.51 (s, 1H), 6.86 (dd, J=5.3, 1.4 Hz, 1H), 6.68-6.66 (m, 1H), 3.89 (s, 3H), 3.04-2.90 (m, 4H), 2.17-2.04 (m, 5H).

LCMS m/z 285.0 (M+H)$^+$ (ES$^+$).

Step B: 5-(2-Methoxypyridin-4-yl)-6-methyl-2,3-dihydro-1H-inden-4-amine

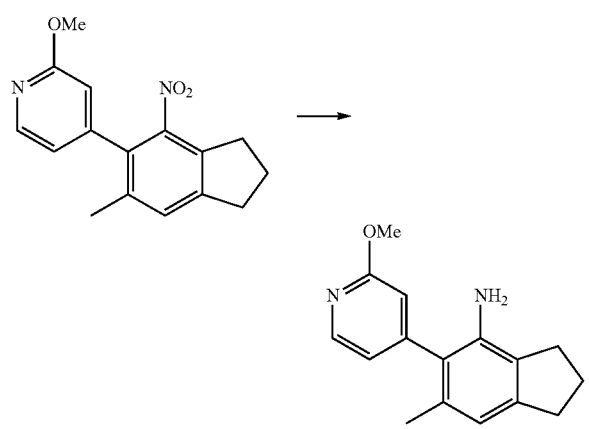

A mixture of 2-methoxy-4-(6-methyl-4-nitro-2,3-dihydro-1H-inden-5-yl)pyridine (186 mg, 0.536 mmol) and 5% Pd—C(Type 87L, 58-5% moisture) (55 mg, 10.72 μmol) in EtOH (2 mL) was hydrogenated at 1 bar for 6 hours. Then the mixture was filtered through Celite® and evaporated to afford the title compound (120 mg, 77%) as a solid.

$^1$H NMR (DMSO-d6) δ 8.24 (d, J=5.2 Hz, 1H), 6.77 (dd, J=5.2, 1.5 Hz, 1H), 6.58 (s, 1H), 6.45 (s, 1H), 4.16 (s, 2H), 3.89 (s, 3H), 2.78 (t, J=7.5 Hz, 2H), 2.64 (t, J=7.4 Hz, 2H), 1.99 (p, J=7.4 Hz, 2H), 1.88 (s, 3H).

LCMS m/z 255.1 (M+H)$^+$ (ES$^+$).

Intermediate A8: 4-Isopropyl-2-methyl-1-(pyridin-4-yl)-1H-imidazol-5-amine

Step A: 2-Methyl-1-((2-(trimethylsilyl)ethoxy)methyl)-1H-imidazole

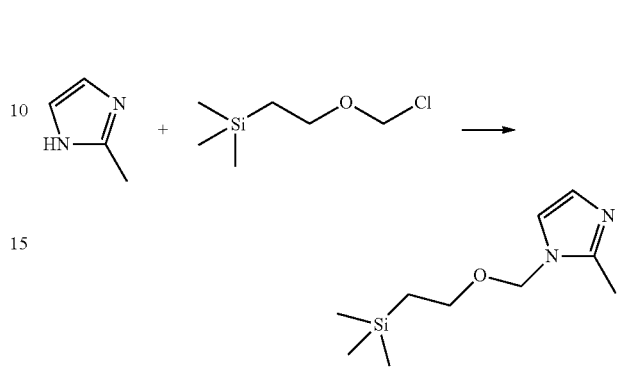

To a solution of NaH (9.74 g, 243.59 mmol, 60 wt % in mineral oil, 1 eq) in DMF (200 mL) was added in portions 2-methyl-1H-imidazole (20 g, 243.59 mmol, 1 eq) at 0° C. The reaction mixture was stirred at 0° C. for 30 minutes. Then (2-(chloromethoxy)ethyl) trimethylsilane (48.73 g, 292.31 mmol, 1.2 eq) was added. The resulting mixture was stirred at 0° C. for 2 hours. The reaction mixture was quenched with ice-water (300 mL), diluted with ethyl acetate (1 L), and washed with saturated aqueous $NH_4Cl$ solution (3×300 mL) and brine (3×300 mL). The organic layers were dried over anhydrous $Na_2SO_4$, filtered and concentrated in vacuo. The residue was purified by column chromatography (SiO$_2$, petroleum ether: ethyl acetate, 5:1 to 1:1) to give the title compound (40 g, 76% yield, 98% purity on LCMS) as a yellow oil.

$^1$H NMR (400 MHz, CDCl$_3$) δ 6.90 (s, 2H), 5.18 (s, 2H), 3.47 (t, 2H), 2.43 (s, 3H), 0.89 (t, 2H) and 0.01 (s, 9H).

LCMS: m/z 213.0 (M+H)$^+$ (ES$^+$).

Step B: 4-Bromo-2-methyl-1-((2-(trimethylsilyl)ethoxy)methyl)-1H-imidazole

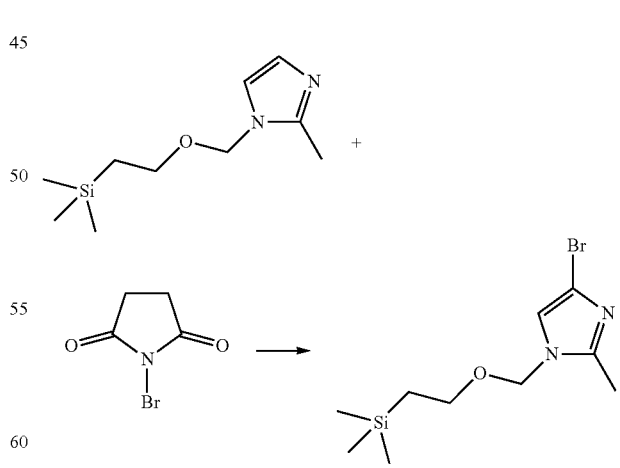

To a solution of 2-methyl-1-((2-(trimethylsilyl)ethoxy)methyl)-1H-imidazole (20 g, 94.18 mmol, 1 eq) in DMF (200 mL) was added NBS (16.76 g, 94.18 mmol, 1 eq) at −20° C. Then the reaction mixture was stirred at −20° C. for 2 hours. The reaction mixture was quenched with saturated aqueous Na₂SO₃ solution (100 mL), diluted with EtOAc (200 mL), and washed with saturated aqueous NH₄Cl solution (3×100 mL) and brine (3×100 mL). The organic layers were dried over anhydrous Na₂SO₄, filtered and concentrated in vacuo. The residue was purified by column chromatography (SiO₂, petroleum ether: ethyl acetate, 10:1 to 5:1) to give the title compound (13.5 g, 41% yield, 84% purity on LCMS) as a yellow oil.

$^1$H NMR (400 MHz, CDCl₃) δ 6.88 (s, 1H), 5.25 (s, 2H), 3.55 (t, 2H), 2.42 (s, 3H), 0.91 (t, 2H) and 0.02 (s, 9H).

LCMS: m/z 292.9 (M+H)⁺ (ES⁺).

Step C: 2-Methyl-4-(prop-1-en-2-yl)-1-((2-(trimethylsilyl)ethoxy)methyl)-1H-imidazole

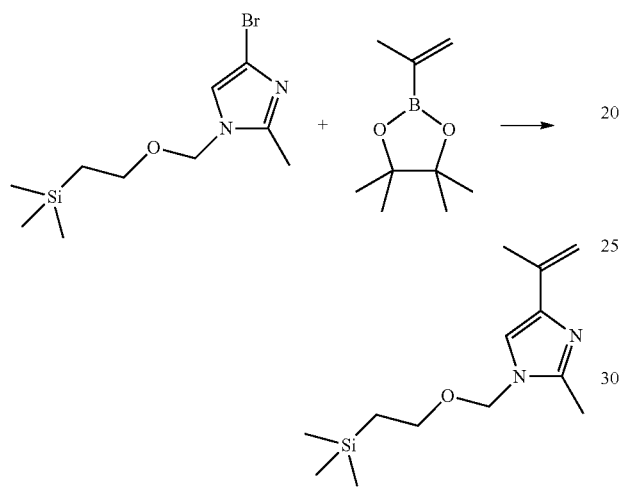

A solution of 4-bromo-2-methyl-1-((2-(trimethylsilyl)ethoxy)methyl)-1H-imidazole (10 g, 28.84 mmol, 1 eq), 4,4,5,5-tetramethyl-2-(prop-1-en-2-yl)-1,3,2-dioxaborolane (5.33 g, 31.72 mmol, 1.1 eq), Pd(dppf)Cl₂ (1.06 g, 1.44 mmol, 0.05 eq) and Na₂CO₃ (6.11 g, 57.68 mmol, 2 eq) in dioxane (100 mL) and H₂O (20 mL) was stirred at 100° C. for 12 hours under N₂. The reaction mixture was diluted with water (100 mL), and then extracted with ethyl acetate (3×100 mL). The organic layers were dried over anhydrous Na₂SO₄, filtered and concentrated in vacuo. The residue was purified by column chromatography (SiO₂, petroleum ether: ethyl acetate, 5:1 to 1:1) to give the title compound (7 g, 96%) as a yellow oil.

$^1$H NMR (400 MHz, CDCl₃) δ 6.88 (s, 1H), 5.23 (s, 2H), 5.20 (s, 1H), 5.14 (s, 1H), 3.52 (t, 2H), 2.48 (s, 3H), 2.08 (s, 3H), 0.93 (t, 2H) and 0.01 (s, 9H).

LCMS: m/z 253.0 (M+H)⁺ (ES⁺).

Step D: 4-Isopropyl-2-methyl-1-((2-(trimethylsilyl)ethoxy)methyl)-1H-imidazole

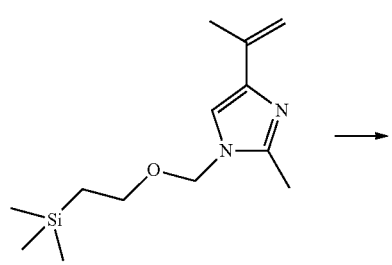

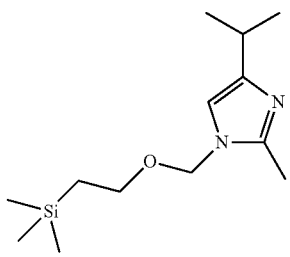

To a solution of 2-methyl-4-(prop-1-en-2-yl)-1-((2-(trimethylsilyl)ethoxy)methyl)-1H-imidazole (7.18 g, 28.44 mmol, 1 eq) in MeOH (100 mL) was added Pd/C (700 mg, 10 wt % loading on activated carbon) under N₂. The suspension was degassed in vacuo and purged with H₂ several times. The mixture was stirred at 25° C. for 12 hours under H₂ (15 psi). Then the reaction mixture was filtered and the filtrate was concentrated in vacuo to give the title compound (8 g, 99% yield, 90% purity on LCMS) as a yellow oil.

$^1$H NMR (400 MHz, CDCl₃) δ 6.66 (s, 1H), 5.15 (s, 2H), 3.49 (t, 2H), 2.95-2.84 (m, 1H), 2.43 (s, 3H), 1.26 (d, 6H), 0.91 (t, 2H) and 0.02 (s, 9H).

LCMS: m/z 255.2 (M+H)⁺ (ES⁺).

Step E: 4-Isopropyl-2-methyl-1H-imidazole

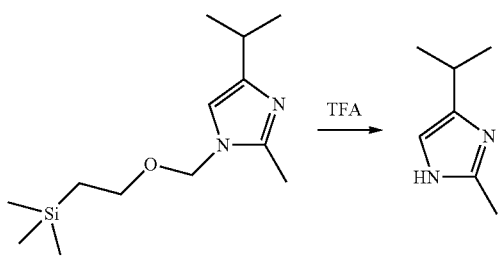

To a solution of 4-isopropyl-2-methyl-1-((2-(trimethylsilyl)ethoxy)methyl)-1H-imidazole (8 g, 31.44 mmol, 1 eq) in DCM (80 mL) was added TFA (123.20 g, 1.08 mol, 34.37 eq) at 25° C. Then the mixture was stirred at 25° C. for 12 hours. The reaction mixture was quenched with ice-water (10 mL) and saturated aqueous NaHCO₃ solution (300 mL). The mixture was extracted with ethyl acetate (2×100 mL). The combined organic layers were washed with brine (2×200 mL), dried over anhydrous Na₂SO₄, filtered and concentrated in vacuo. The residue was purified by column chromatography (SiO₂, ethyl acetate: methanol, 1:0 to 20:1) to give the title compound (3.7 g, 95%) as a yellow oil.

$^1$H NMR (400 MHz, CDCl₃) δ 6.71 (s, 1H), 2.99-2.93 (m, 1H), 2.53 (s, 3H) and 1.27 (d, 6H).

LCMS: m/z 125.3 (M+H)⁺ (ES⁺).

Step F: 4-(4-Isopropyl-2-methyl-1H-imidazol-1-yl)pyridine

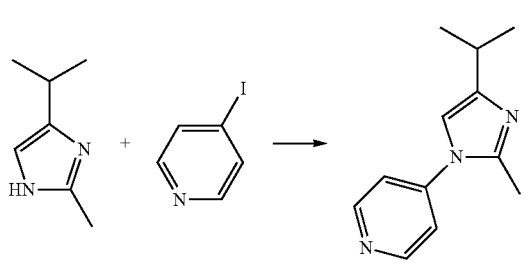

To a solution of 4-isopropyl-2-methyl-1H-imidazole (1.4 g, 11.27 mmol, 1 eq) and 4-iodopyridine (1.85 g, 9.02 mmol, 0.8 eq) in DMF (14 mL) was added with Cu$_2$O (81 mg, 563.68 µmol, 0.05 eq) and Cs$_2$CO$_3$ (7-35 g, 22.55 mmol, 2 eq). The reaction mixture was stirred at 100° C. for 15 hours. Then the reaction mixture was diluted with ethyl acetate (50 mL), and washed with saturated aqueous NH$_4$Cl solution (3×30 mL) and brine (3×30 mL). The organic layers were dried over anhydrous Na$_2$SO$_4$, filtered and concentrated in vacuo. The residue was purified by column chromatography (SiO$_2$, petroleum ether: ethyl acetate, 5:1 to 0:1) to give the title compound (600 mg, 26% yield, 97% purity on LCMS) as a yellow solid.

$^1$H NMR (400 MHz, CDCl$_3$) δ 8.73 (dd, 2H), 7.27 (dd, 2H), 6.77 (s, 1H), 2.93-2.86 (m, 1H), 2.48 (s, 3H) and 1.29 (d, 6H).

LCMS: m/z 202.0 (M+H)$^+$ (ES$^+$).

Step G: 4-(4-Isopropyl-2-methyl-5-nitro-1H-imidazol-1-yl)pyridine

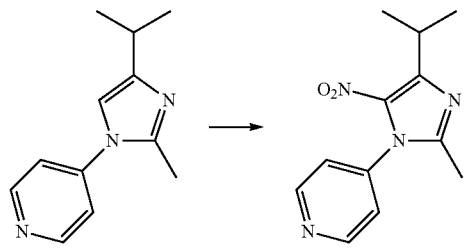 [SMILES: Cc1nc(C(C)C)cn1-c1ccncc1 ; Cc1nc(C(C)C)c([N+](=O)[O-])n1-c1ccncc1]

To a solution of 4-(4-isopropyl-2-methyl-1H-imidazol-1-yl)pyridine (400 mg, 1.93 mmol, 1 eq) in H$_2$SO$_4$ (71.33 mmol, 3.88 mL, 98% purity in solution, 37 eq) was added with HNO$_3$ (5.78 mmol, 400 µL, 65% purity in aqueous solution, 3 eq) at 0° C. Then the reaction mixture was stirred at 25° C. for 12 hours. The reaction mixture was quenched with ice-water (20 mL), and adjusted to pH=8-9 with saturated aqueous NaHCO$_3$ solution. The mixture was extracted with ethyl acetate (3×20 mL). The organic layers were dried over anhydrous Na$_2$SO$_4$, filtered and concentrated in vacuo. The yellow solid was purified by column chromatography (SiO$_2$, petroleum ether: ethyl acetate, 2:1 to 1:1) to give the title compound (400 mg, 84%) as a yellow solid.

$^1$H NMR (400 MHz, CDCl$_3$) δ 8.83 (d, 2H), 7.22 (d, 2H), 3.75-3.69 (m, 1H), 2.25 (s, 3H) and 1.36 (d, 6H).

LCMS: m/z 247.1 (M+H)$^+$ (ES$^+$).

Step H: 4-Isopropyl-2-methyl-1-(pyridin-4-yl)-1H-imidazol-5-amine

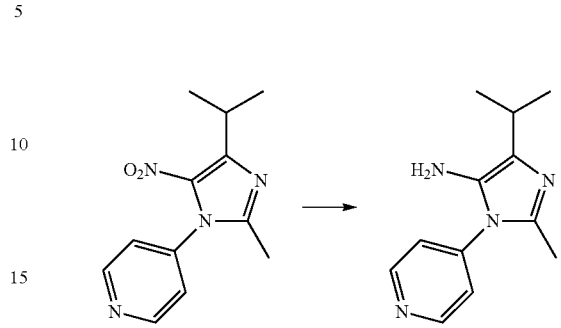

A mixture of 4-(4-isopropyl-2-methyl-5-nitro-1H-imidazol-1-yl)pyridine (400 mg, 1.62 mmol, 1 eq) and Pd/C (40 mg, 10 wt % loading on activated carbon) in MeOH (20 mL) was hydrogenated at 20° C. for 1 hour under H$_2$ (15 psi). Then the reaction mixture was filtered, and the filtrate was concentrated in vacuo. The residue was dissolved in THF (10 mL), and adjusted to pH=3-4 with 4M HCl/dioxane. The resulting mixture was concentrated in vacuo to give the title compound (400 mg, 97%, HCl salt) as a yellow solid, which was used in the next step without further purification.

$^1$H NMR (400 MHz, DMSO-d$_6$) δ 15.02 (s, 1H), 8.99 (d, 2H), 7.90 (d, 2H), 3.25-3.15 (m, 1H), 2.45 (s, 3H) and 1.27 (d, 6H).

LCMS: m/z 217.1 (M+H)$^+$ (ES$^+$).

Intermediate P1: N1,N1,N2-Trimethylpropane-1,2-diamine

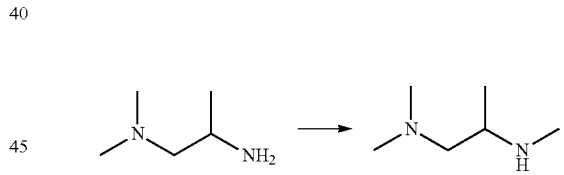

N1,N1-dimethylpropane-1,2-diamine (153 mg, 1.5 mmol) was dissolved in DCM (50 mL) and cooled to 0° C. Ethyl chloroformate (162 mg, 1.5 mmol) was added dropwise and the mixture was allowed to reach room temperature overnight. The reaction mixture was washed with aqueous 1 N NaOH (20 mL), dried over sodium sulfate and evaporated to dryness. The crude oil was taken up in THF (20 mL) and added dropwise to a suspension of lithium aluminium hydride (0.5, 13 mmol) in THF (20 mL) at 0° C. The reaction was refluxed overnight, and subsequently cooled to room temperature and carefully quenched with water. The suspension was filtered and the residue was washed with methanol (10 mL). The filtrates were combined and evaporated to near dryness. The crude product was dissolved in DCM (20 mL), dried over sodium sulfate and evaporated to dryness to yield the title compound (140 mg, 86%) as a yellow oil.

$^1$H NMR (CDCl$_3$) δ 2.59 (m, 1H), 2.39 (s, 3H), 2.05 (m, 1H), 2.19 (s, 6H), 2.01 (m, 1H), 1.40 (s, 1H), 0.95 (d, 3H).

LCMS: m/z 117 (M+H)$^+$ (ES$^+$).

Intermediate P2:
(1-Isopropylazetidin-2-yl)methanamine dihydrochloride

Step A: tert-Butyl ((1-isopropylazetidin-2-yl)methyl)carbamate

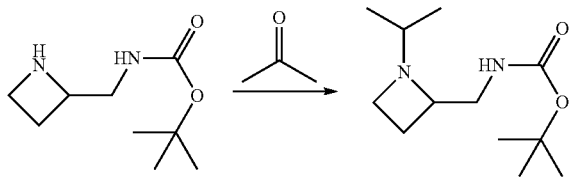

To a solution of tert-butyl (azetidin-2-ylmethyl)carbamate (200 mg, 1.07 mmol) and acetone (84 μL, 1.13 mmol) in acetonitrile (10 mL) was added sodium triacetoxyborohydride (283 mg, 1.34 mmol). The reaction mixture was stirred overnight and then concentrated in vacuo. The crude product was coated on Agilent hydromatrix (a high purity, inert diatomaceous earth sorbent) and was submitted to normal phase flash chromatography using dichloromethane and a mixture of ammonia (3.5 M) in methanol as eluent to afford the title compound (222 mg, 90%) which was used without further purification.

$^1$H NMR (CDCl$_3$) δ 5-75 (bs, 1H), 3.60 (bs, 2H), 3.48-3.34 (m, 1H), 3.18 (d, 1H), 2.98 (q, 1H), 2.71-2.54 (m, 1H), 2.06-1.92 (m, 2H), 1.44 (s, 9H), 1.02 (dd, 6H).

Step B: (1-Isopropylazetidin-2-yl)methanamine dihydrochloride

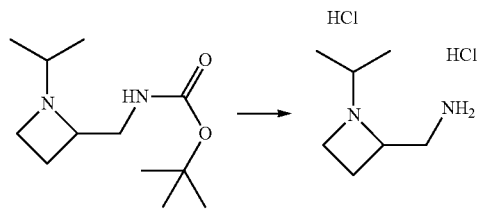

To a solution of tert-butyl ((1-isopropylazetidin-2-yl) methyl)carbamate (83 mg, 0.36 mmol) in dichloromethane (10 mL) was added 4M hydrochloric acid in dioxane (0.9 mL, 36 mmol). After stirring for 6 hours, additional 4M hydrochloric acid in dioxane (0.9 mL, 36 mmol) was added and the reaction stirred over the weekend. The suspension was concentrated in vacuo to afford the title compound (72 mg, quantitative yield) which was used without further purification.

$^1$H NMR (CD$_3$OD) δ 4.83-4.68 (m, 1H), 4.20-3.99 (m, 2H), 3.64-3.45 (m, 3H), 2.73-2.38 (m, 2H), 1.33 (dd, 6H).

Intermediate P3:
3-Methyl-3,8-diazabicyclo[3.2.1]octane dihydrochloride

Step A: tert-Butyl 3-methyl-3,8-diazabicyclo[3.2.1] octane-8-carboxylate

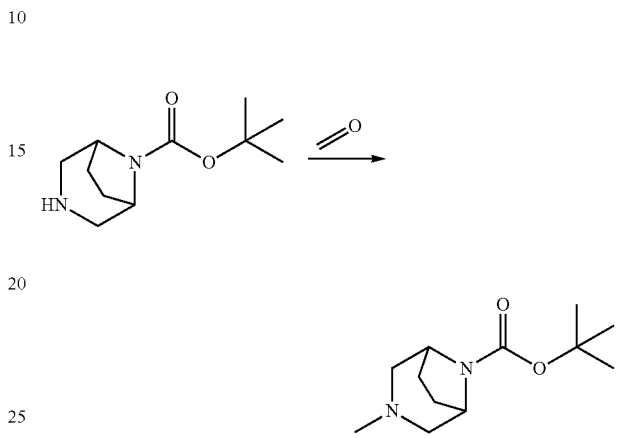

To a solution of tert-butyl 3,8-diazabicyclo[3.2.1]octane-8-carboxylate (84 mg, 0.40 mmol) and formaldehyde (37% in water, stabilized with methanol; 32 μL, 42 mmol) in acetonitrile (10 mL) was added sodium triacetoxyborohydride (0.50 mmol, 106 mg). After stirring overnight, an extra equivalent of formaldehyde (37% in water, stabilized with methanol; 32 μL, 42 mmol) and sodium triacetoxyborohydride (0.50 mmol, 106 mg) were added. After stirring for 3 hours, the reaction mixture was concentrated in vacuo. The crude product was coated on Agilent hydromatrix (a high purity, inert diatomaceous earth sorbent) and was submitted to normal phase flash chromatography using dichloromethane and a mixture of ammonia (3.5 M) in methanol as eluent to afford the title compound (86 mg, 94%).

$^1$H NMR (CDCl$_3$) δ 4.14 (bs, 2H), 2.67 (d, 2H), 2.35-2.13 (m, 5H), 1.91-1.78 (m, 4H), 1.46 (s, 9H).

Step B: 3-Methyl-3,8-diazabicyclo[3.2.1]octane dihydrochloride

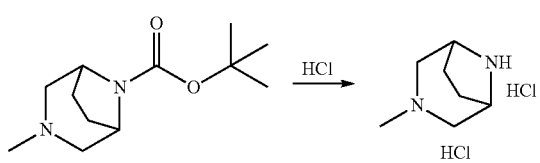

To a solution of tert-butyl 3-methyl-3,8-diazabicyclo [3.2.1]octane-8-carboxylate (86 mg, 0.38 mmol) in dichloromethane (10 mL) was added 4M hydrochloric acid in dioxane (1.9 mL, 7.6 mmol). After stirring over the weekend, the reaction mixture was concentrated in vacuo to afford the title compound (70 mg, 92%) which was used without further purification.

$^1$H NMR (CD$_3$OD) δ 4.34 (s, 2H), 3.73 (d, 2H), 3.55 (d, 2H), 2.94 (s, 3H), 2.37-2.29 (m, 4H).

Intermediate P4: 3-Ethyl-3,8-diazabicyclo[3.2.1]octane dihydrochloride

Step A: tert-Butyl 3-ethyl-3,8-diazabicyclo[3.2.1]octane-8-carboxylate

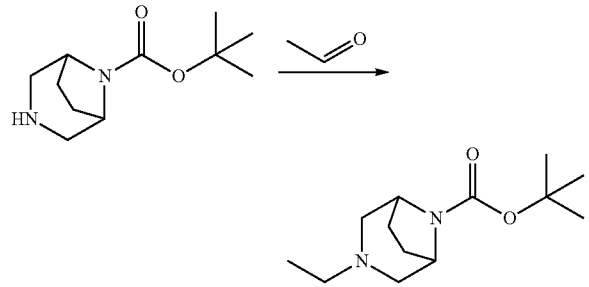

Prepared as described for tert-butyl 3-methyl-3,8-diazabicyclo[3.2.1]octane-8-carboxylate (Intermediate P3, step A) using acetaldehyde instead of formaldehyde to afford the title compound (165 mg, 85%).

$^1$H NMR (CDCl$_3$) δ 3.70 (dd, 2H), 3.35 (d, 2H), 3.20 (dd, 2H), 2.55 (q, 2H), 1.98-1.84 (m, 2H), 1.76-1.56 (m, 2H), 1.44 (s, 9H), 1.15 (t, 3H).

Step B: 3-Ethyl-3,8-diazabicyclo[3.2.1]octane dihydrochloride

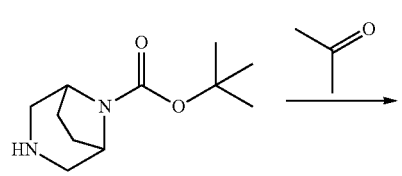

Prepared as described for 3-methyl-3,8-diazabicyclo[3.2.1]octane dihydrochloride (Intermediate P3, step B) from tert-butyl 3-ethyl-3,8-diazabicyclo[3.2.1]octane-8-carboxylate to afford the title compound (140 mg, 95%) which was used without further purification.

$^1$H NMR (CD$_3$OD) δ 4.36 (d, 2H), 3.89-3.74 (m, 2H), 3.73-3.63 (m, 2H), 3.62-3.51 (m, 2H), 2.53 (d, 1H), 2.47-2.38 (m, 1H), 2.36-2.19 (m, 2H), 1.40 (t, 3H).

Intermediate P5: 3-Isopropyl-3,8-diazabicyclo[3.2.1]octane dihydrochloride

Step A: tert-Butyl 3-isopropyl-3,8-diazabicyclo[3.2.1]octane-8-carboxylate

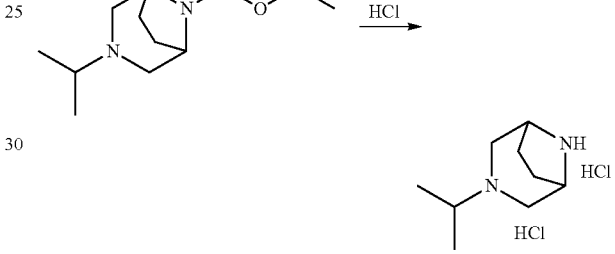

Prepared as described for tert-butyl 3-methyl-3,8-diazabicyclo[3.2.1]octane-8-carboxylate (Intermediate P3, step A) using acetone instead of formaldehyde to afford the title compound (95 mg, 46%).

$^1$H NMR (CDCl$_3$) δ 4.14 (d, 2H), 2.60 (dd, 3H), 2.42 (s, 2H), 1.90-1.70 (m, 4H), 1.45 (d, 9H), 0.98 (d, 6H).

Step B: 3-Isopropyl-3,8-diazabicyclo[3.2.1]octane dihydrochloride

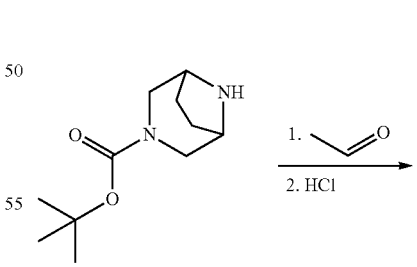

Prepared as described for 3-methyl-3,8-diazabicyclo[3.2.1]octane dihydrochloride (Intermediate P3, step B) from tert-butyl 3-isopropyl-3,8-diazabicyclo[3.2.1]octane-8-carboxylate to afford the title compound (72 mg, quantitative yield) which was used without further purification.

$^1$H NMR (CD$_3$OD) δ 4.35 (d, 2H), 3.73 (d, 2H), 3.61-3.51 (m, 3H), 2.47-2.20 (m, 4H), 1.44 (d, J=6.6 Hz, 6H).

Intermediate P6: 8-Ethyl-3,8-diazabicyclo[3.2.1]octane dihydrochloride

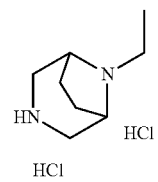

Prepared as described for tert-butyl 3-methyl-3,8-diazabicyclo[3.2.1]octane-8-carboxylate (Intermediate P3, step A)

from tert-butyl 3,8-diazabicyclo[3.2.1]octane-3-carboxylate and acetaldehyde. The intermediate Boc-protected compound was dissolved in dichloromethane (10 mL) and then 4M hydrochloric acid in dioxane (3.3 mL, 13.3 mmol) was added. After stirring over the weekend, the reaction mixture was concentrated in vacuo to afford the title compound (144 mg, 84% yield over two steps).

$^1$H NMR (CD$_3$OD) δ 4.33 (s, 2H), 3.86 (d, 2H), 3.59 (d, 2H), 3.21 (q, 2H), 2.56-2.44 (m, 2H), 2.35-2.22 (m, 2H), 1.43 (t, 3H).

Intermediate P7: 8-Isopropyl-3,8-diazabicyclo[3.2.1]octane dihydrochloride

Step A: tert-Butyl 8-isopropyl-3,8-diazabicyclo[3.2.1]octane-3-carboxylate

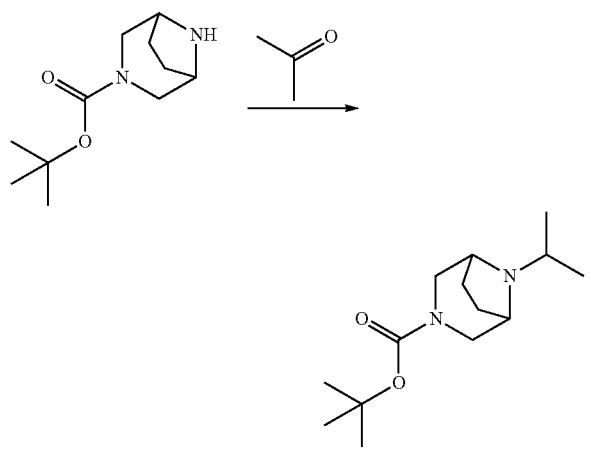

Prepared as described for tert-butyl 3-methyl-3,8-diazabicyclo[3.2.1]octane-8-carboxylate (Intermediate P3, step A) from tert-butyl 3,8-diazabicyclo[3.2.1]octane-3-carboxylate and acetone. The title compound (173 mg, 85%) was used without further purification.

$^1$H NMR (CDCl$_3$) δ 3.81-3.55 (m, 4H), 3.34 (dd, 2H), 2.80 (q, 1H), 1.98 (m, 2H), 1.81-1.66 (m, 2H), 1.45 (s, 9H), 1.25 (d, 6H).

Step B: 8-Isopropyl-3,8-diazabicyclo[3.2.1]octane dihydrochloride

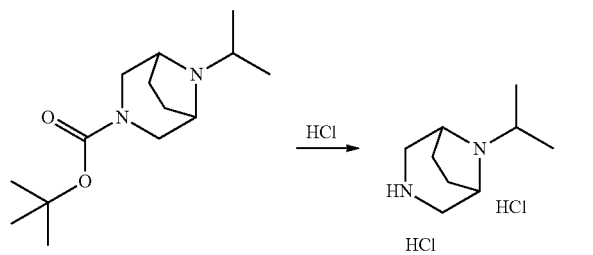 [SMILES: CC(C)N1C2CCC1CN(C(=O)OC(C)(C)C)C2 ; Cl ; CC(C)N1C2CCC1CNC2 ; Cl ; Cl]

Prepared as described for 3-methyl-3,8-diazabicyclo[3.2.1]octane dihydrochloride (Intermediate P3, step B) from tert-butyl 8-isopropyl-3,8-diazabicyclo[3.2.1]octane-3-carboxylate to afford the title compound (143 mg, 91%) which was used without further purification.

$^1$H NMR (CD$_3$OD) δ 4.51 (bs, 2H), 3.89 (d, 2H), 3.57 (d, 2H), 3.43-3.32 (m, 1H), 2.55-2.38 (m, 2H), 2.27 (d, 2H), 1.48 (d, 6H).

Intermediate P8: 8-Cyclopropyl-3,8-diazabicyclo[3.2.1]octane dihydrochloride

Step A: tert-Butyl 8-cyclopropyl-3,8-diazabicyclo[3.2.1]octane-3-carboxylate

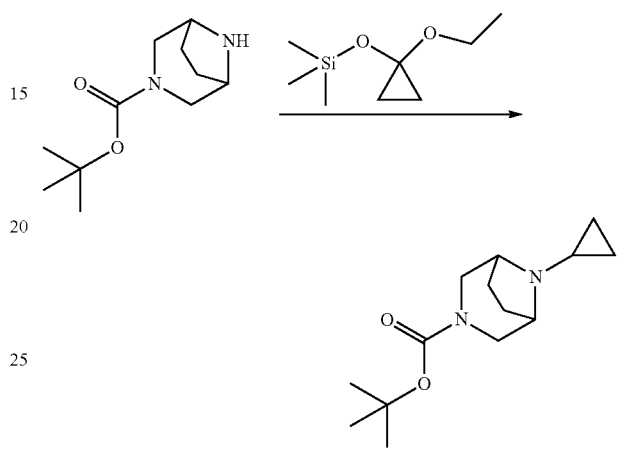

To a solution of tert-butyl (1R',5S')-3,8-diazabicyclo[3.2.1]octane-3-carboxylate (100 mg, 471 μmol) and (1-ethoxycyclopropoxy)trimethylsilane (189 μL, 942 μmol) in tetrahydrofuran (5 mL) and methanol (5 mL) was added acetic acid (62.2 mg, 59.3 μL, 1.04 mmol) followed by sodium cyanoborohydride (44.4 mg, 707 μmol). The reaction mixture was stirred at 50° C. After stirring overnight, more (1-ethoxycyclopropoxy)trimethylsilane (189 μL, 942 μmol), acetic acid (62.2 mg, 59.3 μL, 1.04 mmol) and sodium cyanoborohydride (44.4 mg, 707 μmol) were added. After stirring for 3 days at 50° C., the reaction mixture was concentrated in vacuo. The crude product was coated on Agilent hydromatrix (a high purity, inert diatomaceous earth sorbent) and was submitted to normal phase flash chromatography using dichloromethane and a mixture of ammonia (3.5 M) in methanol as eluent to afford the title compound (118 mg, quantitative yield).

$^1$H NMR (CDCl$_3$) δ 3.87 (td, 1H), 3.82-3.70 (m, 2H), 3.68-3.56 (m, 1H), 3.21 (dd, 2H), 2.02-1.90 (m, 1H), 1.83-1.63 (m, 2H), 1.44 (s, 9H), 1.33-1.16 (m, 2H), 0.78 (s, 2H), 0.54 (d, 2H).

Step B: 8-Cyclopropyl-3,8-diazabicyclo[3.2.1]octane dihydrochloride

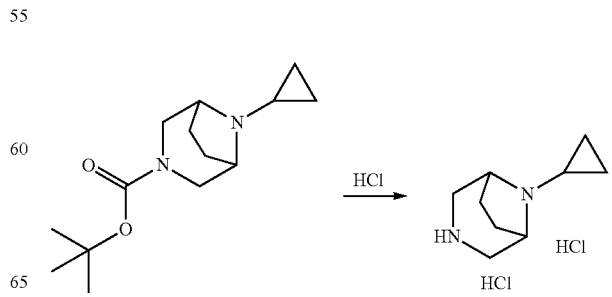

Prepared as described for 3-methyl-3,8-diazabicyclo[3.2.1]octane dihydrochloride (Intermediate P3, step B) from tert-butyl 8-cyclopropyl-3,8-diazabicyclo[3.2.1]octane-3-carboxylate to afford the title compound (106 mg, quantitative yield) which was used without further purification.

$^1$H NMR (CD$_3$OD) δ 4.38 (d, 2H), 3.94 (d, 2H), 3.55 (d, 2H), 2.99 (s, 1H), 2.64 (d, 2H), 2.40-2.24 (m, 2H), 1.35 (d, 2H), 1.01 (d, 2H).

Intermediate P9: (1R,3s,5S)-8-Methyl-8-azabicyclo[3.2.1]octan-3-amine hydrochloride Step A: tert-Butyl ((1R,3s,5S)-8-methyl-8-azabicyclo[3.2.1]octan-3-yl)carbamate

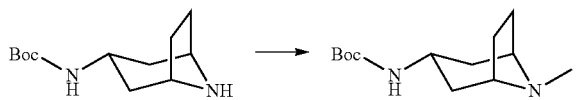 [SMILES: CC(C)(C)OC(=O)NC1CC2CCC(C1)N2 ; CN1C2CCC1CC(NC(=O)OC(C)(C)C)C2]

tert-Butyl ((1R,3s,5S)-8-azabicyclo[3.2.1]octan-3-yl)carbamate (0.20 g, 0.88 mmol) was dissolved in dry acetonitrile (15 mL) and formaldehyde (0.16 ml, 4.41 mmol) was added at room temperature. The reaction mixture was stirred for 30 minutes at room temperature, then sodium triacetoxyborohydride (0.56 g, 2.65 mmol) was added. The solvent was evaporated in vacuo. Purification by silica based column chromatography (DCM:7N NH$_3$ in methanol; 9:1) gave the title compound (0.11 g, 52%) as an off-white solid.

$^1$H NMR (CDCl$_3$) δ 4.46 (s, 1H), 3.76 (s, 1H), 3.20 (s, 2H), 2.30 (s, 3H), 2.17-1.90 (m, 2H), 1.88-1.50 (m, 6H), 1.38 (s, 9H).

Step B: (1R,3s,5S)-8-Methyl-8-azabicyclo[3.2.1]octan-3-amine hydrochloride

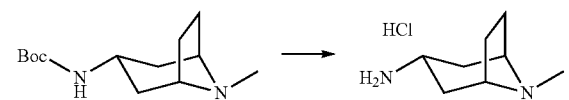

tert-Butyl ((1R,3s,5S)-8-methyl-8-azabicyclo[3.2.1]octan-3-yl)carbamate (0.11 g, 0.42 mmol) was dissolved in a 4N solution of hydrogen chloride in 1,4-dioxane (5 mL) at room temperature. The reaction mixture was stirred overnight at room temperature. The solvent was evaporated in vacuo. The crude product (74 mg, 99%) was used in the next step without further purification.

$^1$H NMR (CD$_3$OD) δ 4.06-3.98 (m, 2H), 3.80-3.56 (m, 1H), 2.81 (s, 3H), 2.48-2.33 (m, 2H), 2.31-2.17 (m, 5H), 2.16-1.96 (m, 3H).

Intermediate P10: (1R,3r,5S)-8-Isopropyl-8-azabicyclo[3.2.1]octan-3-amine hydrochloride Step A: tert-Butyl ((1R,3r,5S)-8-isopropyl-8-azabicyclo[3.2.1]octan-3-yl)carbamate

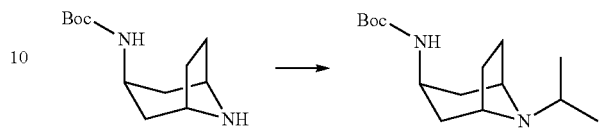

tert-Butyl ((1R,3r,5S)-8-azabicyclo[3.2.1]octan-3-yl)carbamate (0.10 g, 0.44 mmol) was dissolved in acetone (8 mL) and sodium triacetoxyborohydride (0.12 g, 0.55 mmol) was added at room temperature. The reaction mixture was stirred overnight at room temperature. The solvent was evaporated in vacuo. Purification by silica based column chromatography (DCM:7N NH$_3$ in methanol; 9:1) gave the title compound as an off-white solid (0.11 g, 92%).

$^1$H NMR (CDCl$_3$) δ 4.12-3.93 (m, 2H), 3.90-3.70 (m, 1H), 3.23-3.03 (m, 1H), 2.60-2.38 (m, 2H), 2.35-2.20 (m, 2H), 2.14-2.02 (m, 3H), 1.92-1.76 (m, 2H), 1.49-1.34 (m, 15H).

Step B: (1R,3r,5S)-8-Isopropyl-8-azabicyclo[3.2.1]octan-3-amine hydrochloride

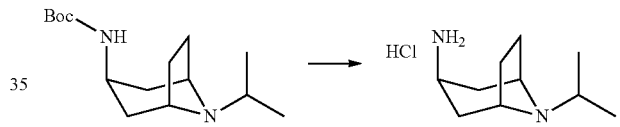

tert-Butyl ((1R,3r,5S)-8-isopropyl-8-azabicyclo[3.2.1]octan-3-yl)carbamate (0.11 g, 0.37 mmol) was dissolved in a 4N solution of hydrogen chloride in 1,4-dioxane (5 mL) at room temperature. The reaction mixture was stirred overnight at room temperature. The solvent was evaporated in vacuo. The crude product (84 mg, quantitative yield) was used in the next step without further purification.

$^1$H NMR (CD$_3$OD) δ 4.31 (s, 1H), 4.16 (s, 1H), 3.83-3.60 (m, 2H), 2.80-2.56 (m, 3H), 10 2.48-2.33 (m, 2H), 2.27-2.07 (m, 4H), 2.03-1.90 (m, 1H), 1.43-1.40 (m, 6H).

Intermediate P11: (1R,3s,5S)—N,N-Diethyl-8-azabicyclo[3.2.1]octan-3-amine hydrochloride Step A: tert-Butyl (1R,3s,5S)-3-(diethylamino)-8-azabicyclo[3.2.1]octane-8-carboxylate

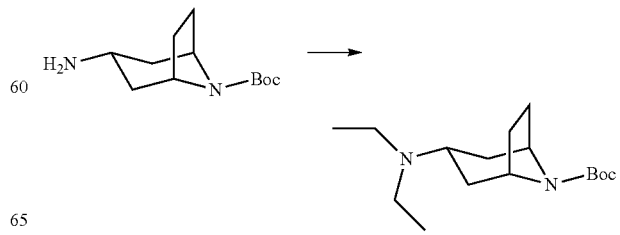

tert-Butyl (1R,3s,5S)-3-amino-8-azabicyclo[3.2.1]octane-8-carboxylate (0.21 g, 0.93 mmol) was dissolved in dry acetonitrile (12 mL) and acetaldehyde (0.12 g, 0.16 mL, 2.8 mmol) was added at room temperature. After 20 minutes sodium triacetoxyhydroborate (0.59 g, 2.8 mmol) was added and the reaction mixture was stirred at room temperature overnight. The solvents were evaporated and the crude mixture was purified by silica based column chromatography (DCM:7N NH$_3$ in DCM, 9:1) to give the title compound (0.22 g, 84%) as a colourless oil.

$^1$H NMR (CDCl$_3$) δ 4.39-3.98 (m, 2H), 3.19-2.98 (m, 1H), 2.62-2.32 (m, 4H), 1.95-1.80 (m, 2H), 1.69-1.48 (m, 6H), 1.41 (s, 9H), 1.07-0.91 (m, 6H).

Step B: (1R,3s,5S)—N,N-Diethyl-8-azabicyclo[3.2.1]octan-3-amine hydrochloride

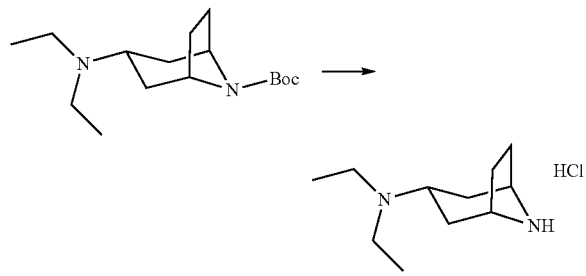

tert-Butyl (1R,3s,5S)-3-(diethylamino)-8-azabicyclo[3.2.1]octane-8-carboxylate (0.22 g, 0.78 mmol) was dissolved in a 4N solution of hydrogen chloride in 1,4-dioxane (8 mL). The reaction mixture was stirred at room temperature overnight. The solvent was evaporated in vacuo. The crude product (0.17 g, 99%) was used in the next step without further purification.

$^1$H NMR (CD$_3$OD) δ 4.03-3.81 (m, 2H), 3.62-3.39 (m, 1H), 3.15-2.78 (m, 5H), 2.02-1.90 (m, 4H), 1.89-1.72 (m, 4H), 1.09-0.98 (m, 6H).

Intermediate P12: tert-Butyl (1R,3s,5S)-3-(dimethylamino)-8-azabicyclo[3.2.1]octane-8-carboxylate

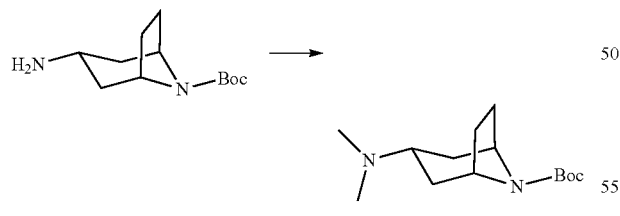

tert-Butyl (1R,3s,5S)-3-amino-8-azabicyclo[3.2.1]octane-8-carboxylate (0.20 g, 0.88 mmol) was dissolved in dry acetonitrile (12 mL) and formaldehyde (80 mg, 98 μL, 2.7 mmol) was added at room temperature. After 20 minutes sodium triacetoxyhydroborate (0.56 g, 2.7 mmol) was added and the reaction mixture was stirred at room temperature overnight. The solvents were evaporated and the crude mixture was purified by silica based column chromatography (DCM:7N NH$_3$ in MeOH; 9:1) to give the title compound (0.23 g, 92%) as a colourless oil.

$^1$H NMR (CDCl$_3$) δ 4.38-4.02 (m, 2H), 2.63-2.45 (m, 1H), 2.16 (s, 6H), 1.93-1.79 (m, 2H), 1.73-1.45 (m, 6H), 1.40 (s, 9H).

Intermediate P13: 1-Isopropylimidazolidine

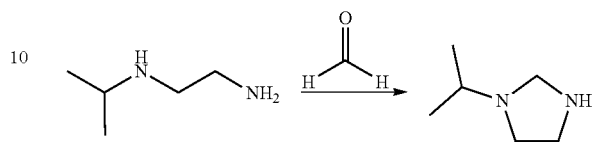

N-Isopropylethylenediamine (0.50 g, 4.89 mmol) was added to a suspension of paraformaldehyde (0.15 g, 4.89 mmol), K$_2$CO$_3$ (2.3 g, 16.6 mmol), and MgSO$_4$ (2.3 g, 19.08 mmol) in CHCl$_3$ (16 mL), under a nitrogen atmosphere at room temperature. The reaction mixture was stirred overnight. The solid was filtered off and solvent was evaporated to give the title compound (0.51 g, 91%). This material was used in the next step without further purification.

$^1$H NMR (CDCl$_3$) δ 3.47 (s, 2H), 3.13-3.01 (m, 2H), 2.68-2.55 (m, 2H), 2.43-2.29 (m, 1H), 1.18-1.03 (m, 6H).

Intermediate P14: (1R,3r,5S)-3-(Pyrrolidin-1-yl)-8-azabicyclo[3.2.1]octane hydrochloride Step A: tert-Butyl (1R,3r,5S)-3-(pyrrolidin-1-yl)-8-azabicyclo[3.2.1]octane-8-carboxylate

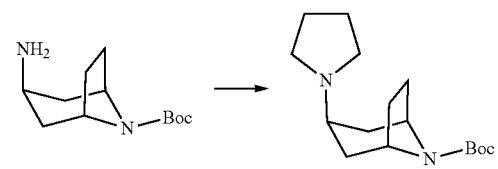 [SMILES: CC(C)(C)OC(=O)N1C2CCC1CC(N)C2 ; CC(C)(C)OC(=O)N1C2CCC1CC(N1CCCC1)C2]

tert-Butyl (1R,3r,5S)-3-amino-8-azabicyclo[3.2.1]octane-8-carboxylate (0.20 g, 0.88 mmol) was dissolved in dry acetonitrile (12 mL). Then potassium iodide (33 mg, 0.20 mmol), potassium carbonate (0.14 g, 1.0 mmol) and 1,4-dibromobutane (0.19 g, 0.10 mL, 0.86 mmol) were added successively. The reaction mixture was heated for 6 hours under reflux. The reaction mixture was cooled down to room temperature and the solvent was evaporated in vacuo. Purification by silica based column chromatography (DCM:7N NH$_3$ in methanol; 9:1) afforded the title compound (0.145 g, 58%) as a colourless oil.

$^1$H NMR (CDCl$_3$) δ 4.23-3.95 (m, 2H), 2.60-2.39 (m, 4H), 2.33-2.15 (m, 1H), 2.15-1.79 (m, 6H), 1.78-1.61 (m, 6H), 1.41 (s, 9H).

Step B: (1R,3r,5S)-3-(Pyrrolidin-1-yl)-8-azabicyclo[3.2.1]octane hydrochloride

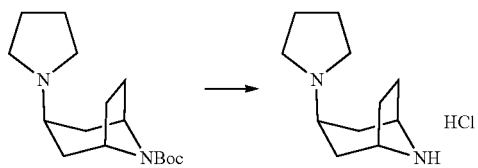 [SMILES: CC(C)(C)OC(=O)N1C2CCC1CC(N1CCCC1)C2 ; C1CCN(C2CC3CCC(C2)N3)C1 ; Cl]

tert-Butyl (1R,3r,5S)-3-(pyrrolidin-1-yl)-8-azabicyclo[3.2.1]octane-8-carboxylate (145 mg, 0.517 mmol) was dissolved in a 4N solution of hydrogen chloride in 1,4-dioxane (10 mL). The reaction mixture was stirred at room temperature overnight. The solvent was evaporated in vacuo. The crude product (112 mg, quantitative yield) was used in the next step without further purification.

$^1$H NMR (CD$_3$OD) δ 4.22-4.05 (m, 2H), 3.85-3.69 (m, 3H), 3.25-3.07 (m, 2H), 2.93-2.66 (m, 2H), 2.37-1.92 (m, 11H).

Intermediate P15: (1R,3r,5S)—N,N-Diethyl-8-azabicyclo[3.2.1]octan-3-amine hydrochloride Step A: tert-Butyl (1R,3r,5S)-3-(diethylamino)-8-azabicyclo[3.2.1]octane-8-carboxylate

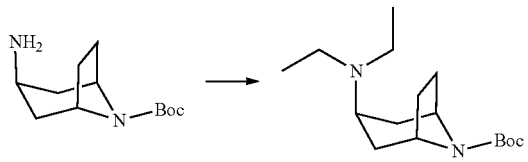 [SMILES: CC(C)(C)OC(=O)N1C2CCC1CC(N)C2 ; CCN(CC)C1CC2CCC(C1)N2C(=O)OC(C)(C)C]

tert-Butyl (1R,3r,5S)-3-amino-8-azabicyclo[3.2.1]octane-8-carboxylate (0.20 g, 0.88 mmol) was dissolved in dry acetonitrile (12 mL) and acetaldehyde (0.16 g, 0.20 mL, 3.5 mmol) was added at room temperature. After 20 minutes sodium triacetoxyhydroborate (0.56 g, 2.65 mmol) was added and the reaction mixture was stirred at room temperature overnight. The crude mixture was purified by silica based column chromatography (DCM:7N NH$_3$ in MeOH; 9:1) to give the title compound (0.17 g, 71%) as a colourless oil.

$^1$H NMR (CDCl$_3$) δ 4.24-4.00 (m, 2H), 2.68-2.42 (m, 5H), 2.31-2.08 (m, 2H), 1.97-1.83 (m, 2H), 1.71-1.57 (m, 2H), 1.40 (s, 9H), 1.40-1.19 (m, 2H), 1.04-0.85 (m, 6H).

Step B: (1R,3r,5S)—N,N-Diethyl-8-azabicyclo[3.2.1]octan-3-amine hydrochloride

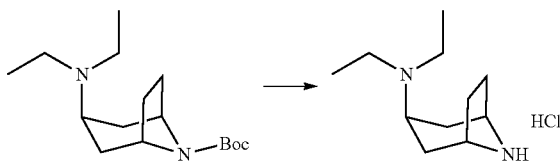 [SMILES: CCN(CC)C1CC2CCC(C1)N2C(=O)OC(C)(C)C ; CCN(CC)C1CC2CCC(C1)N2 ; Cl]

tert-Butyl (1R,3r,5S)-3-(diethylamino)-8-azabicyclo[3.2.1]octane-8-carboxylate (0.17 g, 0.60 mmol) was dissolved in a 4N solution of hydrogen chloride in 1,4-dioxane (10 mL). The reaction mixture was stirred at room temperature overnight. The solvent was evaporated in vacuo. The crude product (0.13 g, 99%) was used in the next step without further purification.

$^1$H NMR (CD$_3$OD) δ 4.25-4.11 (m, 2H), 3.40-3.17 (m, 6H), 2.88-2.73 (m, 2H), 2.30-2.15 (m, 2H), 2.12-2.01 (m, 2H), 1.99-1.86 (m, 2H), 1.43-1.31 (m, 6H).

Intermediate P16: (1R,3r,5S)—N,N-Dimethyl-8-azabicyclo[3.2.1]octan-3-amine hydrochloride Step A: tert-Butyl (1R,3r,5S)-3-(dimethylamino)-8-azabicyclo[3.2.1]octane-8-carboxylate

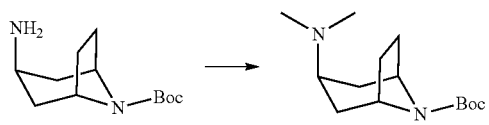 [SMILES: CC(C)(C)OC(=O)N1C2CCC1CC(N)C2 ; CN(C)C1CC2CCC(C1)N2C(=O)OC(C)(C)C]

tert-Butyl (1R,3r,5S)-3-amino-8-azabicyclo[3.2.1]octane-8-carboxylate (0.20 g, 0.88 mmol) was dissolved in dry acetonitrile (12 mL) and formaldehyde (0.11 g, 0.13 mL, 3.5 mmol) was added at room temperature. After 20 minutes sodium triacetoxyhydroborate (0.56 g, 2.65 mmol) was added and the reaction mixture was stirred at room temperature overnight. The crude mixture was purified by silica based column chromatography (DCM:7N NH$_3$ in MeOH, 9:1) to afford the title compound (0.15 g, 68%) as a colourless oil.

$^1$H NMR (CDCl$_3$) δ 4.28-4.01 (m, 2H), 2.21 (s, 6H), 2.17-1.99 (m, 3H), 1.94-1.75 (m, 4H), 1.72-1.51 (m, 2H), 1.44 (s, 9H).

Step B: (1R,3r,5S)—N,N-Dimethyl-8-azabicyclo[3.2.1]octan-3-amine hydrochloride

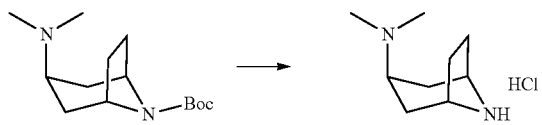 [SMILES: CN(C)C1CC2CCC(C1)N2C(=O)OC(C)(C)C ; CN(C)C1CC2CCC(C1)N2 ; Cl]

tert-Butyl (1R,3r,5S)-3-(dimethylamino)-8-azabicyclo[3.2.1]octane-8-carboxylate (0.13 g, 0.51 mmol) was dissolved in a 4N solution of hydrogen chloride in 1,4-dioxane (8 mL). The reaction mixture was stirred at room temperature overnight. The solvent was evaporated in vacuo. The crude product (97 mg, quantitative yield) was used in the next step without further purification.

$^1$H NMR (CD$_3$OD) δ 4.24-4.07 (m, 2H), 3.64-3.50 (m, 1H), 2.94 (s, 6H), 2.83-2.66 (m, 2H), 2.33-2.14 (m, 3H), 2.13-1.97 (m, 4H).

Intermediate P17: (1R,3s,5S)-8-Isopropyl-8-azabicyclo[3.2.1]octan-3-amine hydrochloride Step A: tert-Butyl ((1R,3s,5S)-8-isopropyl-8-azabicyclo[3.2.1]octan-3-yl)carbamate

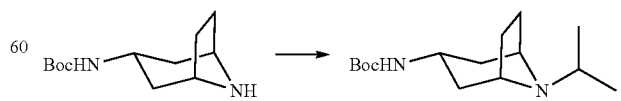

tert-Butyl ((1R,3s,5S)-8-azabicyclo[3.2.1]octan-3-yl)carbamate (0.20 g, 0.88 mmol) was dissolved in acetone (12 mL) and sodium triacetoxyhydroborate (0.56 g, 2.65 mmol) was added. The reaction mixture was stirred at room temperature overnight. The solvents were evaporated and the crude mixture was purified by silica based column chromatography (DCM:7N NH₃ in MeOH; 9:1) to afford the title compound (0.19 g, 79%) as a colourless oil.

¹H NMR (CDCl₃) δ 5.21-4.89 (m, 1H), 4.24-3.79 (m, 3H), 3.21-2.82 (m, 1H), 2.34-2.03 (m, 4H), 2.01-1.78 (m, 4H), 1.50-1.30 (m, 15H).

Step B: (1R,3s,5S)-8-Isopropyl-8-azabicyclo[3.2.1]octan-3-amine hydrochloride

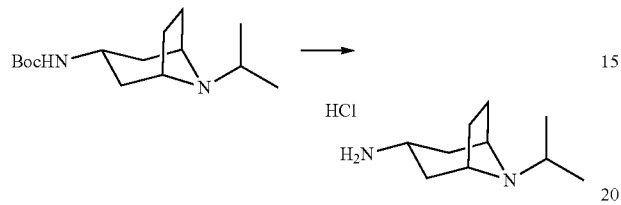

tert-Butyl ((1R,3s,5S)-8-isopropyl-8-azabicyclo[3.2.1]octan-3-yl)carbamate (0.19 g, 0.71 mmol) was dissolved in a 4N solution of hydrogen chloride in 1,4-dioxane (7 mL). The reaction mixture was stirred at room temperature overnight. The solvent was evaporated in vacuo. The crude product (0.14 g, 96%) was used in the next step without further purification.

¹H NMR (CD₃OD) δ 4.51-4.32 (m, 1H), 4.29-4.18 (m, 1H), 4.14-3.99 (m, 1H), 3.83-3.65 (m, 1H), 2.48-1.91 (m, 10H), 1.59-1.37 (m, 6H).

Intermediate P18: (1R,3s,5S)-8-Ethyl-8-azabicyclo[3.2.1]octan-3-amine hydrochloride Step A: tert-Butyl ((1R,3s,5S)-8-ethyl-8-azabicyclo[3.2.1]octan-3-yl)carbamate

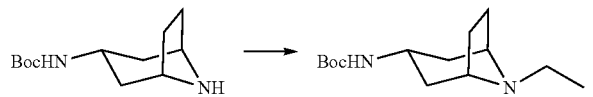

tert-Butyl ((1R,3s,5S)-8-azabicyclo[3.2.1]octan-3-yl)carbamate (0.20 g, 0.88 mmol) was dissolved in dry acetonitrile (12 mL) and acetaldehyde (0.12 g, 0.15 mL, 2.65 mmol) was added at room temperature. After 20 minutes sodium triacetoxyhydroborate (0.56 g, 2.65 mmol) was added and the reaction mixture was stirred at room temperature overnight. The solvents were evaporated and the crude mixture was purified by silica based column chromatography (DCM:7N NH₃ in MeOH; 9:1) to afford the title compound (0.18 g, 82%) as a yellow oil.

¹H NMR (CDCl₃) δ 3.37 (s, 2H), 3.32-3.21 (m, 2H), 2.56-2.45 (m, 2H), 1.99-1.88 (m, 4H), 1.84-1.76 (m, 4H), 1.74-1.61 (m, 9H), 1.19-1.10 (m, 3H).

Step B: (1R,3s,5S)-8-Ethyl-8-azabicyclo[3.2.1]octan-3-amine hydrochloride

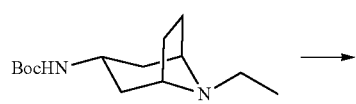

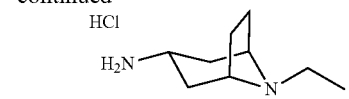

tert-Butyl ((1R,3s,5S)-8-ethyl-8-azabicyclo[3.2.1]octan-3-yl)carbamate (0.10 g, 0.42 mmol) was dissolved in a 4N solution of hydrogen chloride in 1,4-dioxane (5 mL). The reaction mixture was stirred at room temperature overnight. The solvent was evaporated in vacuo. The crude product (79 mg, 97%) was used in the next step without further purification.

¹H NMR (CD₃OD) δ 4.23-4.08 (m, 2H), 3.80-3.68 (m, 2H), 3.19-3.04 (m, 2H), 2.40-2.21 (m, 6H), 2.13-2.05 (m, 2H), 1.48-1.34 (m, 3H).

Intermediate P1: 6-Methyl-3,6-diazabicyclo[3.2.0]heptane dihydrochloride

Step A: tert-Butyl 6-methyl-3,6-diazabicyclo[3.2.0]heptane-3-carboxylate

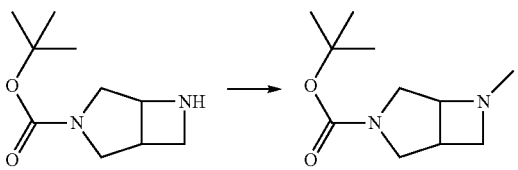

Prepared as described for tert-butyl 3-methyl-3,8-diazabicyclo[3.2.1]octane-8-carboxylate (Intermediate P3, step A) from tert-butyl 3,6-diazabicyclo[3.2.0]heptane-3-carboxylate to afford the title compound (68 mg, 64%).

¹H NMR (CDCl₃) δ 3.79 (dd, 1H), 3.69 (s, 2H), 3.39 (t, 1H), 3.24 (dd, 2H), 3.08 (dd, 1H), 2.97 (dt, 1H), 2.34 (s, 3H), 1.47 (s, 9H).

Step B: 6-Methyl-3,6-diazabicyclo[3.2.0]heptane dihydrochloride

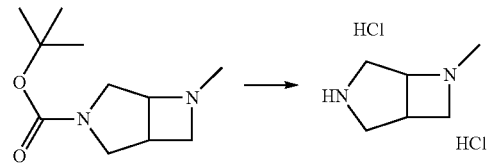

Prepared as described for 3-methyl-3,8-diazabicyclo[3.2.1]octane dihydrochloride (Intermediate P3, step B) from tert-butyl 6-methyl-3,6-diazabicyclo[3.2.0]heptane-3-carboxylate to afford the title compound (59 mg, quantitative yield) which was used without further purification.

¹H NMR (CD₃OD) δ 5.01 (s, 1H), 4.41-4.21 (m, 1H), 4.14 (s, 1H), 3.89-3.66 (m, 2H), 3.62 (t, 2H), 3.49-3.35 (m, 1H), 3.05 (s, 3H).

Intermediate P20: 6-Ethyl-3,6-diazabicyclo[3.2.0]heptane dihydrochloride

Step A: tert-Butyl 6-ethyl-3,6-diazabicyclo[3.2.0]heptane-3-carboxylate

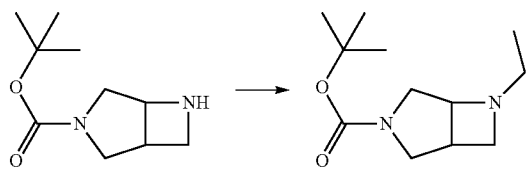 [SMILES: CC(C)(C)OC(=O)N1CC2CNC2C1 ; CCN1CC2CN(C(=O)OC(C)(C)C)CC21]

To a solution of tert-butyl 3,6-diazabicyclo[3.2.0]heptane-3-carboxylate (100 mg, 0.50 mmol) and ethyl iodide (40 μL, 0.50 mmol) in acetonitrile (10 mL) was added potassium carbonate (209 mg, 1.50 mmol). After stirring overnight at room temperature, the suspension was filtered. The residue was washed with methanol. The filtrates were combined and concentrated in vacuo. The crude product was coated on Agilent hydromatrix (a high purity, inert diatomaceous earth sorbent) and was submitted to normal phase flash chromatography using dichloromethane and a mixture of ammonia (3.5 M) in methanol as eluent to afford the title compound (68 mg, 60%).

$^1$H NMR (CDCl$_3$) δ 3.78-3.53 (m, 3H), 3.52-3.40 (m, 1H), 3.23-3.07 (m, 3H), 3.00-2.89 (m, 1H), 2.58-2.46 (m, 2H), 1.46 (s, 9H), 0.96 (t, 3H).

Step B: 6-Ethyl-3,6-diazabicyclo[3.2.0]heptane dihydrochloride

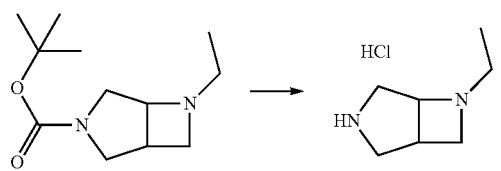

Prepared as described for 3-methyl-3,8-diazabicyclo[3.2.1]octane dihydrochloride (Intermediate P3, step B) from tert-butyl 6-ethyl-3,6-diazabicyclo[3.2.0]heptane-3-carboxylate to afford the title compound (59 mg, quantitative yield) which was used without further purification.

$^1$H NMR (CD$_3$OD) δ 5.07 (s, 1H), 4.30-4.13 (m, 2H), 3.85 (d, 1H), 3.75-3.57 (m, 3H), 3.53-3.35 (m, 3H), 1.27 (t, 3H).

Intermediate P21: 6-Isopropyl-3,6-diazabicyclo[3.2.0]heptane dihydrochloride

Step A: tert-Butyl 6-isopropyl-3,6-diazabicyclo[3.2.0]heptane-3-carboxylate

Prepared as described for tert-butyl 3-methyl-3,8-diazabicyclo[3.2.1]octane-8-carboxylate (Intermediate P3, step A) from tert-butyl 6-methyl-3,6-diazabicyclo[3.2.0]heptane-3-carboxylate and acetone to afford the title compound (79 mg, 65%).

$^1$H NMR (CDCl$_3$) δ 3.94 (bs, 1H), 3.67 (bs, 2H), 3.45-3.29 (m, 2H), 3.27-3.13 (m, 2H), 2.97 (bs, 1H), 2.60 (bs, 1H), 1.47 (s, 9H), 0.97 (dd, 6H).

Step B: 6-Isopropyl-3,6-diazabicyclo[3.2.0]heptane dihydrochloride

Prepared as described for 3-methyl-3,8-diazabicyclo[3.2.1]octane dihydrochloride (Intermediate P3, step B) from tert-butyl 6-isopropyl-3,6-diazabicyclo[3.2.0]heptane-3-carboxylate to afford the title compound (70 mg, quantitative yield) which was used without further purification. 1H NMR (CD$_3$OD) δ 5.22 (t, 1H), 4.42-4.01 (m, 3H), 3.88 (d, 1H), 3.71-3.42 (m, 4H), 1.32 (dd, J=18.5, 6.5 Hz, 6H).

Intermediate P22: 6-Methyl-3,6-diazabicyclo[3.1.1]heptane hydrochloride

Step A: tert-Butyl 6-methyl-3,6-diazabicyclo[3.1.1]heptane-3-carboxylate

To a solution of tert-butyl 3,6-diazabicyclo[3.1.1]heptane-3-carboxylate (100 mg, 1 eq, 504 μmol) and formaldehyde (31 μL, 2.2 eq, 1.10 mmol) in acetonitrile (10 mL) was added sodium triacetoxyborohydride (107 mg, 1 eq, 504 μmol). The suspension was stirred at room temperature overnight and then concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (83 mg, 78%).

$^1$H NMR (CDCl$_3$) δ 3.66-3.48 (m, 4H), 3.37 (dd, 2H), 2.71-2.49 (m, 1H), 2.19 (d, 3H), 1.89 (s, 1H), 1.55-1.43 (m, 9H).

Step B: 6-Methyl-3,6-diazabicyclo[3.1.1]heptane hydrochloride

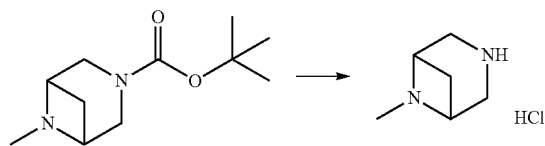

To a solution of tert-butyl 6-methyl-3,6-diazabicyclo[3.1.1]heptane-3-carboxylate (83 mg, 039 mmol, 1 eq) in dichloromethane (8 mL) was added hydrochloric acid in dioxane (4 M, 4.0 mL, 16.0 mmol, 40 eq). The reaction mixture was stirred at room temperature. After stirring for 1.5 hours, a few drops of methanol were added. After stirring overnight, the reaction mixture was concentrated in vacuo to afford the title compound (72 mg, 99%).

$^1$H NMR (DMSO-d$_6$) δ 4.41-4.10 (m, 2H), 3.96 (m, 1H), 3.82 (m, 1H), 3.74-3.58 (m, 2H), 3.30 (s, 3H), 3.04-2.79 (m, 2H).

Intermediate P23: (R)—N-Methyl-1-(1-methylpyrrolidin-2-yl)methanamine

Step A: Methyl methyl-D-prolinate

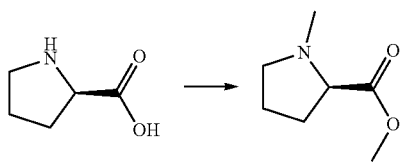

Pd/C (10%) (1.1 g, 0.012 eq, 1.0 mmol) was added to a solution of D-proline (10.0 g, 1 eq, 86.9 mmol) and formaldehyde (37% in water) (7.5 mL, 1 eq, 86.9 mmol) in methanol (200 mL). The mixture was stirred overnight under 2 bar hydrogen. Then the mixture was filtered over Celite® and the filtrate was treated with thionyl chloride (11.4 g, 6.97 mL, 1.1 eq, 95.5 mmol) and refluxed overnight. The reaction mixture was evaporated to dryness, treated with cold 1M Na$_2$CO$_3$ solution (50 mL) and extracted with ethyl acetate (3×100 mL). The combined organic layers were washed with water (20 mL), dried over sodium sulfate and evaporated to dryness to yield the title compound (12.4 g, 100%) as a colourless oil.

$^1$H NMR (CDCl$_3$) δ 3.72 (s, 3H), 3.13 (dt, 1H), 2.93 (dd, 1H), 2.38 (s, 3H), 2.25 (q, 1H), 2.12 (m, 1H), 1.91 (m, 2H), 1.79 (m, 1H).

LCMS: m/z 144 (M+H)$^+$ (ES$^+$).

Step B: (R)—N,1-Dimethylpyrrolidine-2-carboxamide

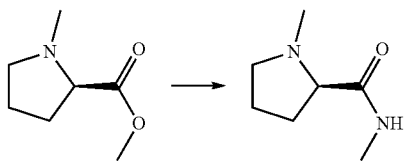

Methyl methyl-D-prolinate (5.5 g, 1 eq, 38 mmol) was dissolved in methylamine (200 mL) in ethanol (33 wt %) and stirred overnight. Removal of the volatiles by rotary evaporation yielded the title compound (5.5 g, 100%) as a clear oil that crystallized upon standing.

$^1$H NMR (CDCl$_3$) δ 7.22 (bs, 1H), 3.03 (m, 1H), 2.83 (dd, 1H), 2.79 (d, 3H), 2.34 (s, 3H), 2.33 (m, 1H), 2.18 (m, 2H), 1.71 (m, 2H).

LCMS: m/z 143 (M+H)$^+$ (ES$^+$).

Step C: (R)—N-Methyl-1-(1-methylpyrrolidin-2-yl)methanamine

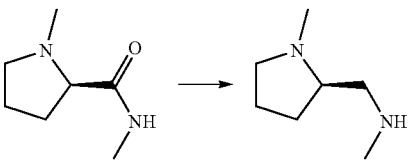

(R)—N,1-Dimethylpyrrolidine-2-carboxamide (5.50 g, 1 eq, 38.7 mmol) was dissolved in THF (80 mL) and cooled to 0° C. Lithium aluminium hydride (2.20 g, 1.5 eq, 58.0 mmol) was carefully added and the mixture was refluxed overnight. The mixture was cooled to 0° C., water (4.18 g, 4.18 mL, 6 eq, 232 mmol) was added dropwise and 33% NaOH solution (2 mL) was added. The suspension was allowed to reach room temperature, stirred for 1 hour and filtered. The filtrate was dried over sodium sulfate and evaporated to dryness, yielding the title compound (5.0 g, 100%) as a clear liquid.

$^1$H NMR (CDCl$_3$) δ 3.03 (dt, 1H), 2.70 (dd, 1H), 2.50 (dd, 1H), 2.41 (s, 3H), 2.35 (s, 3H), 2.22 (m, 1H), 2.18 (m, 2H), 1.92 (m, 1H), 1.63 (m, 2H), 1.20 (bs, 1H).

LCMS: m/z 129 (M+H)$^+$ (ES$^+$).

Intermediate P24: (4-(Dimethylamino)pyridin-1-ium-1-carbonyl)(N,N-dimethyl-sulfamoyl)amide

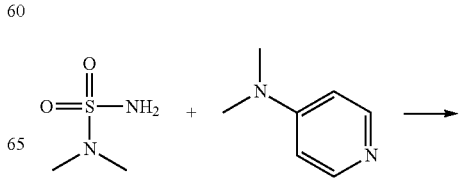

-continued

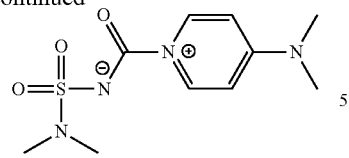

A solution of dimethylaminosulfonamide (993 mg, 8.00 mmol) and DMAP (1.954 g, 16.00 mmol) in MeCN (10 mL) was stirred at room temperature for 10 minutes. Then diphenyl carbonate (1.885 g, 8.80 mmol) was added and the resulting solution was stirred at room temperature for 5 days. The precipitate was filtered off and washed with MTBE. The resulting solid was dried in vacuo (50° C.) to afford the crude title compound (1.45 g, 67%) which was used without further purification.

Intermediate P25: (S)—N-Methyl-1-(1-methylpyrrolidin-2-yl)methanamine

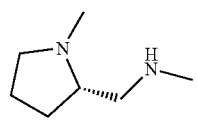

Prepared as described for (R)—N-methyl-1-(1-methylpyrrolidin-2-yl)methanamine (Intermediate P23). 1H NMR (400 MHz, CDCl$_3$) δ 3.05-3.01 (m, 1H), 2.72-2.68 (m, 1H), 2.53-2.48 (m, 1H), 2.44 (s, 3H), 2.32 (s, 3H), 2.28-2.23 (m, 1H), 2.19-2.14 (m, 1H), 1.95-1.88 (m, 1H) and 1.76-1.60 (m, 3H). 1×NH was missing.

Intermediate P26: 1-Methyl-3-[methyl(sulfamoyl)amino]pyrrolidine

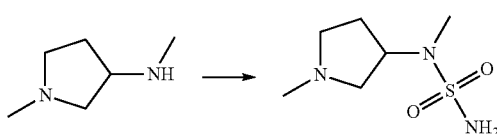

To a solution of N,1-dimethylpyrrolidin-3-amine (4 g, 35.03 mmol, 1 eq) in 1,2-dimethoxyethane (80 mL) was added sulfuric diamide (4.04 g, 42.04 mmol, 1.2 eq) in one portion. The reaction mixture was heated to 90° C. and stirred for 12 hours under N$_2$. Then the reaction mixture was concentrated in vacuo. The residue was purified by column chromatography (SiO$_2$, EtOAc: EtOH, 20:1 to 5:1) to give the title compound (3.5 g, 43% yield, 83% purity on LCMS) as a brown oil.

$^1$H NMR (400 MHz, DMSO-d$_6$) δ 6.65 (s, 2H), 4.31-4.23 (m, 1H), 2.62 (s, 3H), 2.61-2.56 (m, 2H), 2.41-2.36 (m, 1H), 2.20 (s, 3H), 2.18-2.12 (m, 1H), 2.05-1.98 (m, 1H) and 1.78-1.71 (m, 1H).

LCMS: m/z 194.0 (M+H)$^+$ (ES$^+$).

PREPARATION OF EXAMPLES

Example 1: 3-(N-Methyl-N-(1-methylpyrrolidin-3-yl)sulfamoyl)-1-(5-(2-methoxypyridin-4-yl)-2,3-dihydro-1H-inden-4-yl)urea

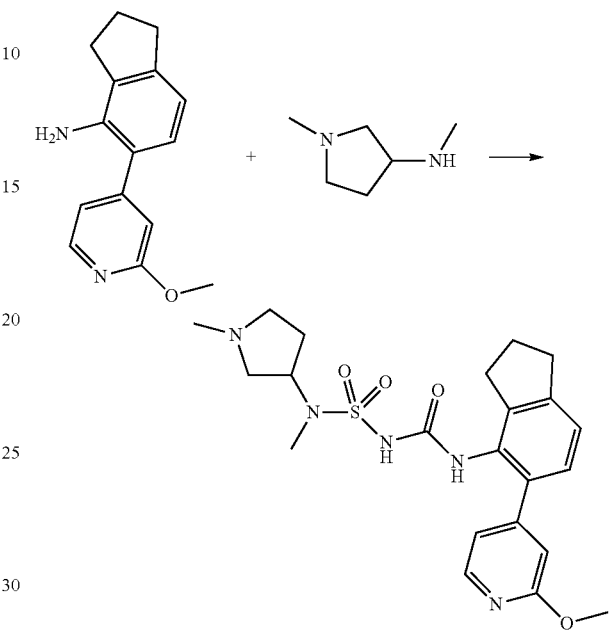

To a cooled (0° C.) solution of chlorosulfonyl isocyanate (59 mg, 0.41 mmol) in DCM (5 mL) was added 5-(2-methoxypyridin-4-yl)-2,3-dihydro-1H-inden-4-amine (Intermediate A2; 100 mg, 0.41 mmol). The mixture was stirred for 10 minutes at 0° C. N,1-dimethylpyrrolidin-3-amine (95 mg, 0.83 mmol) in DCM (5 mL) was added and the reaction was allowed to reach room temperature over 30 minutes. The mixture was evaporated to dryness in vacuo and purified by reversed phase chromatography to afford the title compound (9 mg; 5%) as a white solid.

$^1$H NMR (CD$_3$OD) δ 8.12 (d, 1H), 7.19 (d, 1H), 7.13 (d, 1H), 6.99 (d, 1H), 6.83 (s, 1H), 4.48 (m, 1H), 3.92 (s, 3H), 2.92 (m, 6H), 2.82 (m, 2H), 2.71 (s, 3H), 2.50 (s, 3H), 2.10 (m, 3H) and 1.92 (m, 1H).

LCMS: m/z 460 (M+H)$^+$ (ES$^+$); 458 (M−H)$^-$ (ES$^-$).

Example 2: 3-(N-Methyl-N-((1-methylpyrrolidin-2-yl)methyl) sulfamoyl)-1-(5-(2-methoxypyridin-4-yl)-2,3-dihydro-1H-inden-4-yl)urea

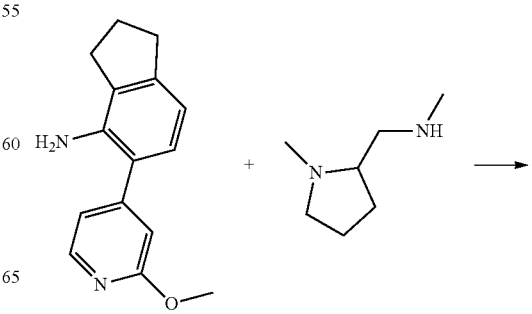

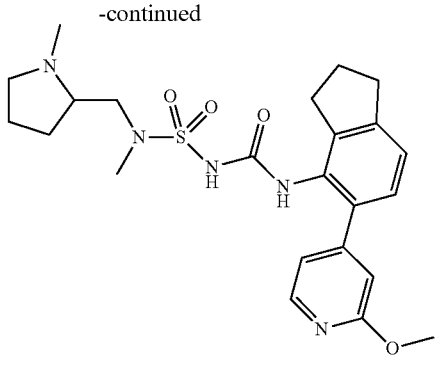

Prepared as described for 3-(N-methyl-N-(1-methylpyrrolidin-3-yl)sulfamoyl)-1-(5-(2-methoxypyridin-4-yl)-2,3-dihydro-1H-inden-4-yl)urea (Example 1), using chlorosulfonyl isocyanate (59 mg, 0.41 mmol), 5-(2-methoxypyridin-4-yl)-2,3-dihydro-1H-inden-4-amine (Intermediate A2; 100 mg, 0.41 mmol) and N-methyl-1-(1-methylpyrrolidin-2-yl)methanamine (racemic Intermediate P23; 107 mg, 0.83 mmol) to afford the title compound (2 mg; 1%) as a white solid.

$^1$H NMR (CD$_3$OD) δ 8.12 (d, 1H), 7.19 (m, 2H), 7.09 (d, 1H), 6.93 (s, 1H), 3.92 (s, 3H), 3.88 (m, 1H), 3.65 (m, 1H), 3.09 (m, 1H), 2.98 (m, 6H), 2.79 (s, 3H), 2.69 (s, 3H), 2.10 (m, 3H), 1.97 (m, 2H) and 1.60 (m, 1H).

LCMS: m/z 474 (M+H)$^+$ (ES$^+$).

Example 3: 3-(N-Methyl-N-((1-methylpyrrolidin-2-yl)methyl) sulfamoyl)-1-(7-fluoro-5-(2-methoxypyridin-4-yl)-2,3-dihydro-1H-inden-4-yl)urea

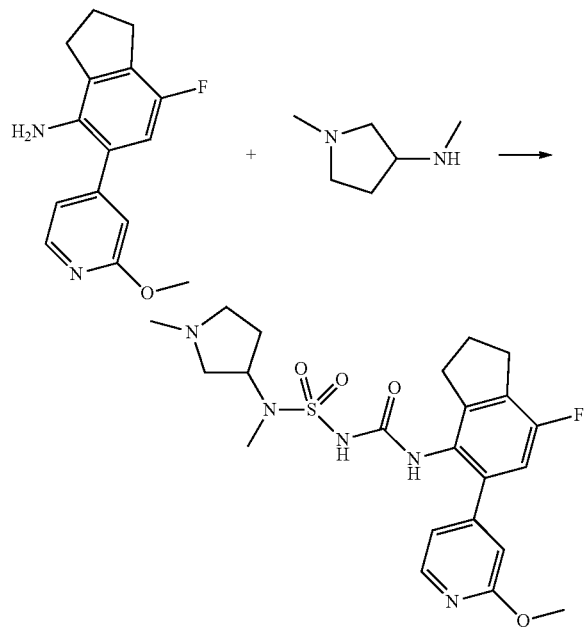

Prepared as described for 3-(N-methyl-N-(1-methylpyrrolidin-3-yl)sulfamoyl)-1-(5-(2-methoxypyridin-4-yl)-2,3-dihydro-1H-inden-4-yl)urea (Example 1), using chlorosulfonyl isocyanate (55 mg, 0.38 mmol), 7-fluoro-5-(2-methoxypyridin-4-yl)-2,3-dihydro-1H-inden-4-amine (Intermediate A1; 100 mg, 0.38 mmol) and N,1-dimethylpyrrolidin-3-amine (95 mg, 0.83 mmol) to afford the title compound (12 mg; 10%) as a white solid.

$^1$H NMR (CD$_3$OD) δ 8.14 (d, 1H), 7.08 (d, 1H), 6.98 (m, 2H), 4.48 (m, 1H), 3.92 (s, 3H), 2.98 (m, 8H), 2.71 (s, 3H), 2.60 (s, 3H), 2.10 (m, 3H) and 1.92 (m, 1H).

LCMS: m/z 479 (M+H)$^+$ (ES$^+$).

Example 4: 3-(N-Methyl-N-((1-methylpyrrolidin-2-yl)methyl) sulfamoyl)-1-(7-fluoro-5-(2-methoxypyridin-4-yl)-2,3-dihydro-1H-inden-4-yl)urea

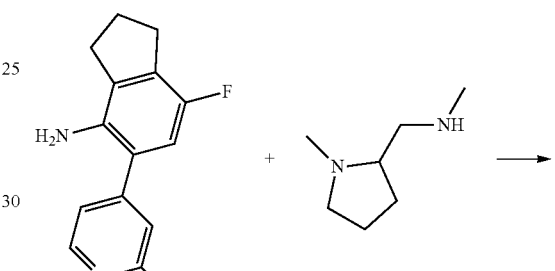

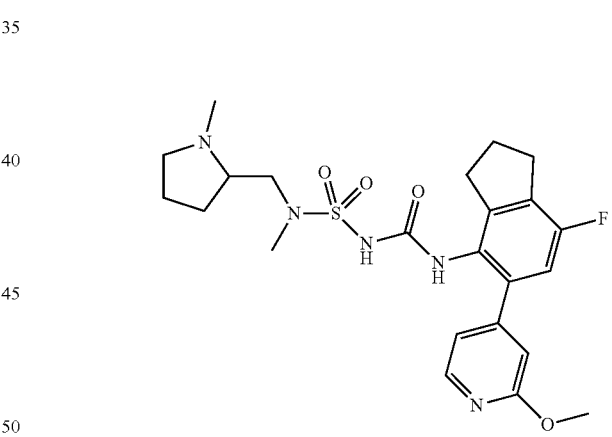

Prepared as described for 3-(N-methyl-N-(1-methylpyrrolidin-3-yl)sulfamoyl)-1-(5-(2-methoxypyridin-4-yl)-2,3-dihydro-1H-inden-4-yl)urea (Example 1), using chlorosulfonyl isocyanate (55 mg, 0.38 mmol), 7-fluoro-5-(2-methoxypyridin-4-yl)-2,3-dihydro-1H-inden-4-amine (Intermediate A1; 100 mg, 0.38 mmol) and N-methyl-1-(1-methylpyrrolidin-2-yl)methanamine (racemic Intermediate P23; 139 mg, 1.16 mmol) to afford the title compound (23 mg; 12%) as a white solid.

$^1$H NMR (CD$_3$OD) δ 8.12 (d, 1H), 7.00 (d, 1H), 6.90 (d, 1H), 6.83 (s, 1H), 3.92 (s, 3H), 3.78 (m, 1H), 3.55 (m, 1H), 3.00 (m, 7H), 2.79 (s, 3H), 2.67 (s, 3H), 2.19 (m, 3H), 2.01 (m, 2H) and 1.62 (m, 1H).

LCMS: m/z 492 (M+H)$^+$ (ES$^+$); 490 (M−H)$^−$ (ES$^−$).

Example 5: (1R,4R)—N-((7-Fluoro-5-(2-methoxypyridin-4-yl)-2,3-dihydro-1H-inden-4-yl)carbamoyl)-5-methyl-2,5-diazabicyclo[2.2.1]heptane-2-sulfonamide

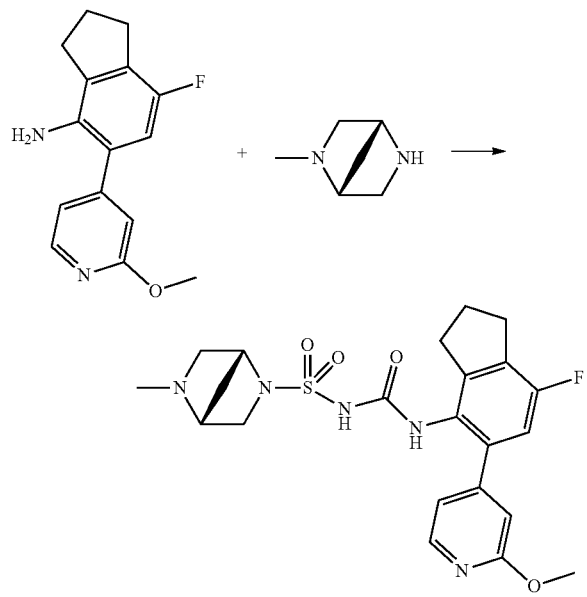

(1R,4R)-2-Methyl-2,5-diazabicyclo[2.2.1]heptane dihydrobromide (50 mg, 0.18 mmol) and sodium hydride (60%) (150 mg, 3.7 mmol) were refluxed for 1 hour in THF (10 mL). The mixture was cooled to room temperature and filtered over Celite®. The filtrate was evaporated to dryness in vacuo and the residue was dissolved in DCM (10 mL), after which DABCO was added (20 mg, 0.18 mmol).

Meanwhile, to a cooled (0° C.) solution of chlorosulfonyl isocyanate (35 mg, 0.25 mmol) in DCM (5 mL) was added 7-fluoro-5-(2-methoxypyridin-4-yl)-2,3-dihydro-1H-inden-4-amine (Intermediate A1; 66 mg, 0.26 mmol). The mixture was stirred for 10 minutes at 0° C.

Both DCM mixtures were combined and allowed to reach room temperature after 1 hour. The mixture was evaporated to dryness in vacuo and purified by reversed phase chromatography to afford the title compound (4 mg; 5%) as a white solid.

$^1$H NMR (CD$_3$OD) δ 8.12 (d, 1H), 7.02 (d, 1H), 6.90 (m, 2H), 4.54 (m, 1H), 4.24 (m, 1H), 3.92 (s, 3H), 3.39 (m, 2H), 2.98 (m, 4H), 2.75 (s, 3H), 2.20 (m, 2H), and 1.64 (m, 2H).

LCMS: m/z 476 (M+H)$^+$ (ES$^+$); 474 (M−H)$^-$ (ES$^-$).

Example 6: 3-Methyl-((2-(dimethylamino)ethyl)sulfamoyl)-1-(1,2,3,5,6,7-hexahydro-s-indacen-4-yl)urea, potassium salt

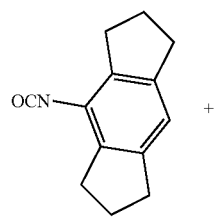

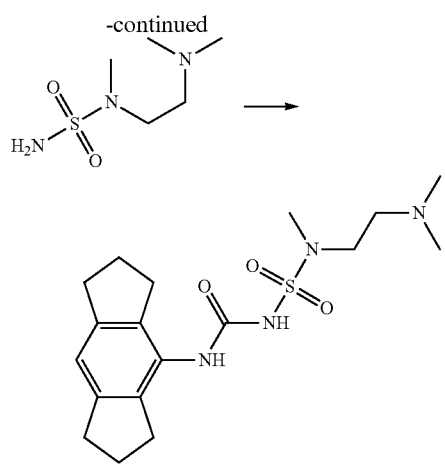

To a solution of [(2-dimethylamino)ethyl](methyl)sulfamoyl-amine (57 mg, 0.31 mmol) in THF (3 mL) was added potassium tert-butoxide (35 mg, 0.31 mmol). The mixture was stirred for 40 minutes. A solution of 4-isocyanato-1,2,3,5,6,7-hexahydro-s-indacene (Intermediate A3) (63 mg, 0.31 mmol) in THF (1 mL) was added and the mixture was stirred overnight at room temperature. The reaction mixture was concentrated in vacuo and DMSO (1 mL) was added. The resulting suspension was filtered over cotton wool and subsequently submitted for purification by reversed phase column chromatography (see "Experimental Methods") to afford the title compound (84 mg, 70%) as a white solid.

$^1$H NMR (CD$_3$OD) δ 6.89 (s, 1H), 3.44 (t, 2H), 3.04 (t, 2H), 2.95-2.74 (m, 11H), 2.67 (s, 6H), 2.03 (m, 4H).

LCMS: m/z 381 (M+H)$^+$ (ES$^+$); 379 (M−H)$^-$ (ES$^-$).

Example 7: 3-Methyl-((2-Methoxyethyl)sulfamoyl)-1-(1,2,3,5,6,7-hexahydro-s-indacen-4-yl)urea, potassium salt

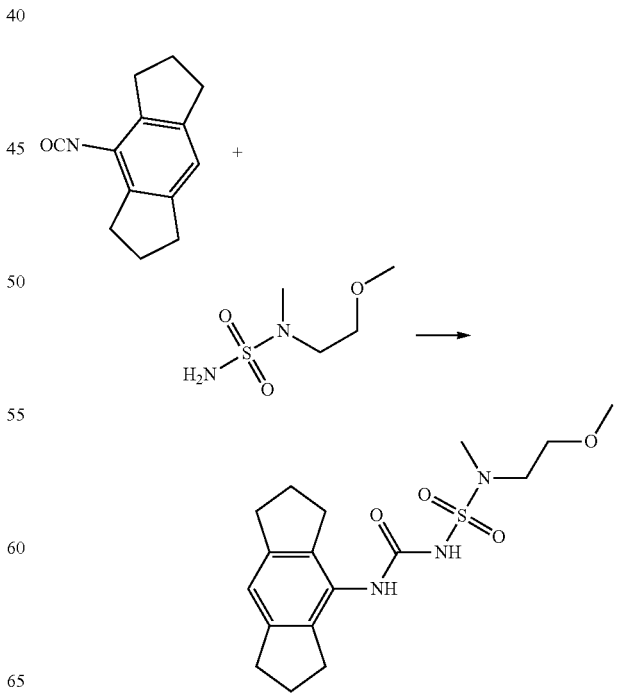

Prepared as described for 3-methyl-((2-(dimethylamino)ethyl)sulfamoyl)-1-(1,2,3,5,6,7-hexahydro-s-indacen-4-yl)urea, potassium salt (Example 6) using [(2-methoxyethyl)(methyl)sulfamoyl]amine (52 mg, 0.31 mmol), KOtBu (35 mg, 0.31 mmol) and 4-isocyanato-1,2,3,5,6,7-hexahydro-s-indacene (Intermediate A3) (62 mg, 0.31 mmol) to afford the title compound (80 mg, 71%) as a white solid.

$^1$H NMR (CD$_3$OD) δ 6.88 (s, 1H), 3.56 (t, 2H), 3.33 (m, 5H), 2.82 (m, 11H), 2.03 (m, 4H).

LCMS: m/z 368 (M+H)$^+$ (ES$^+$); 366 (M−H)$^−$ (ES$^−$).

Example 8: 3-(N-(2-(Dimethylamino)ethyl)sulfamoyl)-1-(1,2,3,5,6,7-hexahydro-s-indacen-4-yl)urea

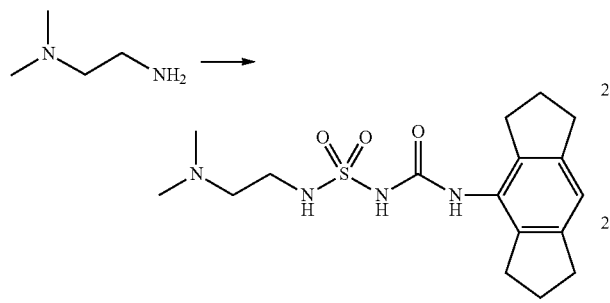

To a cooled (0° C.) solution of N1,N1-dimethylethane-1,2-diamine (102 mg, 1.0 mmol) in THF (10 mL) was added ((1,2,3,5,6,7-hexahydro-s-indacen-4-yl)carbamoyl)sulfamoyl chloride (Intermediate A4) (100 mg, 0.32 mmol). The ice bath was removed and the reaction mixture was stirred whilst being allowed to warm to room temperature overnight. The solvent was removed in vacuo and DMSO (1 mL) was added. The suspension was filtered over cotton wool and subsequently submitted for purification by reversed phase column chromatography (see "Experimental Methods") to afford the title compound (12 mg, 10%) as a white solid.

$^1$H NMR (CD$_3$OD) δ 6.91 (s, 1H), 3.23 (m, 2H), 3.07 (m, 2H), 2.82 (m, 8H), 2.70 (s, 6H), 2.03 (m, 4H).

LCMS: m/z 367 (M+H)$^+$ (ES$^+$); 365 (M−H)$^−$ (ES$^−$).

Example 9: 3-(Dimethylamino)-N-((1,2,3,5,6,7-hexahydro-s-indacen-4-yl) carbamoyl)pyrrolidine-1-sulfonamide, potassium salt

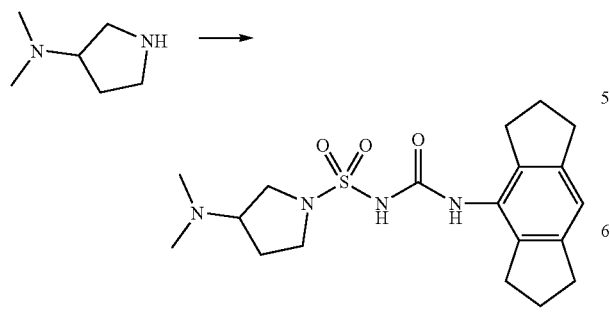

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethylpyrrolidin-3-amine (114 mg, 1.00 mmol) to afford the title compound (5 mg, 4%) as a white solid.

$^1$H NMR (CD$_3$OD) δ 6.91 (s, 1H), 3.80 (dd, 1H), 3.62 (t, 1H), 3.43 (q, 1H), 3.25 (m, 1H), 3.03 (p, 1H), 2.82 (m, 8H), 2.38 (s, 6H), 2.20 (m, 1H), 2.03 (m, 4H), 1.95 (m, 1H).

LCMS: m/z 393 (M+H)$^+$ (ES$^+$); 391 (M−H)$^−$ (ES$^−$).

Example 10: 3-(N-Benzyl-N-(2-(dimethylamino)ethyl)sulfamoyl)-1-(1,2,3,5,6,7-hexahydro-s-indacen-4-yl)urea, potassium salt

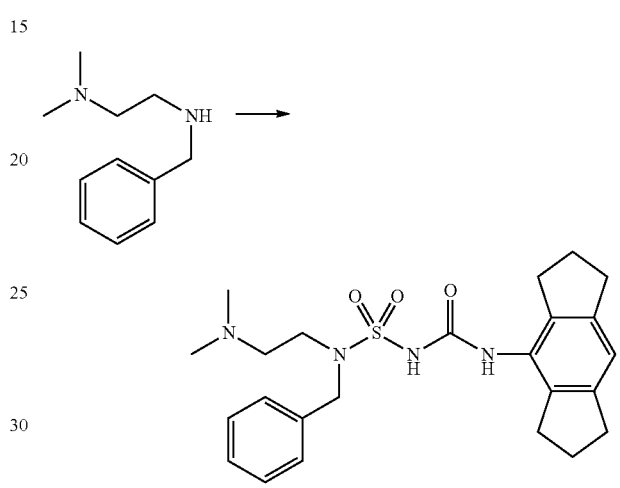

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-benzyl-N2,N2-dimethylethane-1,2-diamine (178 mg, 1.00 mmol) to afford the title compound (10 mg, 7%) as a white solid.

$^1$H NMR (CD$_3$OD) δ 7.48 (d, 2H), 7.38 (m, 3H), 6.91 (s, 1H), 4.31 (s, 2H), 3.46 (t, 2H), 2.82 (m, 8H), 2.71 (t, 2H), 2.59 (s, 6H), 2.03 (m, 4H).

LCMS: m/z 457 (M+H)$^+$ (ES$^+$); 455 (M−H)$^−$ (ES$^−$).

Example 11: 3-(N-Methyl-N-(1-methylpyrrolidin-3-yl)sulfamoyl)-1-(1,2,3,5,6,7-hexahydro-s-indacen-4-yl)urea, potassium salt

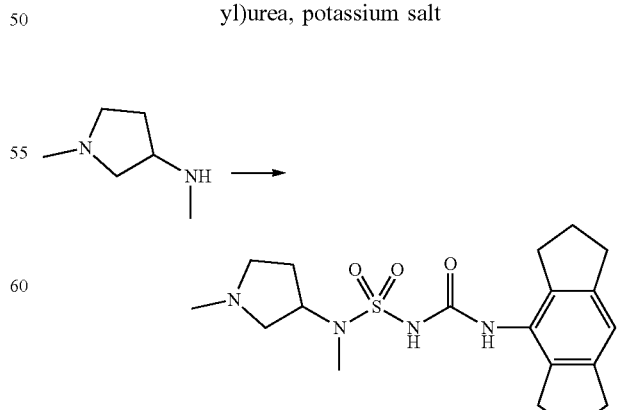

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,1-dimethylpyrrolidin-3-amine (115 mg, 1.00 mmol) to afford the title compound (11 mg, 9%) as a white solid.

¹H NMR (CD₃OD) δ 6.91 (s, 1H), 4.60 (m, 1H), 2.82 (m, 11H), 2.74 (m, 2H), 2.61 (m, 1H), 2.50 (m, 1H), 2.38 (s, 3H), 2.03 (m, 6H).

LCMS: m/z 393 (M+H)⁺ (ES⁺); 391 (M−H)⁻ (ES⁻).

Example 12: 3-(N-(2-(Dimethylamino)ethyl)-N-isobutylsulfamoyl)-1-(1,2,3,5,6,7-hexahydro-s-indacen-4-yl)urea, potassium salt

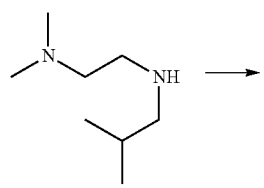

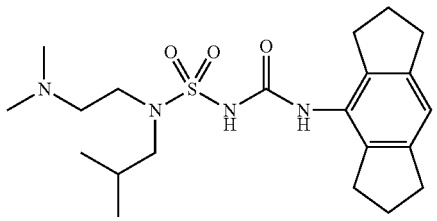

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-isobutyl-N2,N2-dimethylethane-1,2-diamine (144 mg, 1.00 mmol) to afford the title compound (7 mg, 5%) as a white solid.

¹H NMR (CD₃OD) δ 6.91 (s, 1H), 3.51 (t, 2H), 3.10 (t, 2H), 2.95 (d, 2H), 2.82 (m, 14H), 2.03 (m, 4H), 1.90 (m, 1H), 0.99 (m, 6H).

LCMS: m/z 423 (M+H)⁺ (ES⁺); 421 (M−H)⁻ (ES⁻).

Example 13: 3-(N-(2-(Dimethylamino)ethyl)-N-phenethylsulfamoyl)-1-(1,2,3,5,6,7-hexahydro-s-indacen-4-yl)urea, potassium salt

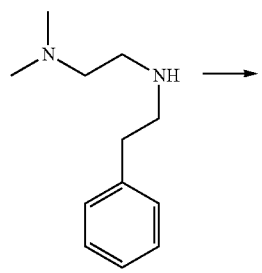

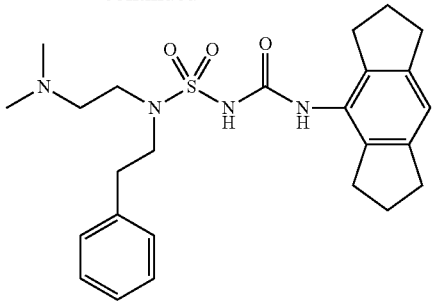

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-dimethyl-N2-phenethylethane-1,2-diamine (192 mg, 1.00 mmol) to afford the title compound (24 mg, 5%) as a white solid.

¹H NMR (CD₃OD) δ 7.21 (m, 5H), 6.91 (s, 1H), 3.60 (m, 2H), 3.41 (m, 2H), 3.10 (t, 2H), 3.01 (t, 2H) 2.82 (m, 8H), 2.76 (s, 6H), 2.03 (m, 4H).

LCMS: m/z 405 (M+H)⁺ (ES⁺); 403 (M−H)⁻ (ES⁻).

Example 14: N-((1,2,3,5,6,7-Hexahydro-s-indacen-4-yl)carbamoyl)-8-methyl-3,8-diazabicyclo[3.2.1]octane-3-sulfonamide, potassium salt

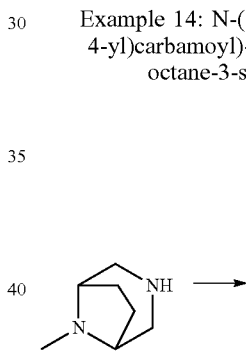

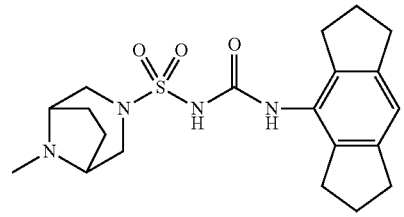

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 8-methyl-3,8-diazabicyclo[3.2.1]octane (128 mg, 1.00 mmol) with triethylamine (0.3 mL, 2.0 mmol) to afford the title compound (0.8 mg, 1%) as a white solid.

¹H NMR (CD₃OD) δ 6.91 (s, 1H), 3.50 (m, 2H), 3.05 (m, 4H), 2.82 (m, 8H), 2.38 (s, 3H) 2.03 (m, 4H), 1.97 (m, 4H).

LCMS: m/z 405 (M+H)⁺ (ES⁺); 403 (M−H)⁻ (ES⁻).

Example 15: 3-(N-(1-(Dimethylamino)propan-2-yl) sulfamoyl)-1-(1,2,3,5,6,7-hexahydro-s-indacen-4-yl) urea, potassium salt

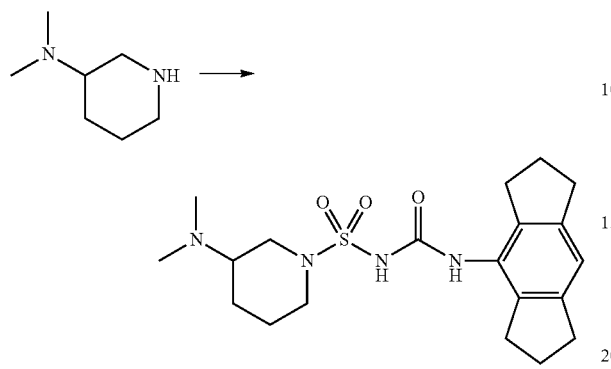

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethylpiperidin-3-amine (130 mg, 1.00 mmol) to afford the title compound (18 mg, 14%) as a white solid.

$^1$H NMR (CD$_3$OD) δ 6.91 (s, 1H), 3.79 (m, 1H), 3.52 (m, 1H), 2.98 (m, 2H), 2.82 (m, 8H), 2.58 (m, 1H), 2.40 (s, 6H) 2.03 (m, 4H), 1.92 (m, 1H), 1.80 (m, 1H), 1.60 (m, 1H), 1.42 (m, 1H).

LCMS: m/z 407 (M+H)$^+$ (ES$^+$); 405 (M−H)$^−$ (ES$^−$).

Example 16: 3-(N-(1-(Dimethylamino)propan-2-yl) sulfamoyl)-1-(1,2,3,5,6,7-hexahydro-s-indacen-4-yl) urea, potassium salt

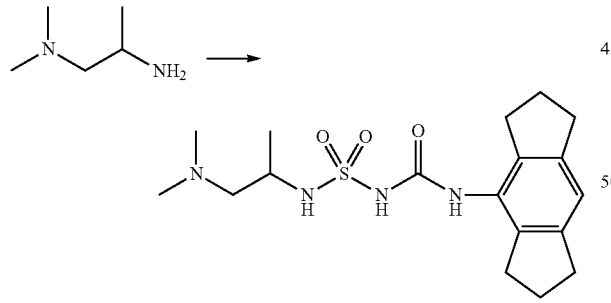

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-dimethylpropane-1,2-diamine (102 mg, 1.00 mmol) to afford the title compound (6 mg, 5%) as a white solid.

$^1$H NMR (CD$_3$OD) δ 6.91 (s, 1H), 3.79 (m, 1H), 2.98 (m, 2H), 2.82 (m, 8H), 2.75 (s, 6H) 2.03 (m, 4H), 1.24 (d, 3H).

LCMS: m/z 381 (M+H)$^+$ (ES$^+$); 379 (M−H)$^−$ (ES$^−$).

Example 17: 3-(Dimethylamino)-N-((1,2,3,5,6,7-hexahydro-s-indacen-4-yl) carbamoyl)azetidine-1-sulfonamide, potassium salt

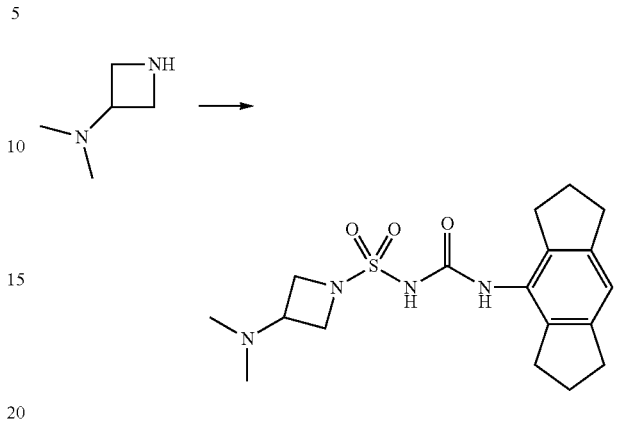

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethylazetidin-3-amine dihydrochloride (178 mg, 1.00 mmol) with triethylamine (0.25 mL, 2 mmol) to afford the title compound (16 mg, 13%) as a white solid.

$^1$H NMR (CD$_3$OD) δ 6.91 (s, 1H), 3.79 (m, 4H), 3.06 (m, 1H), 2.82 (m, 8H), 2.18 (s, 6H) 2.03 (m, 4H).

LCMS: m/z 379 (M+H)$^+$ (ES$^+$); 377 (M−H)$^−$ (ES$^−$).

Example 18: 3-(N-(2-(Diethylamino)ethyl)-N-ethyl-sulfamoyl)-1-(1,2,3,5,6,7-hexahydro-s-indacen-4-yl) urea, potassium salt

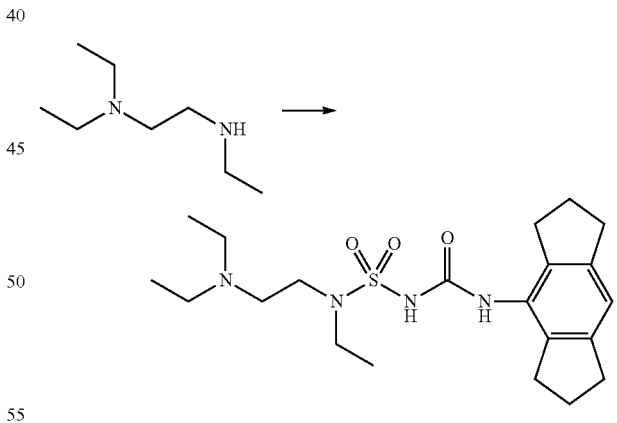

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1,N2-triethylethane-1,2-diamine (148 mg, 1.00 mmol) to afford the title compound (2 mg, 1%) as a white solid.

$^1$H NMR (CD$_3$OD) δ 6.91 (s, 1H), 3.54 (t, 2H), 3.24 (t, 2H), 3.04 (m, 6H), 2.82 (m, 8H), 2.03 (m, 4H), 1.21 (t, 9H).

LCMS: m/z 423 (M+H)$^+$ (ES$^+$); 421 (M−H)$^−$ (ES$^−$).

Example 10: 3-(N-(1-Ethylpiperidin-3-yl)sulfamoyl)-1-(1,2,3,5,6,7-hexahydro-s-indacen-4-yl)urea, potassium salt

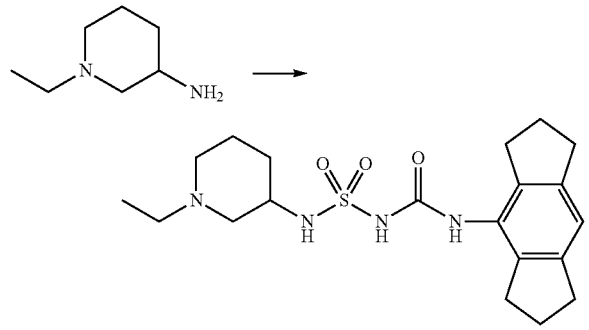

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-ethylpiperidin-3-amine (125 mg, 1.00 mmol) to afford the title compound (4 mg, 3%) as a white solid.

$^1$H NMR (CD$_3$OD) δ 6.91 (s, 1H), 3.41 (m, 1H), 3.20 (m, 1H), 2.82 (m, 8H), 2.43 (m, 4H), 2.03 (m, 7H), 1.95 (s, 1H), 1.79 (m, 1H), 1.60 (m, 1H), 1.22 (m, 1H), 1.10 (t, 3H).

LCMS: m/z 407 (M+H)$^+$ (ES$^+$); 405 (M−H)$^−$ (ES$^−$).

Example 20: 3-(N-((1-Methylpiperidin-2-yl)methyl)sulfamoyl)-1-(1,2,3,5,6,7-hexahydro-s-indacen-4-yl)urea, potassium salt

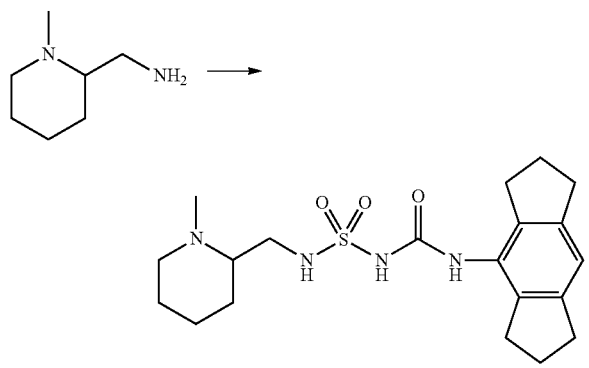

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (1-methylpiperidin-2-yl)methanamine (128 mg, 1.00 mmol) to afford the title compound (8 mg, 6%) as a white solid.

$^1$H NMR (CD$_3$OD) δ 6.91 (s, 1H), 3.51 (m, 1H), 3.18 (m, 1H), 2.82 (m, 14H), 2.03 (m, 4H), 1.95 (s, 1H), 1.70 (m, 6H).

LCMS: m/z 407 (M+H)$^+$ (ES$^+$); 405 (M−H)$^−$ (ES$^−$).

Example 21: 4-Ethyl-N-((1,2,3,5,6,7-hexahydro-s-indacen-4-yl)carbamoyl) piperazine-1-sulfonamide

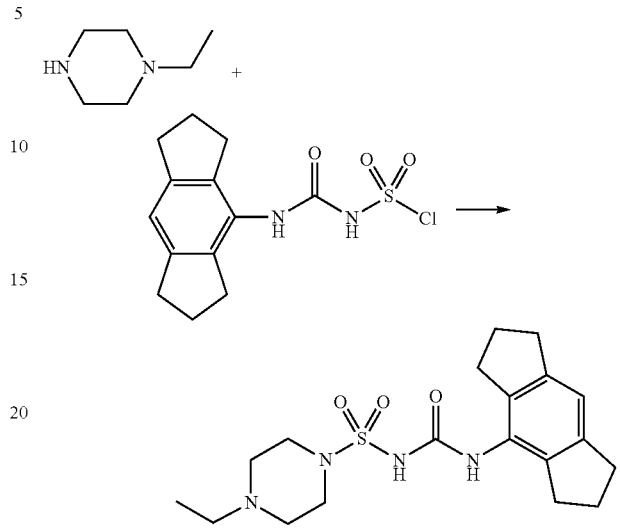

To a solution of 1-ethylpiperazine (36 mg, 0.32 mmol) in dry DCM (6 mL) was added ((1,2,3,5,6,7-hexahydro-s-indacen-4-yl)carbamoyl)sulfamoyl chloride (Intermediate A4) (100 mg, 0.32 mmol) at 0° C. under a nitrogen atmosphere. The mixture was stirred for 1 hour at 0° C. to reach full conversion. The solvent was evaporated in vacuo. Purification by reversed phase column chromatography (see "Experimental Methods") gave the title compound (40 mg, 33%) as a white solid.

$^1$H NMR (CD$_3$OD) δ 6.89 (s, 1H), 3.56 (s, 1H), 3.21 (s, 1H), 3.02-2.92 (m, 2H), 2.91-2.75 (m, 6H), 2.74-2.62 (m, 1H), 2.64-2.37 (m, 9H), 2.18-1.91 (m, 4H), 1.19-1.00 (m, 3H).

LCMS: m/z 393 (M+H)$^+$ (ES$^+$); 391 (M−H)$^−$ (ES$^−$).

Example 22: 3-(N-methyl-N-((1-methylpiperidin-2-yl)methyl)sulfamoyl)-1-(1,2,3,5,6,7-hexahydro-s-indacen-4-yl)urea, potassium salt

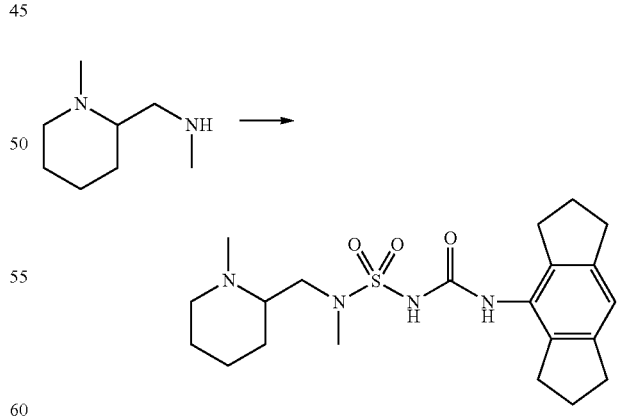

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol), N-methyl-1-(1-methylpiperidin-2-yl)methanamine (70 mg, 0.50 mmol) and triethylamine (50 mg, 0.5 mmol) to afford the title compound (18 mg, 13%) as a white solid.

LCMS: m/z 421 (M+H)⁺ (ES⁺); 419 (M−H)⁻ (ES⁻).

Example 23: 3-(N-(3-(Pyrrolidin-1-yl)azetidin-1-yl) sulfamoyl)-1-(1,2,3,5,6,7-hexahydro-s-indacen-4-yl) urea, potassium salt

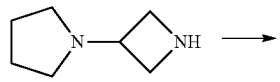

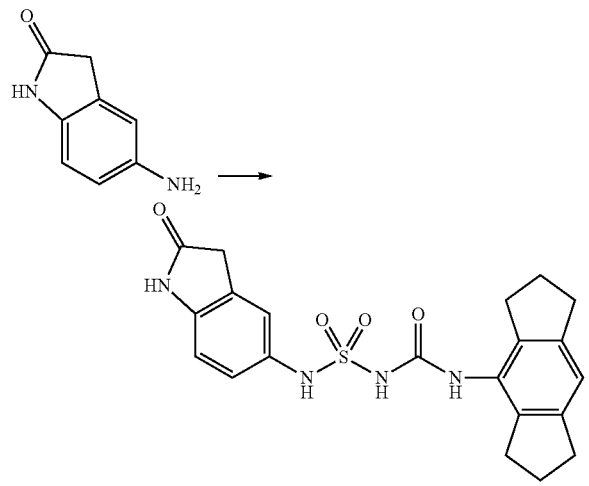

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol), 1-(azetidin-3-yl)pyrrolidine dihydrobromide (125 mg, 0.50 mmol) and triethylamine (0.15 mL, 1.0 mmol) to afford the title compound (8 mg, 6%) as a white solid.

¹H NMR (CD₃OD) δ 6.91 (s, 1H), 4.02 (m, 4H), 3.48 (m, 1H), 2.82 (m, 8H), 2.78 (m, 4H), 2.03 (m, 4H), 1.95 (s, 1H), 1.83 (m, 4H).

LCMS: m/z 405 (M+H)⁺ (ES⁺); 403 (M−H)⁻ (ES⁻).

Example 24: 3-(N-(2-Oxoindolin-5-yl)sulfamoyl)-1-(1,2,3,5,6,7-hexahydro-s-indacen-4-yl)urea, potassium salt Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 5-aminoindolin-2-one (145 mg, 1.00 mmol) with triethylamine (86 mg, 0.85 mmol) to afford the title compound (31 mg, 23%) as a white solid.

¹H NMR (CD₃OD) δ 7.21 (s, 1H), 7.13 (d, 1H), 6.91 (s, 1H), 6.80 (d, 1H), 4.82 (s, 2H), 2.82 (t, 4H), 2.62 (t, 4H), 2.03 (m, 4H).

LCMS: m/z 427 (M+H)⁺ (ES⁺); 425 (M−H)⁻ (ES⁻).

Example 25: 3-(N-((1-Methylpyrrolidin-2-yl)methyl))sulfamoyl)-1-(1,2,3,5,6,7-hexahydro-s-indacen-4-yl)urea, potassium salt

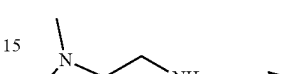

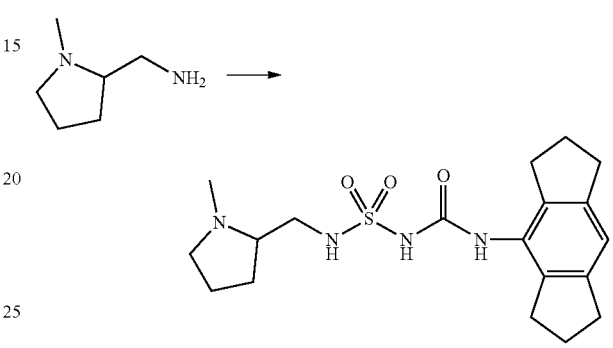

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (1-methylpyrrolidin-2-yl)methanamine (114 mg, 1.00 mmol) to afford the title compound (4 mg, 3%) as a white solid.

LCMS: m/z 393 (M+H)⁺ (ES⁺); 391 (M−H)⁻ (ES⁻).

Example 26: 3-((N-(2-Isopropyl))ethyl)sulfamoyl)-1-(1,2,3,5,6,7-hexahydro-s-indacen-4-yl)urea

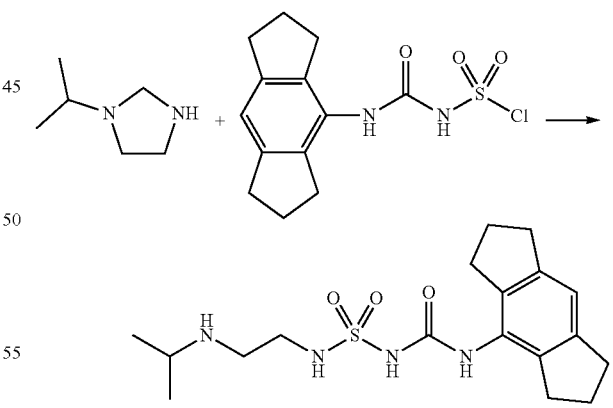

To a solution of 1-isopropylimidazolidine (Intermediate P13) (36 mg, 0.32 mmol) in dry THF (6 mL) at 0° C. was added ((1,2,3,5,6,7-hexahydro-s-indacen-4-yl)carbamoyl) sulfamoyl chloride (Intermediate A4) (100 mg, 0.32 mmol). The mixture was stirred for 1 hour at 0° C. to reach full conversion. The solvent was evaporated in vacuo. Purification by reversed phase column chromatography (see "Experimental Methods") gave the title compound (2 mg, 2%) as a white solid.

¹H NMR (CD₃OD) δ 6.89 (s, 1H), 4.82 (s, 2H), 4.60 (s, 2H), 3.17-3.02 (m, 3H), 2.92-2.71 (m, 8H), 2.14-1.94 (m, 4H), 1.91 (s, 1H), 1.28 (d, J=6.5 Hz, 6H).

LCMS: m/z 381 (M+H)⁺ (ES⁺); 379 (M−H)⁻ (ES⁻).

Example 27: 3-(N-(1-(dimethylamino)propan-2-yl)-N-methyl)sulfamoyl)-1-(1,2,3,5,6,7-hexahydro-s-indacen-4-yl)urea, potassium salt

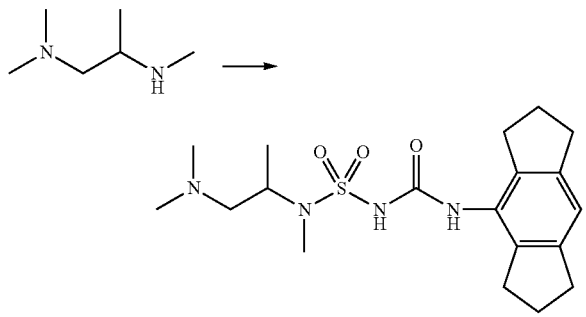

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1,N2-trimethylpropane-1,2-diamine (Intermediate P1) (140 mg, 1.10 mmol) to afford the title compound (5 mg, 4%) as a white solid.

¹H NMR (CD₃OD) δ 6.91 (s, 1H), 3.42 (m, 1H), 3.02 (m, 2H), 2.82 (m, 17H), 2.03 (m, 4H), 1.93 (s, 1H), 1.29 (d, 3H).

LCMS: m/z 395 (M+H)⁺ (ES⁺); 393 (M−H)⁻ (ES⁻).

Example 28: 3-(N-Isopropyl-N-(2-(isopropylamino)ethyl))sulfamoyl)-1-(1,2,3,5,6,7-hexahydro-s-indacen-4-yl)urea, potassium salt

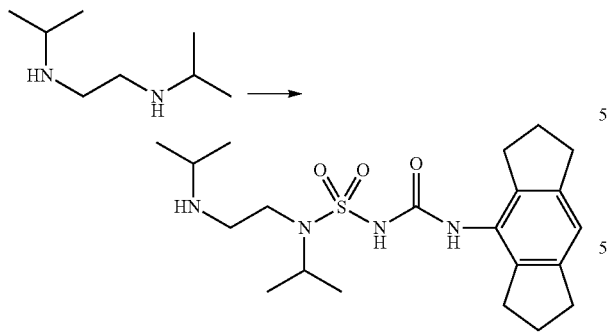

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N2-diisopropylethane-1,2-diamine (140 mg, 1.0 mmol) to afford the title compound (5 mg, 4%) as a white solid.

¹H NMR (CD₃OD) δ 6.91 (s, 1H), 3.62 (m, 2H), 3.38 (m, 2H), 3.18 (m, 2H), 2.82 (m, 8H), 2.17 (s, 1H), 2.03 (m, 4H), 1.90 (s, 1H), 1.35 (d, 12H).

LCMS: m/z 423 (M+H)⁺ (ES⁺); 421 (M−H)⁻ (ES⁻).

Example 20: N-((1,2,3,5,6,7-Hexahydro-s-indacen-4-yl)carbamoyl)-8-isopropyl-3,8-diazabicyclo[3.2.1]octane-3-sulfonamide, potassium salt

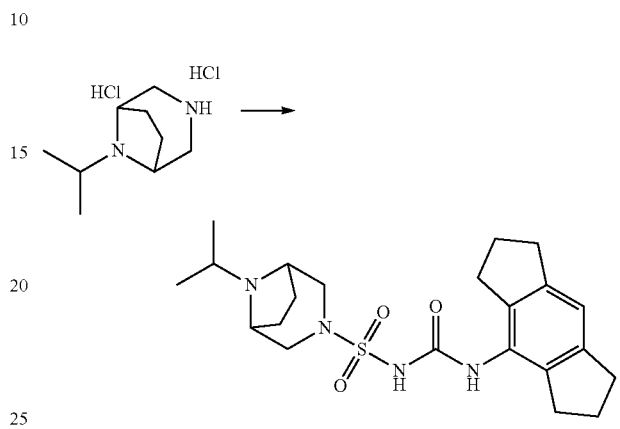

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (98 mg, 0.31 mmol) and 8-isopropyl-3,8-diazabicyclo[3.2.1]octane dihydrochloride (Intermediate P7) (71 mg, 0.31 mmol) to afford the title compound (5 mg, 3%) as a white solid.

¹H NMR (CD₃OD) δ 6.93 (s, 1H), 3.99 (bs, 2H), 3.48 (d, 2H), 3.39-3.32 (m, 2H), 3.20-3.06 (m, 1H), 2.83 (dt, 8H), 2.11-1.98 (m, 8H), 1.27 (d, 6H).

LCMS: m/z 433 (M+H)⁺ (ES⁺); 431 (M−H)⁻ (ES⁻).

Example 30: 3-(N-(2-(Dimethylamino)propyl))sulfamoyl)-1-(1,2,3,5,6,7-hexahydro-s-indacen-4-yl)urea, potassium salt

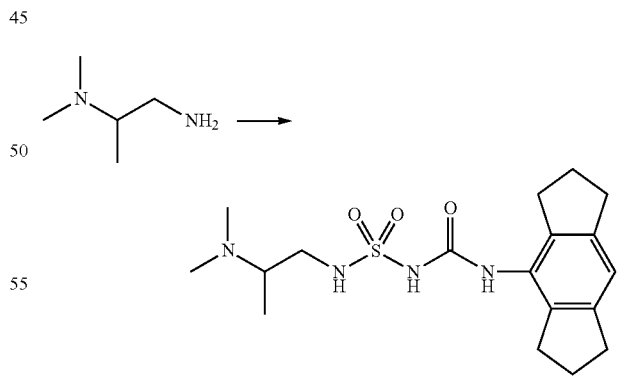

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N2,N2-dimethylpropane-1,2-diamine (102 mg, 1.00 mmol) to afford the title compound (14 mg, 12%) as a white solid.

¹H NMR (CD₃OD) δ 6.91 (s, 1H), 3.13 (m, 1H), 2.98 (m, 1H), 2.82 (m, 9H), 2.37 (s, 6H), 2.17 (s, 1H), 2.03 (m, 4H), 1.05 (d, 3H).
LCMS: m/z 381 (M+H)⁺ (ES⁺); 379 (M–H)⁻ (ES⁻).

Example 31: 3-(N-((1-Methylazetidin-2-yl)methyl))sulfamoyl)-1-(1,2,3,5,6,7-hexahydro-s-indacen-4-yl)urea, potassium salt

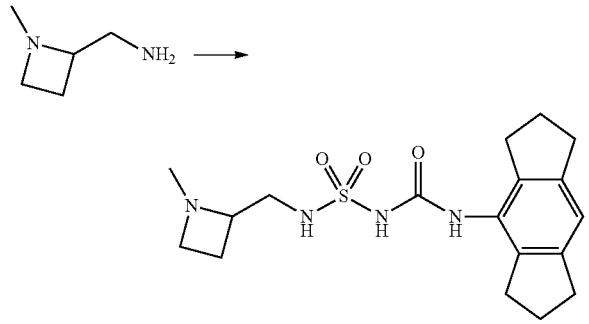

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (1-methylazetidin-2-yl)methanamine (100 mg, 1.00 mmol) to afford the title compound (8 mg, 7%) as a white solid.

¹H NMR (CD₃OD) δ 6.91 (s, 1H), 3.93 (m, 1H), 3.72 (m, 1H), 3.40 (m, 1H), 3.06 (m, 1H), 2.82 (m, 9H), 2.64 (s, 3H), 2.12 (m, 2H), 2.03 (m, 4H), 1.90 (s, 1H).
LCMS: m/z 379 (M+H)⁺ (ES⁺); 377 (M–H)⁻ (ES⁻).

Example 32: 3-(N-Methyl-N-(2-(methylamino)ethyl))sulfamoyl)-1-(1,2,3,5,6,7-hexahydro-s-indacen-4-yl)urea, potassium salt

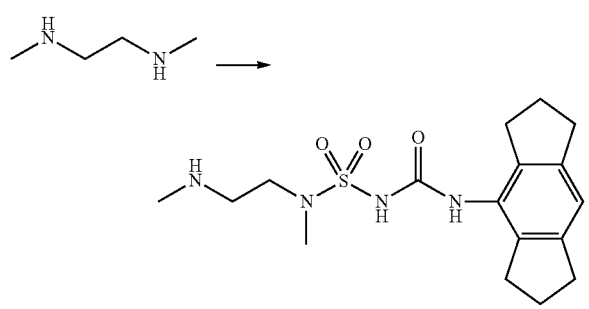

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N2-dimethylethane-1,2-diamine (88 mg, 1.00 mmol) to afford the title compound (12 mg, 10%) as a white solid.

¹H NMR (CD₃OD) δ 6.91 (s, 1H), 3.63 (t, 2H), 3.18 (t, 1H), 3.00 (t, 1H), 2.96 (s, 3H), 2.82 (m, 8H), 2.64 (s, 3H), 2.16 (s, 1H), 2.03 (m, 4H).
LCMS: m/z 367 (M+H)⁺ (ES⁺); 365 (M–H)⁻ (ES⁻).

Example 33: (1R,3r,5S)-8-Isopropyl-8-azabicyclo[3.2.1]octan-3-(N-((1,2,3,5,6,7-hexahydro-s-indacen-4-yl)carbamoyl)-sulfonamide)

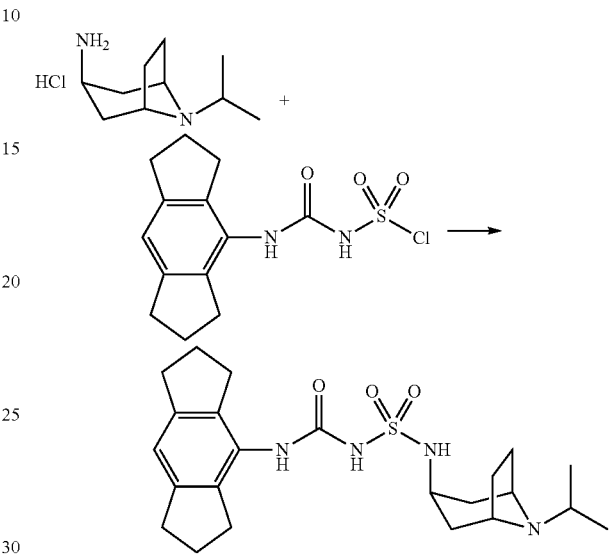

(1R,3r,5S)-8-Isopropyl-8-azabicyclo[3.2.1]octan-3-amine hydrochloride (Intermediate P10) (84 mg, 0.41 mmol) was dissolved in dry THF (10 mL) at 0° C. under a nitrogen atmosphere. Et₃N (0.17 mL, 1.23 mmol) was added, followed by ((1,2,3,5,6,7-hexahydro-s-indacen-4-yl)carbamoyl)sulfamoyl chloride (Intermediate A4) (0.13 g, 0.41 mmol). The reaction mixture was stirred at room temperature overnight under a nitrogen atmosphere. The solvent was evaporated in vacuo. Purification by reversed phase column chromatography (see "Experimental Methods") gave the title compound (5 mg, 5%) as a white solid.

¹H NMR (CD₃OD) δ 6.89 (s, 1H), 4.57 (s, 1H), 4.10 (s, 2H), 3.65-3.50 (m, 1H), 3.18-2.98 (m, 1H), 2.93-2.71 (m, 8H), 2.69-2.45 (m, 2H), 2.44-1.93 (m, 10H), 1.90 (s, 2H), 1.36-1.30 (m, 6H).
LCMS: m/z 447 (M+H)⁺ (ES⁺); 445 (M–H)⁻ (ES⁻).

Example 34: 3-(N-(1-Methylazetidin-3-yl))sulfamoyl)-1-(1,2,3,5,6,7-hexahydro-s-indacen-4-yl)urea, potassium salt

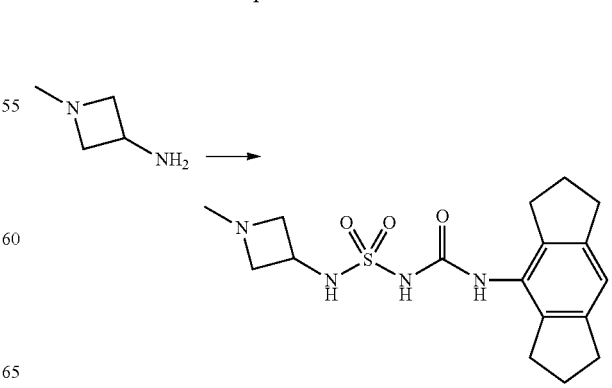

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) and (100 mg, 0.32 mmol) 1-methylazetidin-3-amine (80 mg, 1.00 mmol) to afford the title compound (16 mg, 14%) as a white solid.

$^1$H NMR (CD$_3$OD) δ 6.91 (s, 1H), 4.00 (m, 1H), 3.78 (t, 2H), 3.00 (t, 2H), 2.82 (m, 8H), 2.32 (s, 3H), 2.03 (m, 4H).
LCMS: m/z 365 (M+H)$^+$ (ES$^+$); 363 (M−H)$^−$ (ES$^−$).

Example 35: 3-(N-(2-(Azetidin-1-yl)ethyl)sulfamoyl)-1-(1,2,3,5,6,7-hexahydro-s-indacen-4-yl)urea, potassium salt

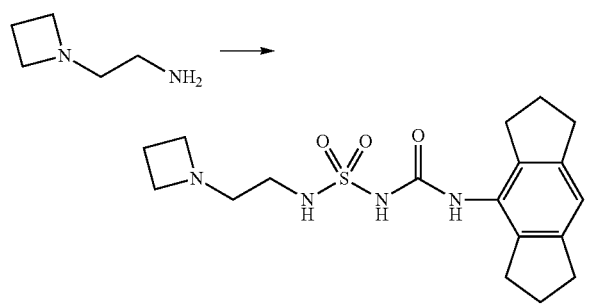

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 2-(azetidin-1-yl)ethan-1-amine (100 mg, 1.00 mmol) to afford the title compound (19 mg, 16%) as a white solid.

$^1$H NMR (CD$_3$OD) δ 6.91 (s, 1H), 3.59 (t, 4H), 3.02 (t, 2H), 2.82 (m, 9H), 2.60 (m, 1H), 2.20 (m, 2H), 2.03 (m, 4H).
LCMS: m/z 379 (M+H)$^+$ (ES$^+$); 377 (M−H)$^−$ (ES$^−$).

Example 16: 3-(N-(1-isopropylpyrrolidin-3-yl)-N-methylsulfamoyl)-1-(1,2,3,5,6,7-hexahydro-s-indacen-4-yl)urea, potassium salt

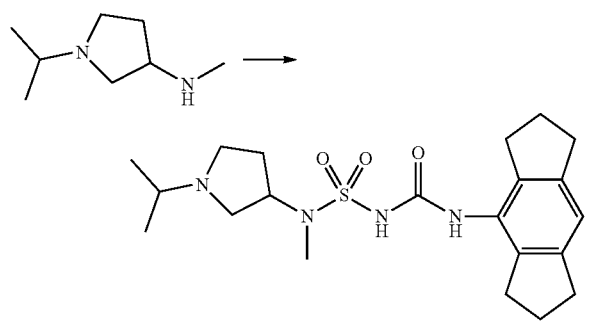

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-isopropyl-N-methylpyrrolidin-3-amine (142 mg, 1.00 mmol) to afford the title compound (20 mg, 15%) as a white solid.

$^1$H NMR (CD$_3$OD) δ 6.91 (s, 1H), 4.55 (m, 1H), 3.24 (m, 1H), 3.03 (t, 2H), 2.82 (m, 8H), 2.70 (m, 2H), 2.60 (m, 1H), 2.40 (s, 3H), 2.10 (m, 1H), 2.03 (m, 4H), 1.18 (d, 6H).
LCMS: m/z 421 (M+H)$^+$ (ES$^+$); 419 (M−H)$^−$ (ES$^−$).

Example 17: N-((1,2,3,5,6,7-Hexahydro-s-indacen-4-yl)carbamoyl)-3-methyl-3,8-diazabicyclo[3.2.1]octane-8-sulfonamide, potassium salt

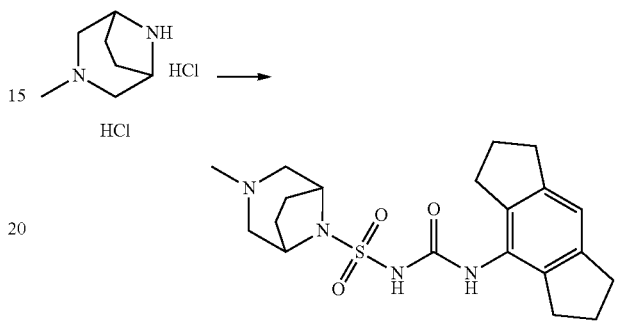

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (110 mg, 0.35 mmol) and 3-methyl-3,8-diazabicyclo[3.2.1]octane dihydrochloride (Intermediate P3) (70 mg, 0.35 mmol) to afford the title compound (1 mg, 0.6%) as a white solid.

$^1$H NMR (CD$_3$OD) δ 6.92 (s, 1H), 4.15 (bs, 2H), 2.92-2.62 (m, 10H), 2.40 (d, 2H), 2.26 (s, 3H), 2.16-1.98 (m, 6H), 1.92-1.74 (m, 2H).
LCMS: m/z 405 (M+H)$^+$ (ES$^+$); 403 (M−H)$^−$ (ES$^−$).

Example 38: N-((1,2,3,5,6,7-Hexahydro-s-indacen-4-yl)carbamoyl)-3-isopropyl-3,8-diazabicyclo[3.2.1]octane-8-sulfonamide, potassium salt

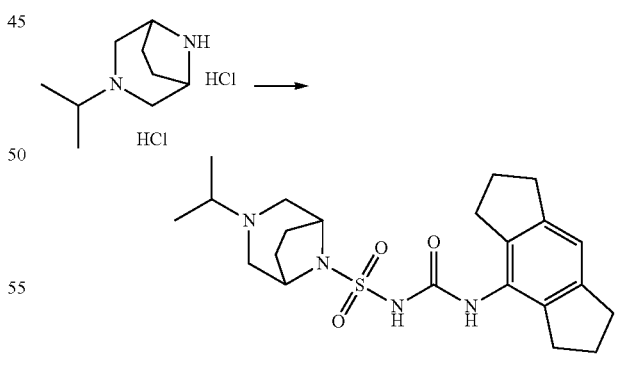

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (147 mg, 0.46 mmol) and 3-isopropyl-3,8-diazabicyclo[3.2.1]octane dihydrochloride (Intermediate P5) (72 mg, 0.46 mmol) to afford the title compound (4 mg, 1%) as a white solid.

¹H NMR (CD₃OD) δ 6.96 (s, 1H), 4.20 (s, 2H), 2.91-2.56 (m, 13H), 2.05 (p, 6H), 1.94-1.81 (m, 2H), 1.04 (d, 6H).
LCMS: m/z 433 (M+H)⁺ (ES⁺); 431 (M−H)⁻ (ES⁻).

Example 39: 3-(N-(2-(Dimethylamino)ethyl)-N-ethylsulfamoyl))-1-(1,2,3,5,6,7-hexahydro-s-indacen-4-yl)urea, potassium salt

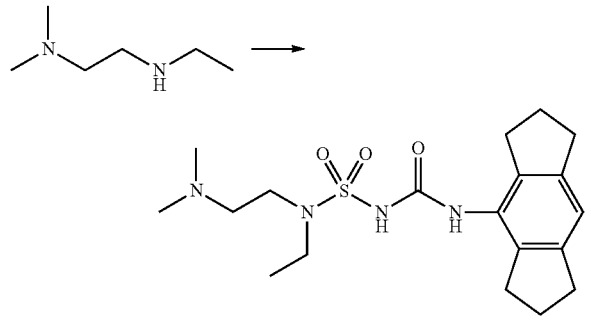

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-ethyl-N2,N2-dimethylethane-1,2-diamine (155 mg, 1.3 mmol) to afford the title compound (2 mg, 2%) as a white solid.

¹H NMR (CD₃OD) δ 6.91 (s, 1H), 3.52 (t, 2H), 3.25 (t, 2H), 3.10 (m, 2H), 2.82 (m, 8H), 2.70 (s, 6H), 2.03 (m, 4H), 1.21 (t, 3H).
LCMS: m/z 395 (M+H)⁺ (ES⁺); 393 (M−H)⁻ (ES⁻).

Example 40: 3-(N-(2-(Diethylamino)ethyl)sulfamoyl))-1-(1,2,3,5,6,7-hexahydro-s-indacen-4-yl) urea, potassium salt

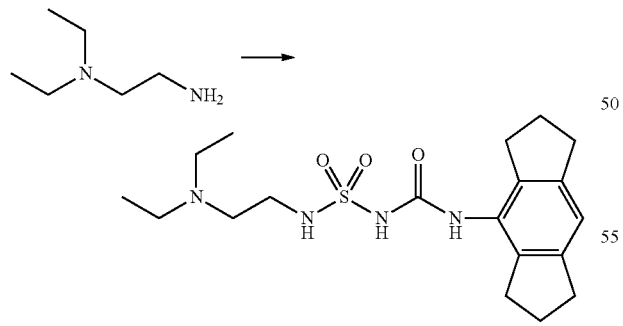

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-diethylethane-1,2-diamine (115 mg, 1.00 mmol) to afford the title compound (10 mg, 8%) as a white solid.

¹H NMR (CD₃OD) δ 6.91 (s, 1H), 3.27 (m, 2H), 3.20 (s, 1H), 3.00 (m, 5H), 2.82 (m, 8H), 2.03 (m, 4H), 1.19 (t, 6H).
LCMS: m/z 395 (M+H)⁺ (ES⁺); 393 (M−H)⁻ (ES⁻).

Example 41: N-(2-((N-((1,2,3,5,6,7-Hexahydro-s-indacen-4-yl)carbamoyl) sulfamoyl)(methyl)amino) ethyl)-N-methylacetamide, potassium salt

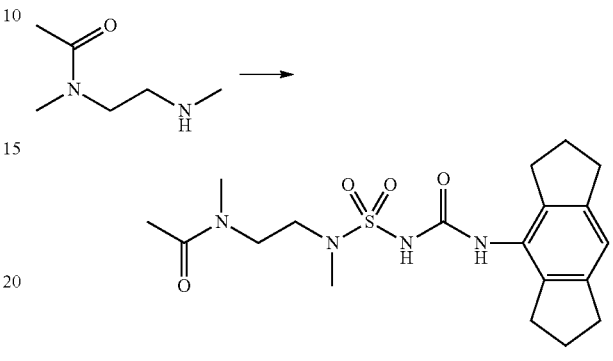

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N-methyl-N-(2-(methylamino)ethyl)acetamide (130 mg, 1.00 mmol) to afford the title compound (7 mg, 6%) as a white solid.

¹H NMR (CD₃OD) δ 6.91 (s, 1H), 3.55 (m, 2H), 3.39 (m, 2H), 3.10 (s, 3H), 2.90 (s, 3H), 2.82 (m, 8H), 2.03 (m, 7H).
LCMS: m/z 409 (M+H)⁺ (ES⁺); 407 (M−H)⁻ (ES⁻).

Example 42: 3-((Dimethylamino)methyl)-N-((1,2,3,5,6,7-hexahydro-s-indacen-4-yl)carbamoyl)piperidine-1-sulfonamide, potassium salt

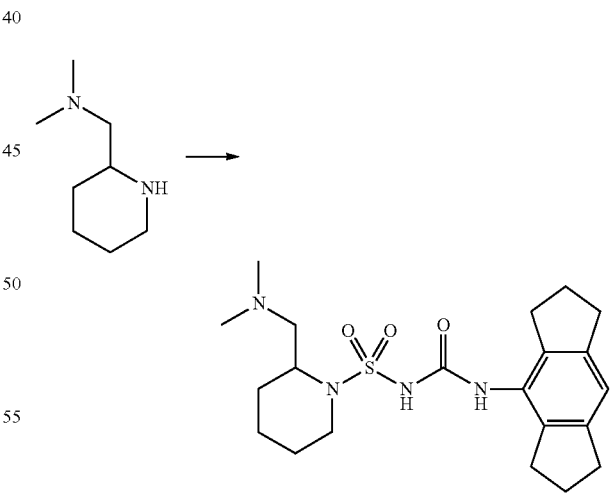

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethyl-1-(piperidin-2-yl)methanamine (142 mg, 1.00 mmol) to afford the title compound (11 mg, 8%) as a white solid.

¹H NMR (CD₃OD) δ 6.91 (s, 1H), 4.42 (m, 1H), 3.95 (m, 1H), 3.70 (d, 1H), 3.45 (t, 1H), 3.05 (t, 1H), 2.82 (m, 8H), 2.66 (s, 6H), 2.21 (s, 1H), 2.03 (m, 4H), 1.80 (m, 1H), 1.60 (m, 4H).

LCMS: m/z 421 (M+H)⁺ (ES⁺); 419 (M−H)⁻ (ES⁻).

Example 43: (1R,4R)—N-((1,2,3,5,6,7-Hexahydro-s-indacen-4-yl) carbamoyl)-5-methyl-2,5-diazabicyclo[2.2.1]heptane-2-sulfonamide, potassium salt

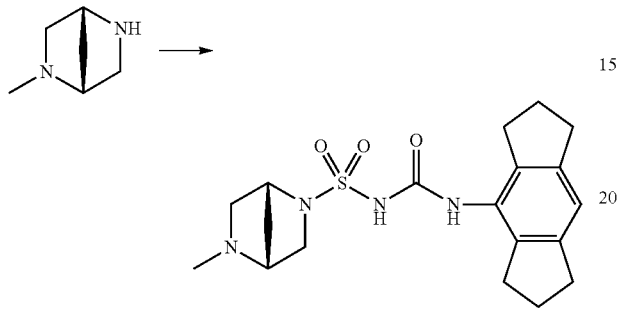

To a solution of (1R,4R)-2-methyl-2,5-diazabicyclo[2.2.1]heptane dihydrobromide (100 mg, 0.36 mmol) in THF (10 mL) under N₂ atmosphere was added sodium hydride (40%) (30 mg, 0.75 mmol). The reaction mixture was refluxed for 30 minutes. After cooling to room temperature, DABCO (100 mg, 89 mmol), triethylamine (0.5 g, 0.7 mL, mmol) and ((1,2,3,5,6,7-hexahydro-s-indacen-4-yl)carbamoyl)sulfamoyl chloride (Intermediate A4) (100 mg, 0.32 mmol) were added. The mixture was stirred for 4 hours at room temperature. Potassium tert-butoxide (100 mg, 0.89 mmol) was added and the mixture was stirred for 5 minutes. The solvent was removed in vacuo and DMSO (1 mL) was added. The suspension was filtered over cotton wool and subsequently submitted for purification by reversed phase column chromatography (see "Experimental Methods") to afford the title compound (21 mg, 18%) as a white solid.

¹H NMR (CD₃OD) δ 6.91 (s, 1H), 4.29 (s, 1H), 3.62 (s, 1H), 3.42 (dd, 2H), 3.05 (m, 2H), 2.82 (m, 11H), 2.03 (m, 4H), 1.56 (s, 2H).

LCMS: m/z 391 (M+H)⁺ (ES⁺); 389 (M−H)⁻ (ES⁻).

Example 44: 3-(N-(1-Methylpyrrolidin-3-yl))sulfamoyl)-1-(1,2,3,5,6,7-hexahydro-s-indacen-4-yl)urea, potassium salt

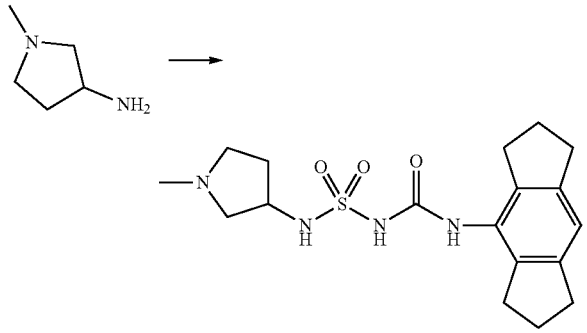

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-methylpyrrolidin-3-amine (100 mg, 1.00 mmol) to afford the title compound (38 mg, 31%) as a white solid.

¹H NMR (CD₃OD) δ 6.91 (s, 1H), 3.95 (m, 1H), 3.01 (dd, 1H), 2.82 (m, 8H), 2.56 (m, 3H), 2.38 (s, 3H), 2.22 (m, 1H), 2.03 (m, 6H), 1.80 (m, 1H).

LCMS: m/z 379 (M+H)⁺ (ES⁺); 377 (M−H)⁻ (ES⁻).

Example 45: 3-(N-(2-(3-(but-3-yn-1-yl)-3H-diazirin-3-yl)ethyl))sulfamoyl)-1-(1,2,3,5,6,7-hexahydro-s-indacen-4-yl)urea, potassium salt

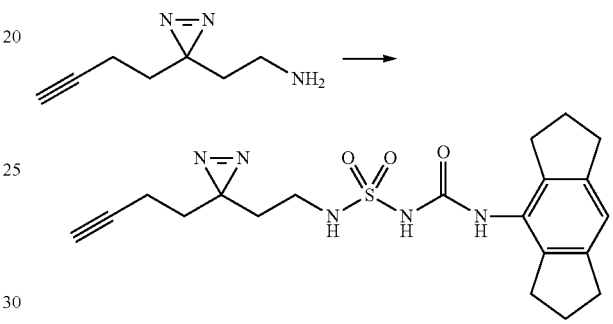

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 2-(3-(but-3-yn-1-yl)-3H-diazirin-3-yl)ethan-1-amine (116 mg, 0.85 mmol) with triethylamine (86 mg, 0.85 mmol) to afford the title compound (22 mg, 17%) as a white solid.

¹H NMR (CD₃OD) δ 6.91 (s, 1H), 2.82 (m, 8H), 2.62 (t, 2H), 2.24 (dt, 1H), 2.03 (m, 6H), 1.62 (m, 4H).

LCMS: m/z 416 (M+H)⁺ (ES⁺); 414 (M−H)⁻ (ES⁻).

Example 46: N-((1,2,3,5,6,7-Hexahydro-s-indacen-4-yl)carbamoyl)-[1,3'-biazetidine]-1'-sulfonamide, potassium salt

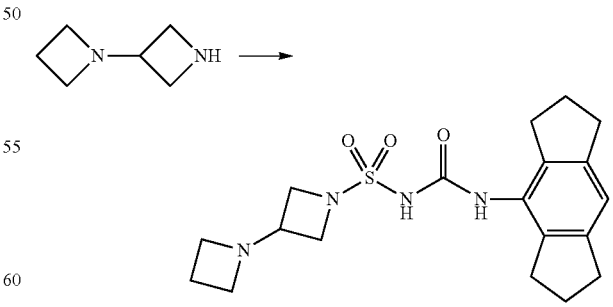

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1,3'- biazetidine bis(2,2,2-trifluoroacetate) (100 mg, 0.29 mmol) with DABCO (200 mg, 1.78 mmol) to afford the title compound (9 mg, 8%) as a white solid.
$^1$H NMR (CD$_3$OD) δ 6.91 (s, 1H), 3.80 (m, 1H), 2.82 (m, 16H), 2.03 (m, 6H).
LCMS: m/z 391 (M+H)$^+$ (ES$^+$); 389 (M–H)$^-$ (ES$^-$).

Example 47: 3-(N-((1-Ethylazetidin-2-yl)methyl)sulfamoyl)-1-(1,2,3,5,6,7-hexahydro-s-indacen-4-yl)urea, potassium salt

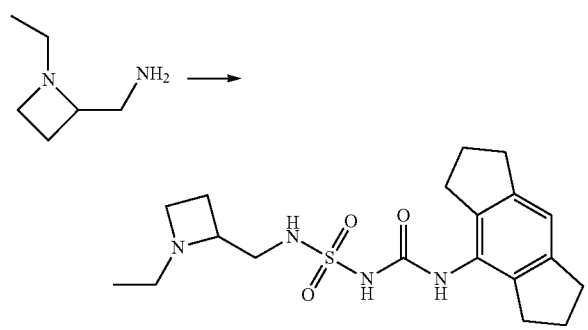

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (127 mg, 0.263 mmol, purity 80%) and (1-ethylazetidin-2-yl)methanamine (commercial from enamine; 30 mg, 0.26 mmol) except that before removal of the solvent potassium tert-butoxide (1.0 equivalent) was added. This afforded the title compound as the potassium salt (9 mg, 7%) as a white solid.
$^1$H NMR (CD$_3$OD) δ 6.89 (s, 1H), 4.24-4.10 (m, 1H), 3.95-3.77 (m, 1H), 3.63-3.46 (m, 3H), 3.26-3.06 (m, 2H), 2.83 (q, 8H), 2.42-2.28 (m, 1H), 2.21 (d, 1H), 2.02 (p, 4H), 1.13 (t, 3H).
LCMS: m/z 393 (M+H)$^+$ (ES$^+$); 391 (M–H)$^-$ (ES$^-$).

Example 48: 3-(N-(4-(Dimethylamino)butyl)sulfamoyl)-1-(1,2,3,5,6,7-hexahydro-s-indacen-4-yl)urea, potassium salt

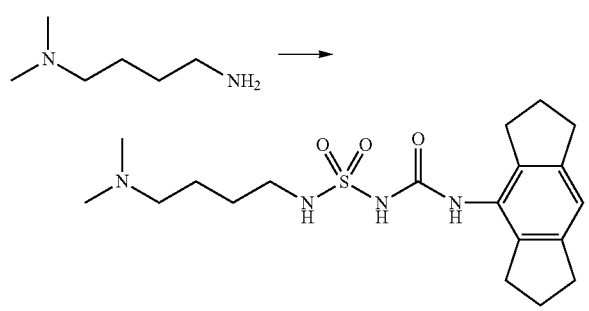

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-dimethylbutane-1,4-diamine (116 mg, 1.0 mmol) to afford the title compound (20 mg, 16%) as a white solid.
$^1$H NMR (CD$_3$OD) δ 6.91 (s, 1H), 3.07 (t, 2H), 2.82 (m, 8H), 2.62 (m, 2H), 2.42 (s, 6H), 2.03 (m, 4H), 1.60 (m, 4H).
LCMS: m/z 395 (M+H)$^+$ (ES$^+$); 393 (M–H)$^-$ (ES$^-$).

Example 49: 3-(3-((Diethylamino)pyrrolidine)-1-sulfamoyl)-1-(1,2,3,5,6,7-hexahydro-s-indacen-4-yl)urea, potassium salt

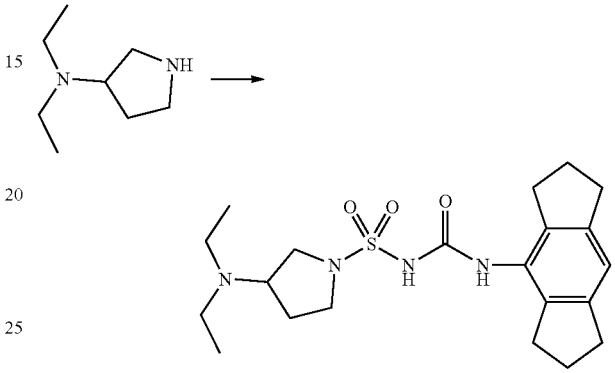

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-diethylpyrrolidin-3-amine (142 mg, 1.0 mmol) to afford the title compound (21 mg, 16%) as a white solid.
$^1$H NMR (CD$_3$OD) δ 6.91 (s, 1H), 3.66 (m, 1H), 3.40 (m, 3H), 3.17 (m, 1H), 2.82 (m, 8H), 2.67 (q, 4H), 2.13 (m, 1H), 2.03 (m, 4H), 1.80 (m, 1H), 1.80 (t, 6H).
LCMS: m/z 421 (M+H)$^+$ (ES$^+$); 419 (M–H)$^-$ (ES$^-$).

Example 50: 3-(N-((1-Isopropylazetidin-2-yl)methyl)sulfamoyl)-1-(1,2,3,5,6,7-hexahydro-s-indacen-4-yl)urea, potassium salt

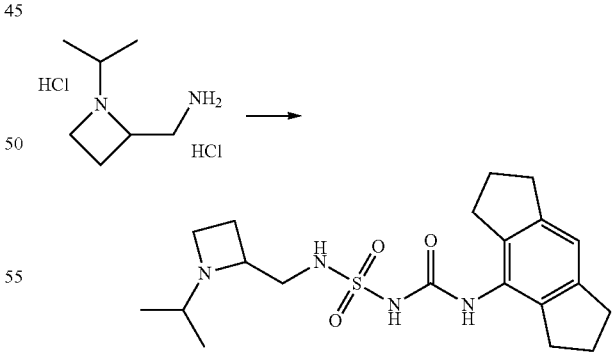

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (170 mg, 0.54 mmol) and (1-isopropylazetidin-2-yl)methanamine dihydrochloride (Intermediate P2) (72 mg, 0.36 mmol) except that triethylamine (3.0 equivalent) was added to the reaction mixture and except that before removal of the solvent potassium tert-butoxide (3.0 equivalent) was added. This afforded the title compound as the potassium salt (34 mg, 21%) as a white solid.

$^1$H NMR (CD$_3$OD) δ 6.89 (s, 1H), 4.32-4.15 (m, 1H), 3.82 (m, 1H), 3.57 (q, 1H), 3.47 (dd, 1H), 3.24-3.15 (m, 2H), 2.83 (q, 8H), 2.43-2.16 (m, 2H), 2.02 (p, 4H), 1.22 (d, 3H), 1.12 (d, 3H).

LCMS: m/z 407 (M+H)$^+$ (ES$^+$); 405 (M−H)$^−$ (ES$^−$).

Example 51: 3-(N,N-Bis(2-(dimethylamino)ethyl) sulfamoyl)-1-(1,2,3,5,6,7-hexahydro-s-indacen-4-yl) urea, potassium salt

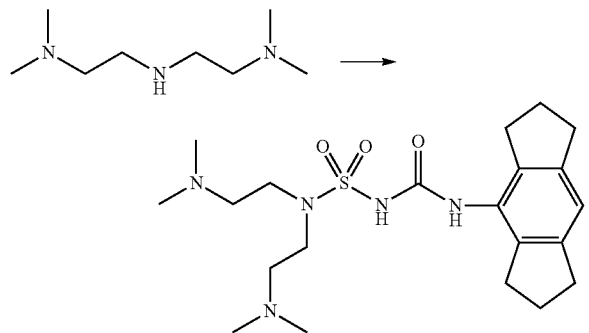

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-(2-(dimethylamino)ethyl)-N2,N2-dimethylethane-1,2-diamine (100 mg, 0.7 mmol) to afford the title compound (14 mg, 11%) as a white solid.

$^1$H NMR (CD$_3$OD) δ 6.91 (s, 1H), 3.55 (t, 4H), 3.10 (t, 4H), 2.82 (m, 8H), 2.71 (s, 12H), 2.03 (m, 4H).

LCMS: m/z 438 (M+H)$^+$ (ES$^+$); 436 (M−H)$^−$ (ES$^−$).

Example 52: 3-(N-(1-Methylpiperidin-3-yl)sulfamoyl)-1-(1,2,3,5,6,7-hexahydro-s-indacen-4-yl)urea, potassium salt

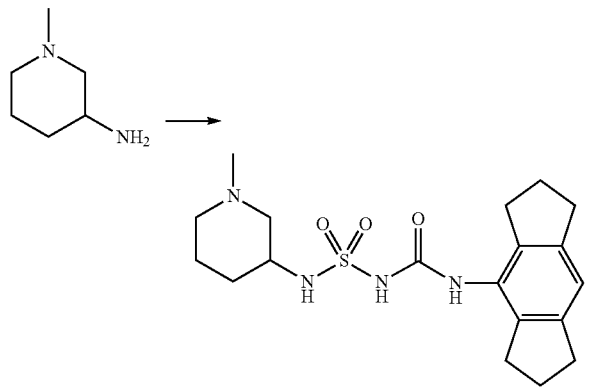

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-methylpiperidin-3-amine (114 mg, 1.0 mmol) to afford the title compound (16 mg, 13%) as a white solid.

$^1$H NMR (CD$_3$OD) δ 6.91 (s, 1H), 3.50 (t, 2H), 3.40 (m, 1H), 3.05 (d, 1H), 2.82 (m, 8H), 2.63 (d, 1H), 2.23 (s, 3H), 2.03 (m, 5H), 1.75 (m, 1H), 1.60 (m, 1H), 1.20 (m, 1H).

LCMS: m/z 391 (M+H)$^+$ (ES$^+$); 393 (M−H)$^−$ (ES$^−$).

Example 53: 3-(N-(2-(Diethylamino)ethyl)-N-methyl)sulfamoyl)-1-(1,2,3,5,6,7-hexahydro-s-indacen-4-yl)urea, potassium salt

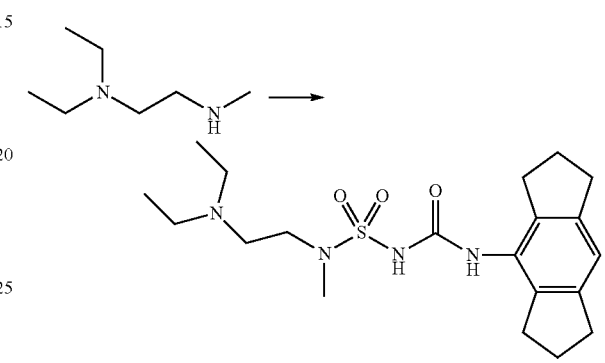

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-diethyl-N2-methylethane-1,2-diamine (130 mg, 1.0 mmol) to afford the title compound (3 mg, 3%) as a white solid.

$^1$H NMR (CD$_3$OD) δ 6.91 (s, 1H), 3.50 (t, 2H), 3.20 (q, 2H), 3.19 (q, 4H), 2.82 (m, 11H), 2.03 (m, 4H), 1.23 (t, 6H).

LCMS: m/z 409 (M+H)$^+$ (ES$^+$); 407 (M−H)$^−$ (ES$^−$).

Example 54: 3-((N-(4-Hydroxybutyl))sulfamoyl)-1-(1,2,3,5,6,7-hexahydro-s-indacen-4-yl)urea, potassium salt

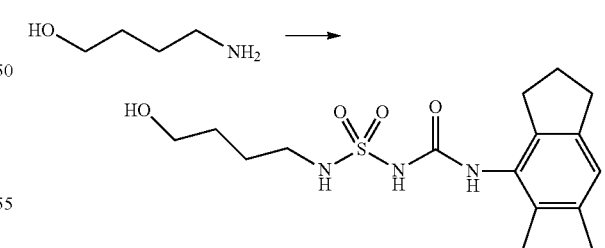

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 4-aminobutan-1-ol (116 mg, 1.0 mmol) with triethylamine (0.15 g, 0.2 mL, 0.14 mmol) to afford the title compound (33 mg, 26%) as a white solid.

¹H NMR (CD₃OD) δ 6.91 (s, 1H), 3.58 (m, 2H), 3.0 (t, 1H), 2.82 (m, 10H), 2.03 (m, 4H), 1.60 (m, 4H).
LCMS: m/z 368 (M+H)⁺ (ES⁺); 366 (M–H)⁻ (ES⁻).

Example 55: 3-((N-(1-Methyl-1H-pyrazol-3-yl))sulfamoyl)-1-(1,2,3,5,6,7-hexahydro-s-indacen-4-yl)urea, potassium salt

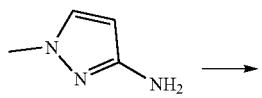

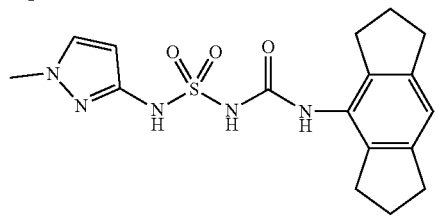

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol), 1-methyl-1H-pyrazol-3-amine (97 mg, 1.0 mmol) and triethylamine (0.15 g, 0.2 mL, 0.14 mmol) to afford the title compound (19 mg, 16%) as a white solid.
¹H NMR (CD₃OD) δ 7.38 (s, 1H), 6.91 (s, 1H), 6.17 (s, 1H), 3.75 (s, 3H), 2.82 (m, 8H), 2.03 (m, 4H).
LCMS: m/z 376 (M+H)⁺ (ES⁺); 374 (M–H)⁻ (ES⁻).

Example 56: (1R,3r,5S)-8-Methyl-8-azabicyclo[3.2.1]octan-3-(N-((1,2,3,5,6,7-hexahydro-s-indacen-4-yl)carbamoyl)-sulfonamide)

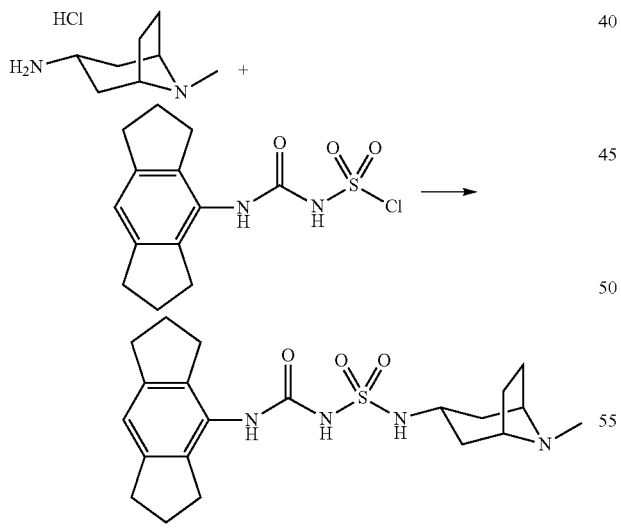

(1R,3s,5S)-8-Methyl-8-azabicyclo[3.2.1]octan-3-amine hydrochloride (Intermediate P9) (74 mg, 0.42 mmol) was dissolved in dry THF (10 mL) at 0° C. under a nitrogen atmosphere. Et₃N (0.31 mL) was added, followed by ((1,2,3,5,6,7-hexahydro-s-indacen-4-yl)carbamoyl)sulfamoyl chloride (Intermediate A4) (0.13 g, 0.42 mmol). The reaction mixture was stirred at room temperature overnight under nitrogen atmosphere. The solvent was evaporated in vacuo. Purification by reversed phase column chromatography (see "Experimental Methods") gave the title compound (14 mg, 5%) as a white solid.
¹H NMR (CD₃OD) δ 6.99 (s, 1H), 4.26-4.02 (m, 1H), 3.79-3.59 (m, 3H), 2.91-2.73 (m, 9H), 2.68 (s, 3H), 2.31-2.16 (m, 2H), 2.13-1.88 (m, 11H).
LCMS: m/z 419 (M+H)⁺ (ES⁺).

Example 57: 3-(N-(2-(Dimethylamino)-2-methylpropyl)sulfamoyl)-1-(1,2,3,5,6,7-hexahydro-s-indacen-4-yl)urea, potassium salt

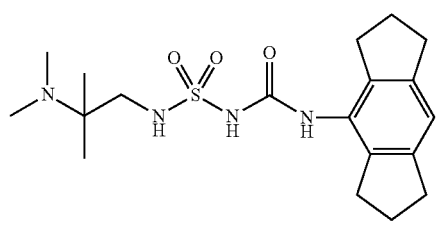

To a solution of ((1,2,3,5,6,7-hexahydro-s-indacen-4-yl)carbamoyl)sulfamoyl chloride (Intermediate A4) (100 mg, 0.32 mmol) in THF (10 mL) under N₂ atmosphere was added N2,N2,2-trimethylpropane-1,2-diamine (116 mg, 1.0 mmol). The mixture was stirred for 4 hours at room temperature. Potassium tert-butoxide (100 mg, 0.89 mmol) was added and the reaction mixture was stirred for 5 minutes. The solvent was removed in vacuo and DMSO (1 mL) was added. The suspension was filtered over cotton wool and subsequently submitted for purification by reversed phase column chromatography (see "Experimental Methods") to afford the title compound (11 mg, 9%) as a white solid.
¹H NMR (CD₃OD) δ 6.91 (s, 1H), 3.75 (t, 1H), 2.82 (m, 8H), 2.55 (s, 6H), 2.20 (s, 2H), 2.03 (m, 4H), 1.55 (m, 1H), 1.20 (s, 6H).
LCMS: m/z 395 (M+H)⁺ (ES⁺); 393 (M–H)⁻ (ES⁻).

Example 58: 3-(N-(2-(Dimethylamino)ethyl)-N-(3-phenylpropyl) sulfamoyl)-1-(1,2,3,5,6,7-hexahydro-s-indacen-4-yl)urea, potassium salt

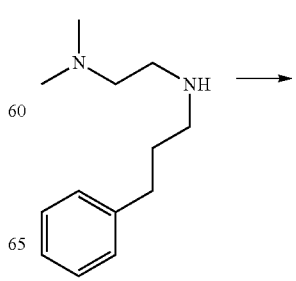

-continued

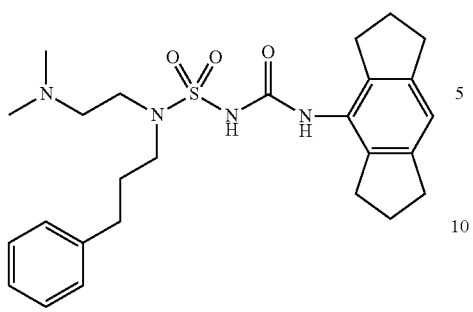

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-dimethyl-N2-(3-phenylpropyl)ethane-1,2-diamine (206 mg, 1.00 mmol) to afford the title compound (16 mg, 10%) as a white solid.

$^1$H NMR (CD$_3$OD) δ 7.20 (m, 5H), 6.91 (s, 1H), 3.59 (t, 2H), 3.23 (m, 2H), 3.18 (t, 2H), 2.82 (m, 14H), 2.63 (t, 2H), 2.03 (m, 6H).

LCMS: m/z 485 (M+H)$^+$ (ES$^+$); 483 (M−H)$^-$ (ES$^-$).

Example 59: 3-(N-(1-(Dimethylamino)-2-methylpropan-2-yl)sulfamoyl)-1-(1,2,3,5,6,7-hexahydro-s-indacen-4-yl)urea, potassium salt Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1,2-trimethylpropane-1,2-diamine (116 mg, 1.00 mmol) to afford the title compound (14 mg, 11%) as a white solid.

$^1$H NMR (CD$_3$OD) δ 6.91 (s, 1H), 2.98 (s, 6H), 2.82 (m, 8H), 2.40 (m, 2H), 2.03 (m, 4H), 1.47 (s, 6H).

LCMS: m/z 395 (M+H)$^+$ (ES$^+$); 393 (M−H)$^-$ (ES$^-$).

Example 60: 3-(N-(1-(Dimethylamino)-2-methylpropan-2-yl)sulfamoyl)-1-(1,2,3,5,6,7-hexahydro-s-indacen-4-yl)urea, potassium salt

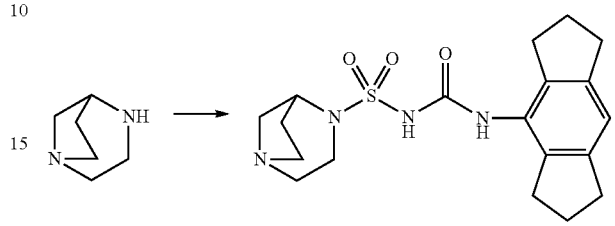

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1,4-diazabicyclo[3.2.1]octane dihydrochloride (110 mg, 0.60 mmol) with DABCO (107 mg, 0.95 mmol) to afford the title compound (6 mg, 5%) as a white solid.

$^1$H NMR (CD$_3$OD) δ 6.91 (s, 1H), 4.34 (m, 1H), 3.40 (m, 1H), 3.22 (m, 1H), 3.04 (m, 4H), 2.82 (m, 8H), 2.73 (m, 1H), 2.60 (m, 1H), 2.31 (m, 1H), 2.03 (m, 4H), 1.95 (m, 1H).

LCMS: m/z 391 (M+H)$^+$ (ES$^+$); 389 (M−H)$^-$ (ES$^-$).

Example 61: 8-Ethyl-N-((1,2,3,5,6,7-hexahydro-s-indacen-4-yl)carbamoyl)-3,8-diazabicyclo[3.2.1]octane-3-sulfonamide, potassium salt

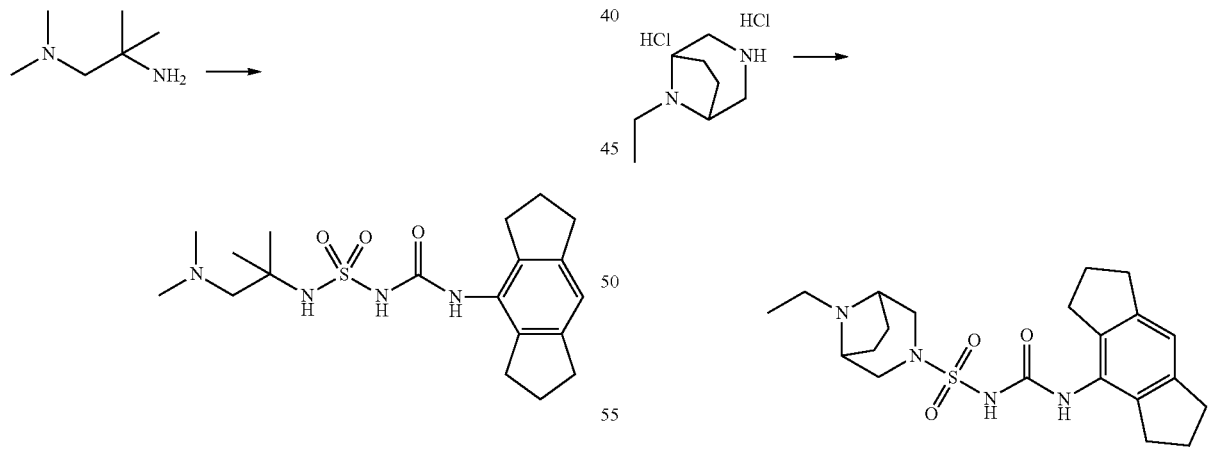

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (107 mg, 0.34 mmol) and 8-ethyl-3,8-diazabicyclo[3.2.1]octane dihydrochloride (Intermediate P6) (72 mg, 0.34 mmol) to afford the title compound (0.9 mg, 0.5%) as a white solid.

LCMS: m/z 419 (M+H)$^+$ (ES$^+$); 417 (M−H)$^-$ (ES$^-$).

Example 62: 3-Ethyl-N-((1,2,3,5,6,7-hexahydro-s-indacen-4-yl)carbamoyl)-3,8-diazabicyclo[3.2.1]octane-8-sulfonamide, potassium salt

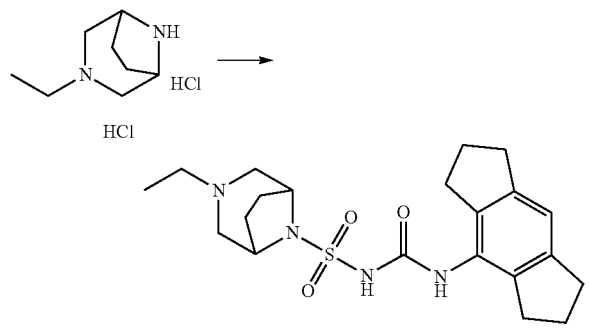

To a suspension of 3-ethyl-3,8-diazabicyclo[3.2.1]octane dihydrochloride (Intermediate P4) (60 mg, 0.28 mmol) in anhydrous tetrahydrofuran (10 mL) cooled at 0° C. was added sodium hydride (24 mg, 0.59 mmol). The suspension was then heated to 50° C. After heating for 1.5 hours, 1,4-diazabicyclo[2.2.2]octane (94 mg, 0.84 mmol) was added. After heating for 0.5 hour, the reaction mixture was cooled to 0° C. and then ((1,2,3,5,6,7-hexahydro-s-indacen-4-yl)carbamoyl)sulfamoyl chloride (Intermediate A4) (176 mg, 0.56 mmol) was added. The reaction mixture was stirred overnight at room temperature and then potassium tert-butoxide (189 mg, 1.68 mmol) was added. After stirring for 15 minutes, the solvent was removed in vacuo and DMSO (1 mL) was added. The suspension was filtered over cotton wool and subsequently submitted for purification by reversed phase column chromatography (see "Experimental Methods") to afford the title compound (0.5 mg, 0.4%) as a white solid.

LCMS: m/z 419 (M+H)$^+$ (ES$^+$); 417 (M−H)$^−$ (ES$^−$).

Example 63: (1R,3s,5S)-8-isopropyl-8-azabicyclo[3.2.1]octan-3-(N-((1,2,3,5,6,7-hexahydro-s-indacen-4-yl)carbamoyl)-sulfonamide)

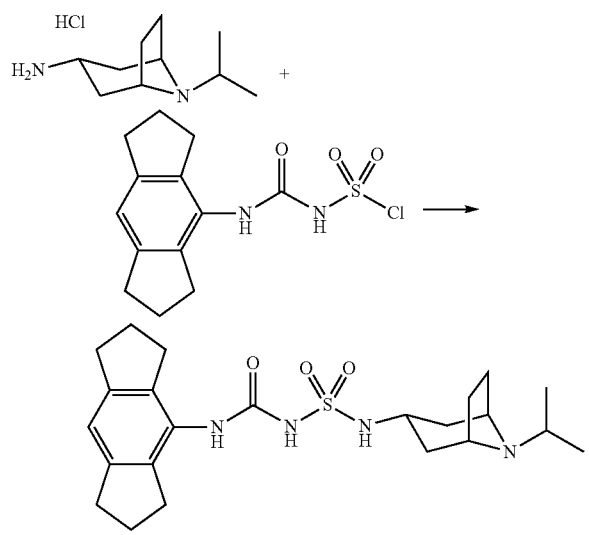

(1R,3s,5S)-8-Isopropyl-8-azabicyclo[3.2.1]octan-3-amine hydrochloride (Intermediate P17) (0.14 g, 0.71 mmol) was dissolved in dry THF (10 mL) under a nitrogen atmosphere and triethylamine (0.21 g, 0.30 mL, 2.1 mmol) was added, followed by ((1,2,3,5,6,7-hexahydro-s-indacen-4-yl)carbamoyl)sulfamoyl chloride (Intermediate A4) (0.22 g, 0.70 mmol). The reaction mixture was stirred at room temperature overnight under a nitrogen atmosphere. The solvent was evaporated in vacuo. Purification by reversed phase column chromatography (see "Experimental Methods") gave the title compound (3 mg, 2%) as a white solid.

$^1$H NMR (CD$_3$OD) δ 6.92 (s, 1H), 4.60 (s, 2H), 4.14 (s, 2H), 2.93-2.72 (m, 8H), 2.30-2.09 (m, 4H), 2.09-1.81 (m, 11H), 1.49-1.21 (m, 6H).

LCMS: m/z 447 (M+H)$^+$ (ES$^+$); 446 (M−H)$^−$ (ES$^−$).

Example 64: (1R,3r,5S)-3-(Diethylamino)-N-((1,2,3,5,6,7-hexahydro-s-indacen-4-yl)carbamoyl)-8-azabicyclo[3.2.1]octane-8-sulfonamide

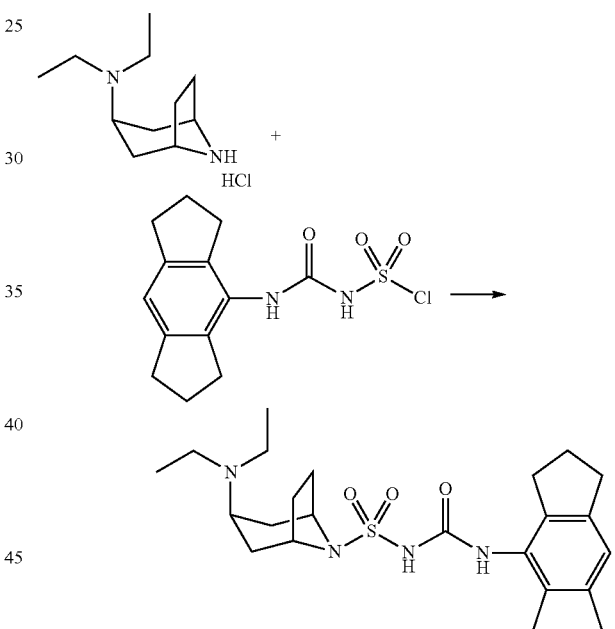

(1R,3r,5S)—N,N-Diethyl-8-azabicyclo[3.2.1]octan-3-amine hydrochloride (Intermediate P15) (0.13 g, 0.60 mmol) was dissolved in dry THF (10 mL) under a nitrogen atmosphere and triethylamine (0.18 g, 0.25 mL, 1.81 mmol) was added, followed by ((1,2,3,5,6,7-hexahydro-s-indacen-4-yl)carbamoyl)sulfamoyl chloride (Intermediate A4) (0.19 g, 0.60 mmol). The reaction mixture was stirred at room temperature overnight under a nitrogen atmosphere. The solvent was evaporated in vacuo. Purification by reversed phase column chromatography (see "Experimental Methods") gave the title compound (7 mg, 3%) as a white solid.

$^1$H NMR (CD$_3$OD) δ 6.90 (s, 1H), 4.42-4.26 (m, 2H), 3.60-3.41 (m, 1H), 3.14-2.92 (m, 5H), 2.92-2.77 (m, 9H), 2.73-2.56 (m, 2H), 2.37-2.19 (m, 2H), 2.14-1.94 (m, 4H), 1.75-1.54 (m, 2H), 1.50-1.29 (m, 2H), 1.28-1.15 (m, 6H).

LCMS: m/z 461 (M+H)$^+$ (ES$^+$).

Example 65: 3-(N-(1-Isopropyl-1H-pyrazol-4-yl)sulfamoyl)-1-(1,2,3,5,6,7-hexahydro-s-indacen-4-yl)urea, potassium salt

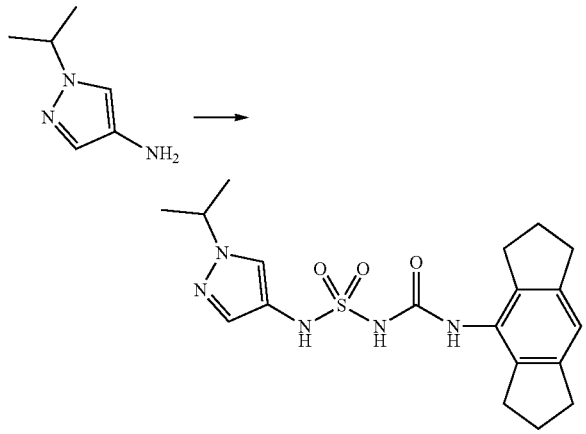

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-isopropyl-1H-pyrazol-4-amine (97 mg, 1.0 mmol) with triethylamine (0.1 g, 0.14 mL, 1.0 mmol) to afford the title compound (16 mg, 12%) as a white solid.

$^1$H NMR (CD$_3$OD) δ 7.42 (s, 1H), 6.91 (s, 1H), 6.19 (s, 1H), 4.18 (m, 1H), 2.82 (m, 8H), 1.41 (d, 6H).

LCMS: m/z 404 (M+H)$^+$ (ES$^+$); 402 (M–H)$^-$ (ES$^-$).

Example 66: 3-((R)—N-Methyl-N-(1-methylpyrrolidin-3-yl)sulfamoyl)-1-(1,2,3,5,6,7-hexahydro-s-indacen-4-yl)urea, potassium salt

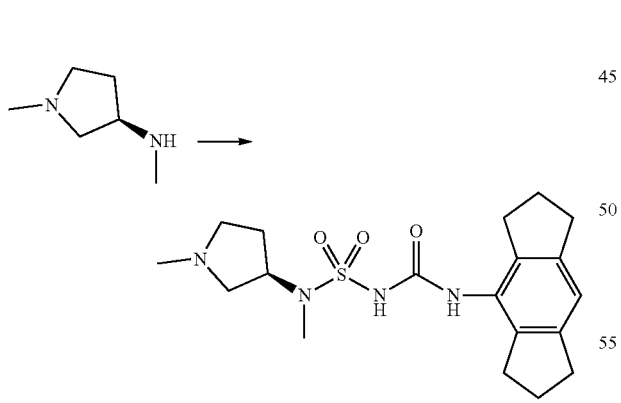

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (R)—N,1-dimethylpyrrolidin-3-amine (116 mg, 1.00 mmol) with triethylamine (100 mg, 100 mmol) to afford the title compound (36 mg, 9%) as a white solid.

$^1$H NMR (CD$_3$OD) δ 6.91 (s, 1H), 4.60 (m, 1H), 2.82 (m, 11H), 2.74 (m, 2H), 2.61 (m, 1H), 2.50 (m, 1H), 2.38 (s, 3H), 2.03 (m, 6H).

LCMS: m/z 393 (M+H)$^+$ (ES$^+$); 391 (M–H)$^-$ (ES$^-$).

Example 67: (1S,4S)—N-((1,2,3,5,6,7-Hexahydro-s-indacen-4-yl)carbamoyl)-5-methyl-2,5-diazabicyclo[2.2.1]heptane-2-sulfonamide, potassium salt

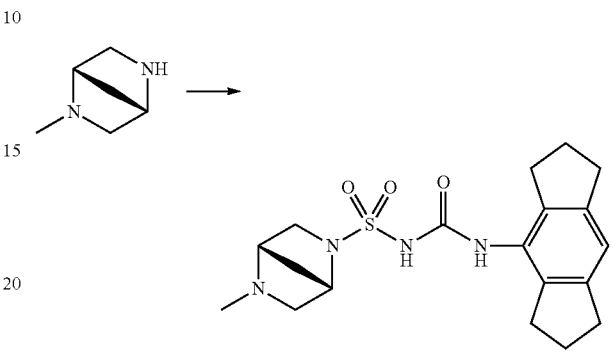

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (S)—N,1-dimethylpyrrolidin-3-amine (116 mg, 1.00 mmol) with triethylamine (100 mg, 100 mmol) to afford the title compound (20 mg, 16%) as a white solid.

$^1$H NMR (CD$_3$OD) δ 6.91 (s, 1H), 4.29 (s, 1H), 3.62 (s, 1H), 3.42 (dd, 2H), 3.05 (m, 2H), 2.82 (m, 11H), 2.03 (m, 4H), 1.55 (m, 2H).

LCMS: m/z 391 (M+H)$^+$ (ES$^+$); 389 (M–H)$^-$ (ES$^-$).

Example 68: 3-(N-(1-(Dimethylamino)-2-methylpropan-2-yl)sulfamoyl)-1-(1,2,3,5,6,7-hexahydro-s-indacen-4-yl)urea, potassium salt

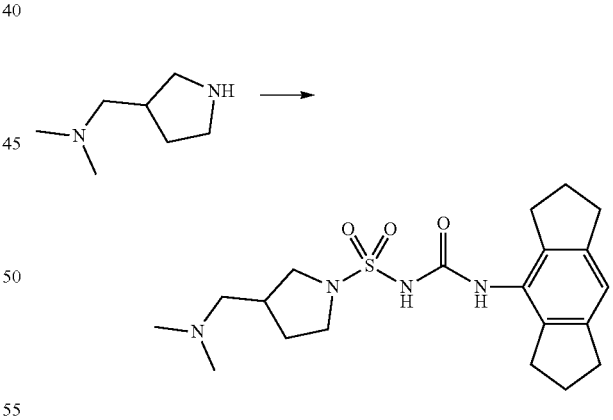

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethyl-1-(pyrrolidin-3-yl)methanamine dihydrochloride (80 mg, 0.40 mmol) with triethylamine (100 mg, 1.0 mmol) to afford the title compound (27 mg, 21%) as a white solid.

$^1$H NMR (CD$_3$OD) δ 6.91 (s, 1H), 3.58 (m, 1H), 3.42 (m, 1H), 3.37 (m, 1H), 3.03 (m, 1H), 2.82 (m, 10H), 2.42 (m, 1H), 2.23 (s, 6H), 2.03 (m, 5H), 1.61 (m, 1H).

LCMS: m/z 407 (M+H)$^+$ (ES$^+$); 405 (M–H)$^-$ (ES$^-$).

Example 6A: 3-(N-((1-Methylazetidin-3-yl)methyl)sulfamoyl)-1-(1,2,3,5,6,7-hexahydro-s-indacen-4-yl)urea, potassium salt

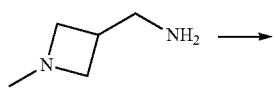

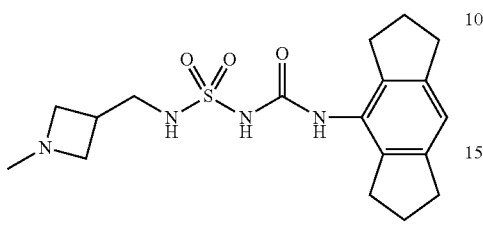

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N-((1-methylazetidin-3-yl)methyl) (100 mg, 0.98 mmol) with triethylamine (100 mg, 1.0 mmol) to afford the title compound (12 mg, 10%) as a white solid.

$^1$H NMR (CD$_3$OD) δ 6.91 (s, 1H), 3.58 (t, 2H), 3.20 (t, 2H), 3.12 (d, 2H), 2.82 (m, 8H), 2.72 (m, 1H), 2.40 (s, 3H), 2.03 (m, 4H).

LCMS: m/z 379 (M+H)$^+$ (ES$^+$); 377 (M–H)$^-$ (ES$^-$).

Example 70: (1R,3r,5S)—N-((1,2,3,5,6,7-Hexahydro-s-indacen-4-yl) carbamoyl)-3-(pyrrolidin-1-yl)-8-azabicyclo[3.2.1]octane-8-sulfonamide

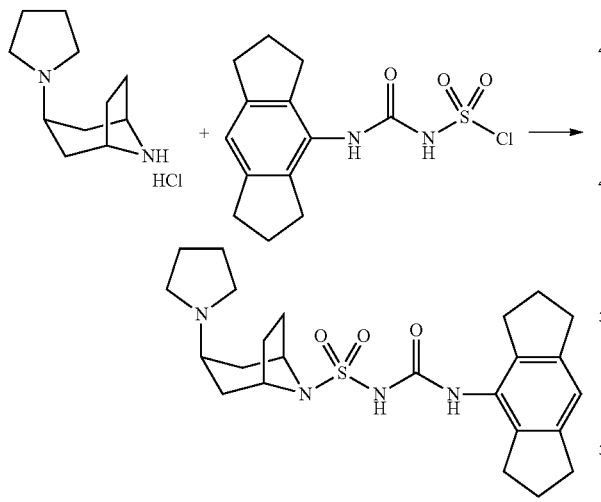

(1R,3r,5S)-3-(Pyrrolidin-1-yl)-8-azabicyclo[3.2.1]octane hydrochloride (Intermediate P14) (112 mg, 0.517 mmol) was dissolved in dry THF (10 mL) under a nitrogen atmosphere and triethylamine (157 mg, 0.216 mL, 1.55 mmol) was added, followed by ((1,2,3,5,6,7-hexahydro-s-indacen-4-yl)carbamoyl)sulfamoyl chloride (Intermediate A4) (163 mg, 0.518 mmol). The reaction mixture was stirred at room temperature overnight under a nitrogen atmosphere. The solvent was evaporated in vacuo.

Purification by reversed phase column chromatography (see "Experimental Methods") gave the title compound (13 mg, 5%) as a white solid.

$^1$H NMR (CD$_3$OD) δ 6.92 (s, 1H), 4.36-4.11 (m, 2H), 3.02-2.91 (m, 5H), 2.90-2.75 (m, 9H), 2.60-2.41 (m, 2H), 2.30-2.13 (m, 2H), 2.11-1.98 (m, 5H), 1.96-1.85 (m, 4H), 1.84-1.69 (m, 2H), 1.67-1.47 (m, 2H).

LCMS: m/z 459 (M+H)$^+$ (ES$^+$); 457 (M–H)$^-$ (ES$^-$).

Example 71: 3-(N-(2-(tert-Butylamino)ethyl)sulfamoyl)-1-(1,2,3,5,6,7-hexahydro-s-indacen-4-yl)urea, potassium salt

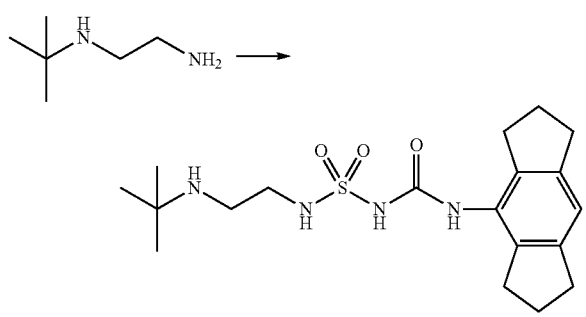

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-(tert-butyl)ethane-1,2-diamine (100 mg, 0.86 mmol) with triethylamine (100 mg, 1.0 mmol) to afford the title compound (16 mg, 13%) as a white solid.

$^1$H NMR (CD$_3$OD) δ 6.91 (s, 1H), 3.27 (t, 2H), 3.05 (t, 2H), 2.82 (m, 8H), 2.03 (m, 4H), 1.25 (s, 9H).

LCMS: m/z 395 (M+H)$^+$ (ES$^+$).

Example 72: N-((1,2,3,5,6,7-Hexahydro-s-indacen-4-yl)carbamoyl)-[1,3'-bipyrrolidine]-1'-sulfonamide, potassium salt

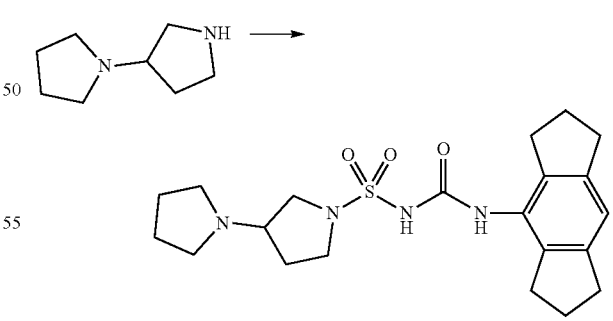

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1,3'-bipyrrolidine (140 mg, 1.00 mmol) to afford the title compound (39 mg, 29%) as a white solid.

¹H NMR (CD₃OD) δ 6.91 (s, 1H), 3.62 (dd, 1H), 3.42 (m, 1H), 3.39 (m, 1H), 3.19 (m, 1H), 2.99 (m, 1H), 2.82 (m, 8H), 2.62 (m, 4H), 2.17 (m, 1H), 2.03 (m, 4H), 1.87 (m, 1H), 1.80 (m, 4H).
LCMS: m/z 419 (M+H)⁺ (ES⁺).

Example 73: 3-(Azetidin-1-yl)-N-((1,2,3,5,6,7-hexahydro-s-indacen-4-yl) carbamoyl)pyrrolidine-1-sulfonamide, potassium salt

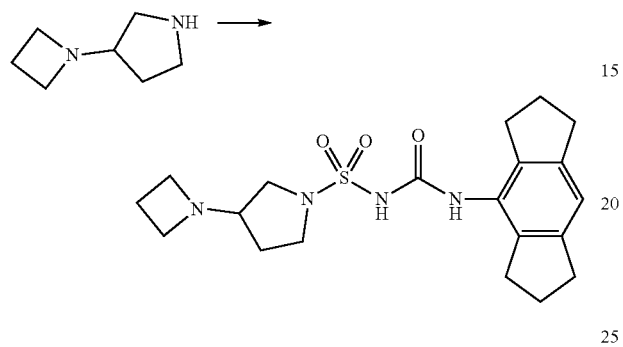

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 3-(azetidin-1-yl)pyrrolidine (100 mg, 0.79 mmol) with triethylamine (100 mg, 1.0 mmol) to afford the title compound (0.9 mg, 0.7%) as a white solid.
¹H NMR (CD₃OD) δ 6.91 (s, 1H), 3.58 (t, 2H), 3.50 (m, 2H), 3.40 (m, 3H), 3.12 (m, 2H), 2.82 (m, 8H), 2.20 (m, 2H), 2.03 (m, 6H).
LCMS: m/z 405 (M+H)⁺ (ES⁺).

Example 74: (1R,3s,5S)-8-Ethyl-8-azabicyclo[3.2.1]octan-3-(N-((1,2,3,5,6,7-hexahydro-s-indacen-4-yl) carbamoyl)-sulfonamide)

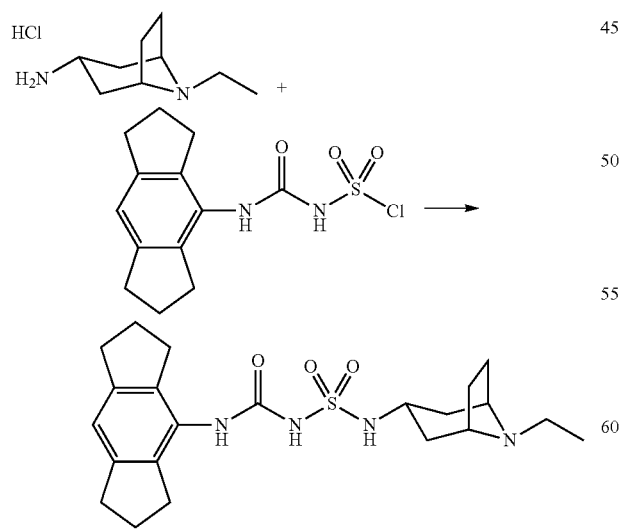

(1R,3s,5S)-8-Ethyl-8-azabicyclo[3.2.1]octan-3-amine hydrochloride (Intermediate P18) (79 mg, 0.42 mmol) was dissolved in dry THF (10 mL) under a nitrogen atmosphere and triethylamine (0.13 g, 0.20 mL, 1.25 mmol) was added, followed by ((1,2,3,5,6,7-hexahydro-s-indacen-4-yl)carbamoyl)sulfamoyl chloride (Intermediate A4) (0.13 g, 0.42 mmol). The reaction mixture was stirred at room temperature overnight under a nitrogen atmosphere. The solvent was evaporated in vacuo.
Purification by reversed phase column chromatography (see "Experimental Methods") gave the title compound (2 mg, 1%) as a white solid.
¹H NMR (CD₃OD) δ 6.92 (s, 1H), 3.94 (s, 2H), 3.12-2.96 (m, 3H), 2.93-2.74 (m, 9H), 2.34-2.15 (m, 5H), 2.13-1.99 (m, 7H), 1.98-1.77 (m, 2H), 1.39-1.24 (m, 3H).
LCMS: m/z 433 (M+H)⁺ (ES⁺).

Example 75: 8-Cyclopropyl-N-((1,2,3,5,6,7-hexahydro-s-indacen-4-yl) carbamoyl)-3,8-diazabicyclo[3.2.1]octane-3-sulfonamide, potassium salt

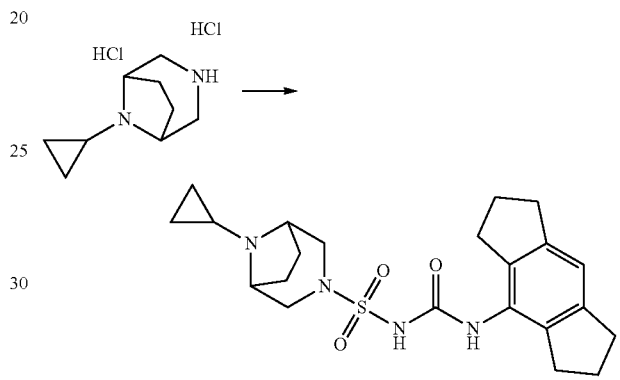

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (222 mg, 0.70 mmol) and 8-cyclopropyl-3,8-diazabicyclo[3.2.1]octane dihydrochloride (Intermediate P8) (106 mg, 0.47 mmol) to afford the title compound (2.1 mg, 1%) as a white solid.
¹H NMR (CD₃OD) δ 6.95 (s, 1H), 3.42-3.34 (m, 4H), 3.26-3.17 (m, 2H), 2.82 (dt, 8H), 2.14-1.95 (m, 7H), 1.83 (d, 2H), 0.55-0.37 (m, 4H).
LCMS: m/z 431 (M+H)⁺ (ES⁺).

Example 76: 3-((S)—N-Methyl-N-(1-methylpyrrolidin-3-yl)sulfamoyl)-1-(1,2,3,5,6,7-hexahydro-s-indacen-4-yl)urea, potassium salt

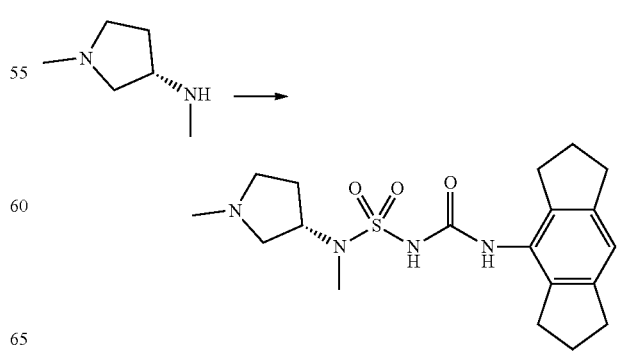

Prepared as described for (1R,4R)—N-((1,2,3,5,6,7-hexahydro-s-indacen-4-yl)carbamoyl)-5-methyl-2,5-diazabicyclo[2.2.1]heptane-2-sulfonamide, potassium salt (Example 43) using ((1,2,3,5,6,7-hexahydro-s-indacen-4-yl)carbamoyl)sulfamoyl chloride (Intermediate A4) (100 mg, 0.32 mmol) and (1S,4S)-2-methyl-2,5-diazabicyclo[2.2.1]heptane dihydrobromide (100 mg, 0.36 mmol) to afford the title compound (12 mg, 3%) as a white solid.

$^1$H NMR (CD$_3$OD) δ 6.91 (s, 1H), 4.60 (m, 1H), 2.82 (m, 11H), 2.74 (m, 2H), 2.61 (m, 1H), 2.50 (m, 1H), 2.38 (s, 3H), 2.03 (m, 6H).

LCMS: m/z 393 (M+H)$^+$ (ES$^+$); 391 (M−H)$^-$ (ES$^-$).

Example 77: (1R,3s,5S)-3-(Dimethylamino)-N-((1,2,3,5,6,7-hexahydro-s-indacen-4-yl)carbamoyl)-8-azabicyclo[3.2.1]octane-8-sulfonamide

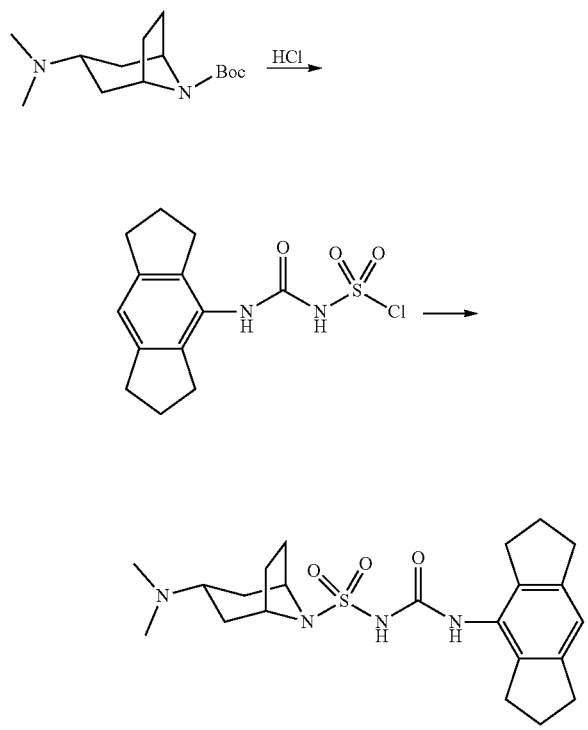

tert-Butyl (1R,3s,5S)-3-(dimethylamino)-8-azabicyclo[3.2.1]octane-8-carboxylate (Intermediate P12) (0.23 g, 0.90 mmol) was dissolved in a 4N solution of hydrogen chloride in 1,4-dioxane (8 mL). The reaction mixture was stirred overnight at room temperature. The solvent was evaporated in vacuo. The crude mixture (0.17 g, 0.90 mmol) was dissolved in dry THF (10 mL) under a nitrogen atmosphere and triethylamine (0.27 g, 0.38 mL, 2.7 mmol) was added, followed by ((1,2,3,5,6,7-hexahydro-s-indacen-4-yl)carbamoyl)sulfamoyl chloride (Intermediate A4) (0.28 g, 0.90 mmol). The reaction mixture was stirred at room temperature overnight under a nitrogen atmosphere. The solvent was evaporated in vacuo. Purification by reversed phase column chromatography (see "Experimental Methods") gave the title compound (24 mg, 6%) as a white solid.

$^1$H NMR (CD$_3$OD) δ 6.95 (s, 1H), 4.06 (s, 2H), 2.96-2.80 (m, 7H), 2.71 (s, 6H), 2.36 (s, 1H), 2.15-1.99 (m, 6H), 1.96-1.70 (m, 7H), 1.66-1.56 (m, 2H).

LCMS: m/z 433 (M+H)$^+$ (ES$^+$).

Example 78: (1R,3s,5S)-3-(Diethylamino)-N-((1,2,3,5,6,7-hexahydro-s-indacen-4-yl)carbamoyl)-8-azabicyclo[3.2.1]octane-8-sulfonamide

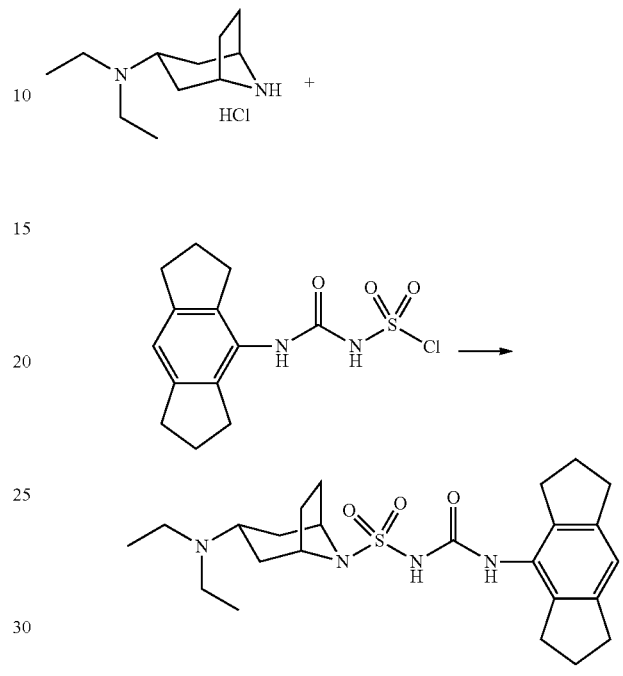

(1R,3s,5S)—N,N-Diethyl-8-azabicyclo[3.2.1]octan-3-amine hydrochloride (Intermediate P11) (0.17 g, 0.78 mmol) was dissolved in dry THF (10 mL) under a nitrogen atmosphere and triethylamine (0.32 g, 0.43 mL, 3.1 mmol) was added, followed by ((1,2,3,5,6,7-hexahydro-s-indacen-4-yl)carbamoyl)sulfamoyl chloride (Intermediate A4) (0.25 g, 0.78 mmol). The reaction mixture was stirred at room temperature overnight under a nitrogen atmosphere. The solvent was evaporated in vacuo. Purification by reversed phase column chromatography (see "Experimental Methods") gave the title compound (17 mg, 5%) as a white solid.

$^1$H NMR (CD$_3$OD) δ 6.90 (s, 1H), 4.40-4.19 (m, 2H), 3.61-3.42 (m, 1H), 3.18-2.91 (m, 4H), 2.93-2.67 (m, 8H), 2.35-2.10 (m, 2H), 2.10-1.84 (m, 8H), 1.75-1.61 (m, 2H), 1.32-1.12 (m, 6H).

LCMS: m/z 461 (M+H)$^+$ (ES$^+$); 459 (M−H)$^-$ (ES$^-$).

Example 7A: (1R,3r,5S)-3-(Dimethylamino)-N-((1,2,3,5,6,7-hexahydro-s-indacen-4-yl)carbamoyl)-8-azabicyclo[3.2.1]octane-8-sulfonamide

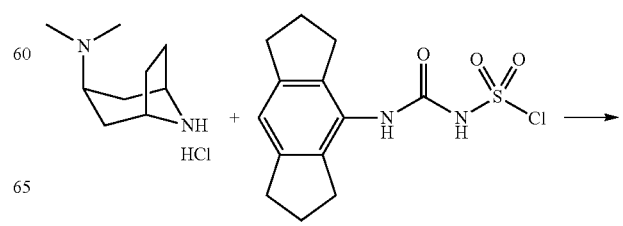

-continued

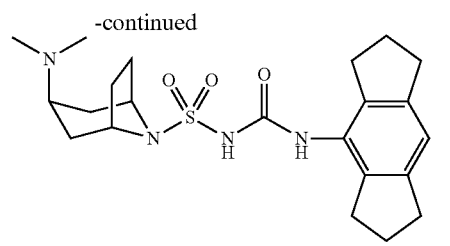
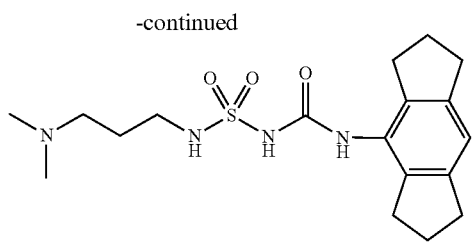

(1R,3r,5S)—N,N-Dimethyl-8-azabicyclo[3.2.1]octan-3-amine hydrochloride (Intermediate P16) (0.13 g, 0.51 mmol) was dissolved in dry THF (10 mL) under a nitrogen atmosphere and triethylamine (0.15 g, 0.21 mL, 1.53 mmol) was added, followed by ((1,2,3,5,6,7-hexahydro-s-indacen-4-yl)carbamoyl)sulfamoyl chloride (Intermediate A4) (0.16 g, 0.51 mmol). The reaction mixture was stirred at room temperature overnight under a nitrogen atmosphere. The solvent was evaporated in vacuo. Purification by reversed phase column chromatography (see "Experimental Methods") gave the title compound (17 mg, 8%) as a white solid.

$^1$H NMR (CD$_3$OD) δ 6.92 (s, 1H), 4.41-4.19 (m, 2H), 2.94-2.76 (m, 11H), 2.56-2.43 (m, 7H), 2.27-2.16 (m, 2H), 2.14-1.96 (m, 5H), 1.81-1.62 (m, 2H), 1.57-1.39 (m, 2H).

LCMS: m/z 433 (M+H)$^+$ (ES$^+$); 431 (M−H)$^−$ (ES$^−$).

Example 80: 3-(N-Methyl-N-((1-methylpyrrolidin-2-yl)methyl)sulfamoyl)-1-(1,2,3,5,6,7-hexahydro-s-indacen-4-yl)urea, potassium salt

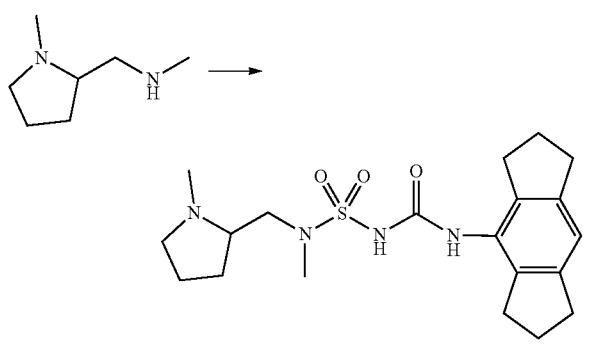

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N-methyl-1-(1-methylpyrrolidin-2-yl)methanamine (racemic Intermediate P23; 128 mg, 1.00 mmol) to afford the title compound (9 mg, 7%) as a white solid.

$^1$H NMR (CD$_3$OD) δ 6.91 (s, 1H), 3.58 (m, 2H), 3.22 (m, 2H), 2.82 (m, 15H), 2.03 (m, 8H).

LCMS: m/z 407 (M+H)$^+$ (ES$^+$); 405 (M−H)$^−$ (ES$^−$).

Example 81: 3-(N-(3-(Dimethylamino)propyl)sulfamoyl)-1-(1,2,3,5,6,7-hexahydro-s-indacen-4-yl)urea, potassium salt

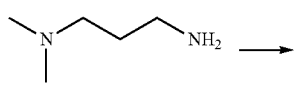

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1,N1-dimethylpropane-1,3-diamine (102 mg, 1.00 mmol) to afford the title compound (26 mg, 22%) as a white solid.

$^1$H NMR (CD$_3$OD) δ 6.91 (s, 1H), 3.16 (t, 2H), 2.82 (m, 10H), 2.60 (s, 6H), 2.03 (m, 4H), 1.81 (t, 2H).

LCMS: m/z 381 (M+H)$^+$ (ES$^+$); 379 (M−H)$^−$ (ES$^−$).

Example 82: 2-((Dimethylamino)methyl)-N-((1,2,3,5,6,7-hexahydro-s-indacen-4-yl)carbamoyl)pyrrolidine-1-sulfonamide, potassium salt

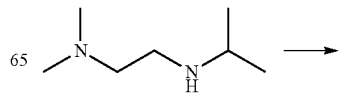

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N,N-dimethyl-1-(pyrrolidin-2-yl)methanamine (128 mg, 1.00 mmol) to afford the title compound (26 mg, 20%) as a white solid.

$^1$H NMR (CD$_3$OD) δ 6.91 (s, 1H), 4.36 (m, 1H), 3.51 (m, 1H), 3.21 (m, 1H), 3.05 (m, 2H), 2.82 (m, 14H), 2.60 (s, 6H), 2.03 (m, 9H), 1.54 (m, 1H).

LCMS: m/z 407 (M+H)$^+$ (ES$^+$); 405 (M−H)$^−$ (ES$^−$).

Example 83: 3-(N-(2-(Dimethylamino)ethyl)-N-isopropylsulfamoyl)-1-(1,2,3,5,6,7-hexahydro-s-indacen-4-yl)urea, potassium salt

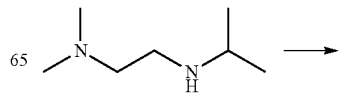

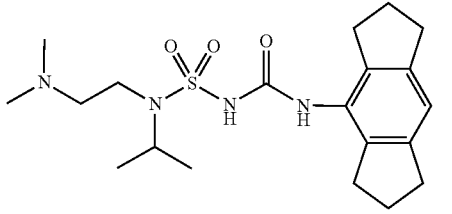

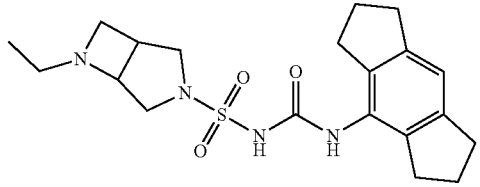

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N1-isopropyl-N2,N2-dimethylethane-1,2-diamine (130 mg, 1.00 mmol) to afford the title compound (9 mg, 7%) as a white solid.
$^1$H NMR (CD$_3$OD) δ 6.91 (s, 1H), 4.12 (m, 1H), 3.43 (t, 2H), 3.19 (t, 2H), 2.82 (m, 14H), 2.03 (m, 4H), 1.21 (s, 6H).
LCMS: m/z 409 (M+H)$^+$ (ES$^+$); 407 (M–H)$^-$ (ES$^-$).

Example 84: 3-(N-Methyl-N-((1-methylazetidin-3-yl)methyl)sulfamoyl)-1-(1,2,3,5,6,7-hexahydro-s-indacen-4-yl)urea, potassium salt

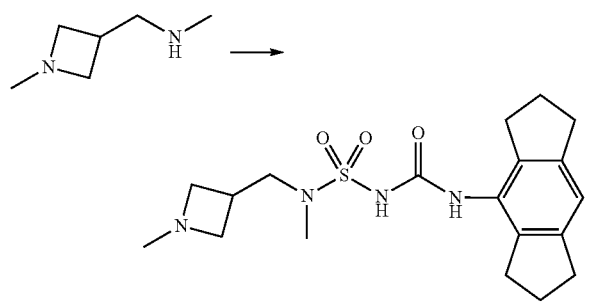

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and N-methyl-1-(1-methylazetidin-3-yl)methanamine (116 mg, 1.02 mmol) to afford the title compound (15 mg, 12%) as a white solid.
$^1$H NMR (CD$_3$OD) δ 6.91 (s, 1H), 4.07 (m, 4H), 3.43 (m, 2H), 2.97 (m, 1H), 2.87 (s, 3H), 2.82 (m, 8H), 2.80 (s, 3H), 2.03 (m, 4H).
LCMS: m/z 393 (M+H)$^+$ (ES$^+$); 391 (M–H)$^-$ (ES$^-$).

Example 8t: 6-Ethyl-N-((1,2,3,5,6,7-hexahydro-s-indacen-4-yl)carbamoyl)-3,6-diazabicyclo[3.2.0]heptane-3-sulfonamide

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (142 mg, 0.45 mmol), 6-ethyl-3,6-diazabicyclo[3.2.0]heptane dihydrochloride (Intermediate P20) (59 mg, 0.30 mmol) and triethylamine (0.12 mL, 0.9 mmol) to afford the title compound (0.9 mg, 0.7%) as a white solid.
$^1$H NMR (CD$_3$OD) δ 6.90 (s, 1H), 3.81 (m, 1H), 3.57-3.50 (m, 2H), 3.28-3.12 (m 4H), 3.10-3.04 (m, 1H), 2.89-2.77 (m, 10H), 2.09-1.98 (m, 4H), 1.14 (t, 3H).
LCMS: m/z 405 (M+H)$^+$ (ES$^+$); 403 (M–H)$^-$ (ES$^-$).

Example 86: N-((1,2,3,5,6,7-Hexahydro-s-indacen-4-yl)carbamoyl)-6-methyl-3,6-diazabicyclo[3.2.0]heptane-3-sulfonamide

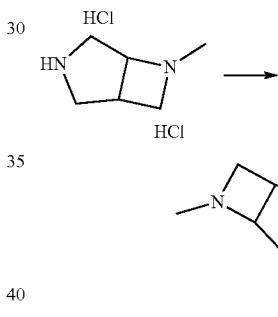

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (151 mg, 0.48 mmol), 6-methyl-3,6-diazabicyclo[3.2.0]heptane dihydrochloride (Intermediate P19) (59 mg, 0.32 mmol) and triethylamine (0.13 mL, 0.96 mmol) to afford the title compound (3 mg, 2%) as a white solid.
$^1$H NMR (CD$_3$OD) δ 6.91 (s, 1H), 4.71-4.59 (m, 1H), 4.05-3.93 (m, 1H), 3.89-3.71 (m, 2H), 3.52 (d, 2H), 3.25-3.00 (m, 2H), 2.92-2.70 (m, 11H), 2.08-1.95 (m, 4H).
LCMS: m/z 391 (M+H)$^+$ (ES$^+$); 389 (M–H)$^-$ (ES$^-$).

Example 87: N-((1,2,3,5,6,7-Hexahydro-s-indacen-4-yl)carbamoyl)-6-isopropyl-3,6-diazabicyclo[3.2.0]heptane-3-sulfonamide, potassium salt

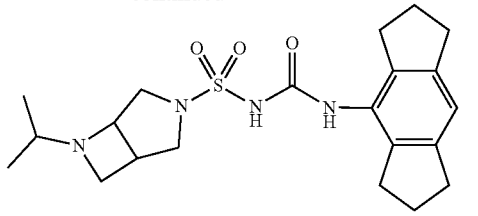

Prepared as described for (1R,4R)—N-((1,2,3,5,6,7-hexahydro-s-indacen-4-yl)carbamoyl)-5-methyl-2,5-diazabicyclo[2.2.1]heptane-2-sulfonamide, potassium salt (Example 43) using ((1,2,3,5,6,7-hexahydro-s-indacen-4-yl)carbamoyl)sulfamoyl chloride (Intermediate A4) (100 mg, 0.32 mmol), 6-isopropyl-3,6-diazabicyclo[3.2.0]heptane dihydrochloride (Intermediate P21) (121 mg, 0.57 mmol), triethylamine (96 mg, 0.95 mmol), sodium hydride (60%) (19 mg, 0.32 mmol) and DABCO (100 mg, 0.63 mmol) to afford the title compound (1 mg, 1%) as a white solid.

$^1$H NMR (CD$_3$OD) δ 6.91 (s, 1H), 4.34 (m, 1H), 3.61 (m, 2H), 3.41 (m, 2H), 3.12 (m, 3H), 3.04 (m, 1H), 2.82 (m, 8H), 2.03 (m, 4H), 1.01 (d, 3H), 0.98 (d, 2H).

LCMS: m/z 419 (M+H)$^+$ (ES$^+$); 417 (M–H)$^-$ (ES$^-$).

Example 88: 3-((S)—N-(1-Methylpyrrolidin-3-yl)sulfamoyl)-1-(1,2,3,5,6,7-hexahydro-s-indacen-4-yl)urea, potassium salt

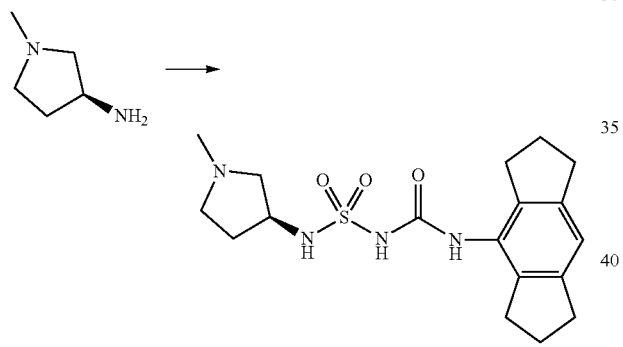

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (S)-1-methylpyrrolidin-3-amine (100 mg, 1.00 mmol) to afford the title compound (4 mg, 3%) as a white solid.

$^1$H NMR (CD$_3$OD) δ 6.91 (s, 1H), 3.95 (m, 1H), 3.01 (dd, 1H), 2.82 (m, 8H), 2.56 (m, 3H), 2.38 (s, 3H), 2.22 (m, 1H), 2.03 (m, 6H), 1.80 (m, 1H).

LCMS: m/z 379 (M+H)$^+$ (ES$^+$); 377 (M–H)$^-$ (ES$^-$).

Example 89: 3-((R)—N-(1-Methylpyrrolidin-3-yl)sulfamoyl)-1-(1,2,3,5,6,7-hexahydro-s-indacen-4-yl)urea, potassium salt

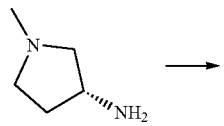

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (R)-1-methylpyrrolidin-3-amine (100 mg, 1.00 mmol) to afford the title compound (11 mg, 9%) as a white solid.

$^1$H NMR (CD$_3$OD) δ 6.91 (s, 1H), 3.95 (m, 1H), 3.01 (dd, 1H), 2.82 (m, 8H), 2.56 (m, 3H), 2.38 (s, 3H), 2.22 (m, 1H), 2.03 (m, 6H), 1.80 (m, 1H).

LCMS: m/z 379 (M+H)$^+$ (ES$^+$); 377 (M–H)$^-$ (ES$^-$).

Example 90: N-((1,2,3,5,6,7-Hexahydro-s-indacen-4-yl)carbamoyl)-4-methyl-1,4-diazepane-1-sulfonamide, potassium salt

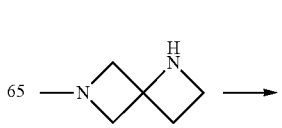

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-methyl-1,4-diazepane (114 mg, 1.00 mmol) to afford the title compound (13 mg, 10%) as a white solid.

$^1$H NMR (CD$_3$OD) δ 6.91 (s, 1H), 3.55 (m, 2H), 3.48 (t, 2H), 2.99 (m, 2H), 2.82 (m, 8H), 2.67 (m, 2H), 2.40 (s, 3H), 2.03 (m, 4H), 1.95 (m, 2H).

LCMS: m/z 393 (M+H)$^+$ (ES$^+$); 391 (M–H)$^-$ (ES$^-$).

Example 91: N-((1,2,3,5,6,7-Hexahydro-s-indacen-4-yl)carbamoyl)-6-methyl-1,6-diazaspiro[3.3]heptane-1-sulfonamide, potassium salt

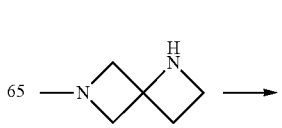

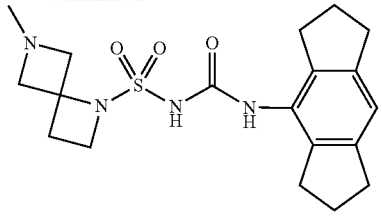
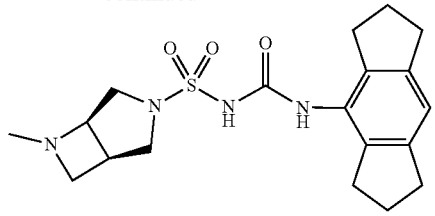

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 6-methyl-1,6-diazaspiro[3.3]heptane (114 mg, 1.00 mmol) to afford the title compound (4 mg, 3%) as a white solid.

$^1$H NMR (CD$_3$OD) δ 6.91 (s, 1H), 4.50 (d, 2H), 4.05 (d, 2H), 3.73 (t, 2H), 2.82 (m, 8H), 2.78 (s, 3H), 2.42 (t, 2H), 2.03 (m, 4H).

LCMS: m/z 391 (M+H)$^+$ (ES$^+$); 389 (M−H)$^−$ (ES$^−$).

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (116 mg, 0.37 mmol) and (1S,5R)-6-methyl-3,6-diazabicyclo[3.2.0]heptane 2,2,2-trifluoroacetate (125 mg, 0.37 mmol) with DABCO (124 mg, 1.10 mmol) to afford the title compound (1 mg, 1%) as a white solid.

$^1$H NMR (CD$_3$OD) δ 6.85 (s, 1H), 3.98 (m, 1H), 3.60 (d, 1H), 3.40 (t, 1H), 3.20 (m, 1H), 3.05 (m, 2H), 2.95 (m, 1H), 2.82 (m, 9H), 2.30 (s, 3H), 2.03 (m, 4H).

LCMS: m/z 391 (M+H)$^+$ (ES$^+$); 389 (M−H)$^−$ (ES$^−$).

Example 92: (1S,5S)—N-((1,2,3,5,6,7-Hexahydro-s-indacen-4-yl)carbamoyl)-6-methyl-3,6-diazabicyclo[3.2.0]heptane-3-sulfonamide, potassium salt Example 94: N-((1,2,3,5,6,7-Hexahydro-s-indacen-4-yl)carbamoyl)-3-methyl-3,6-diazabicyclo[3.2.0]heptane-6-sulfonamide, potassium salt

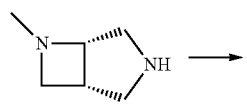

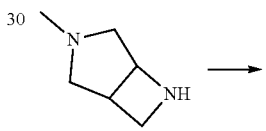

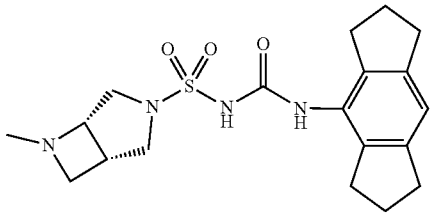

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (116 mg, 0.37 mmol) and (1R,5S)-6-methyl-3,6-diazabicyclo[3.2.0]heptane 2,2,2-trifluoroacetate (125 mg, 0.37 mmol) with DABCO (124 mg, 1.10 mmol) to afford the title compound (22 mg, 15%) as a white solid.

$^1$H NMR (CD$_3$OD) δ 6.89 (s, 1H), 4.08 (m, 1H), 3.67 (d, 1H), 3.50 (t, 1H), 3.15 (m, 1 Ho, 2.99 (m, 1H), 2.82 (m, 12H), 2.40 (s, 3H), 2.03 (m, 4H).

LCMS: m/z 391 (M+H)$^+$ (ES$^+$); 389 (M−H)$^−$ (ES$^−$).

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 3-methyl-3,6-diazabicyclo[3.2.0]heptane (100 mg, 0.89 mmol) to afford the title compound (1.3 mg, 1%) as a white solid.

$^1$H NMR (CD$_3$OD) δ 6.91 (s, 1H), 4.17 (t, 1H), 3.59 (d, 2H), 3.42 (m, 1H), 3.18 (m, 1H), 2.82 (m, 14H), 2.70 (m, 1H), 2.03 (m, 4H).

LCMS: m/z 391 (M+H)$^+$ (ES$^+$).

Example 93: (1R,5R)—N-((1,2,3,5,6,7-Hexahydro-s-indacen-4-yl)carbamoyl)-6-methyl-3,6-diazabicyclo[3.2.0]heptane-3-sulfonamide, potassium salt Example 95: 3-((R)—N-Methyl-N-((1-methylpyrrolidin-2-yl)methyl) sulfamoyl)-1-(1,2,3,5,6,7-hexahydro-s-indacen-4-yl)urea, potassium salt

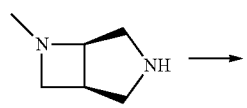

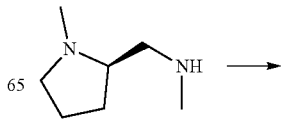

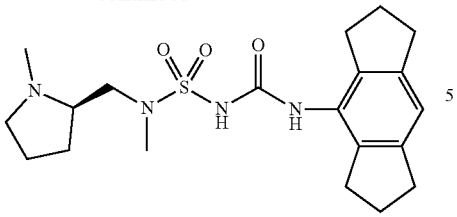

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and (R)—N-methyl-1-(1-methylpyrrolidin-2-yl)methanamine (Intermediate P23; 100 mg, 0.90 mmol) to afford the title compound (6 mg, 5%) as a white solid.

$^1$H NMR (CD$_3$OD) δ 6.91 (s, 1H), 3.78 (d, 2H), 3.42 (m, 1H), 3.08 (m, 2H), 2.82 (m, 14H), 2.20 (m, 2H), 2.03 (m, 6H).

LCMS: m/z 408 (M+H)$^+$ (ES$^+$).

Example 96: N-((1,2,3,5,6,7-Hexahydro-s-indacen-4-yl)carbamoyl)-1-methylhexahydropyrrolo[3,4-b]pyrrole-5(1H)-sulfonamide, potassium salt

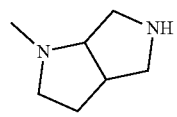 

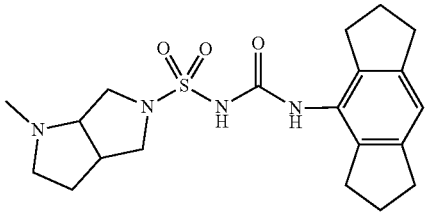

Prepared as described for 3-(N-(2-(dimethylamino)-2-methylpropyl)sulfamoyl)-1-(1,2,3,5,6,7-hexahydro-s-indacen-4-yl)urea, potassium salt (Example 57) using ((1,2,3,5,6,7-hexahydro-s-indacen-4-yl)carbamoyl)sulfamoyl chloride (Intermediate A4) (100 mg, 0.32 mmol) and 1-methyloctahydropyrrolo[3,4-b]pyrrole (80 mg, 0.63 mmol) with triethylamine (73 mg, 0.72 mmol) to afford the title compound (14 mg, 11%) as a white solid.

$^1$H NMR (CD$_3$OD) δ 6.91 (s, 1H), 3.41 (d, 1H), 3.22 (d, 1H), 3.17 (m, 3H), 3.05 (m, 1H), 2.99 (m, 1H), 2.82 (m, 10H), 2.42 (s, 3H), 2.12 (m, 1H), 2.03 (m, 4H).

LCMS: m/z 405 (M+H)$^+$ (ES$^+$); 403 (M−H)$^−$ (ES$^−$).

Example 97: N-((1,2,3,5,6,7-Hexahydro-s-indacen-4-yl)carbamoyl)-1-methyloctahydro-6H-pyrrolo[3,4-b]pyridine-6-sulfonamide

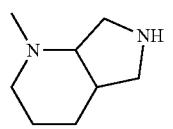 

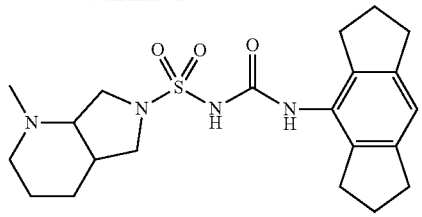

Chlorosulfonyl isocyanate (81.7 mg, 1 eq, 0.58 mmol) was dissolved in DCM (20 mL) under N$_2$ atmosphere and cooled to 0° C. 1,2,3,5,6,7-Hexahydro-s-indacen-4-amine (100 mg, 1 eq, 0.58 mmol) was added and the mixture was stirred for 10 minutes. 1-Methyloctahydro-1H-pyrrolo[3,4-b]pyridine (100 mg, 1.24 eq, 0.72 mmol) and TEA (0.1 mL, 1 eq, 0.7 mmol) were added and the mixture was allowed to reach room temperature over 1 hour. The suspension was evaporated to near dryness and submitted for reversed phase column chromatography to afford the title compound (32 mg, 13%) as a white solid.

$^1$H NMR (CD$_3$OD) δ 6.91 (s, 1H), 3.78 (d, 1H), 3.50 (m, 2H), 3.38 (t, 1H), 3.07 (m, 1H), 2.82 (m, 10H), 2.48 (m, 1H), 2.41 (s, 3H), 2.03 (m, 4H), 1.60 (m, 4H).

LCMS: m/z 419 (M+H)$^+$ (ES$^+$).

Example 98: N-((1,2,3,5,6,7-Hexahydro-s-indacen-4-yl)carbamoyl)-1-methyloctahydro-6H-pyrrolo[2,3-c]pyridine-6-sulfonamide

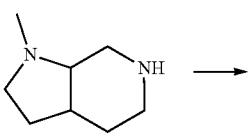

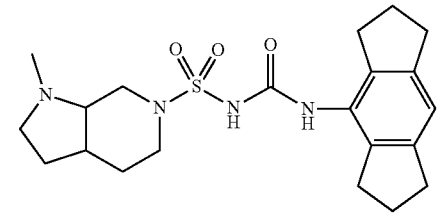

Prepared as described for N-((1,2,3,5,6,7-hexahydro-s-indacen-4-yl)carbamoyl)-1-methyloctahydro-6H-pyrrolo[3,4-b]pyridine-6-sulfonamide (Example 97) using chlorosulfonyl isocyanate (49 mg, 0.35 mmol), 1,2,3,5,6,7-hexahydro-s-indacen-4-amine (60 mg, 0.35 mmol) and 1-methyloctahydro-1H-pyrrolo[2,3-c]pyridine (100 mg, 0.73 mmol) with triethylamine (73 mg, 0.72 mmol) to afford the title compound (8 mg, 6%) as a white solid.

$^1$H NMR (CD$_3$OD) δ 6.91 (s, 1H), 4.09 (d, 1H), 3.58 (m, 1H), 3.43 (m, 1H), 2.99 (m, 2H), 2.82 (m, 10H), 2.79 (s, 3H), 2.42 (m, 1H), 2.12 (m, 1H), 2.03 (m, 4H), 1.63 (m, 3H).

LCMS: m/z 419 (M+H)$^+$ (ES$^+$); 417 (M−H)$^−$ (ES$^−$).

Example 99: N-((1,2,3,5,6,7-Hexahydro-s-indacen-4-yl)carbamoyl)-5-methylhexahydropyrrolo[3,4-c]pyrrole-2(1H)-sulfonamide

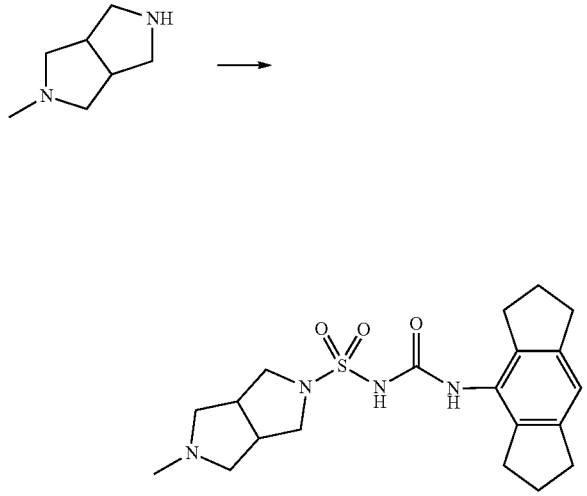

Prepared as described for N-((1,2,3,5,6,7-hexahydro-s-indacen-4-yl)carbamoyl)-1-methyloctahydro-6H-pyrrolo[3,4-b]pyridine-6-sulfonamide (Example 97) using chlorosulfonyl isocyanate (82 mg, 0.58 mmol), 1,2,3,5,6,7-hexahydro-s-indacen-4-amine (100 mg, 0.58 mmol) and 2-methyloctahydropyrrolo[3,4-c]pyrrole (146 mg, 1.15 mmol) with triethylamine (73 mg, 0.72 mmol) to afford the title compound (4 mg, 2%) as a white solid.

$^1$H NMR (CD$_3$OD) δ 6.91 (s, 1H), 3.38 (m, 2H), 3.23 (m, 4H), 3.12 (m, 4H), 2.82 (m, 8H), 2.65 (s, 3H), 2.03 (m, 4H).

LCMS: m/z 405 (M+H)$^+$ (ES$^+$); 403 (M−H)$^−$ (ES$^−$).

Example 100: N-((1,2,3,5,6,7-Hexahydro-s-indacen-4-yl)carbamoyl)-6-methyl-3,6-diazabicyclo[3.1.1]heptane-3-sulfonamide

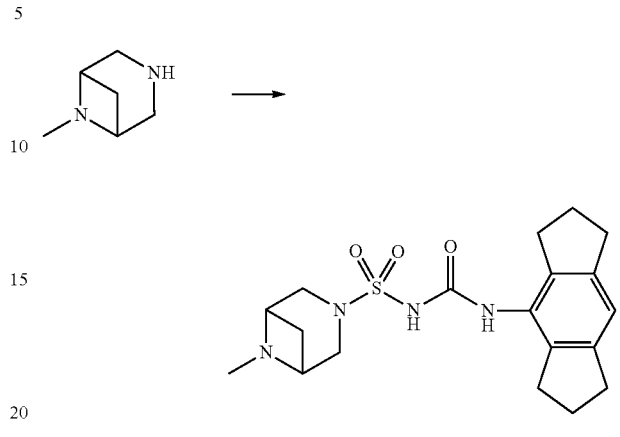

Chlorosulfonyl isocyanate (81.7 mg, 1 eq, 0.58 mmol) was dissolved in DCM (20 mL) under N$_2$ atmosphere and cooled to 0° C. 1,2,3,5,6,7-Hexahydro-s-indacen-4-amine (100 mg, 1 eq, 0.58 mmol) was added and the mixture was stirred for 10 minutes. 6-Methyl-3,6-diazabicyclo[3.1.1]heptane hydrochloride (Intermediate P22) (100 mg, 1.15 eq, 0.67 mmol), pre-treated with NaH (69 mg, 1.73 mmol) and DABCO (129 mg, 1.15 mmol) in DCM (5 mL), was added and the mixture was allowed to reach room temperature over 1 hour. The suspension was evaporated to near dryness and submitted for reversed phase column chromatography to afford the title compound (2 mg, 1%) as a white solid.

$^1$H NMR (CD$_3$OD) δ 6.91 (s, 1H), 3.85 (m, 2H), 3.62 (m, 2H), 2.82 (m, 15H), 2.03 (m, 4H).

LCMS: m/z 391 (M+H)$^+$ (ES$^+$).

The compounds of examples 101-108 were synthesised by methods analogous to those outlined above and below.

TABLE 1

| | $^1$H NMR and MS data | | | |
|---|---|---|---|---|
| Ex | Structure and Name | 1H NMR spectrum | MS | MW |
| 101 | 3-(N-Methyl-N-(1-methylpyrrolidin-3-yl)sulfamoyl)-1-(5-(2-cyanopyridin-4-yl)-4-fluoro-6-isopropylphenyl)urea | $^1$H NMR (Methanol-d$_4$) δ 8.71 (dd, 1H), 7.97 (d, 1H), 7.73 (dd, 1H), 7.19 (dd, 1H), 7.02 (dd, 1H), 4.44 (q, 1H), 3.09-3.00 (m, 2H), 3.00-2.91 (m, 2H), 2.91-2.71 (m, 1H), 2.64 (s, 3H), 2.59 (s, 3H), 2.05 (dq, 1H), 1.98-1.82 (m, 1H), 1.35-1.16 (m, 6H). | m/z 475.2 (M + H)$^+$ (ES$^+$) | 474.56 |

TABLE 1-continued

¹H NMR and MS data

| Ex | Structure and Name | 1H NMR spectrum | MS | MW |
|---|---|---|---|---|
| 102 | 3-(N-Methyl-N-(1-methylpyrrolidin-2-yl)methyl)sulfamoyl)-1-(5-(2-cyanopyridin-4-yl)-4-fluoro-6-isopropylphenyl)urea | ¹H NMR (Methanol-d₄) δ 8.73 (d, 1H), 8.03 (d, 1H), 7.78 (d, 1H), 7.21 (dd, 1H), 7.07 (dd, 1H), 4.57 (m, 1H), 3.37-3.07 (m, 3H), 2.91 (m, 2H), 2.79 (s, 3H), 2.65 (s, 3H), 2.22-1.83 (m, 4H), 1.25 (dd, 6H). | m/z 489.2 (M + H)⁺ (ES⁺) | 488.58 |
| 103 | 3-(N-Methyl-N-(1-methylpyrrolidin-3-yl)sulfamoyl)-1-(5-(2-cyanopyridin-4-yl)-2,3-dihydro-1H-inden-4-yl)urea | ¹H NMR (Methanol-d₄) δ 8.68 (dd, 1H), 7.95 (dd, 1H), 7.73 (dd, 1H), 7.32-7.14 (m, 3H), 4.51 (q, 1H), 3.26-3.13 (m, 1H), 3.11-2.89 (m, 6H), 2.70 (d, 6H), 2.14 (m, 3H), 2.09-1.89 (m, 1H). | m/z 455.2 (M + H)⁺ (ES⁺) | 454.55 |
| 104 | N-((5-(2-Cyanopyridin-4-yl)-2,3-dihydro-1H-inden-4-yl)carbamoyl)-1-methylhexahydropyrrolo[3,4-b]pyrrole-5(1H)-sulfonamide | ¹H NMR (Methanol-d₄) δ 8.67 (dd, 1H), 7.95 (dd, 1H), 7.73 (dd, 1H), 7.21 (q, 2H), 3.62-3.40 (m, 2H), 3.16-2.88 (m, 9H), 2.81 (dt, 1H), 2.72 (s, 3H), 2.38-2.25 (m, 1H), 2.25-2.04 (m, 2H), 1.57 (dd, 1H). | m/z 467.2 (M + H)⁺ (ES⁺) | 466.56 |
| 105 | N-((2-(2-Cyanopyridin-4-yl)-4-fluoro-6-isopropylphenyl)carbamoyl)-1-methylhexahydropyrrolo[3,4-b]pyrrole-5(1H)-sulfonamide | ¹H NMR (Methanol-d₄) δ 8.71 (dd, 1H), 7.97 (d, 1H), 7.74 (dd, 1H), 7.19 (dd, 1H), 7.02 (dd, 1H), 3.46 (dd, 2H), 3.04-2.86 (m, 6H), 2.88-2.73 (m, 1H), 2.68 (s, 3H), 2.32-2.21 (m, 1H), 1.67-1.41 (m, 1H), 1.37-1.13 (m, 6H). | m/z 487.2 (M + H)⁺ (ES⁺) | 486.57 |

TABLE 1-continued

<sup>1</sup>H NMR and MS data

| Ex | Structure and Name | 1H NMR spectrum | MS | MW |
|---|---|---|---|---|
| 106 | 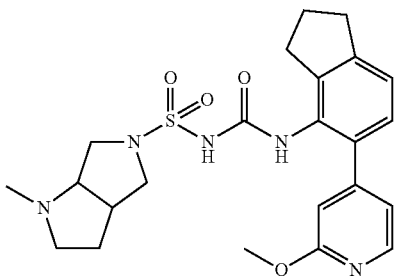<br>N-((5-(2-Methoxypyridin-4-yl)-2,3-dihydro-1H-inden-4-yl)carbamoyl)-1-methylhexahydropyrrolo[3,4-b]pyrrole-5(1H)-sulfonamide, potassium salt | $^1$H NMR (Methanol-$d_4$) δ 8.12 (dd, 1H), 7.27-7.10 (m, 2H), 7.02 (dd, 1H), 6.85 (d, 1H), 3.93 (s, 3H), 3.55 (dd, 2H), 3.18-3.05 (m, 3H), 2.96 (dt, 6H), 2.80 (dt, 1H), 2.72 (s, 3H), 2.30 (dt, 1H), 2.11 (p, 2H), 1.62 (ddd, 1H). | m/z 472.2 (M + H)$^+$ (ES$^+$) | 471.58 |
| 107 | 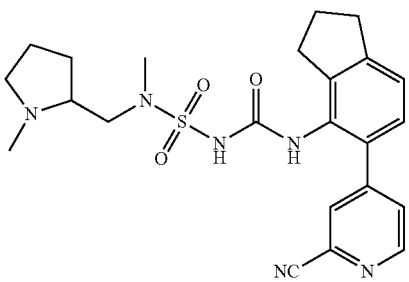<br>3-(N-Methyl-N-((1-methylpyrrolidin-2-yl)methyl)sulfamoyl)-1-(5-(2-cyanopyridin-4-yl)-2,3-dihydro-1H-inden-4-yl)urea | $^1$H NMR (Methanol-$d_4$) δ 8.68 (dd, 1H), 8.03 (dd, 1H), 7.78 (dd, 1H), 7.23 (d, 2H), 3.72 (dd, 1H), 3.51 (d, 1H), 3.19-3.09 (m, 1H), 3.09-2.91 (m, 6H), 2.79 (s, 3H), 2.71 (s, 3H), 2.13 (p, 2H), 1.99 (m, 3H), 1.65 (m, 1H). | m/z 469.4 (M + H)$^+$ (ES$^+$) | 468.58 |
| 108 | 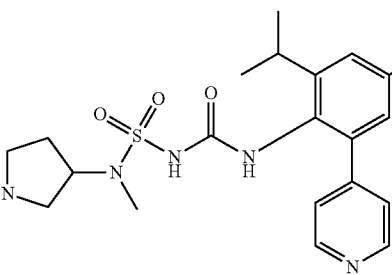<br>3-(N-Methyl-N-(1-methylpyrrolidin-3-yl)sulfamoyl)-1-(5-(pyridin-4-yl)-4-fluoro-6-isopropylphenyl)urea | $^1$H NMR (300 MHz, Methanol-$d_4$) δ 8.57 (d, 2H), 7.52 (d, 2H), 7.18 (dd, 1H), 6.98 (dd, 1H), 4.43 (m, 1H), 2.98-2.82 (m, 3H), 2.80-2.70 (m, 2.62 (s, 3H), 2.54 (s, 3H), 2.05-1.80 (m, 2H), 1.22 (d, 6H). | m/z 450.2 (M + H)$^+$ (ES$^+$) m/z 448.2 (M − H)$^−$ (ES$^−$) | 449.55 |

Example 109: 1-(5-Isopropyl-2-methyl-3-(4-pyridyl)imidazol-4-yl)-3-(methyl-(1-methylpyrrolidin-3-yl)sulfamoyl)urea

Step A: (4-(Dimethylamino)pyridin-1-ium-1-carbonyl)(N-methyl-N-(1-methylpyrrolidin-3-yl)sulfamoyl)amide

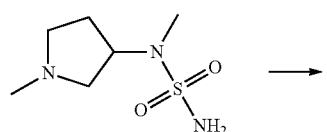 →

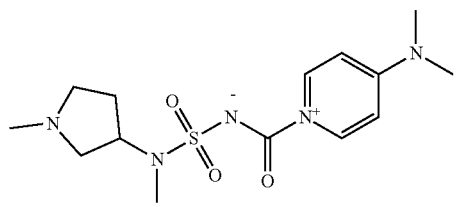

A solution of N,N-dimethylpyridin-4-amine (366 mg, 3.00 mmol, 2 eq) and 1-methyl-3-[methyl(sulfamoyl)amino]pyrrolidine (Intermediate P26) (0.29 g, 1.50 mmol, 1 eq) in MeCN (8 mL) was stirred at 20° C. for 30 minutes. Then diphenyl carbonate (353 mg, 1.65 mmol, 1.1 eq) was added.

The resulting mixture was stirred at 20° C. for 12 hours. The mixture (theoretical amount: 0.53 g, crude) was used directly in the next step.

Step B: 1-(5-Isopropyl-2-methyl-3-(4-pyridyl)imidazol-4-yl)-3-(methyl-(1-methylpyrrolidin-3-yl)sulfamoyl)urea

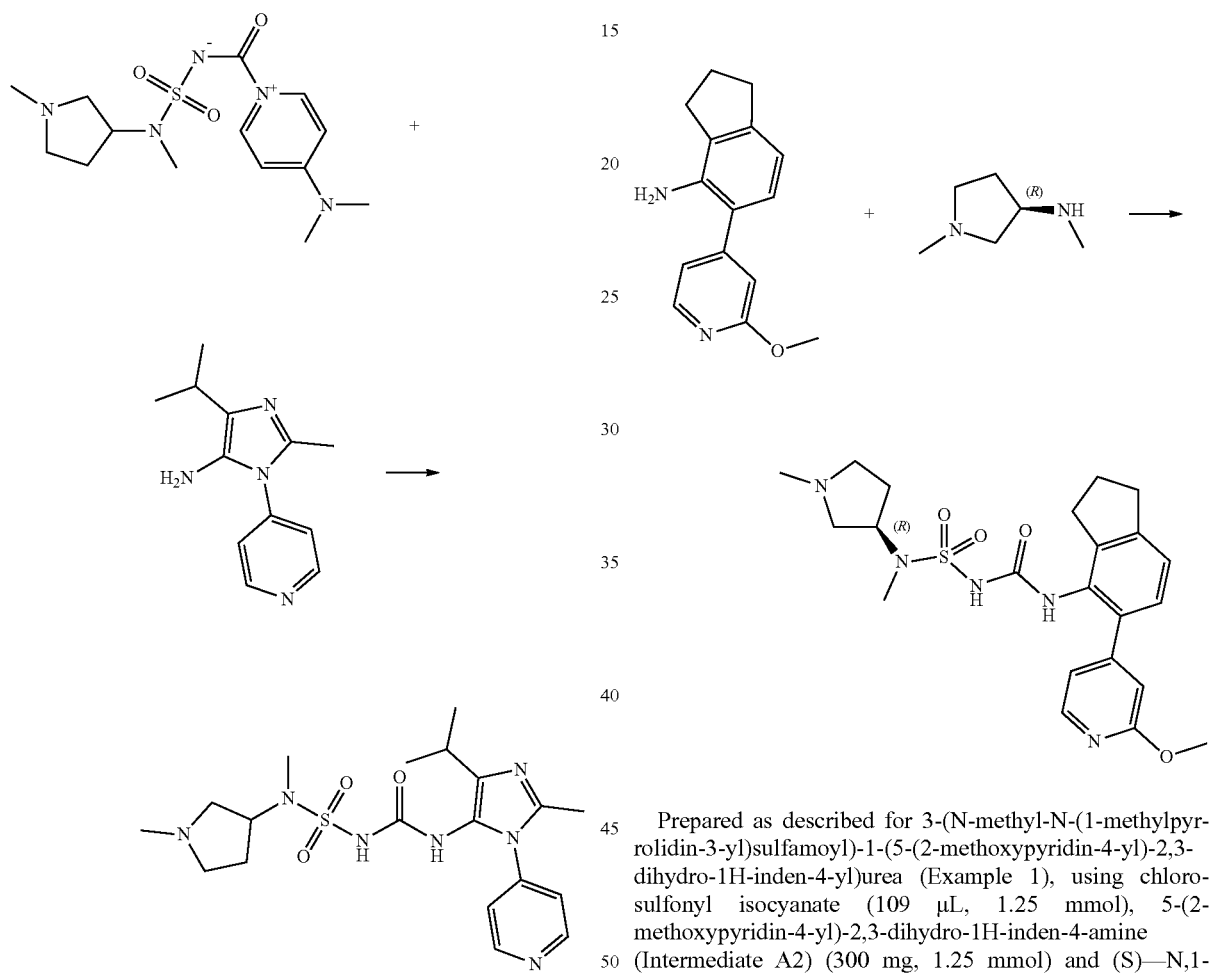

To a mixture of 4-isopropyl-2-methyl-1-(pyridin-4-yl)-1H-imidazol-5-amine (Intermediate A8) (0.2 g, 791.32 μmol, 1 eq, HCl salt) in MeCN (1 mL) was added a solution of (4-(dimethylamino)pyridin-1-ium-1-carbonyl)(N-methyl-N-(1-methylpyrrolidin-3-yl)sulfamoyl)amide (the reaction mixture of step A) in MeCN (8 mL). The resulting mixture was heated to 70° C. and stirred for 30 minutes under $N_2$. Then the reaction mixture was concentrated in vacuo. The residue was purified by reversed phase flash chromatography (0.1% $NH_3 \cdot H_2O$-MeCN) and then further purified by prep HPLC (column: Waters XBridge C18, 150 mm×25 mm×5 μm; mobile phase [A: water (10 mM $NH_4HCO_3$), B: MeCN]; B %: 1%-15%, 10 minutes) to give the title compound (25.13 mg, 7% yield over two steps, 100% purity on LCMS) as a white solid.

$^1$H NMR (400 MHz, $CD_3OD$) δ 8.70 (d, J=6.0 Hz, 2H), 7.50-7.48 (m, 2H), 4.48-4.44 (m, 1H), 3.30-2.92 (m, 5H), 2.74 (s, 3H), 2.63 (s, 3H), 2.29 (s, 3H), 2.15-1.98 (m, 2H), 1.27 (d, J=6.8 Hz, 6H). 2×NH were missing.

LCMS: m/z 436.1 (M+H)$^+$ (ES$^+$).

Example 110: (R)-3-(N-Methyl-N-(1-methylpyrrolidin-3-yl)sulfamoyl)-1-(5-(2-methoxypyridin-4-yl)-2,3-dihydro-1H-inden-4-yl)urea, potassium salt Prepared as described for 3-(N-methyl-N-(1-methylpyrrolidin-3-yl)sulfamoyl)-1-(5-(2-methoxypyridin-4-yl)-2,3-dihydro-1H-inden-4-yl)urea (Example 1), using chlorosulfonyl isocyanate (109 μL, 1.25 mmol), 5-(2-methoxypyridin-4-yl)-2,3-dihydro-1H-inden-4-amine (Intermediate A2) (300 mg, 1.25 mmol) and (S)—N,1-dimethylpyrrolidin-3-amine (0.19 mL, 1.50 mmol), except that a solution of (S)—N,1-dimethylpyrrolidin-3-amine and triethylamine (0.21 mL, 1.50 mmol) in DCM (5 mL) was added to the reaction mixture and the reaction was allowed to reach room temperature over one hour. Then the mixture was evaporated to dryness in vacuo. The residue was suspended in tetrahydrofuran, and then potassium tert-butoxide (280 mg, 2.50 mmol) was added. The suspension was sonicated for 15 minutes and then concentrated in vacuo. The crude product was purified by reversed phase chromatography to afford the title compound (24 mg, 4%) as a white solid.

$^1$H NMR ($CD_3OD$) δ 8.11 (dd, 1H), 7.19 (d, 1H), 7.12 (d, 1H), 7.02 (dd, 1H), 6.85 (d, 1H), 4.49 (p, 1H), 3.93 (s, 3H), 2.95 (dt, 5H), 2.87-2.77 (m, 3H), 2.71 (s, 3H), 2.50 (s, 3H), 2.18-2.02 (m, 3H), 1.89 (dq, 1H).

LCMS: m/z 460 (M+H)$^+$ (ES$^+$).

Example 11: (S)-3-(N-methyl-N-(1-methylpyrrolidin-3-yl)sulfamoyl)-1-(5-(2-methoxypyridin-4-yl)-2,3-dihydro-1H-inden-4-yl)urea, potassium salt

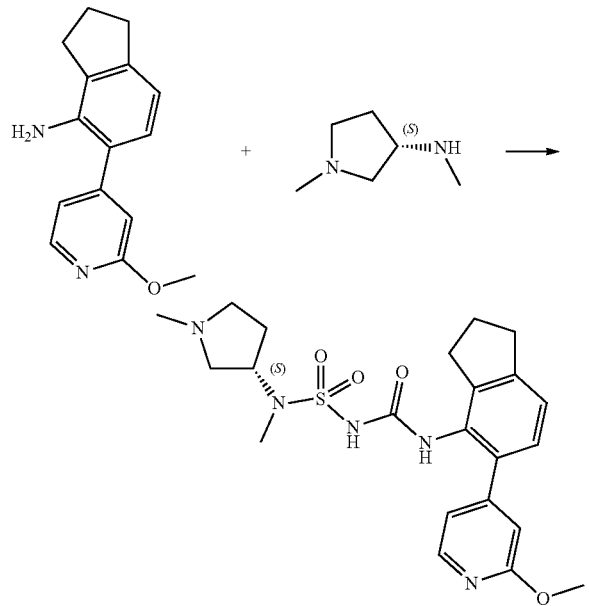

Prepared as described for 3-(N-methyl-N-(1-methylpyrrolidin-3-yl)sulfamoyl)-1-(5-(2-methoxypyridin-4-yl)-2,3-dihydro-1H-inden-4-yl)urea (Example 1), using chlorosulfonyl isocyanate (109 µL, 1.25 mmol), 5-(2-methoxypyridin-4-yl)-2,3-dihydro-1H-inden-4-amine (Intermediate A2) (300 mg, 1.25 mmol) and (R)—N,1-dimethylpyrrolidin-3-amine (0.19 mL, 1.50 mmol), except that a solution of (R)—N,1-dimethylpyrrolidin-3-amine and triethylamine (0.21 mL, 1.50 mmol) in DCM (5 mL) was added to the reaction mixture and the reaction was allowed to reach room temperature over one hour. Then the mixture was evaporated to dryness in vacuo. The residue was suspended in tetrahydrofuran, and then potassium tert-butoxide (280 mg, 2.50 mmol) was added. The suspension was stirred for 10 minutes and then concentrated in vacuo. The crude product was purified by reversed phase chromatography to afford the title compound (55 mg, 9%) as a white solid.

$^1$H NMR (CD$_3$OD) δ 8.11 (d, 1H), 7.20 (d, 1H), 7.12 (d, 1H), 7.01 (dd, 1H), 6.85 (d, 1H), 4.49 (p, 1H), 3.93 (s, 3H), 3.07-2.79 (m, 8H), 2.72 (s, 3H), 2.52 (s, 3H), 2.08 (dp, 3H), 1.91 (dq, 1H).

LCMS: m/z 460 (M+H)$^+$ (ES$^+$).

Example 112: (R)—(N-Methyl-N-((1-methylpyrrolidin-2-yl)methyl) sulfamoyl)((1,2,3,5-tetrahydro-s-indacen-4-yl)carbamoyl)amide, potassium salt

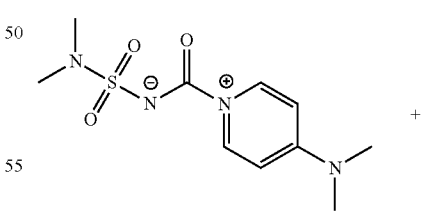

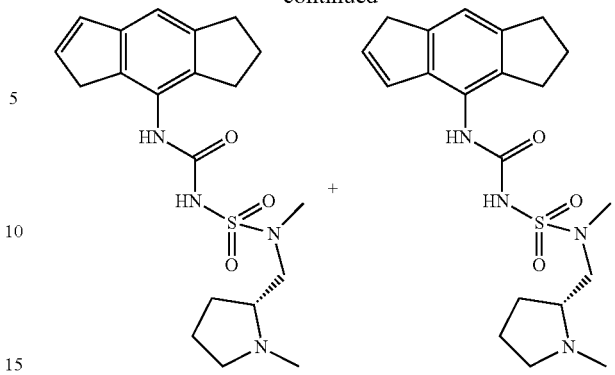

1,2,3,5-Tetrahydro-s-indacen-4-amine (Intermediate A5; 50 mg, 0.29 mmol) was dissolved in anhydrous THF (12.5 mL). The mixture was cooled in a bath of ice with brine. Next, chlorosulfonyl isocyanate (25 µL, 0.29 mmol) was added dropwise. After stirring for 10 minutes on ice, (R)—N-methyl-1-(1-methylpyrrolidin-2-yl)methanamine (Intermediate P23; 169 mg, 0.99 mmol) was added dropwise. After another 15 minutes stirring on ice, potassium tert-butoxide (66 mg, 0.58 mmol) was added. After 5 minutes, the reaction mixture was concentrated in vacuo. The crude was dissolved in methanol and submitted for reversed phase purification using acetonitrile and water as eluent. The fractions containing the product were combined and lyophilized. The yellowish solid that was obtained was submitted for prep LC-MS purification. The product fractions were lyophilized to afford the title compound (33 mg; 26%) as a yellowish solid.

$^1$H NMR (CD$_3$OD) δ 7.21-7.02 (m, 1H), 6.88-6.72 (m, 1H), 6.54-6.37 (m, 1H), 3.88-3.71 (m, 1H), 3.71-3.56 (m, 1H), 3.52-3.40 (m, 1H), 3.32-3.28 (m, 2H), 3.29-3.22 (m, 1H), 3.12-2.97 (m, 1H), 2.98-2.81 (m, 10H), 2.27-2.14 (m, 1H), 2.14-1.96 (m, 5H).

LCMS: m/z 405 (M+H)$^+$ (ES$^+$); 403 (M−H)$^−$ (ES$^−$).

Example 113: N-((6-Methyl-5-(2-((1-methylpiperidin-4-yl)oxy)pyridin-4-yl)-2,3-dihydro-1H-inden-4-yl)carbamoyl)N,N-dimethylsulfamide

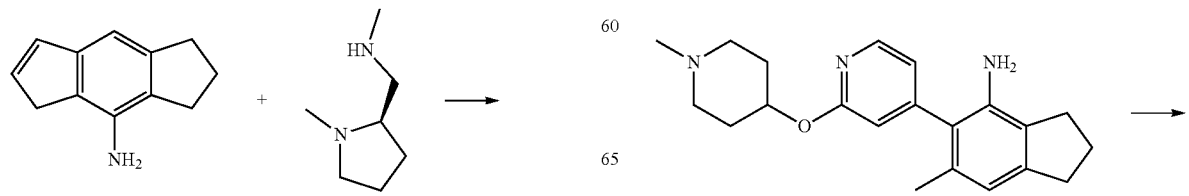

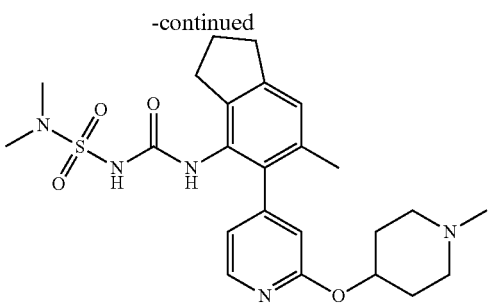

6-Methyl-5-(2-((1-methylpiperidin-4-yl)oxy)pyridin-4-yl)-2,3-dihydro-1H-inden-4-amine (Intermediate A6; 58 mg, 0.172 mmol) was added to a suspension of (4-(dimethylamino)pyridin-1-ium-1-carbonyl)(N,N-dimethylsulfamoyl)amide (Intermediate P24; 47 mg, 0.173 mmol) in MeCN (1 mL). The reaction was stirred at 60° C. for 1 hour, then cooled to room temperature and stirred for 72 hours. The reaction mixture was concentrated in vacuo and purified by basic prep HPLC (10-40% MeCN in water) to afford the title compound (17 mg, 19%) as a white solid.

$^1$H NMR (DMSO-d6) δ 8.19 (d, J=5.2 Hz, 1H), 7.46 (br s, 1H), 7.10 (s, 1H), 6.72 (dd, J=5.2, 1.4 Hz, 1H), 6.52 (s, 1H), 5.04-4.95 (m, 1H), 2.90 (t, J=7.4 Hz, 2H), 2.77-2.69 (m, 4H), 2.64 (s, 6H), 2.28-2.16 (m, 5H), 2.09-1.94 (m, 7H), 1.73-1.64 (m, 2H). One exchangeable proton not observed.

LCMS m/z 488.4 (M+H)$^+$ (ES$^+$); 486.3 (M−H)$^-$ (ES$^-$).

Example 14: N-((5-(2-Methoxypyridin-4-yl)-6-methyl-2,3-dihydro-1H-inden-4-yl)carbamoyl)(N,N-dimethylsulfamoyl)amide

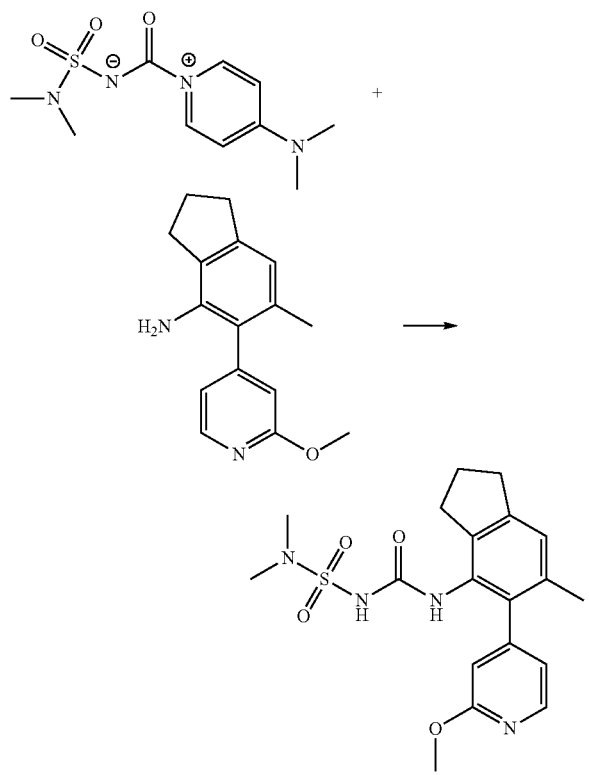

5-(2-Methoxypyridin-4-yl)-6-methyl-2,3-dihydro-1H-inden-4-amine (Intermediate A7; 38 mg, 0.149 mmol) was added to a suspension of (4-(dimethylamino)pyridin-1-ium-1-carbonyl)(N,N-dimethylsulfamoyl)amide (Intermediate P24; 41 mg, 0.151 mmol) in MeCN (1 mL) and the reaction mixture was stirred at 60° C. for 1 hour. The volatiles were evaporated, and the crudes dissolved in DMSO (1 mL), filtered and purified by basic prep HPLC (20-50% MeCN in water) to afford the title compound (17 mg, 28%) as a white solid.

$^1$H NMR (DMSO-d6) δ 9.66 (br s, 1H), 8.22 (d, J=5.2 Hz, 1H), 7.46 (s, 1H), 7.11 (s, 1H), 6.75 (dd, J=5-3, 1.4 Hz, 1H), 6.59 (s, 1H), 3.89 (s, 3H), 2.90 (t, J=7.4 Hz, 2H), 2.76-2.70 (m, 2H), 2.66 (s, 6H), 2.05-1.96 (m, 5H).

LCMS m/z 405.2 (M+H)$^+$ (ES$^+$).

Example 115: 3-((S)—N-Methyl-N-((-1-methylpyrrolidin-2-yl)methyl) sulfamoyl)-1-(1,2,3,5,6,7-hexahydro-s-indacen-4-yl)urea, sodium salt Step A: 3-((S)—N-Methyl-N-((-1-methylpyrrolidin-2-yl)methyl) sulfamoyl)-1-(1,2,3,5,6,7-hexahydro-s-indacen-4-yl)urea

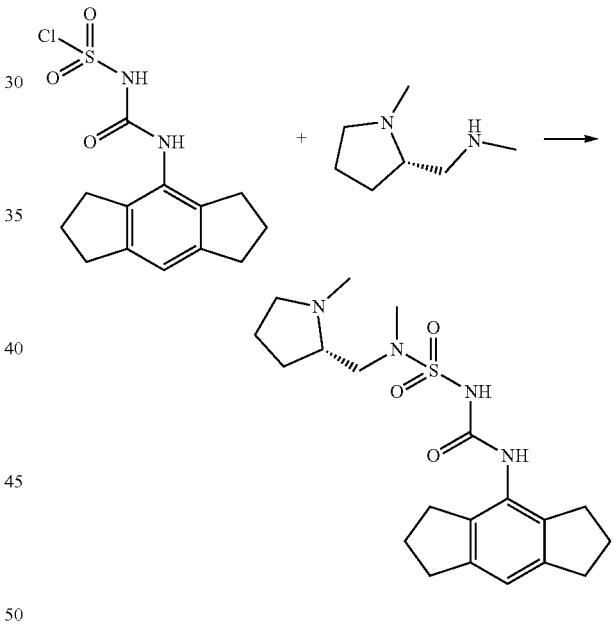

To a solution of (S)—N-methyl-1-(1-methylpyrrolidin-2-yl)methanamine (Intermediate P25) (1.02 g, 7.94 mmol, 5 eq) in THF (4 mL) was added ((1,2,3,5,6,7-hexahydro-s-indacen-4-yl)carbamoyl)sulfamoyl chloride (Intermediate A4) (0.5 g, 1.59 mmol, 1 eq) in THF (1 mL). The reaction mixture was stirred at 0° C. for 10 minutes. Then the reaction mixture was concentrated in vacuo. The residue was purified by prep-HPLC (column: Waters XBridge C18, 150 mm×25 mm×5 μm; mobile phase [A: water (10 mM NH$_4$HCO$_3$), B: MeCN]; B %: 19%-49%, 10 minutes) to give the title compound (33 mg, 5% yield, 98.8% purity on HPLC) as a white solid.

$^1$H NMR (400 MHz, CD$_3$OD) δ 6.92 (s, 1H), 3.80-3.70 (m, 2H), 3.51-3.45 (m, 1H), 3.30-3.24 (m, 1H), 3.10-3.03 (m, 1H), 2.91 (s, 3H), 2.89-2.77 (m, 11H), 2.24-2.18 (m, 1H) and 2.13-1.94 (m, 7H). 2×NHs were missing.

LCMS: m/z 407.2 (M+H)$^+$ (ES$^+$).

Step B: 3-((S)—N-Methyl-N-((-1-methylpyrrolidin-2-yl)methyl) sulfamoyl)-1-(1,2,3,5,6,7-hexahydro-s-indacen-4-yl)urea, sodium salt

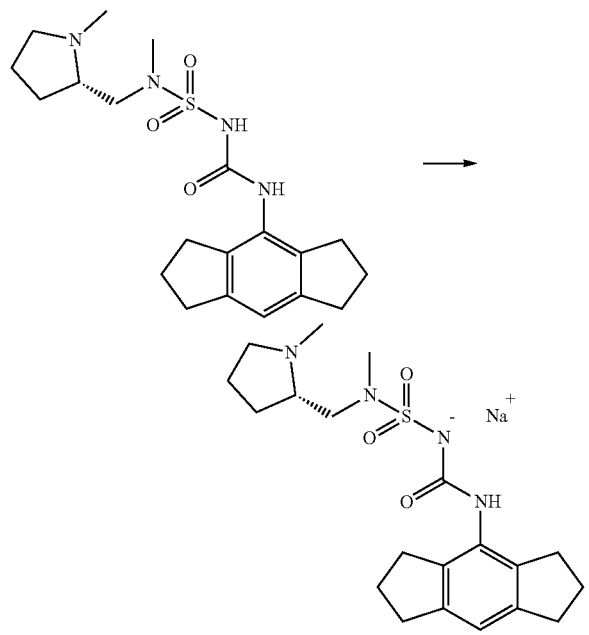

To a solution of 3-((S)—N-methyl-N-((-1-methylpyrrolidin-2-yl)methyl) sulfamoyl)-1-(1,2,3,5,6,7-hexahydro-s-indacen-4-yl)urea (30 mg, 73.79 μmol, 1 eq) in THF (10 mL) was added t-BuONa (7 mg, 73.79 μmol, 1 eq) at 0° C. The reaction mixture was stirred at 5° C. for 30 minutes. Then the reaction mixture was concentrated in vacuo and lyophilized to give the title compound (20.92 mg, 65% yield, 98.1% purity on HPLC) as a white solid.

$^1$H NMR (400 MHz, CD$_3$OD) δ 6.87 (s, 1H), 3.32-3.31 (m, 1H), 3.12-3.03 (m, 2H), 2.86-2.80 (m, 11H), 2.58-2.55 (m, 1H), 2.42 (s, 3H), 2.31-2.26 (m, 1H), 2.07-1.99 (m, 5H) and 1.77-1.67 (m, 3H). 1×NH was missing.

LCMS: m/z 407.4 (M−Na+2H)$^+$ (ES$^+$).

Examples—Biological Studies

NLRP and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C., 5% CO$_2$
4. Add 5 μl nigericin (Sigma #N7143) (FAC 5 μM) to all wells
5. Incubate for 1 hr at 37° C., 5% CO$_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

| | 96-well Plate Man | | | | | | | | | | |
|---|---|---|---|---|---|---|---|---|---|---|---|
| 1 | 2 | 3 | 4 | 5 | 6 | 7 | 8 | 9 | 10 | 11 | 12 |
| A High | Comp 1 | Comp 2 | Comp 3 | Comp 4 | Comp 5 | Comp 6 | Comp 7 | Comp 8 | Comp 9 | Comp 10 | Low |
| B High | Comp 1 | Comp 2 | Comp 3 | Comp 4 | Comp 5 | Comp 6 | Comp 7 | Comp 8 | Comp 9 | Comp 10 | Low |
| C High | Comp 1 | Comp 2 | Comp 3 | Comp 4 | Comp 5 | Comp 6 | Comp 7 | Comp 8 | Comp 9 | Comp 10 | Low |
| D High | Comp 1 | Comp 2 | Comp 3 | Comp 4 | Comp 5 | Comp 6 | Comp 7 | Comp 8 | Comp 9 | Comp 10 | Low |
| E High | Comp 1 | Comp 2 | Comp 3 | Comp 4 | Comp 5 | Comp 6 | Comp 7 | Comp 8 | Comp 9 | Comp 10 | Low |
| F High | Comp 1 | Comp 2 | Comp 3 | Comp 4 | Comp 5 | Comp 6 | Comp 7 | Comp 8 | Comp 9 | Comp 10 | Low |
| G High | Comp 1 | Comp 2 | Comp 3 | Comp 4 | Comp 5 | Comp 6 | Comp 7 | Comp 8 | Comp 9 | Comp 10 | Low |
| H High | Comp 1 | Comp 2 | Comp 3 | Comp 4 | Comp 5 | Comp 6 | Comp 7 | Comp 8 | Comp 9 | Comp 10 | Low |
| High | MCC950(10 uM) | | | | Compound 8-point | | | | | | |
| Low | Drug free control | | | | half-log dilution | | | | | | |

The results of the pyroptosis assay performed are summarised in Table 2 below as THP $IC_{50}$.

Human Whole Blood IL-1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add 10 μl nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 2 below as HWB $IC_{50}$.

TABLE 2

| Example No | THP $IC_{50}$ | HWB $IC_{50}$ |
|---|---|---|
| 1 | ++++ | ++++ |
| 2 | ++++ | ++++ |
| 3 | ++++ | ++++ |
| 4 | ++++ | ++++ |
| 5 | ++++ | ++++ |
| 6 | ++++ | ++++ |
| 7 | +++ | ND |
| 8 | +++ | ++++ |
| 9 | ++++ | ++++ |
| 10 | ++ | ++ |
| 11 | ++++ | ++++ |
| 12 | ++ | ND |
| 13 | +++ | ND |
| 14 | ++++ | ++++ |
| 15 | ++++ | ++++ |
| 16 | ++ | ND |
| 17 | +++ | ND |
| 18 | ++ | ND |
| 19 | +++ | ND |
| 20 | ++++ | ++++ |
| 21 | ++ | ND |
| 22 | ++++ | ND |
| 23 | ++ | ND |
| 24 | + | ND |
| 25 | +++ | ++++ |
| 26 | ++++ | +++ |
| 27 | +++ | ND |
| 28 | ++++ | ++++ |
| 29 | ++++ | ++++ |
| 30 | +++ | ++++ |
| 31 | ++++ | ++++ |
| 32 | ++ | ND |
| 33 | ++ | ND |
| 34 | ++++ | ++++ |
| 35 | ++ | +++ |
| 36 | ++++ | +++ |
| 37 | ++++ | +++ |
| 38 | ++++ | +++ |
| 39 | ++++ | +++ |
| 40 | +++ | ++++ |
| 41 | ++ | ND |
| 42 | ++ | ND |
| 43 | ++++ | ++++ |
| 44 | +++ | ++++ |
| 45 | ++++ | + |
| 46 | +++ | ++ |
| 47 | +++ | +++ |
| 48 | +++ | ND |
| 49 | ++++ | ++++ |
| 50 | ++++ | ++++ |
| 51 | + | ND |
| 52 | ++++ | ++++ |
| 53 | ++ | ND |
| 54 | ++ | ND |
| 55 | +++ | ND |
| 57 | ++ | ND |
| 58 | ++++ | ++ |
| 59 | ++ | ND |
| 60 | +++ | ND |
| 61 | ++++ | ++++ |
| 62 | ++++ | +++ |
| 63 | +++ | ND |
| 64 | ++++ | ND |
| 65 | ++++ | ++ |
| 66 | ++++ | ++++ |
| 67 | +++ | ND |
| 68 | ++++ | +++ |
| 69 | +++ | ND |
| 70 | +++ | ND |
| 71 | ++++ | +++ |
| 72 | ++++ | ++++ |
| 73 | +++ | ++ |
| 74 | ++ | ND |
| 75 | ++++ | ++ |
| 76 | ++++ | ++++ |
| 77 | + | ND |
| 78 | ++ | ND |
| 79 | ++++ | ++++ |
| 80 | ++++ | ++++ |
| 81 | ++++ | ++++ |
| 82 | ++ | ND |
| 83 | +++ | ++ |
| 84 | ++++ | +++ |
| 85 | ++++ | ++++ |
| 86 | ++++ | ++++ |
| 87 | ++++ | ++ |
| 88 | +++ | ++++ |
| 89 | ++++ | ++++ |
| 90 | +++ | ++++ |
| 91 | +++ | ++ |
| 92 | ++++ | ++++ |
| 93 | ++++ | ++++ |
| 94 | ++++ | +++ |
| 95 | ++++ | ++++ |
| 96 | ++++ | ++++ |
| 97 | ++++ | ++++ |
| 98 | ++ | ++ |
| 99 | ++ | ND |
| 100 | ++++ | ND |
| 101 | ++ | ND |
| 102 | ++ | ND |
| 103 | ++++ | ++++ |
| 104 | +++ | ++++ |
| 105 | + | ND |
| 106 | ++++ | ++++ |
| 107 | +++ | ++++ |
| 108 | ++++ | ++++ |
| 109 | + | ND |
| 110 | ++++ | ++++ |
| 111 | ++++ | ++++ |
| 112 | +++ | ++ |
| 113 | ++++ | ++++ |
| 114 | ++++ | +++ |
| 115 | ++++ | +++ |

$NLRP_3$ inhibitory activity (≤0.5 μM = '++++', ≤1 μM = '+++', ≤5 μM = '++', ≤10 μM = '+', not determined = 'ND').

PK Protocol

Pharmacokinetic parameters were determined in male Sprague Dawley rats (Charles River, UK, 250-350 g; or Vital River Laboratory Animal Technology Co Ltd, Beijing, China, 7-9 weeks old). Animals were individually housed during the study and maintained under a 12 h light/dark cycle.

For intravenous administration, compounds were formulated as a solution in water or DMSO:PBS [10:90] in 2 mL/kg dosing volume and administered via tail or jugular vein. For oral administration, compounds were formulated as a solution in 0.5% w/v methyl cellulose in water in 5 mL/kg dosing volume and administered orally.

Serial blood samples (about 120-300 μL) were taken from each animal at each of 8 time-points post dose (0.083, 0.25, 0.5, 1, 2, 4, 8 and 24 h) or at each of 12 time-points post dose (0.03, 0.1, 0.17, 0.25, 0.5, 1, 2, 4, 6, 8, 12 and 24 h) or pre-dose and at each of 9 time-points post dose (0.25, 0.5, 1, 2, 4, 6, 8, 12 and 24 h). Samples were held on ice for no longer than 30 minutes before centrifugation (10,000 rpm (8,385 g) for 3 minutes; or 5,696 rpm (3,000 g) for 15 minutes) for plasma generation. Plasma was frozen on dry ice prior to bioanalysis. PK parameters were generated from LC-MS/MS data using Dotmatics or Phoenix WinNonlin 6.3 software.

TABLE 3

PK data (intravenous administration)

| Example No | Dose (mg/kg) | AUC (ng · hr/mL) | $T_{1/2}$ (hr) | $V_{dss}$ (L/kg) | Cl (mL/min/kg) |
|---|---|---|---|---|---|
| 1 | 0.96 | 1318.7 | 11.1 | 8.69 | 12.6 |
| 3 | 1.27 | 1024 | 2.55 | 1.89 | 20.7 |
| 6 | 0.08 | 7271.1 | 2.7 | 0.35 | 2.3 |
| 8 | 1.3 | 2291.0 | 4.0 | 0.61 | 7.3 |
| 11 | 0.4 | 5661.0 | 2.7 | 0.59 | 2.9 |
| 20 | 1.32 | 2355.0 | 1.2 | 0.4 | 7.1 |
| 36 | 0.94 | 5909.7 | 1.1 | 0.23 | 2.8 |
| 66 | 1.48 | 6762 | 3.44 | 0.43 | 3.7 |
| 96 | 1.75 | 5149 | 1.14 | 0.45 | 5.7 |
| 106 | 1.86 | 5154 | 5.61 | 0.84 | 6.0 |
| 110 | 1 | 835 | 3.9 | 1.6 | 20 |
| 111 | 1 | 979 | 4.8 | 1.3 | 17 |

TABLE 4

PK data (oral administration)

| Example No | Dose (mg/kg) | $C_{max}$ (ng/mL) | AUC (ng · hr/mL) | $T_{max}$ (hr) | $T_{1/2}$ (hr) | Cl/F (mL/min/kg) | Bioavailability (%) |
|---|---|---|---|---|---|---|---|
| 110 | 3 | 277 | 1020 | 0.67 | 3.4 | 50 | 41 |
| 111 | 3 | 318 | 1376 | 0.67 | 4.0 | 38 | 47 |

As is evident from the results presented in Table 2, surprisingly in spite of the structural differences versus the prior art compounds, the compounds of the invention show high levels of NLRP3 inhibitory activity in the pyroptosis assay and in the human whole blood assay.

As is evident from the results presented in Tables 3 and 4, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (ID):

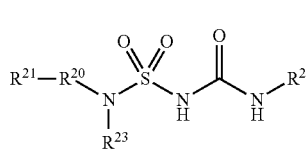

Formula (ID)

or a pharmaceutically acceptable salt or solvate thereof, wherein:

$R^{20}$ is selected from a bond, —$CH_2$— or —$CH_2CH_2$—;

$R^{21}$ is a 4- to 6-membered saturated heterocyclic group comprising one or two ring nitrogen atoms, wherein the heterocyclic group may optionally be substituted with one or two $C_1$-$C_4$ alkyl groups;

$R^{23}$ is selected from hydrogen or $C_1$-$C_4$ alkyl;

and $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein $R^2$ may optionally be further substituted.

2. The compound or the pharmaceutically acceptable salt or solvate thereof as claimed in claim 1, selected from the group consisting of:

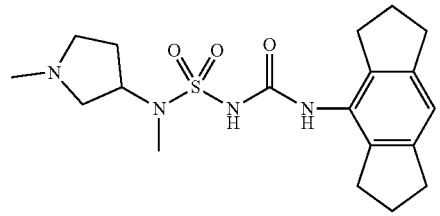

189
-continued
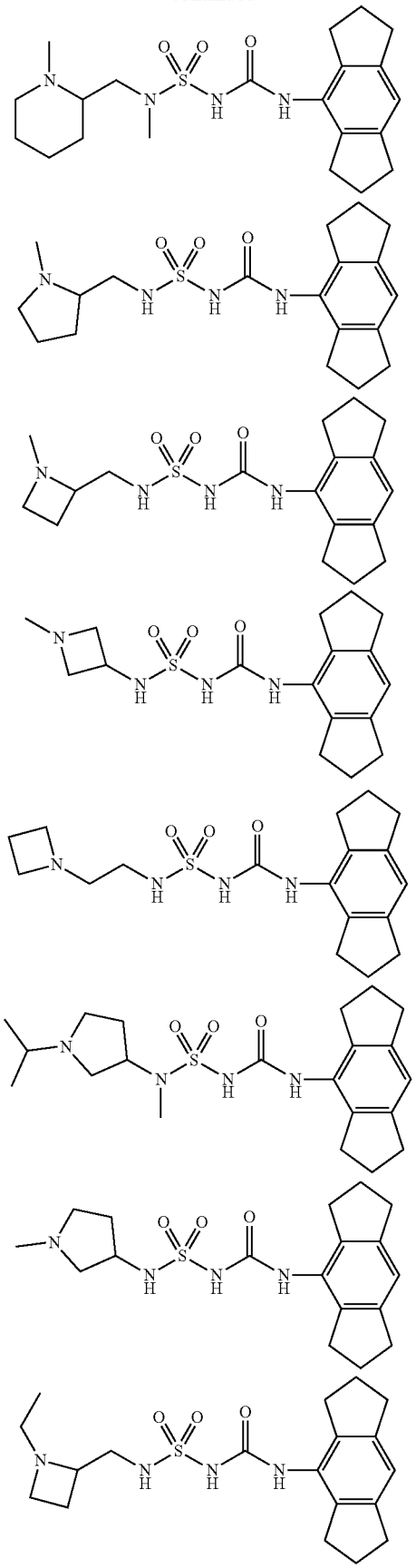
190
-continued
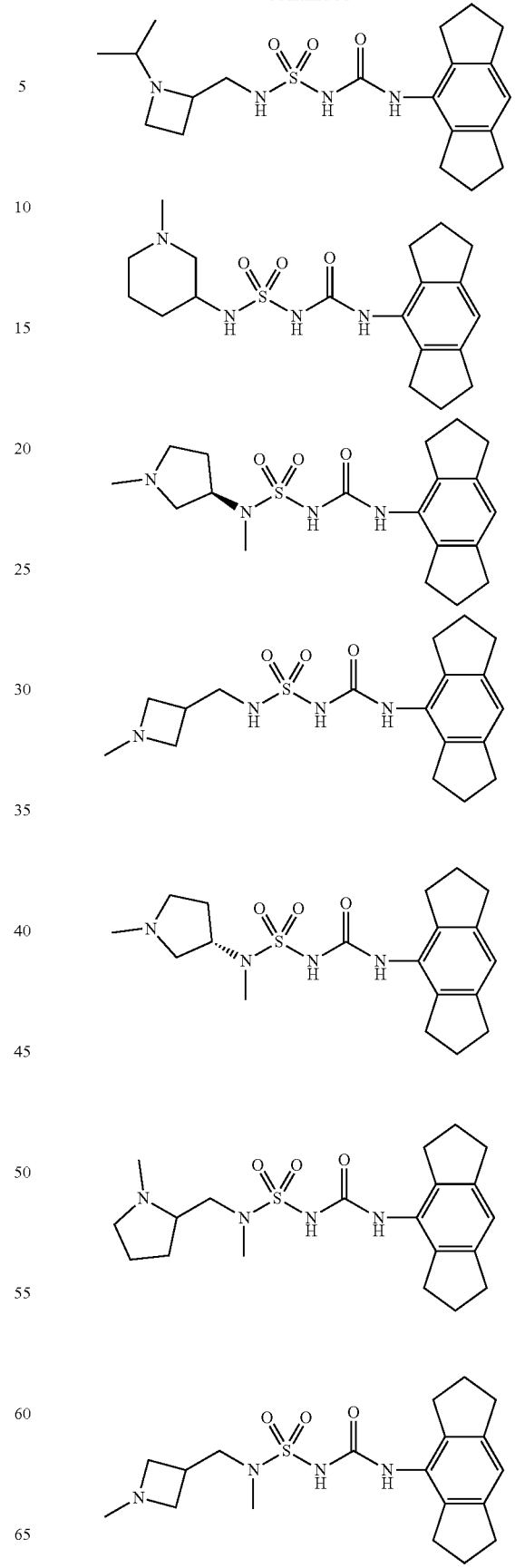

-continued

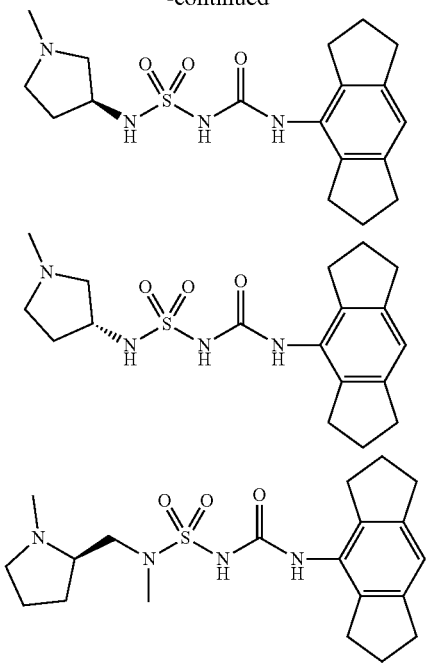

and pharmaceutically acceptable salts and solvates of any of the foregoing.

3. A pharmaceutical composition comprising the compound or the pharmaceutically acceptable salt or solvate thereof as claimed in claim 1, and a pharmaceutically acceptable excipient.

4. A method of treating a disease, disorder or condition in a subject, the method comprising the step of administering an effective amount of the compound or the pharmaceutically acceptable salt or solvate thereof as claimed in claim 1 to the subject, thereby treating the disease, disorder or condition, wherein the disease, disorder or condition is responsive to NLRP3 inhibition, and the disease, disorder or condition is selected from Alzheimer's disease, Parkinson's disease, asthma, chronic obstructive pulmonary disease, type 2 diabetes, atherosclerosis, gout, pseudo-gout, metabolic syndrome, myocardial infarction, aortic aneurysm, atrial fibrillation and hypertension.

5. The method as claimed in claim 4, wherein the compound is administered as a pharmaceutical composition further comprising a pharmaceutically acceptable excipient.

6. A method of inhibiting NLRP3 in a subject, comprising administering the compound or the pharmaceutically acceptable salt or solvate thereof as claimed in claim 1 to the subject thereby inhibiting NLRP3.

7. A method of analysing inhibition of NLRP3 or an effect of inhibition of NLRP3 by a compound, comprising contacting a cell or non-human animal with the compound or the pharmaceutically acceptable salt or solvate thereof as claimed in claim 1, and analysing inhibition of NLRP3 or an effect of inhibition of NLRP3 in the cell or non-human animal by the compound.

8. The compound or the pharmaceutically acceptable salt or solvate thereof as claimed in claim 1, wherein $R^{21}$ is a 4- to 6-membered saturated heterocyclic group selected from an azetidinyl, pyrrolidinyl, imidazolinyl, pyrazolinyl, piperidinyl or piperazinyl group, all optionally substituted with one or two $C_1$-$C_3$ alkyl groups.

* * * * *